US005955347A

United States Patent [19]
Lowe

[11] Patent Number: 5,955,347
[45] Date of Patent: Sep. 21, 1999

[54] METHODS AND PRODUCTS FOR THE SYNTHESIS OF OLIGOSACCHARIDE STRUCTURES ON GLYCOPROTEINS, GLYCOLIPIDS, OR AS FREE MOLECULES, AND FOR THE ISOLATION OF CLONED GENETIC SEQUENCES THAT DETERMINE THESE STRUCTURES

[75] Inventor: John B. Lowe, Ann Arbor, Mich.

[73] Assignee: The Regents of the University of Michigan, Ann Arbor, Mich.

[21] Appl. No.: 08/696,731

[22] Filed: Aug. 14, 1996

Related U.S. Application Data

[62] Division of application No. 08/393,246, Feb. 23, 1995, Pat. No. 5,595,900, which is a continuation of application No. 08/220,433, Mar. 30, 1994, abandoned, which is a division of application No. 07/914,281, Jul. 20, 1992, Pat. No. 5,324,663, which is a continuation-in-part of application No. 07/715,900, Jun. 19, 1991, abandoned, which is a continuation-in-part of application No. 07/627,621, Dec. 12, 1990, abandoned, which is a continuation-in-part of application No. 07/479,858, Feb. 14, 1990, abandoned.

[51] Int. Cl.$^6$ .............................. C12N 15/54; C12N 1/21; C12N 15/63; C12N 9/10
[52] U.S. Cl. ................... 435/252.3; 435/193; 435/320.1; 536/23.2
[58] Field of Search .......................... 536/23.2; 435/193, 435/320.1, 252.3

[56] References Cited

U.S. PATENT DOCUMENTS

| | | | |
|---|---|---|---|
| 4,205,129 | 5/1980 | Podolsky et al. ....................... | 435/193 |
| 4,411,994 | 10/1983 | Gilbert et al. .............................. | 435/71 |
| 4,438,200 | 3/1984 | Taubman et al. ......................... | 435/193 |
| 4,593,004 | 6/1986 | Boross et al. ............................ | 435/181 |
| 4,634,665 | 1/1987 | Axel et al. ................................ | 435/68 |
| 4,745,055 | 5/1988 | Schenk et al. .............................. | 435/7 |
| 5,324,663 | 6/1994 | Lowe .................................. | 435/320.1 |

FOREIGN PATENT DOCUMENTS

| | | |
|---|---|---|
| WO 90/13300 | 11/1990 | WIPO . |
| WO 94/23021 | 10/1994 | WIPO . |

OTHER PUBLICATIONS

Lowe et al, FASEB Abstract Form, "Blood Group H α–2–L–Fucosyltransferase Expressed in Mouse Cells After Stable Transfection with Human DNA", (1988).

Kukowska–Latallo et al, (Sep. 22, 1988 Submission to UCLA Glycobiology Symposium).

Ernst et al, (Sep. 22, 1988 Submission to UCLA Glycobiology Symposium).

Lowe et al, (Sep. 22, 1988 Submission to UCLA Glycobiology Symposium).

Ernst et al, *J. Biol. Chem.*, "Stable Expression of Blood Group H Determinants and GDP–L–fucose:β–D–Galactoside 2–α–L–Fucosyltransferase in Mouse Cells after Transfection with Human DNA", (1989) 264, pp. 3436–3447.

Rajan et al, *J. Biol. Chem.*, "A Cloned Human DNA Restriction Fragment Determines Expression of GDP–L–Fucose:β–D–Galactoside 2–α–L–fucosyltransferase in Transfected Cells", (1989) 264, pp. 11158–11167.

Larsen et al, *Proc. Natl. Acad. Sci.*, "Molecular Cloning, Sequence and Expression of a Human GDP–L–fucose:β–D–galactoside 2–α–L–fucosyltransferase cDNA that can Form the H Blood Group Antigen", (1990) 87, pp. 6674–6678.

Larsen et al, *Proc. Natl. Acad. Sci.*, "Isolation of a cDNA Encoding a Murine UDPgalactose:β–D–galactosyl–1, 4–N–acetyl–D–glucosaminide α–1,3–galactosyltransferase: Expression Cloning by Gene Transfer", (1989) 86, pp. 8227–8231.

Graham et al, *Virology*, "A New Technique for the Assay of Infectivity of Human Adenovirus 5 DNA", (1973) 52, pp. 456–467.

Kukowska–Latallo et al, *Genes & Devel.*, "A Cloned Human cDNA determines expression of a Mouse Stage–Specific Embryonic Antigen and the Lewis Blood Group α(1,3/1, 4)fucosyltransferase", (1990) 4, pp. 1288–1303.

Weber et al, *Mol. Cell. Biol.*, "Molecular Cloning and Biological Characterization of a Human Gene, ERCC2, That Corrects the Nucleotide Excision Repair Defect in CHO UV5 Cells", (1988) 8, pp. 1137–1146.

Ripka et al, *Biochem. & Biophys. Res. Comm.*, "DNA–Mediated Transformation of N–Acetylglucosaminyltransferase I Activity into an Enzyme Deficient Cell Line", (1989), 159, pp. 554–560.

Ripka et al, (preprint) "Co–transformation of Lec1 CHO Cells with N–Acetylgucosaminyltransferase I Activity and a Selectable Marker".

Chao et al, *Science*, "Gene Transfer and Molecular Cloning of the Human NGF Receptor", (1986), 232, pp. 518–521.

(List continued on next page.)

*Primary Examiner*—Rebecca E. Prouty
*Attorney, Agent, or Firm*—Oblon, Spivak, McClelland, Maier & Neustadt, P.C.

[57] ABSTRACT

A method for isolating a gene, comprising:

(i) isolating a cell possessing a post-translational characteristic of interest, said post-translational characteristic being the presence of a membrane-bound oligosaccharide or polysaccharide of interest on the surface of said cell, the presence of a soluble oligosaccharide or polysaccharide of interest in an extract of said cell, or the presence of a particularly glycosyltransferase activity in an extract of said cell;

(ii) creating a genetic library of either cDNA or genomic DNA from the genetic material of said isolated cell;

(iii) transforming host cells with said genetic library; and (iv) screening said transformed host cells for a host cell containing said post-translational characteristic, thereby obtaining a cell containing said gene, is disclosed. The method can be used to obtain genes encoding glycosyltransferases.

18 Claims, 43 Drawing Sheets

OTHER PUBLICATIONS

Kavathas et al, *Proc. Natl. Acad. Sci.,* "Stable Transformation of Mouse L Cells for Human Membrane T–Cell Differentiation Antigens, HLA and $\beta_2$–microglobulin: Selection by Fluorescence–activated Cell Sorting", (1983), 80, pp. 524–528.

Southern et al, *J. Mol. Appl. Genet.,* "Transformation of Mammalian Cells to Antibiotic Resistance with a Bacterial Gene Under Control of the SV40 Early Region Promoter", (1982), 1, pp. 327–341.

Kuhn et al, *Cell,* "Gene Transfer, Expression, and Molecular Cloning of the Human Transferrin Receptor Gene", (1984), 37, pp. 95–103.

Wigler et al, *Cell,* "Biochemical Transfer of Single–Copy Eucaryotic Genes Using Total Cellular DNA as Donor", (1978), 14, pp. 725–731.

Littman et al, *Cell,* "The Isolation and Sequence of the Gene Encoding T8: A Molecule Defining Functional Classes of T Lymphocytes", (1985), 40, pp. 237–246.

Toone et al, *Tetrahedron Rep.,* (1989) "Enzyme–Catalyzed Synthesis of Carbohydrates" pp. 5365–5422.

Hodgson, *Bio/Techn.,* "Capitalizing in Carbohydrates", (1990), 8, pp. 83–111 (partial).

Stinson, *C&EN,* "Controlled Linkage Techniques for Monosaccharides Introduced", (1989), Aug. 28, 1989, pp. 25–26.

*C&EN,* "Yale Carbohydrate Technology Licensed", (1990), Jan. 15, 1990, pp. 7–8.

Shaper et al, *Proc. Natl. Acad. Sci.,* "Bovine Galactosyltransferase: Identification of a Clone by Direct Immunological Screening of a cDNA Expression Library", (1986), 83, pp. 1573–1577.

Appert et al, *Biochem. Biophys. Res. Comm.,* "Isolation of a cDNA Coding for Human Galactosyltransferase", (1986), 139, pp. 163–168.

Narimatsu et al, *Proc. Natl. Acad. Sci,* "Cloning and Sequencing of cDNA of Bovine N–acetylglucosamine ($\beta$1–4)galactosyltransferase", (1986), 83, 4720–4724.

Prieels et al, *J. Biol. Chem.,* "Purification of the Lewis Blood Group N–Acetylglucosaminide $\alpha$1–4 Fucosyltransferase and an N–Acetylglucosaminide $\alpha$1–3 Fucosyltransferase from Human Milk", (1981) 256, pp. 10456–10463.

Eppenberger–Castori et al, *Glycoconjugate J,* "Purification of the N–Acetylglucosaminide $\alpha$(1–3/4) Fucosyltransferase of Human Milk", (1989), 6, pp. 101–114.

Elices et al, *J. Biol. Chem.,* "Purification and Characterization of UDP–Gal"$\beta$–D–Gal(1,4)–D–GlcNAc $\alpha$(1,3)–Galactosyltransferase from Ehrlich Ascites Tumor Cells", (1986) 261, pp. 6064–6072.

Blanken et al, *J. Biol. Chem.,* "Biosynthesis of Terminal Gal$\alpha$1–3Gal$\beta$1–4GlcNAc–R Oligosaccharide Sequences on Glyconconjugates", (1985), 260, pp. 12927–12934.

Beyer et al, *J. Biol. Chem.,* "Purification to Homogeneity of the H Blood Gropu $\beta$–Galactoside $\alpha$1–2 Fucosyltransferase from Porcine Submaxillary Gland", (1980), 255, pp. 5364–5372.

Beyer et al, *J. Biol. Chem.,* "Enzymatic Properties of the $\beta$–Galactoside $\alpha$1–2 Fucosyltransferase from Porcine Submaxillary Gland", (1980), 255, pp. 5373–5379.

Weinstein et al, *J. Biol. Chem.,* "Primary Structure of $\beta$–Galactoside $\alpha$2,6–Sialyltransferase", (1987), 262, pp. 17735–17743.

Weinstein et al, *J. Biol. Chem.,* "Purification of a Gal$\beta$1–4GlcNAc $\alpha$2–6 Sialyltransferase and a Gal$\beta$1–3(4)GlcNAc $\alpha$2–3 Sialyltransferase to Homogeneity from Rat Liver", (1982), 257, pp. 13835–13844.

Creeger et al, *Meth. Enz.,* "Complex Carbohydrates", (1982), 83, pp. 326–331 (ed. V. Ginsborg).

Natsuka et al, *J. Biol. Chem.,* "Molecular Cloning of a cDNA Encoding a Novel Human Leukocyte $\alpha$–1,3–Fucosyltransferase Capable of Synthesising the Sialyl Lewis x Determinant", (1994), 269(24), pp. 16789–16794.

Natsuka et al, *J. Biol. Chem.,* (*Additions and Corrections*), "Molecular Cloning of a cDNA Encoding a Novel Human Leukocyte $\alpha$–1,3–Fucosyltransferase Capable of Synthesising the Sialyl Lewis x Determinant", (1994), 269(32), p. 20806.

Sasaki et al, *J. Biol. Chem.,* "Expression Cloning of a Novel $\alpha$–1,3–Fucosyltransferase that is Involved in Biosynthesis of the Sialyl Lewis x Carbohydrate Determinant in Leukocytes", (1994), 269(20), pp. 14730–14737.

Sarnesto et al, *J. Biol. Chem.,* "Purification of the $\beta$–N–Acetylglucosaminide $\alpha$1–3–Fucosyltransferase from Human Serum", (1992),267, pp. 2745–2752.

Mollicone et al, *Eur. J. Biochem.,* "Acceptor Specificity and Tissue Distribution of Three Human $\alpha$–3–fucosyltransferases", (1990), 191, pp. 169–176.

Holmes et al, *J. Biol. Chem.,* "Biosynthesis of the Sialyl–Le$^x$ Determinant Carried by Type 2 Chain Glycosphingolipids (IV$^3$NeuAcIII$^3$FucnLe$_4$, VI$^3$NEuAcV$^3$FucnLc$_6$, and VI$^3$NeuAcIII$^3$V$^3$Fuc$_2$nLc$_6$) in Human Lung Carcinoma PC9 Cells", (1986), 261, pp. 3737–3743.

Weston et al, *J. Cell. Biochem,* "Defining a Glycosyltransferase Gene Family: Cloning and Expression of a Gene Encoding a GDP–Fucose: N–Acetylglucosaminide 3–$\alpha$–L–Fucosyltransferase Homologous to But Distinct from Known Human $\alpha$(1,3)Fucosyltransferases", (1992), p. 150.

Holmes et al, *J. Biol. Chem.,* "Enzymatic Basis for the Accumulation of Glycolipids with X and Dimeric X Determinants in Human Lung Cancer Cells (NCI–H69)", (1985), 260, pp. 7619–7627.

Koszdin et al, *Biochem. and Biophys. Res. Comm.,* "The Cloning and Expression of a Human $\alpha$–1,3 Fucosyltransferase Capable of Forming the E–Selectin Ligand", (1992), 187, pp. 152–157.

Nishihara et al, *Biochem. and Biophys. Res. Comm.,* "Human $\alpha$–1,3 Fucosyltransferase (FucT–VI) Gene is Located at Only 13 Kb 3' to the Lewis Type Fucosyltransferase (FucT–III) Gene on Chromosome 19", (1993), 190, pp. 42–46.

Mulligan et al, *J. Exp. Med.,* "Protective Effects of Sialylated Oligosaccharides in Immune Complex–induced Acute Lung Injury", (1993), 178, pp. 623–631.

Mulligan et al, *Nature,* "Protective Effects of Oligosaccharides in P–selectin–dependent Lung Injury", (1993), 364, pp. 149–151.

B.W. Weston et al., "Molecular Cloning of a Fourth Member of a Human Alpha(1,3)Fucosyltransferase Gene Family", J. Biol. Chem. 267(34): 24575–24584, Dec. 1992.

B.W. Weston et al., "Isolation of a Novel Human Alpha(1, 3)Fucosyltransferase Gene and Molecular Comparison to the Human Lewis Blood Group Alpha(1,3/1,4)Fucosyltransferase", J. Biol. Chem. 267(6): 4152–4160, Feb. 1992.

FIG. 1A

```
Sequence I
      -72 AGGAAACCTGCC
  -60 ATGGCCTCCTGGTGAGCTGTCCTCATCCACTGCTGCCTCTCCAGATACTCTGACCC 1     M  D  P  L  G  A  A  K  P  Q  W  P  W  R  R  C  L  A  A  L
    1 ATGGATCCCCTGGGTGCAGCCAAGCCACAATGGCCATGGCGCGTGTGCTGGCCGCACTG 21     L  F  Q  L  L  V  A  V  C  F  F  S  Y  L  R  V  S  R  D  D
   61 CTATTTCAGCTGCTGGTGGCTGTGTGTTTCTTCTCTTACCTGCGTGTGTCCCGAGACGAT 41     A  T  G  S  P  R  A  P  S  G  S  S  R  Q  D  T  T  P  T  R
  121 GCCACTGGATCCCCTAGGGCTCCCAGTGGGTCCTCCCGACAGGACACCACTCCCACCCGC 61     P  T  L  L  I  L  L  W  T  W  P  F  H  I  P  V  A  L  S  R
  181 CCCACCCTCCTGATCCTGCTATGGACATGGCCTTTCCACATCCCTGTGGCTCTGTCCCGC 81     C  S  E  M  V  P  G  T  A  D  C  H  I  T  A  D  R  K  V  Y
  241 TGTTCAGAGATGGTGCCCGGCACAGCCGACTGCCACATCACTGCCGACCGCAAGGTGTAC 101     P  Q  A  D  T  V  I  V  H  H  W  D  I  M  S  N  P  K  S  R
  301 CCACAGGCAGACACGGTCATCGTGCACCACTGGGATATCATGTCCAACCCTAAGTCACGC 121     L  P  P  S  P  R  P  Q  G  Q  R  W  I  W  F  N  L  E  P  P
  361 CTCCCACCTTCCCCGAGGCCCCAGGGGCAGCGCTGGATCTGGTTCAACTTGGAGCCACCC 141     P  N  C  Q  H  L  E  A  L  D  R  Y  F  N  L  T  M  S  Y  R
  421 CCTAACTGCCAGCACCTGGAAGCCCTGGACAGATACTTCAATCTTCACCATGTCCTACCGC 161     S  D  S  D  I  F  T  P  Y  G  W  L  E  P  W  S  G  Q  P  A
  481 AGCGACTCCGACATCTTCACGCCCTACGGCTGGCTGGAGCCGTGGTCCGGCCAGCCTGCCA 181     H  P  P  L  N  L  S  A  K  T  E  L  V  A  W  A  V  S  N  W
  541 CACCCACCGCTCAACCTCTCGGCCAAGACCGAGCTGGTGGCCTGGGCCGTGTCCAACTGG
```

FIG. 1B

```
201  K   P   D   S   A   R   V   R   Y   Y   Q   S   L   Q   A   H   L   K   V   D
601  AAGCCGGACTCAGCCAGGGTGCGCTACTACCAGAGCCTGCAGGCTCATCTCAAGGTGGAC

221  V   Y   G   R   S   H   K   P   L   P   K   G   T   M   M   E   T   L   S   R
661  GTGTACGGACGCTCCCACAAGCCCCTGCCCAAGGGGACCATGATGGAGACGCTGTCCCGG

241  Y   K   F   Y   L   A   F   E   N   S   L   H   P   D   Y   I   T   E   K   L
721  TACAAGTTCTACCTGGCCTTCGAGAACTCCTTGCACCCCGACTACATCACCGAGAAGCTG

261  W   R   N   A   L   E   A   W   A   V   P   V   V   L   G   P   S   R   S   N
781  TGGAGGAACGCCCTGGAGGCCTGGGCCGTGCCCGTGGTGCTGGGCCCCAGCAGAAGCAAC

281  Y   E   R   F   L   P   P   D   A   F   I   H   V   D   D   F   Q   S   P   K
841  TACGAGAGGTTCCTGCCACCCGACGCCTTCATCCACGTGGACGACTTCCAGAGCCCCAAG

301  D   L   A   R   Y   L   Q   E   L   D   K   D   H   A   R   Y   L   S   Y   F
901  GACCTGGCCCGGTACCTGCAGGAGCTGGACAAGGACCACGCCCGCTACCTGAGCTACTTT

321  R   W   R   E   T   L   R   P   R   S   F   S   W   A   L   D   F   C   K   A
961  CGCTGGCGGGAGACGCTGCGGCCTCGGTCCTTCAGCTGGGCACTGGACTTCTGCAAGGCC

341  C   W   K   L   Q   Q   E   S   R   Y   Q   T   V   R   S   I   A   A   W   F
1021 TGCTGGAAACTGCAGCAGGAATCCAGGTACCAGACGGTGCGCAGCATAGCGGCTTGGTTC

361  T   *
1081 ACCTGAGAGGCCGGCATGGTGCCTGGGCTGCGCGGGAACCTCATCTGCCTGGGGCCTCACC

1141 TGCTGGAGTCCTTGTGGCCAACCCTCTCTCTTACCTGGGACCTCACACGCTGGGCTTCA

1201 CGGCTGCCAGGAGCCCTCTCCCCTCCAGAAGACTTGCCTGCTAGGGACCTCGCCTGCTGGG

1261 GACCTCGCCTGTTGGGACCTCACCTGCTGGGACCTGCTGGGACCTTGGCTGC
```

```
1321 TGGAGGCTGCACCTACTGAGGATGTCGGGGTCGGGGACTTTACCTGCTGGGACCTGCTC
1381 CCAGAGACCTTGCCACACTGAATCTCACCTGCTGGGACCTTCACCTGGAGGCCCTGGG
1441 CCCTGGGAACTGGCTTACTTGGGCCCCACCCGGAGTGATGGTTCTGGCTGATTTGTT
1501 TGTGATGTTGTTAGCCGCCTGTGAGGGTGCAGAGAGATCATCACGGCACGGTTTCCAGA
1561 TGTAATACTGCAAGGAAAAATGATGACGTGTCTCCTCACTCTAGAGGGGTTGGTCCCATG
1621 GGTTAAGAGCTCACCCCAGGTTCTCACCTCAGGGGTTAAGAGCTCAGAGTTCAGACAGGT
1681 CCAAGTTCAAGCCCAGGACCCAGACCACCACTTATAGGGTACACAGGTGGATCGACTGTAAATGAGG
1741 ACTTCTGAACATTCCAAATATTCTGGGGTTGAGGGAAATTGCTGCTGTCTACAAATGC
1801 CAAGGGTGGACAGGCCTGTGGCTCACGCCTGTAATTCCAGCACTTTGGGAGGCTGAGGT
1861 AGGAGGATTGATTGAGGCCAACAGTTAAAGACCAGCCTGGTCAATATAGCAAGACCACGT
1921 CTCTAAATAAAAAATAAGGCCGGCCAGAAAAAAAAAAAAAAAA
```

Sequence II

```
-276  CCTTCCCTTGTAGACTCTTCTTGGAATGAGAAGTAC
-240  CGATTCTGCTGAAGACCTCGGCTCTCAGGCTCTTGGGAGTTGGAACCCTGTACCTTCCTT
-180  TCCTCTGCTGAGCCCTGCCTCCTTAGGCAGGCCAGAGCTCGACAGAACTCGGTTGCTTTG
-120  CTGTTTGCTTTGGAGGAACACAGCTGACGATGAGGCTGACTTTGAACTCAAGAGATCTG
 -60  CTTACCCCAGTCTCCTGGAATTAAAGGCCTGTACTACATTGCCTGGACCTAAGATTTTC

1        M  I  T  M  L  Q  D  L  H  V  N  K  I  S  M  S  R  S  K  S
   1  ATGATCACTATGCTTCAAGATCTTCATGTCAACAAGATCTCAAGATCCAAGTCA

21        E  T  S  L  P  S  S  R  S  G  S  Q  E  K  I  M  N  V  K  G
  61  GAAACAAGTCTTCCATCCTCTCAAGATCTGGATCACAGGAGAAATAATGAATGTCAAGGA

41        K  V  I  L  L  M  L  I  V  S  T  V  V  V  F  W  E  Y  V
 121  AAAGTAATCCTGTTGATGCTGATTGTCTCAACCGTGGTTGTCGTGTTTTGGGAATATGTC

61        N  R  I  P  E  V  G  E  N  R  W  Q  K  D  W  F  P  S  W
 181  AACAGAATTCCAGAGGTTGGTGAGAACAGATGGCAGAAGGACTGGTTCCCAAGCTGG

81        F  K  N  G  T  H  S  Y  Q  E  D  N  V  E  G  R  R  E  K  G
 241  TTTAAAAATGGGACCCACAGTTATCAAGAAGACAACGTAGAAGGACGGAGAGAAAAGGGT

101        R  N  G  D  R  I  E  E  P  Q  L  W  D  W  F  N  P  K  N  R
 301  AGAAATGGAGATCGCATTGAAGAGCCTCAGCTGTGGGACTGGTTCAATCCAAAGAACCGC

121        P  D  V  L  T  V  T  P  W  K  A  P  I  V  W  E  G  T  Y  D
 361  CCGGATGTTTTGACAGTGACCCCGTGGAAGGCGCCGATTGTGTGGGAAGGCACTTATGAC
```

FIG. 2B

```
141  T  A  L  L  E  K  Y  Y  A  T  Q  K  L  T  V  G  L  T  V  F
421  ACAGCTCTGCTGGAAAAGTACTACGCCACACAGAAACTCACTGTGGGGCTGACAGTGTTT

161  A  V  G  K  Y  I  E  H  Y  L  E  D  F  L  E  S  A  D  M  U
481  GCTGTGGGAAAGTACATTGAGCATTACTTAGAAGACTTTCTGGAGTCTGCTGACATGTAC

181  F  M  V  G  H  R  V  I  F  Y  V  M  I  D  D  T  S  R  M  P
541  TTCATGGTTGGCCATCGGGTCATATTTTACGTCATGATAGACACCTCCCGGATGCCT

201  V  V  H  L  N  P  L  H  S  L  Q  V  F  E  I  R  S  E  K  R
601  GTCGTGCACCTGAACCCTCTACAGTTCTTACAAGTCTTTGAGATCAGGTCTGAGAAGAGG

221  W  Q  D  I  S  M  M  R  M  K  T  I  G  E  H  I  L  A  H  I
661  TGGCAGGATATCAGCATGATGGGAGCATGAAGACCATTGGGGAGCACATCCTGGCCCACATC

241  Q  H  E  V  D  F  L  F  C  M  D  V  D  Q  V  F  Q  D  N  F
721  CAGCACGAGGTCGACTTCCTCTTCTGCATGGACGTGGATCAAGTCTTTCAAGACAACTTC

261  G  V  E  T  L  G  Q  L  V  A  Q  L  Q  A  W  Y  K  A  S
781  GGGGTGGAAACTCTGGGCCAGCTGGTAGCACAGCTCCAGGCCTGGTGGTACAAGGCCAGT

281  P  E  K  F  T  Y  E  R  R  E  L  S  A  A  Y  I  P  F  G  E
841  CCCGAGAAGTTCACCTATGAGAGGCGGGAACTGTCGGCCGCGTACATTCCATTCGGAGAG

301  G  D  F  Y  Y  H  A  A  I  F  G  G  T  P  T  H  I  L  N  L
901  GGGGATTTTTACTACCACGCGGCCATTTTTGGAGGAACGCCTACTCACATTCTCAACCTC

321  T  R  E  C  F  K  G  I  L  Q  D  K  K  H  D  I  E  A  Q  W
961  ACCAGGGAGTGCTTTAAGGGGATCCTCCAGGACAAGAAACATGACATAGAAGCCCAGTGG

341  H  D  E  S  H  L  N  K  Y  F  L  F  N  K  P  T  K  I  L  S
1021 CATGATGAGAGCCACCTCAACAAATACTTCCTTTTCAACAAACCCACTAAAATCCTATCT
```

```
361        P  E  Y  C  W  D  Y  Q  I  G  L  P  S  D  I  K  S  V  K  V
1081    CCAGAGTATTGCTGGGACTATCAGATAGGCCTTGCCTTCAGATATTAAAAGTGTCAAGGTA

381        A  W  Q  T  K  E  Y  N  L  V  R  N  N  V  *
1141    GCTTGGCAGACAAAAGAGTATAATTTGGTTAGAAATAATGTCTGACTTCAAATTGTGATG

1201    GAAACTTGACACTATTTCTAACCA
```

Sequence III

```
         10         20         30         40         50         60
GAATTCCATCGTGGCAAGGCAGCCCTGAATGGATGATGTAACCTGGGGTCCTTTCAATGG 70         80         90        100        110        120
AGGGCCAGACTCCTGGGTCTAGGGATGAGGGGAGGATCGGGTTAGCTGGGACCCA 130        140        150        160        170        180
GGTGAAAGGGCTGGGGCCCACATTCCTGAGTCTCAGAGAGAAGGATCTGGGGTCTCAA 190        200        210        220        230        240
GCACCTGAGTCGGAGGGAGGGGGTGCTGGGCTCCTGGAAAAACCACCTCTTGGACCAT 250        260        270        280        290        300
CTATGCAGATCACGCAGAACAAGAGAAATTTCTGCGCCCCATCTGAATTTCTAAGTTTGG 310        320        330        340        350        360
GGGGAGGGCGTGATCTGACACTGAGGTTCCTTGATCCTCAGCAAGGCGGCAATTGCTGTA 370        380        390        400        410        420
TGAAAGAAGGACCGCATCTGAGACACAAGTATCCTGCCTTGGAAGCCTCTCACCTGGCC 430        440        450        460        470        480
GTGGGCCAACCTCAACCTCATCTGTCCCTGCTCAGATGCTCAGACCCTGGACATCCCAGC 490        500        510        520        530        540
CTCCTCCTCCCTGATGCAATCCTGGTGTTTCTTTCACCAGAGAAGCCATCCCAGGCCCAG 550        560        570        580        590        600
GCAGGTGCTCCTGAAATAACCTGGGGGAGGGGTGGCTGAAAGTCCCTGACTGGAGTTGG 610        620        630        640        650        660
CAGCCAAGCCAGGCCCTGAGTGGGCACCCAGAGAGGAAGACAGGTTGGCTAATTTCCTGG
```

FIG. 3B

```
         670        680        690        700        710        720
AGCCCCTAAGGGTGCAAGGGTAGGCCTTCTGTGTCTGAGGGAGGAGGGCTGGGGCTCTGG 730        740        750        760        770        780
ACTCCTGGGTCTGAGGGAGGAGGGGTGGGGGCCTGGACTCCTGGGTCTGAGGGAGGAGG 790        800        810        820        830        840
GTCTGGGCCTGTACTCCTGGATCTGAGGGAGGAGGGGCTGGGAACTTGGGCTCCTGGGT 850        860        870        880        890        900
CTGAGGGAGGAGGAGCTTTGGTCTGAGGGAGTCCTGGGTCTGAGGGAGTAGGGGCTAGGGAT 910        920        930        940        950        960
CTGGACTCGTGGGTGTGAGGAAGGAGGGGCTGGGGTCCTGGGACTCCTGGGTCTGAGGAAG 970        980        990       1000       1010       1020
GAGGGGCAGGGGGCTTGGACTCCTGGGTCTGAGGAAGGAGGGGCCCGGAGCCTGGACTCC 1030       1040       1050       1060       1070       1080
TAAGTCTGAGGGAGGAGGGGTCTGGGGGCCTGGACTGCTGGGGTGTGAGCACAAGGGTCTGG 1090       1100       1110       1120       1130       1140
GTGCTGGGAGTCCCGAGCCTGGGGAGATGATGGTTAAACTTCTGGGAATCAAGTCAAACT 1150       1160       1170       1180       1190       1200
CCTGAGTCTTTGACATTGATGTATCTTGAATGGGAGGGTCAGTCTGTGGGAAGGATTAC 1210       1220       1230       1240       1250       1260
CCAGGTGCCGAGGCAAGACTGAAGGCACAAACTGTTTCAGTATAATAAAGAAAATAGT 1270       1280       1290       1300       1310       1320
TAGAATAAGAATAGTTATCATACAAATTAGATATAGAGATGATCATGGACAGTATCAATC
```

FIG. 3C

```
1330      1340      1350      1360      1370      1380
ATTAGTGTAAACATTATTAATCATTAGCTATTACTTTTATTCTTTGTTGTATAAACTAATA 1390      1400      1410      1420      1430      1440
TAACCAGAAACAACCGGTGGTATAGGGTCAGTGTACTGAAGGACATTGTGAGAAGTGA 1450      1460      1470      1480      1490      1500
CCTAGAAGGCAAGAGGTGAGCCTTCTGTCACACCGGCATAAGGGCCTCTTGAGGGCTCCT 1510      1520      1530      1540      1550      1560
TGGTCAAGGGGAACGCCAGTGTCTGGGAAGGCACCCGTTACTCAGCAGACCACGAAAGG 1570      1580      1590      1600      1610      1620
GAATCTCCTTTTCTTGGAGGAGTCAGGAACACTCTGCTCCACCAGCTTCTTGTGGAGG 1630      1640      1650      1660      1670      1680
CTGGGTATTATCTAGGCCCTGCCCGCAGTCATCCTGCTGTGCTGTGCTTCAATGGTCACGC 1690      1700      1710      1720      1730      1740
TCCTTGTCCTCTTGCATTTCCTCCCGTACTCCTGGTTCCTCTTTGAAGTTCGTAGTAGA 1750      1760      1770      1780      1790      1800
TAGCGGTAGAAGAAATAGTGAAAGCCTTTTTTTTTTTTTTTGAGGCGGAGTCTCGCTC 1810      1820      1830      1840      1850      1860
TGTCCCCAGGCTGGAGTGCAGTGGCGTGATCTCGGCTCACTGCAATCTCCGCCTCCTGG 1870      1880      1890      1900      1910      1920
GTTCACACCATTCTCCTGCCTCACCCTCCCAAATAGCTAGGACTACAGGCGCCCTCCACC 1930      1940      1950      1960      1970      1980
ACGCGCCCGATAATTTTTTGTATTTTTAGTAGAGACAGGGTTTCACCGTGTTAGCCAGG
```

FIG. 3D

```
       1990       2000       2010       2020       2030       2040
ATGGCCTCCACTTCCTGACCTTGTGATCCGCCCGCCTCAGCCTCCCAAAGTGCTGGGATT 2050       2060       2070       2080       2090       2100
ACAGGCGTGAGCCACCGCGCCCGCCGAAATAGTGAAAGTCTTAAAGTCTTTGATCTTTC 2110       2120       2130       2140       2150       2160
TTATAAGTGCAGAGAAGAAACGCTGACATATGCTGCCTTCTCTTTCTGCTTCGGCTGCC 2170       2180       2190       2200       2210       2220
TAAAAGGGAAGGCCCCCTGTCCCATGATCACGTGACTTGCTTGACCTTATCAGTCATTT 2230       2240       2250       2260       2270       2280
GGACGACTCACCCTCCTTATCCTGCCCCCCTTGTCTTGTATACAATAAATATCAGCGCG 2290       2300       2310       2320       2330       2340
CCCAGCCATTCGGGGCCACTACCGGTCTCTGCGTCTTGATGGTAGTGGTCCCCGGCCC 2350       2360       2370       2380       2390       2400
AGCTGTTTTCTCTTTATCTCTTTGTCTTGTGTCTTTATTTCTTACAATCTCTCCTCTCCT 2410       2420       2430       2440       2450       2460
CACAGGGGAAGAACACCCGACAAAGCCCGTAGGGCTGGACCCTACGTTAGCCTGCC 2470       2480       2490       2500       2510       2520
CTGCTCGGGGGTTGGCGATGCTGGAGGTGGGCCTTGGACCAGAGAAAATGCTTTAATTAGG 2530       2540       2550       2560       2570       2580
TGACAAGCGGGCAGAGGCCTTTGTCTGGCGCCAGCCACGCCCCCGCTGACGGCG 2590       2600       2610       2620       2630       2640
TGGGAAACAGACCCTGTTCCACTCCGGTCTCCAGCCCTTGGAATGGTTGCCTTCGTGCAGT
```

FIG. 3E

```
2650      2660      2670      2680      2690      2700
GCAGGTCTGGAAAGTAGCAGTTTGGCACGGGACCCTAGAATTCCCCAAAAGGAGTGACTA 2710      2720      2730      2740      2750      2760
GGGGCTGGGATTCTGGAATTTGAGTGTGTGGACGGTGAGGCGGGGGGGTGTGGGAGATCGGAG 2770      2780      2790      2800      2810      2820
ACCCTGGTGGGCGCGGGAGCACCTGCAGGCTGGAGGCCCTCGCCGCTCCGGCGGCAGCC 2830      2840      2850      2860      2870      2880
TGGCAAACAGGTTCTCCATCCCCCAGGAGACGCGGCAGAGGGCGACGATCGCTCCACT 2890      2900      2910      2920      2930      2940
CGCCCGGACCAGGTGCGGGGGCCCTGCCCAGCCGCTGGGGCGTGGCCAGGCTCGAAGCAC 2950      2960      2970      2980      2990      3000
CCAGGTGTCGGGGGCCGACTCTAAGCCCTGGCACCGGAAGAGAGAGGGCGGGATTGGA 3010      3020      3030      3040      3050      3060
CCTCCCGGCTCCAGCATTGCAAACTGGGCGCTCCGTCTCCTGGTCCACGCAATGATGCTGC 3070      3080      3090      3100      3110      3120
GGCTGCTCAGAAGCCAGGTAGCCCTGCCCTGGGTGAAGCCTTCGCGCAGGTCAATGACGGG 3130      3140      3150      3160      3170      3180
GCGGAGGGGCAGGGCGCGGTCCCCTGCATCCCCGATCTGGGGAGCGGTGGGCCCAGGGGC 3190      3200      3210      3220      3230      3240
CATCGCCTTAGCCCCTGGGCGCTCGGCGCCAAGTGACGGGGCGGGGCTCCACCTTC 3250      3260      3270      3280      3290      3300
CAGCCATCCGCCCGGCCCGGGAGGGCGGGACGCTGCGAGACTCCCGGCGCCCTCTCCT
```

FIG. 3F

```
3310      3320      3330      3340      3350      3360
TCCTCTCCTCCCCAAGCCCTGCTGCCAGTCCGGACACAGGCTGCGCGGAGGGGAGGGCTGC 3370      3380      3390      3400      3410      3420
CGGGCCGGATAGCCGGACGCCTGGCGTTCCAGGGGCGGCCGGATGTGGCCTGCCTTTGCG 3430      3440      3450      3460      3470      3480
GAGGGTGCGCTCCGGCCACGAAAAGCGGACTGTGGATCTGCCACCTGCAAGCAGCTCGGC 3490      3500      3510      3520      3530      3540
TAAGTGGGACTGCCCCACTCAGTTGTTCCTGGACCCAGGAACAACTCCTTCAGAACCA 3550      3560      3570      3580      3590      3600
GGAGGTGCACCCCCAACCTCTTCTCCAGGTCTCTTCCTAAGGCCCTAGGAATCTCCGCCACC 3610      3620      3630      3640      3650      3660
TCCCCAGCCATTACTCCTCCAGGAACCAAGATGCTCCTTCCGCTCCTGACCCTCCAGCCT 3670      3680      3690      3700      3710      3720
CTCTGTTTTACTTGAACTATCGTTTCCCATCACCACCTCTGTGGTGGATTTTGCGCCTC 3730      3740      3750      3760      3770      3780
ACAGACAGGTACTCCTGAGAAACAGGCTGGTGGAAGAGTCCAGTATCAGCGGAACTTASC 3790      3800      3810      3820      3830      3840
AGGAGGGGAGACTCGAGATTCCTTCAGGAAAGTGTAGGAACCTGGACCACTTTCTTTTT 3850      3860      3870      3880      3890      3900
TTTTTTTTTTTTTTTTAAGACAGGGTCCCTCTCTGTCGCGCAAGCTGGAGTGCAGTCAG 3910      3920      3930      3940      3950      3960
CGGTGCTATCGGCGGCTCATTGTGAGCTCCGGGGATCCTCCCGCCTTAGCATCCGGTGTAG
```

FIG. 36

```
     3970      3980      3990      4000      4100      4200
CTGAGACCACAGACATGTGCCACCATGCCAAGCTAATTTTATTTATTTTTTTGGAGAC 4300      4400      4500      4600      4700      4800
GGAGTTTCACTCTTGTTGCCCAGGCTGGAGTGTAATGGCATGATCTCAGCTCACCGCAAC 4090      4100      4110      4120      4130      4140
TCCCGCCCCCCGGGTTCAGGCGATTCTCCTGCCTCAGCCTCCGAGTGGCTGGGATTACA 4150      4160      4170      4180      4190      4200
GGCATGCGCCACCATGCCCGGCTAATTTTGTATTTTAAGTAGAGACAGGGTTTCTCCACG 4210      4220      4230      4240      4250      4260
TTGGTCAGGCTGGTCTCGAACTCCCAAGGTGATCCAACCTCAGGTGATCCAACCCACCTTGGCCTCCCAAA 4270      4280      4290      4300      4310      4320
GTGCTGGGATTACAGGTGTGAGCCACCGCGCCCTGGCCCATGCCAAGCTAATTTTAAAATT 4330      4340      4350      4360      4370      4380
TTTTTGTAAGAGTGCTCTGTTGCCCAGGCTGATCTTGAACTCCTGGGCTCAAGGGATCCT 4390      4400      4410      4420      4430      4440
CCCATCTCAGCCTCCCAATATGCTGGGATTACAGGTGTGAGCCACAGTGCCCAGCCAAAC 4450      4460      4470      4480      4490      4500
CATGGCTATCTTGAAAACCACTTGTCTTCCCAGTCCCCATGCCCCGAAATTCCAAGGCTCT 4510      4520      4530      4540      4550      4560
CATCCCCTGAAACCTAGGACTCAGGCTCTCCCTACCTCAGCCCCAGGAGTCTAAACCTTTA 4570      4580      4590      4600      4610      4620
ACTTCCTCTTTCCCTGGGACTAAGGAGTGCTGCACCCCAGGCGCCTCCCTTACCCCACAT
```

FIG. 3H

```
     4630      4640      4650      4660      4670      4680
CCCTCCTCAGCCTCCCCCTCCTCAGCCTCAGTGCATTTGCTAATTCGCCTTTCCTCCCCTG 4690      4700      4710      4720      4730      4740
CAGCCATGTGGCTCCGGAGCCATCGTCAGCTCTGCCTGGCCTTCCTGCTAGTCTGTGTCC
     MetTrpLeuArgSerHisArgGlnLeuCysLeuAlaPheLeuLeuValCysValL 4750      4760      4770      4780      4790      4800
TCTCTGTAATCTTCTTCCTCCATATCCATCAAGACAGCTTTCCACATGGCCTAGGCCTGT
euSerValIlePhePheLeuHisIleHisGlnAspSerPheProHisGlyLeuGlyLeuS 4810      4820      4830      4840      4850      4860
CGATCCTGTGTCCAGACCGCGCTGGTGACACCCCAGTGGCCATCTTCTGCCTGCCGG
erIleLeuCysProAspArgLeuValThrProProValAlaIlePheCysLeuProG 4870      4880      4890      4900      4910      4920
GTACTGGCGATGGGCCCCAACGCTCTACCTCTTCCTGTCCCCAGCACCCTGCTTCCCTCTCCG
lyThrAlaMetGlyProAsnAlaSerSerCysProGlnHisProAlaSerLeuSerG 4930      4940      4950      4960      4970      4980
GCACCTGACTGTCTACCCCAATGGCCGGTTTGGTAATCAGATGGGACAGTATGCCACGC
lyThrTrpThrValTyrProAsnGlyArgPheGlyAsnGlnMetGlyGlnTyrAlaThrL 4990      5000      5010      5020      5030      5040
TGCTGGCTCTGCCCAGCTCAACGGCCGCCGGGCCCTTTATCCTGCCTGCCATGCCG
euLeuAlaLeuAlaGlnLeuAsnGlyArgArgAlaPheIleLeuProAlaMetHisAlaA 5050      5060      5070      5080      5090      5100
CCCTGGCCCCGGTATTCCGACATCACCCTGCCCGTGCTGGCCCCAGAAGTGGACAGCCGCA
laLeuAlaProValPheArgIleThrLeuProValLeuAlaProGluValAspSerArgT 5110      5120      5130      5140      5150      5160
CGCCGTGGGGGAGCTGCAGCTTCACGATGGATGTCGGAGGAGTACGCGGACTTGAGAG
hrProTrpArgGluLeuGlnLeuHisAspTrpMetSerGluGluTyrAlaAspLeuArgA
```

FIG. 31

```
      5170           5180           5190           5200           5210           5220
ATCCTTCCTGAAGCTCTCTGGCTTCCCCTGCTCTCTTGGACTTTCTTCCACCATCTCCGGG
spProPheLeuLysSerGlyPheProCysSerTrpThrPhePheHisHisLeuArgG 5230           5240           5250           5260           5270           5280
AACAGATCCGCAGAGAGTTCACCCTGCACGACCACCTTCGGGAAGAGGGCAGAGTGTGC
luGlnIleArgArgGluPheThrLeuHisAspHisLeuArgGluAlaGlnSerValL 5290           5300           5310           5320           5330           5340
TGGGTCAGCTCCGCCTGGGCCGCACAGGGACCGCCCGCCACCTTTGTCGGCGTCCACG
euGlyGlnLeuArgLeuGlyArgThrGlyAspArgProArgThrPheValGlyValHisV 5350           5360           5370           5380           5390           5400
TGCGCCGTGGGGACTATCTGCAGGTTATGCCTCAGCGCTGGAAGGGTGTGGTGGGCGACA
alArgArgGlyAspTyrLeuGlnValMetProGlnArgTrpLysGlyValValGlyAspS 5410           5420           5430           5440           5450           5460
GCGCCTACCTCCGGCAGGCCATGGACTGGTTCCGGGCACGGCACGAAGCCCCCGTTTTCG
erAlaTyrLeuArgGlnAlaMetAspTrpPheArgAlaArgHisGluAlaProValPheV 5470           5480           5490           5500           5510           5520
TGGTCACCAGCAACGGCATGGAGTGGTGTAAAGAAAACATCGACACCTCCCAGGGCGATG
alValThrSerAsnGlyMetGluTrpCysLysGluAsnIleAspThrSerGlnGlyAspV 5530           5540           5550           5560           5570           5580
TGACGTTTGCTGGGGATGGACAGGAGGCTACACCGTGGAAAGACTTTGCCCTGCTCACAC
alThrPheAlaGlyAspGlyGlnGluAlaThrProTrpLysAspPheAlaLeuLeuThrG
```

FIG. 3J

```
                5590          5600          5610          5620          5630          5640
          AGTGCAACCACCACCATTATGACCATTGGCACCTTCGGCCTTCTGGGCTGCCTGCCTACCTGGCTG
          lnCysAsnHisThrIleMetThrIleGlyThrPheGlyTyrPheAlaAlaTyrLeuAlaG 5650          5660          5670          5680          5690          5700
          GCGGAGACACTGTCTACCTGGCCAACTTCACCCTGCCAGAGACTCTGAGTTCCTGAAGATCT
          lyGlyAspThrValTyrLeuAlaAsnPheThrLeuProAspSerGluPheLeuLysIleP 5710          5720          5730          5740          5750          5760
          TTAAGCCGGAGGGGCCTTCCTGCCCAGTGGGTGGGCATTAATGCAGACTTGTCTCCAC
          heLysProGluAlaPheLeuProGluTrpValGlyLeuAsnAlaAspLeuSerProL 5770          5780          5790          5800          5810          5820
          TCTGGACATTGGCTAAGCCTTGAGAGCCAGGGAGACTTTCTGAAGTAGCCTGATCTTTCT
          euTrpThrLeuAlaLysProEnd 5830          5840          5850          5860          5870          5880
          AGAGCCAGCAGTACGTGGCTTCAGAGGCCTGGCATCTTCTGGAGAAGCTTGTGGTGTTCC 5890          5900          5910          5920          5930          5940
          TGAAGCAAATGGGTGCCCGTATCCAGAGTGATTCTAGTTGGGAGAGTTGGAGAGAAGGGG 5950          5960          5970          5980          5990          6000
          GACGTTTCTGGAACTGTCTGAATATTCTAGAACTAGCAAAACATCTTTTCCTGATGGCTG 6010          6020          6030          6040          6050          6060
          GCAGGCAGTTCTAGAAGCCACAGTGCCCACCTGCTCTTCCCAGCCCATATCTACAGTACT 6070          6080          6090          6100          6110          6120
          TCCAGATGGCTGCCCCCAGGAATGGGAACTCTCCCTGGTCTACTCTAGAAGAGGGGT 6130          6140          6150          6160          6170          6180
          TACTTCTCCCCTGGGTCCTCCAAAGACTGAAGGAGCATATGATTGCTCCAGAGCAAGCAT
```

FIG.3K

```
6190       6200       6210       6220       6230       6240
TCACCAAGTCCCCTTCTGTGTTCTGGAGTGATTCTAGAGGGAGACTTGTTCTAGAGAGG 6250       6260       6270       6280       6290       6300
ACCAGGTTTGATGCCTGTGAAGAACCCTGCAGGGCCCTTATGGACAGGATGGGGTTCTGG 6310       6320       6330       6340       6350       6360
AAATCCAGATAACTAAGGTGAAGAATCTTTTTAGTTTTTTTTTTTTTTTGGAGACAG 6370       6380       6390       6400       6410       6420
GGTCTCGCTCTGTTGCCCAGGCTGGAGTGCAGTGGCGTGATCTTGGCTCACTGCAACTTC 6430       6440       6450       6460       6470       6480
CGCCTCCTGTGTTCAAGCGATTCTCCTGTCTCAGCCTCCTGAGTAGATGGGACTACAGGC 6490       6500       6510       6520       6530       6540
ACAGGCCATTATGCCTGGCTAATTTTTGTATTTTTAGTAGAGACAGGGTTTCACCATGTT 6550       6560       6570       6580       6590       6600
GGCCCGGATGGTCTCGATCTCCTGACCTTGTCATCCACCTGTCTTGGCCTCCCAAAGTGC 6610       6620       6630       6640       6650       6660
TGGGATTACTGGCATGAGCACCACTGTGCCCAGCCCGGATATTTTTTTAATTATTATTT 6670       6680       6690       6700       6710       6720
ATTTATTTATTTATTGAGACGGAGTCTTGCTCTGTAGCCCAGGCCAGAGTGCAGTGGCGC 6730       6740       6750       6760       6770       6780
GATCTCAGCTCACTGCAAGCTCTGCCTCCCGGGTTCATGCCATTCTGCCTCAGCCTCCTG 6790       6800       6810       6820       6830       6840
AGTAGCTGGGACTACAGGCGCCCGCCACCACGCCCCGGCTAATTTTTTGTATTTTTAGT
```

FIG.3L

```
        6850                6860                6870                6880                6890                6900
AGAGACGGGGTTTCATCGTGTTAACCAGAGATGGTTCTCGATCTCCTGACCTCGTGATCTGC 6910                6920                6930                6940                6950                6960
CCACCTCGGCCTCCCACAGTGCTGGGATTACCGGCGTGAGCCACCATGCCTGGCCCGGAT 6970                6980                6990                7000                7010                7020
AATTTTTTTAATTTTTGTAGAGACGAGGTCTTGTGATATTGCCCAGGCTGTCTCTTCAAC 7030                7040                7050                7060                7070                7080
TCCTGGGCTCAAGCAGTCCTCCCACCTTGGCCTCCCAGAATGCTGGGTTTATAGATGTGA 7090                7100                7110                7120                7130                7140
GCCAGCACACCGGGCCAAGTGAAGAATCTAATGAATGTGCAACCTAATTGTAGCATCTAA 7150                7160                7170                7180                7190                7200
TGAATGTTCCACCATTGCTGGAAAAATTGAGATGGAAAACAAACCATCTCTAGTTGGCCA 7210                7220                7230                7240                7250                7260
GCGTCTTGCTCTGTTCACAGTCTCTGGAAAAGCTGGGTAGTGGTGAGCAGAGCGGGAC 7270                7280                7290                7300                7310                7320
TCTGTCCAACAAGCCCCACAGCCCCCTCAAAGACTTTTTTTGTTTTTGAGCAGACAG 7330                7340                7350                7360                7370                7380
GCTAAAAATGTGAACGTGGGGTGAGGGATCACTGCCAAAATGTACAGCTTCTGGAGCAGA 7390                7400                7410                7420                7430                7440
ACTTTCCAGGGATCCAGGGACACTTTTTTTAAAGCTCATAAACTGCCAAGAGCTCCATA 7450                7460                7470                7480                7490                7500
TATTGGGTGTGAGTTCAGGTTGCCTCTCACAATGAAGGAAGTTGGTCTTTGTCTGCAGGT
```

FIG. 3M

```
       7510      7520      7530      7540      7550      7560
GGGCTGCTGAGGGTCTGGGATCTGTTTTCTGGAAGTGTGCAGGTATAAACACACCCTCTG 7570      7580      7590      7600      7610      7620
TGCTTGTGACAAACTGGCAGGTACCGTGCTCATTGCTAACCACTGTCTGTCCCTGAACTC 7630      7640      7650      7660      7670      7680
CCAGAACCACTACATCTGGCTTTGGGCAGGTCTGAGATAAAACGATCTAAAGGTAGGCAG 7690      7700      7710      7720      7730      7740
ACCCTGGACCCCAGCCTCAGATCCAGGCAGGAGCACGAGGTCTGGCCAAGGTGGACGGGGT 7750      7760      7770      7780      7790      7800
TGTCGAGATCTCAGGAGCCCCTGCTGTTTTTTGGAGGGTGAAAGAAGAAACCTTAAACA 7810      7820      7830      7840      7850      7860
TAGTCAGCTTCTGATCACATCCCCTGTCTACTCATCCAGACCCCATGCCTGTAGGCTTATC 7870      7880      7890      7900      7910      7920
AGGGAGTTACAGTTACAATTGTTACAGTACTGTTCCCAACTCAGCTGCCACGGGTGAGAG 7930      7940      7950      7960      7970      7980
AGCAGGAGGTATGAATTAAAAGTCTACACAGCACTAACCCGTGTCTCTGTAGCTTTTTGGA 7990      8000      8010      8020      8030      8040
GCCAGAGCCACTGTGTATGTGTGTGTGGGTTTGTGTGTGTGTGTGTGTGTGTGTGTGTGT 8050      8060      8070      8080      8090      8100
AAGAGAGTGGAGGAAAAGGTGGGGTACTTCTGAAGACTTTTATTTTTTATTTTTAATTAATTT 8110      8120      8130      8140      8150      8160
ATTTTTTTCAGAGATCGAGTCTTGCTCTGTGGCCCAGGCTGGAGTGCAGTAGTGTGATC
```

8170
TCGGCCCCACTGCAA

FIG. 3N

```
  10         20         30         40         50         60
   *          *          *          *          *          *
CTGCA GAGAG CGCCA CCCGG AAGCC ACTTT TATAG AAGCT TTTAC ACACA ATGCT TGATT 70         80         90        100        110        120
   *          *          *          *          *          *
TTTTT TTTTT TTTTC CGAGA CGGAG TCTCG CTTTG TCGCC CAGGC TGGAG TGCAG TGGCG 130        140        150        160        170        180
   *          *          *          *          *          *
CGATC TGGGC TCACT GCAAG CTCCG CCTCC TGGGT TGACG CCATT CTCCT GCCTC AGCTT 190        200        210        220        230        240
   *          *          *          *          *          *
CCCGA GTAGC TGGGA CTACA GGCGC CCGCC ACCAA GCCTG GCTAA TTTTT TTTTA TTTTT 250        260        270        280        290        300
   *          *          *          *          *          *
AGTGG AGACA GAGTT TCACC GTGTT AGCCA GGATG GTCTC GATCT CCTGA CCTCG GGATC 310        320        330        340        350        360
   *          *          *          *          *          *
CGCCC GCCTC GGCCT CCCAA AGTGC TGGGA GTATA GGCGT GAGCC ACCGC GCCTG GCCTA 370        380        390        400        410        420
   *          *          *          *          *          *
TACTT GATTT TTAAT GAAAA CATTC TTAAA TTCAT ATGGC TAACG CAAAT TTATT TTCTG 430        440        450        460        470        480
   *          *          *          *          *          *
TAGGC ATAAC ATCAA AAACA CCTGG CAGGA CTGCC CCATT CCCAG CACTG TCTAG TTCTC
```

FIG. 4A

```
         490        500        510        520        530        540
          *          *          *          *          *          *
CCCTA GTATC AGTGG GACTC CACTG ATGCA CAGCT GTGAT CTACT AAAAC TTCTC TCAAA
         550        560        570        580        590        600
          *          *          *          *          *          *
ACTTT CTCCT CTCCT TAGGT CAGCA GCCCC GCCCC TGATC TATTT GGAAA TCCCC TGAAT
         610        620        630        640        650        660
          *          *          *          *          *          *
AAAAG TTGAA TATCA TAAAC CAAAG CGAAC ACCCA GAAAT TCAAA CCCGT AGGTA
         670        680        690        700        710        720
          *          *          *          *          *          *
AAAAA TTTCT CAAGT GACTG TAGAC GTAGA TGTCT CCAGT GTCGC CTAAT AAGGT AGAAG
         730        740        750        760        770        780
          *          *          *          *          *          *
AGGCC AGTGC GATAC TGTCT TTACA CCCTT AACTT GGGTG CTAGA ATATT TATCT TCGTC
         790        800        810        820        830        840
          *          *          *          *          *          *
ATCAT TTTAT CATCC AAACT ATTTT GCATA ACTTT CATGG GTGCA GAAAA TGTTT TTTAA
         850        860        870        880        890        900
          *          *          *          *          *          *
GTGCT TGGTA AAATT AATAG TGATA TTCAT TCATT CATCT CACTG AACAG GCAAT AAATT
         910        920        930        940        950        960
          *          *          *          *          *          *
CCTTG ACGAC AAGGG CCTTG GGGGG GGCCA CATCT TCATC TTTGG TTTAT GAGTC CTGTG
```

FIG. 4B

```
        970         980         990        1000        1010        1020
          *           *           *           *           *           *
CGTCT TGGTA CAAGC AATAC TACTA TGAGC CGGCA AGTCA GACTT ATTTG GTAGG GGACC 1030        1040        1050        1060        1070        1080
          *           *           *           *           *           *
AAAGG AAAGA ACATG TTTTG ATTGC TAAGA AAACA TTTTG TTCTC TATTC TTTAC TGGGC 1090        1100        1110        1120        1130        1140
          *           *           *           *           *           *
TGGCA GGCAA AGGAA ATGTT CTTAT GAGCA CTCAC ATTGA AAACT TAAGT TCTTC ACCAA 1150        1160        1170        1180        1190        1200
          *           *           *           *           *           *
ATGCA GAGAC TCTGA AGGCC ACGCC GCTGC GGGCT GCCTC CACAA TTCGA CCGTC TCGGC 1210        1220        1230        1240        1250        1260
          *           *           *           *           *           *
GGGCC ACGAG ATCCT GGCCA CGGAT GCGGT GGCCG CGCCT CTGCT CGCAC GTTCC CCCGG 1270        1280        1290        1300        1310        1320
          *           *           *           *           *           *
CCTCT GGACT CCCTC CCTCC CTCAA TCCCT CGGCG GGCGT CGCTG GCGGG TGGCT 1330        1340        1350        1360        1370        1380
          *           *           *           *           *           *
AGGCC CAACG GCAGG AAGCC GACGC TATCC TCCGT TCCGC GGGCC CGGGT CCGCC TTCCG 1390        1400        1410        1420        1430        1440
          *           *           *           *           *           *
TCTGT TCTAG GGCCT GCTCC TGCGC GGCAG CTGCT TTAGA AGGTC TCGAG CCTCC TGTAC
```

FIG. 4C

```
        1450       1460       1470       1480       1490       1500
          *          *          *          *          *          *
CTTCC CAGGG ATGAA CCGGG CCTTC CCTCT GGAAG GCGAG GGTTC GGGCC ACAGT GAGCG 1510       1520       1530       1540       1550       1560
          *          *          *          *          *          *
AGGGC CAGGG CGGTG GGCGC GCGCA GAGGG AAACC GGATC AGTTG AGAGA GAATC AAGAG 1570       1580       1590       1600       1610       1620
          *          *          *          *          *          *
TAGCG GATGA GGCGC TTGTG GGGCG CGGCC CGGAA GCCCT CGGGC GCGGG CTGGG AGAAG 1630       1640       1650       1660       1670       1680
          *          *          *          *          *          *
GAGTG GGCGG AGGCG CCGCA GGAGG CTCCC CGGGC CTGGT CGGGC CGGCT GGGCC CCGGG 1690       1700       1710       1720       1730       1740
          *          *          *          *          *          *
CGCAG TGGAA GAAAG GGACG GGCGG TGCCC GGTTG GGCGT CCTGG CCAGC TCACC TTGCC 1750       1760       1770       1780       1790       1800
          *          *          *          *          *          *
CTGGC GGCTC GCCCC GCCCG GCACT TGGGA GGAGC AGGGC AGGGC CCGCG GCCTT TGCAT 1810       1820       1830       1840       1850       1860
          *          *          *          *          *          *
TCTGG GACCG CCCCC TTCCA TTCCC GGGCC AGCGG GGCAG CGACG GCTGG AGCCG 1870       1880       1890       1900       1910       1920
          *          *          *          *          *          *
CAGCT ACAGC ATGAG AGCCG GTGCC GCTCC TCCAC GCCTG CGGAC GCGTG GCGAG CGGAG
```

```
              1930        1940        1950        1960        1970
                *           *           *           *           *
         GCAGC GCTGC CTGTT CGCGC C ATG GGG GCA CCG TGG GGC TCG CCG ACG GCG GCG
                                    Met Gly Ala Pro Trp Gly Ser Pro Thr Ala Ala 1980        1990        2000        2010        2020
      *           *           *           *           *
GCG GGC GGG CGG CGC GGG TGG CGC CGA GGC CGG GGG CTG CCA ACC GTC TGT
Ala Gly Gly Arg Arg Gly Trp Arg Arg Gly Arg Gly Leu Pro Thr Val Cys 2040        2050        2060        2070        2080
           *           *           *           *           *
GTG CTG GCG GCC GGC TTG ACG TGT ACG GCG CTG ATC ACC TAC GCT TGC TGG
Val Leu Ala Ala Gly Leu Thr Cys Thr Ala Leu Ile Thr Tyr Ala Cys Trp 2030           2090        2100        2110        2120        2130
  *              *           *           *           *           *
GGG CAG CTG CCG CCG CCC TGG CCC TGG GCG TCG CCA ACC CCG TCG CCG GTG GGC
Gly Gln Leu Pro Pro Pro Trp Pro Trp Ala Ser Pro Thr Pro Ser Arg Pro Val Gly 2140        2150        2160        2170        2180        2190
           *           *           *           *           *           *
CTG CTG CTG TGG GAG CCC TTC GGG GGG CGC GAT AGC GCC CCG AGG CCG CCC
Val Leu Leu Trp Glu Pro Phe Gly Gly Arg Asp Ser Ala Pro Arg Pro Pro 2200        2210        2220        2230        2240
                *           *           *           *           *
CCT GAC TGC CCG CTG CGC TTC AAC ATC AGC GGC TGC CGC CTG CTC ACC GAC CGC
Pro Asp Cys Pro Leu Arg Phe Asn Ile Ser Gly Cys Arg Leu Leu Thr Asp Arg 2250        2260        2270        2280        2290
      *           *           *           *           *
GCG TCC TAC GGA GAG GCT CAG GCC GTG CTT TTC CAC CAC CGC GAC CTC GTG AAG
Ala Ser Tyr Gly Glu Ala Gln Ala Val Leu Phe His His Arg Asp Leu Val Lys
```

FIG. 4F

```
      2300        2310        2320        2330        2340        2350
        *           *           *           *           *           *
      GGG CCC CCC GAC TGG CCC CCG CCC TGG GGC ATC CAG GCG CAC ACT GCC GAG GAG
      Gly Pro Pro Asp Trp Pro Pro Pro Trp Gly Ile Gln Ala His Thr Ala Glu Glu 2360        2370        2380        2390        2400
        *           *           *           *           *
      GTG GAT CTG CGC GTG TTG GAC TAC GAG GAG GCA GCG GCG GCA GAA GCC CTG
      Val Asp Leu Arg Val Leu Asp Tyr Glu Glu Ala Ala Ala Ala Glu Ala Leu 2410        2420        2430        2440        2450        2460
        *           *           *           *           *           *
      GCG ACC TCC AGC CCC AGG CCC CCG GGC CAG CGC TGG GTT TGG ATG AAC TTC GAG
      Ala Thr Ser Ser Pro Arg Pro Pro Gly Gln Arg Trp Val Trp Met Asn Phe Glu 2470        2480        2490        2500        2510
        *           *           *           *           *
      TCG CCC TCG CAC TCC CCG GGG CTG CGA AGC CTG GCA AGT AAC CTC TTC TAC AAC TGG
      Ser Pro Ser His Ser Pro Gly Leu Arg Ser Leu Ala Ser Asn Leu Phe Tyr Asn Trp 2520        2530        2540        2550        2560
        *           *           *           *           *
      ACG CTC TCC TAC CGG GCG GCG GAC TCG GAC GTC TTT GTG CCT TAT GGC TAC CTC TAC
      Thr Leu Ser Tyr Arg Ala Asp Ser Asp Val Phe Val Pro Tyr Gly Tyr Leu Tyr 2570        2580        2590        2600        2610        2620
        *           *           *           *           *           *
      CCC AGA AGC CAC CCC GGC GAC CCG CCC TCA GGC CTG GCC CCG CCA CTG TCC AGG
      Pro Arg Ser His Pro Gly Asp Pro Pro Ser Gly Leu Ala Pro Leu Ser Arg 2630        2640        2650        2660        2670
        *           *           *           *           *
      AAA CAG GGG CTG GTG GCA TGG GTG GTG AGC CAC TGG GAC GAG CGC CAG GCC CGG
      Lys Gln Gly Leu Val Ala Trp Val Val Ser His Trp Asp Glu Arg Gln Ala Arg
```

FIG. 4G

```
      2680        2690        2700        2710        2720        2730
       *           *           *           *           *           *
GTC CGC TAC TAC CAA CTG AGC CAA CAT GTG ACC GTG GAC GTG TTC GGC CGG
Val Arg Tyr Tyr Gln Leu Ser Gln His Val Thr Val Asp Val Phe Gly Arg 2740        2750        2760        2770        2780
       *           *           *           *           *
CGC GGG CCC GGG CAG CCG GTG CCC GAA ATT GGG CTC CTG CAC ACA GTG GCC CGC
Gly Gly Pro Gly Gln Pro Val Pro Glu Ile Gly Leu Leu His Thr Val Ala Arg 2790        2800        2810        2820        2830
       *           *           *           *           *
TAC AAG TTC TAC CTG GCT TTC GAG AAC TCG CAG CAC CTG GAT TAT ATC ACC GAG
Tyr Lys Phe Tyr Leu Ala Phe Glu Asn Ser Gln His Leu Asp Tyr Ile Thr Glu 2840        2850        2860        2870        2880        2890
       *           *           *           *           *           *
AAG CTC TGG CGC AAC GCG TTG CTC GCT GGG CTG TTT GTG CCC CGC GGT GTG CTG GGC CCA
Lys Leu Trp Arg Asn Ala Leu Leu Ala Gly Phe Val Pro Arg Gly Val Leu Gly Pro 2900        2910        2920        2930        2940
       *           *           *           *           *
GAC CGT GCC AAC TAC GAG CGC TTT GTG CCC CGC GGC GCC TTC ATC CAC GTG GAC
Asp Arg Ala Asn Tyr Glu Arg Phe Val Pro Arg Gly Ala Phe Ile His Val Asp 2950        2960        2970        2980        2990        3000
       *           *           *           *           *           *
GAC TTC CCA AGT GCC TCC TCC CTG GCC TCG TAC CTG CTT TTC GAC CGC AAC
Asp Phe Pro Ser Ala Ser Ser Leu Ala Ser Tyr Leu Leu Phe Asp Arg Asn 3010        3020        3030        3040        3050
       *           *           *           *           *
CCC GCG GTC TAT CGC CGT TAC TTC CAC TGG CGC CGG AGC TAC GCT GTC CAC ATC
Pro Ala Val Tyr Arg Arg Tyr Phe His Trp Arg ARg Ser Tyr Ala Val His Ile
```

FIG. 4H

```
      3060             3070             3080             3090             3100
        *                *                *                *                *
ACC TCC TTC TGG GAC GAG CCT TGG TGC CGG GTG TGC CAG GCT GTA CAG AGG GCT
Thr Ser Phe Trp Asp Glu Pro Trp Cys Arg Val Cys Gln Ala Val Gln Arg Ala 3110             3120             3130             3140             3150             3160
        *                *                *                *                *                *
GGG GAC CGG CCC AAG AGC ATA CGG AAC TTG GCC AGC TGG TTC GAG CGG TGA A
Gly Asp Arg Pro Lys Ser Ile Arg Asn Leu Ala Ser Trp Phe Glu Arg ***

3170             3180             3190             3200             3210             3220
        *                *                *                *                *                *
GCCGC GCTCC CCTGG AAGCG GGGGA ACCCA GGCCA AGTTG TCAGC TTTTT GATCC TCTAC 3230             3240             3250             3260             3270             3280
        *                *                *                *                *                *
TGTGC ATCTC CTTGA CGGCC ATGGG GCATC AGTAA GTTCT TCAAA CACCC ATTTT TGCTC 3290             3300             3310             3320             3330             3340
        *                *                *                *                *                *
TATGG GAAAA AAACG ATTTA CCAAT TAATA TTACT CAGCA CAGAG ATGGG GGCCC GGTTT 3350             3360             3370             3380             3390             3400
        *                *                *                *                *                *
CCATA TTTTT TGCAC AGCTA GCAAT TGGGC TCCCT TTGCT GCTGA TGGGC ATCAT TGTTT 3410             3420             3430             3440             3450             3460
        *                *                *                *                *                *
AGGGG TGAAG GAGGG GGTTC TTCCT CACCT TGTAA CCAGT GCAGA AATGA AATAG CTTAG 3470             3480             3490             3500             3510             3520
        *                *                *                *                *                *
CGGCA AGAAG CCGTT GAGGC GGTTT CCTGA ATTTC CCCAT CTGCC ACAGG CCATA TTTGT
```

```
              3530           3540           3550           3560           3570           3580
                *              *              *              *              *              *
          GGCCC GTGCA GCTTC CAAAT CTCAT ACACA ACTGT TCCCG ATTCA CGTTT TTCTG GACCA 3590           3600           3610           3620           3630           3640
                *              *              *              *              *              *
          AGGTG AAGCA AATTT GTGGT TGTAG AAGGA GCCTT GTTGG TGGAG AGTGG AAGGA CTGTG

GCTGC AG
```

```
pFT-3 DNA      CCGCTGCGCTTCAACATCAGCGGCTGCCGCCTGCTCACCGACCGCGCGTCCTA
pFT-3 AA    87 P  L  R  F  N  I  S  G  C  R  L  L  T  D  R  A  S  Y104
Lewis AA    83 E  M  V  P  G  T  A  D  C  H  I  T  A  D  R  K  V  Y100 pFT-3 DNA      CGGAGAGGCTCAGGCCGTGCTTTTCCACCACCGCGACCTCGTGAAGGGCCCC
pFT-3 AA   105 G  E  A  Q  A  V  L  F  H  H  R  D  L  V  K  G  P  121
Lewis AA   101 P  Q  A  D  T  V  I  V  H  H  W  D  I  M  S  N  P  117 pFT-3 DNA      CCGACTGGCCCCCCGCCCTGGGCATCCAGGCGCACACTGCCGAG
pFT-3 AA   122 P  D  W  P  P  P  W  G  I  Q  A  H  T  A  E  136
Lewis AA   118 K  S  R  L  P  P  .  .  .  .  .  .  .  .  .  123 pFT-3 DNA      GAGGTGGATCTGCGCGTGTTGGACTACGAGGAGGCAGCGGCGGCAGAAGC
pFT-3 AA   137 E  V  D  L  R  V  L  D  Y  E  E  A  A  A  A  E  A154
Lewis AA   124 .  .  .  .  .  .  .  .  .  .  .  .  .  .  .  .124 pFT-3 DNA      CCTGGCGACCTCCAGCCCCAGGCCCCGGCCTGGGTTTGGATGAACT
pFT-3 AA   155 L  A  T  S  S  P  R  P  P  G  Q  R  W  V  W  M  N  171
Lewis AA   124 .  .  .  S  P  R  P  .  Q  G  .  Q  R  W  I  W  F  N  136 pFT-3 DNA      TCGAGTCGCCCCTCGCACTCCCCGGGCTGCGAAGCCTGGCAAGT
pFT-3 AA   172 F  E  S  P  S  H  S  P  G  L  R  S  L  A  S  186
Lewis AA   137 L  E  P  P  N  C  Q  H  L  E  A  L  D  .  150
```

FIG. 5B

```
pFT-3 DNA  AACCTCTTCAACTGAACTGGAGCGCTCTCCTACCGGGGACTGGAGCGTCTTTGTGCC
pFT-3 AA   187 N  L  F  N  W  T  L  S  Y  R  A  D  S  D  V  F  V  P204
Lewis AA   151 R  Y  F  N  L  T  M  S  Y  R  D  S  D  I  F  T  P168 pFT-3 DNA  TTATGGCTACCTCTACCCCAGAAGC---CACCCCGGGCGACCCGCCCTCAGGCC
pFT-3 AA   205 Y  G  Y  L  Y  P  R  S  .  H  P  G  D  P  P  S  G  220
Lewis AA   169 Y  G  W  L  E  P  W  S  G  Q  P  A  H  P  P  .    183 pFT-3 DNA  TGGCCCCGCCACTGTCCAGGAAACAGGGGCTGGTGGCATGGGTG
pFT-3 AA   221 L  A  P  P  L  S  R  K  Q  G  L  V  A  W  V  235
Lewis AA   184 L  N  .  .  L  S  A  K  T  E  L  V  A  W  A  196 pFT-3 DNA  GTGAGCCACTGGGACGAGCGCCAGGCCCGGGTCCGCTACTACCACCAACTGAG
pFT-3 AA   236 V  S  H  W  D  E  R  Q  A  R  V  R  Y  Y  H  Q  L  S253
Lewis AA   197 V  S  N  W  .  K  P  D  S  A  R  V  R  Y  Y  Q  S  L  Q214 pFT-3 DNA  CCAACATGTGACCGTGGACGTGTTCGGGCGACGTGTTCGGCCGGGGCCCGGGCAGCCGGTGC
pFT-3 AA   254 Q  H  V  T  V  D  V  F  G  R  G  G  P  G  Q  P  V  270
Lewis AA   215 A  H  L  K  V  D  .  V  Y  G  R  S  .  H  K  P  L  229 pFT-3 DNA  CCGAAATTGGGCTCCTGCACACAGTGGCCCGCTACAAGTTCTAC
pFT-3 AA   271 P  E  I  G  L  L  H  T  V  A  R  Y  K  F  Y  285
Lewis AA   230 P  K  G  T  M  M  E  T  L  .  S  R  Y  K  F  Y  244
```

```
pFT-3 DNA        TGCCGGGTGTGCCAGGCTGTACAGAGGGCTGGGACCGGCCCAAGAGCATACG
pFT-3 AA     380 C R V C Q—A V—Q R A G D R P K S I R397
Lewis AA     338 C · · K · A C W K L · Q Q E S · R · Y Q · T V R354 pFT-3 DNA        GAACTTGGCCAGCTGTGGTTCGAGCGGGTGA
pFT-3 AA     398 N L A S W—F E R 405
Lewis AA     355 · S I · A A W · F · T · 361
```

FIG. 5E

Sequence VI

```
-120  TTTATGACAAGCTGTGTCATAAATTATAACAGCTTCTCTCAGGACACTGTGGCCAGGAAG

-60  TGGGTGATCTTCCTTAATGACCCTCACTCCTCCTCTCCTCTTCCCAGCTACTCTGACCC

M  D  P  L  G  P  A  K  P  Q  W  L  W  R  R  C  L  A  G  L
   1  ATGGATCCCCTGGGCCCAGCCAAGCCACAGTGGCTGTGGCGCCGCTGTGGCTCTGGCCGGCTG
      ATGGATCCCCTGGTGCAGCCAAGCCACAAATGGCCACAATGGCCGTGTCTGGCCGCACTG
                                       A                       P                A

L  F  Q  L  V  A  V  C  F  F  S  Y  L  R  V  S  R  D  D
  61  CTGTTTCAGCTGCTGGTGGCTGTGTGTTTCTTCTCCTACTTGCGTGTGTCCCGAGACGAT
      CTATTTCAGCTGCTGGTGGCTGTGTGTTCTTCTCCTACCTGCGTGTGTCCCGAGACGAT
                                                P

A  T  G  S  P  R  P  G  L  M  A  V  E  P  V  T  G  A  P  N
 121  GCCACTGGATCCCCTAGGCCAGGGGCTTATGGCAGTGGAACCTGTCACCGGGGCTCCCAAT
      GCCACTGGATCCCCTAGG------------------------------GCTCCCAGT
                                                                                    S

G  S  R  C  Q  D  S  M  A  T  P  A  H  P  T  L  L  I  L  L
 181  GGGTCCCGCTGCCAGGACAGCATGGCGACCCCTGCCACCCACCCTACTGATCCTGCTG
      GGGTCCTCCGACAGGAGACACC----ACTCCCACCCGCCCCACCCCTCCTGATCCTGCTA
            S  R              T                T  R                 T
```

```
      W   T   W   P   F   N   T   P   V   A   L   P   R   C   S   E   M   V   P   G
241  TGGACGTGGCCTTTTAACACACCCGTGGCTCTGCCCCGTGCTCAGAGATGGTGCCCGGC
     TGGACATGGCCTTTCCACATCCCTGTGTGGCTCTGTTCAGAGATGGTGCCCGGC
                     H   I                      S

A   A   D   C   N   I   T   A   D   S   S   V   Y   P   Q   A   D   A   V   I
301  GCGGCCGACTGCAACATCACTGCCGACTCCAGTGTGTACCCACAGGCAGACGCGGTCATC
     ACAGCCGACTGCCACATCACTGCCGACTGCCAAGGTGTACCCACACAGGCAGACACGGTCATC
                 H                                       T       R   K

V   H   H   W   D   I   M   Y   N   P   S   A   N   L   P   P   T   R   P
361  GTGCACCACTGGGATATCATGTACAACCCCAGTGCCAACCTCCCGCCCCCCACCAGGCCG
     GTGCACCACTGGGATATCATGTCCAACCCCTAAGTCACGGCCCTCCCACCTTCCCGAGGCCG
                                         S                   K   S   R       S   P

Q   G   Q   R   W   I   W   F   S   M   E   S   P   S   N   C   R   H   L   E
421  CAGGGGCAGCGCTGGATCTGGTTCAGCATGGAGTCCCCCAGCAACTGCCGGCACCTGGAA
     CAGGGGCAGCGCTGGATCTGGTTCAACTTGGAGCCACCCCTAACTGCCAGCACCTGGAA
                                 N   L                       P   P       Q

A   L   D   G   Y   F   N   L   T   M   S   Y   R   S   D   S   D   I   F   T
481  GCCCTGGACGGATACTTCAATCTCACCATGTCCTACCGCAGGCACTCCGACATCTTCACG
     GCCCTGGACAGATACTTCAATCTCACCATGTCCTACCGCAGGCACTCCGACATCTTCACG
                 R

P   Y   G   W   L   E   P   W   S   G   Q   P   A   H   P   P   L   N   L   S
541  CCCTACGGCTGGCTGGAGCCGTGGTCCGGCCAGCCTGCCCACCCGCTCAACCTCTCG
     CCCTACGGCTGGCTGGAGCCGTGGTCCGGCCAGCCTGCCCACCCGCTCAACCTCTCG
```

FIG. 6C

```
       A  K  T  E  L  V  A  W  A  V  S  N  W  K  P  D  S  A  R  V
601    GCCAAGACGAGCTGGTGGCCTGGGCGGTGTCCAACTGGAAGCCGGACTCGGCCAGGGTG
       GCCAAGACGAGCTGGTGGCCTGGGCGGTGTCCAACTGGAAGCCGGACTCGGCCAGGGTG

R  Y  Y  Q  S  L  Q  A  H  L  K  V  D  V  Y  G  R  S  H  K
661    CGCTACTACCAGAGCCTGCAGGCTCATCTCAAGGTGGACGTGTACGGACGCTCCCACAAG
       CGCTACTACCAGAGCCTGCAGGCTCATCTCAAGGTGGACGTGTACGGACGCTCCCACAAG

P  L  P  K  G  T  M  M  E  T  L  S  R  Y  K  F  Y  L  A  F
721    CCCCTGCCCAAGGGGACCATGATGGAGACGCTGTCCCGGTACAAGTTCTATCTGGCCTTC
       CCCCTGCCCAAGGGGACCATGATGGAGACGCTGTCCCGGTACAAGTTCTACCTGGCCTTC

E  N  S  L  H  P  D  Y  I  T  E  K  L  W  R  N  A  L  E  A
781    GAGAACTCCTTGCACCCCGACTACATCACCGAGAAGCTGTGGAGGAACGCCCTGGAGGCC
       GAGAACTCCTTGCACCCCGACTACATCACCGAGAAGCTGTGGAGGAACGCCCTGGAGGCC

W  A  V  P  V  V  L  G  P  S  R  S  N  Y  E  R  F  L  P  P
841    TGGGCCGTGCCCGTGGTGCTGGGCCCCAGCAGAAGCAACTACGAGAGGTTCCTGCCGCCC
       TGGGCCGTGCCCGTGGTGCTGGGCCCCAGCAGAAGCAACTACGAGAGGTTCCTGCCACCC

D  A  F  I  H  V  D  D  F  Q  S  P  K  D  L  A  R  Y  L  Q
901    GACGCCTTCATCCACGTGGATGACTTCCAGAGCCCCAAGGACCTGGCCCGGTACCTGCAG
       GACGCCTTCATCCACGTGGACGACTTCCAGAGCCCCAAGGACCTGGCCCGGTACCTGCAG

E  L  D  K  D  H  A  R  Y  L  S  Y  F  R  W  R  E  T  L  R
961    GAGCTGGACAAGGACCACGCCCGCTACCTGAGCTACTTTCGCTGGCGGGAGACGCTGCGG
       GAGCTGGACAAGGACCACGCCCGCTACCTGAGCTACTTTCGCTGGCGGGAGACGCTGCGG
```

```
         P   R   S   F   S   W   A   L   A   F   C   K   A   C   W   K   L   Q   Q   E
1021   CCTCGCTCCTTCAGCTGGGCACTGGCTTTCTGCAAGGCCTGCTGGAAGCTGCAGCAGGAA
       CCTCGCTCCTTCAGCTGGGCACTGGGCTTTCTGCAAGGCCTGCTGGAAACTGCAGCAGGAA
                                         D
         S   R   Y   Q   T   V   R   S   I   A   A   W   F   T   U
1081   TCCAGGTACCAGACGGTGCGCAGCATAGCGGCTTGGTTCACCTGAGAGGCCGGCATGGGG
       TCCAGGTACCAGACGGTGCGCAGCATAGCGGCTTGGTTCACCTGA

1141   CCTGGGCTGCCAGGGACCTCACTTTCCCAGGGCCTCACCTACCTAGGGTC // TCTAGA
```

```
α(1,3)FT AA            S E M V P G T A D C N I T A D R K V Y P
α(1,3)FT DNA (241)     TCAGAGATGGTGCCTGGCACGGCTGACTGCAACATCACTGCCGACCGCAAGGTGTATCCA
                       ||||||||||||||||||| ||| ||||| |||| || || |||| |||||||| |||||
Lewis FT DNA           TCAGAGATGGTGCCGGGCACAGCCGACTGCACCATGCCGACTGCCAAGGTGTACCCA α(1,3)FT AA            Q A D A V I V H H R E V M Y N P S A Q L
α(1,3)FT DNA (301)     CAGGCAGACGCGGTCATCGTGCACCACCGAGAGGTCATGTACAACCCCAGTGCCCAGCTC
                       ||||||||| ||||||||||||||||||   ||| ||||||||| ||| ||||| |
Lewis FT DNA           CAGGCAGACACGGTCATCGTGCACCACTGTGCACCATCATGTCCAACCCTAAGTCACGCCTC α(1,3)FT AA            P R S P R R Q G Q R W I W F S M E S P S
α(1,3)FT DNA (361)     CCACGCTCTCCCCGAGGCGGCAGGGCCAGCGATGGATCTGGTTCAGCATGGAGTCCCAAGC
                       ||||| ||||||||||||| |||||||||||| |||||||||||||||| ||||||||||
Lewis FT DNA           CCACCTTCCCCGAGGCCGCAGGGGCCAGGGGCCAGCGGATCTGGTTCAACTTGGAGCCACCCCT α(1,3)FT AA            H C W Q L K A M D G Y F N L T M S Y R S
α(1,3)FT DNA (421)     CACTGCTGGCAGCTGAAAGCCATGGACGGATACTTCAATCTTCACCATGTCCTACCGCAGC
                       |||||||||||||||  ||||||| ||||| ||||||||||||| ||||||||||||||
Lewis FT DNA           AACTGCCAGCACCTGGAAGCCCTGGACAGATACTTCAATCTTCACCATGTCCTACCGCAGC α(1,3)FT AA            D S D I F T P Y G W L E P W S G Q P A H
α(1,3)FT DNA (481)     GACTCCGACATCTTCACGCCCTACGGCTGGCTGGAGCCCTGGTCCGGCCAGCCTGCCCAGC
                       ||||||||||||||||||||||||||||||||||||||||||||||||||||||||||||
Lewis FT DNA           GACTCCGACATCTTCACGCCCTACGGCTGGCTGGAGCCCTGGTCCGGCCAGCCTGCCCAC
```

```
α(1,3)FT AA             P  P  L  N  L  S  A  K  T  E  L  V  A  W  A  V  S  N  W  G
α(1,3)FT DNA (541)     CCACCGCTCAACCTCTCGGCCAAGACCGAGCTGGTGGCCTGGGCAGTGTCCAACTGGGGG
                       |||||||||||||||||||||||||||||||||||||||||||| ||||||||||||  |
Lewis FT DNA           CCACCGCTCAACCTCTCGGCCAAGACCGAGCTGGTGGCCTGGGCGGTGTCCAACTGGAAG α(1,3)FT AA             P  N  S  A  R  V  R  Y  Y  Q  S  L  Q  A  H  L  K  V  D  V
α(1,3)FT DNA (601)     CCAAACTCCGCCAGGGTGCGCTACTACCAGAGCCTGCAGGCCCATCTCAAGGTGGACGTG
                       ||  |||| ||||||||||||||||||||||||||||||||| ||||||||||||||||||
Lewis FT DNA           CCGGACTCAGCCAGGGTGCGCTACTACCAGAGCCTGCAGGCTCATCTCAAGGTGGACGTG α(1,3)FT AA             Y  G  R  S  H  K  P  L  P  Q  G  T  M  M  E  T  L  S  R  Y
α(1,3)FT DNA (661)     TACGGACGCTCCCACAAGCCCCTGCCCCAGGGAACCATGATGGAGACGCTGTCCCGGTAC
                       ||||||||||||||||||||||||||| |||| |||||||||||||||||||||||||||
Lewis FT DNA           TACGGACGCTCCCACAAGCCCCTGCCCAAGGGGACCATGATGGAGACGCTGTCCCGGTAC α(1,3)FT AA             K  F  Y  L  A  F  E  N  S  L  H  P  D  Y  I  T  E  K  L  W
α(1,3)FT DNA (721)     AAGTTCTATCTGGCCTTCGAGAACTCCTTGCACCCCGACTACATCACCGAGAAGCTGTGG
                       |||||||| |||||||||||||||||||||||||||||||||||||||||||||||||||
Lewis FT DNA           AAGTTCTACCTGGCCTTCGAGAACTCCTTGCACCCCGACTACATCACCGAGAAGCTGTGG α(1,3)FT AA             R  N  A  L  E  A  W  A  V  P  V  V  L  G  P  S  R  S  N  Y
α(1,3)FT DNA (781)     AGGAACGCCCTGGAGGCCTGGGCCGTGCCCGTGGTGCTGGGCCCCAGCAGAAGCAACTAC
                       ||||||||||||||||||||||||||||||||||||||||||||||||||||||||||||
Lewis FT DNA           AGGAACGCCCTGGAGGCCTGGGCCGTGCCCGTGGTGCTGGGCCCCAGCAGAAGCAACTAC
```

FIG. 7C

```
                        E  R  F  L  P  P  D  A  F  I  H  V  D  D  F  Q  S  P  K  D
α(1,3)FT AA
α(1,3)FT DNA  (841)    GAGAGGTTCCTGCCACCCGACGCCTTCATCCACGTGGACGACTTCCAGAGCCCCAAGGAC
Lewis FT DNA            GAGAGGTTCCTGCCACCCGACGCCTTCATCCACGTGGACGACTTCCAGAGCCCCAAGGAC L  A  R  Y  L  Q  E  L  D  K  D  H  A  R  Y  L  S  Y  F  R
α(1,3)FT AA
α(1,3)FT DNA  (901)    CTGGCCCGGTACCTGCAGGAGCTGGACAAGGACCACGCCCGCTACCTGAGCTACTTTCGC
Lewis FT DNA            CTGGCCCGGTACCTGCAGGAGCTGGACAAGGACCACGCCCGCTACCTGAGCTACTTTCGC W  R  E  T  L  R  P  R  S  F  S  W  A  L  A  F  C  K  A  C
α(1,3)FT AA
α(1,3)FT DNA  (961)    TGGCGGGAGACGCTGCGCCCTCGCTCCTTCAGCTGGGCACTCGCTTTCTGCAAGGCCTGC
Lewis FT DNA            TGGCGGGAGACGCTGCGCCCTCGCTCCTTCAGCTGGGCACTGGATTTCTGCAAGGCCTGC W  K  L  Q  E  E  S  R  Y  Q  T  R  G     I  A  A  W  F  Stop
α(1,3)FT AA
α(1,3)FT DNA (1021)    TGGAAACTGCAGGAGGAATCCAGGTACCAGACACGCGGC...ATAGCGGCTTGGTTCACCTGA
Lewis FT DNA            TGGAAACTGCAGGAGGAATCCAGGTACCAGACACGCGGC...ATAGCGGCTTGGTTCACCTGA Lewis FT DNA    GAGGCTGGTGTGGGCCTGGCCTGCCAGGAACCTCATTTCCTGGGCCTCACCTGAGTG
                GGGGCCTCATCTACCTAAGGACTCGTTTGCCTGAAGCTTCACCTGCCTGAGGACTCACCT
                GCCTGGGACGGTCACCTGTTGCAGCTTCACCTGGGATTCACCTACCTGGTCCTC
                ACTTTCCTGGGCCCTCACCCTGGCTTCCAGGAGCGTCTTCGGTGCCAGGTCTTCCCTTACCTGGA
                TTTCACATGCTGGCTTCCAGGAGCGTCCCCTGGCTGTTGGGGACTTTACCTGCTGGGACCTGCT
                CTGGGGACTTTGCCTACTGGCTTCCACACTGAATCTCACCTGCTAGGAGCCTCACCTGAGCCTCAC
                CCCAGAGACCTTCCACACTGAATCTCACCTGCTAGGAGCCTCACCTGGGACCTCAC
                CCTGGAGGCACTGGGCCCTGGGAACT
```

FIG. 7D

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 2043 base pairs
      (B) TYPE: nucleic acid
      (C) STRANDEDNESS: unknown
      (D) TOPOLOGY: unknown (ii) MOLECULE TYPE: cDNA (iv) ANTI-SENSE: NO (xi) SEQUENCE DESCRIPTION: SEQ ID NO:1:

```
AGGAAACCTG CCATGGCCTC CTGGTGAGCT GTCCTCATCC ACTGCTCGCT GCCTCTCCAG      60

ATACTCTGAC CCATGGATCC CCTGGGTGCA GCCAAGCCAC AATGGCCATG GCGCCGCTGT     120

CTGGCCGCAC TGCTATTTCA GCTGCTGGTG GCTGTGTGTT TCTTCTCCTA CCTGCGTGTG     180

TCCCGAGACG ATGCCACTGG ATCCCCTAGG GCTCCCAGTG GGTCCTCCCG ACAGGACACC     240

ACTCCCACCC GCCCCACCCT CCTGATCCTG CTATGGACAT GGCCTTTCCA CATCCCTGTG     300

GCTCTGTCCC GCTGTTCAGA GATGGTGCCC GGCACAGCCG ACTGCCACAT CACTGCCGAC     360

CGCAAGGTGT ACCCACAGGC AGACACGGTC ATCGTGCACC ACTGGGATAT CATGTCCAAC     420

CCTAAGTCAC GCCTCCCACC TTCCCCGAGG CCGCAGGGGC AGCGCTGGAT CTGGTTCAAC     480

TTGGAGCCAC CCCCTAACTG CCAGCACCTG GAAGCCCTGG ACAGATACTT CAATCTCACC     540

ATGTCCTACC GCAGCGACTC CGACATCTTC ACGCCCTACG GCTGGCTGGA GCCGTGGTCC     600

GGCCAGCCTG CCCACCCACC GCTCAACCTC TCGGCCAAGA CCGAGCTGGT GGCCTGGGCG     660

GTGTCCAACT GGAAGCCGGA CTCAGCCAGG GTGCGCTACT ACCAGAGCCT GCAGGCTCAT     720
```

```
CTCAAGGTGG ACGTGTACGG ACGCTCCCAC AAGCCCCTGC CCAAGGGGAC CATGATGGAG      780

ACGCTGTCCC GGTACAAGTT CTACCTGGCC TTCGAGAACT CCTTGCACCC CGACTACATC      840

ACCGAGAAGC TGTGGAGGAA CGCCCTGGAG GCCTGGGCCG TGCCCGTGGT GCTGGGCCCC      900

AGCAGAAGCA ACTACGAGAG GTTCCTGCCA CCCGACGCCT TCATCCACGT GGACGACTTC      960

CAGAGCCCCA AGGACCTGGC CCGGTACCTG CAGGAGCTGG ACAAGGACCA CGCCCGCTAC     1020

CTGAGCTACT TTCGCTGGCG GGAGACGCTG CGGCCTCGCT CCTTCAGCTG GCACTGGAT     1080

TTCTGCAAGG CCTGCTGGAA ACTGCAGCAG GAATCCAGGT ACCAGACGGT GCGCAGCATA     1140

GCGGCTTGGT TCACCTGAGA GGCCGGCATG GTGCCTGGGC TGCCGGGAAC CTCATCTGCC     1200

TGGGGCCTCA CCTGCTGGAG TCCTTTGTGG CCAACCCTCT CTCTTACCTG GGACCTCACA     1260

CGCTGGGCTT CACGGCTGCC AGGAGCCTCT CCCCTCCAGA AGACTTGCCT GCTAGGGACC     1320

TCGCCTGCTG GGGACCTCGC CTGTTGGGGA CCTCACCTGC TGGGGACCTC ACCTGCTGGG     1380

GACCTTGGCT GCTGGAGGCT GCACCTACTG AGGATGTCGG CGGTCGGGGA CTTTACCTGC     1440

TGGGACCTGC TCCCAGAGAC CTTGCCACAC TGAATCTCAC CTGCTGGGGA CCTCACCCTG     1500

GAGGGCCCTG GGCCCTGGGG AACTGGCTTA CTTGGGGCCC CACCCGGGAG TGATGGTTCT     1560

GGCTGATTTG TTTGTGATGT TGTTAGCCGC CTGTGAGGGG TGCAGAGAGA TCATCACGGC     1620

ACGGTTTCCA GATGTAATAC TGCAAGGAAA AATGATGACG TGTCTCCTCA CTCTAGAGGG     1680

GTTGGTCCCA TGGGTTAAGA GCTCACCCCA GGTTCTCACC TCAGGGGTTA AGAGCTCAGA     1740

GTTCAGACAG GTCCAAGTTC AAGCCCAGGA CCACCACTTA TAGGGTACAG GTGGGATCGA     1800

CTGTAAATGA GGACTTCTGG AACATTCCAA ATATTCTGGG GTTGAGGGAA ATTGCTGCTG     1860

TCTACAAAAT GCCAAGGGTG GACAGGCGCT GTGGCTCACG CCTGTAATTC CAGCACTTTG     1920

GGAGGCTGAG GTAGGAGGAT TGATTGAGGC CAAGAGTTAA AGACCAGCCT GGTCAATATA     1980

GCAAGACCAC GTCTCTAAAT AAAAAATAAT AGGCCGGCCA GGAAAAAAAA AAAAAAAAA     2040

AAA                                                                 2043

(2) INFORMATION FOR SEQ ID NO:2:

(i) SEQUENCE CHARACTERISTICS:
        (A) LENGTH: 361 amino acids
        (B) TYPE: amino acid
        (D) TOPOLOGY: unknown (ii) MOLECULE TYPE: protein (xi) SEQUENCE DESCRIPTION: SEQ ID NO:2:

Met Asp Pro Leu Gly Ala Ala Lys Pro Gln Trp Pro Trp Arg Arg Cys
1               5                   10                  15

Leu Ala Ala Leu Leu Phe Gln Leu Leu Val Ala Val Cys Phe Phe Ser
            20                  25                  30

Tyr Leu Arg Val Ser Arg Asp Asp Ala Thr Gly Ser Pro Arg Ala Pro
        35                  40                  45

Ser Gly Ser Ser Arg Gln Asp Thr Thr Pro Thr Arg Pro Thr Leu Leu
    50                  55                  60

Ile Leu Leu Trp Thr Trp Pro Phe His Ile Pro Val Ala Leu Ser Arg
65                  70                  75                  80

Cys Ser Glu Met Val Pro Gly Thr Ala Asp Cys His Ile Thr Ala Asp
                85                  90                  95

Arg Lys Val Tyr Pro Gln Ala Ser Thr Val Ile Val His His Trp Asp
            100                 105                 110

Ile Met Ser Asn Pro Lys Ser Arg Leu Pro Pro Ser Pro Arg Pro Gln
```

```
                115                 120                 125
Gly Gln Arg Trp Ile Trp Phe Asn Leu Glu Pro Pro Asn Cys Gln
            130                 135                 140
His Leu Glu Ala Leu Asp Arg Tyr Phe Asn Leu Thr Met Ser Tyr Arg
145                 150                 155                 160
Ser Asp Ser Asp Ile Phe Thr Pro Tyr Gly Trp Leu Glu Pro Trp Ser
                165                 170                 175
Gly Gln Pro Ala His Pro Pro Leu Asn Leu Ser Ala Lys Thr Glu Leu
            180                 185                 190
Val Ala Trp Ala Val Ser Asn Trp Lys Pro Asp Ser Ala Arg Val Arg
            195                 200                 205
Tyr Tyr Gln Ser Leu Gln Ala His Leu Lys Val Asp Val Tyr Gly Arg
210                 215                 220
Ser His Lys Pro Leu Pro Lys Gly Thr Met Met Glu Thr Leu Ser Arg
225                 230                 235                 240
Tyr Lys Phe Tyr Leu Ala Phe Glu Asn Ser Leu His Pro Asp Tyr Ile
                245                 250                 255
Thr Glu Lys Leu Trp Arg Asn Ala Leu Glu Ala Trp Ala Val Pro Val
            260                 265                 270
Val Leu Gly Pro Ser Arg Ser Asn Tyr Glu Arg Phe Leu Pro Pro Asp
            275                 280                 285
Ala Phe Ile His Val Asp Asp Phe Gln Ser Pro Lys Asp Leu Ala Arg
            290                 295                 300
Tyr Leu Gln Glu Leu Asp Lys Asp His Ala Arg Tyr Leu Ser Tyr Phe
305                 310                 315                 320
Arg Trp Arg Glu Thr Leu Arg Pro Arg Ser Phe Ser Trp Ala Leu Asp
                325                 330                 335
Phe Cys Lys Ala Cys Trp Lys Leu Gln Gln Glu Ser Arg Tyr Gln Thr
            340                 345                 350
Val Arg Ser Ile Ala Ala Trp Phe Thr
            355                 360

(2) INFORMATION FOR SEQ ID NO:3:

(i) SEQUENCE CHARACTERISTICS:
        (A) LENGTH: 1500 base pairs
        (B) TYPE: nucleic acid
        (C) STRANDEDNESS: unknown
        (D) TOPOLOGY: unknown (ii) MOLECULE TYPE: cDNA (iv) ANTI-SENSE: NO (xi) SEQUENCE DESCRIPTION: SEQ ID NO:3:

CCTTCCCTTG TAGACTCTTC TTGGAATGAG AAGTACCGAT TCTGCTGAAG ACCTCGCGCT        60

CTCAGGCTCT GGGAGTTGGA ACCCTGTACC TTCCTTTCCT CTGCTGAGCC CTGCCTCCTT       120

AGGCAGGCCA GAGCTCGACA GAACTCGGTT GCTTTGCTGT TTGCTTTGGA GGGAACACAG       180

CTGACGATGA GGCTGACTTT GAACTCAAGA GATCTGCTTA CCCCAGTCTC CTGGAATTAA       240

AGGCCTGTAC TACATTTGCC TGGACCTAAG ATTTTCATGA TCACTATGCT TCAAGATCTC       300

CATGTCAACA AGATCTCCAT GTCAAGATCC AAGTCAGAAA CAAGTCTTCC ATCCTCAAGA       360

TCTGGATCAC AGGAGAAAAT AATGAATGTC AAGGGAAAAG TAATCCTGTT GATGCTGATT       420

GTCTCAACCG TGGTTGTCGT GTTTTGGGAA TATGTCAACA GAATTCCAGA GGTTGGTGAG       480

AACAGATGGC AGAAGGACTG GTGGTTCCCA AGCTGGTTTA AAAATGGGAC CCACAGTTAT       540
```

```
CAAGAAGACA ACGTAGAAGG ACGGAGAGAA AAGGGTAGAA ATGGAGATCG CATTGAAGAG      600

CCTCAGCTAT GGGACTGGTT CAATCCAAAG AACCGCCCGG ATGTTTTGAC AGTGACCCCG      660

TGGAAGGCGC CGATTGTGTG GGAAGGCACT TATGACACAG CTCTGCTGGA AAAGTACTAC      720

GCCACACAGA AACTCACTGT GGGGCTGACA GTGTTTGCTG TGGGAAAGTA CATTGAGCAT      780

TACTTAGAAG ACTTTCTGGA GTCTGCTGAC ATGTACTTCA TGGTTGGCCA TCGGGTCATA      840

TTTTACGTCA TGATAGACGA CACCTCCCGG ATGCCTGTCG TGCACCTGAA CCCTCTACAT      900

TCCTTACAAG TCTTTGAGAT CAGGTCTGAG AAGAGGTGGC AGGATATCAG CATGATGCGC      960

ATGAAGACCA TTGGGGAGCA CATCCTGGCC CACATCCAGC ACGAGGTCGA CTTCCTCTTC     1020

TGCATGGACG TGGATCAAGT CTTTCAAGAC AACTTCGGGG TGGAAACTCT GGGCCAGCTG     1080

GTAGCACAGC TCCAGGCCTG GTGGTACAAG GCCAGTCCCG AGAAGTTCAC CTATGAGAGG     1140

CGGGAACTGT CGGCCGCGTA CATTCCATTC GGAGAGGGGG ATTTTTACTA CCACGCGGCC     1200

ATTTTTGGAG GAACGCCTAC TCACATTCTC AACCTCACCA GGGAGTGCTT TAAGGGGATC     1260

CTCCAGGACA AGAAACATGA CATAGAAGCC CAGTGGCATG ATGAGAGCCA CCTCAACAAA     1320

TACTTCCTTT TCAACAAACC CACTAAAATC CTATCTCCAG AGTATTGCTG GGACTATCAG     1380

ATAGGCCTGC CTTCAGATAT TAAAAGTGTC AAGGTAGCTT GGCAGACAAA AGAGTATAAT     1440

TTGGTTAGAA ATAATGTCTG ACTTCAAATT GTGATGGAAA CTTGACACTA TTTCTAACCA     1500
```

(2) INFORMATION FOR SEQ ID NO:4:

(i) SEQUENCE CHARACTERISTICS:
        (A) LENGTH: 394 amino acids
        (B) TYPE: amino acid
        (D) TOPOLOGY: unknown (ii) MOLECULE TYPE: protein (xi) SEQUENCE DESCRIPTION: SEQ ID NO:4:

```
Met Ile Thr Met Leu Gln Asp Leu His Val Asn Lys Ile Ser Met Ser
1               5                  10                  15

Arg Ser Lys Ser Glu Thr Ser Leu Pro Ser Ser Arg Ser Gly Ser Gln
            20                  25                  30

Glu Lys Ile Met Asn Val Lys Gly Lys Val Ile Leu Leu Met Leu Ile
        35                  40                  45

Val Ser Thr Val Val Val Phe Trp Glu Tyr Val Asn Arg Ile Pro
    50                  55                  60

Glu Val Gly Glu Asn Arg Trp Gln Lys Asp Trp Phe Pro Ser Trp
65                  70                  75              80

Phe Lys Asn Gly Thr His Ser Tyr Gln Glu Asp Asn Val Glu Gly Arg
                85                  90                  95

Arg Glu Lys Gly Arg Asn Gly Asp Arg Ile Glu Glu Pro Gln Leu Trp
            100                 105                 110

Asp Trp Phe Asn Pro Lys Asn Arg Pro Asp Val Leu Thr Val Thr Pro
        115                 120                 125

Trp Lys Ala Pro Ile Val Trp Glu Gly Thr Tyr Asp Thr Ala Leu Leu
    130                 135                 140

Glu Lys Tyr Tyr Ala Thr Gln Lys Leu Thr Val Gly Leu Thr Val Phe
145                 150                 155                 160

Ala Val Gly Lys Tyr Ile Glu His Tyr Leu Glu Asp Phe Leu Glu Ser
                165                 170                 175

Ala Asp Met Tyr Phe Met Val Gly His Arg Val Ile Phe Tyr Val Met
            180                 185                 190
```

```
Ile Asp Asp Thr Ser Arg Met Pro Val Val His Leu Asn Pro Leu His
        195                 200                 205

Ser Leu Gln Val Phe Glu Ile Arg Ser Glu Lys Arg Trp Gln Asp Ile
    210                 215                 220

Ser Met Met Arg Met Lys Thr Ile Gly Glu His Ile Leu Ala His Ile
225                 230                 235                 240

Gln His Glu Val Asp Phe Leu Phe Cys Met Asp Val Asp Gln Val Phe
                245                 250                 255

Gln Asp Asn Phe Gly Val Glu Thr Leu Gly Gln Leu Val Ala Gln Leu
            260                 265                 270

Gln Ala Trp Trp Tyr Lys Ala Ser Pro Glu Lys Phe Thr Tyr Glu Arg
        275                 280                 285

Arg Glu Leu Ser Ala Ala Tyr Ile Pro Phe Gly Glu Gly Asp Phe Tyr
    290                 295                 300

Tyr His Ala Ala Ile Phe Gly Gly Thr Pro Thr His Ile Leu Asn Leu
305                 310                 315                 320

Thr Arg Glu Cys Phe Lys Gly Ile Leu Gln Asp Lys Lys His Asp Ile
                325                 330                 335

Glu Ala Gln Trp His Asp Glu Ser His Leu Asn Lys Tyr Phe Leu Phe
            340                 345                 350

Asn Lys Pro Thr Lys Ile Leu Ser Pro Glu Tyr Cys Trp Asp Tyr Gln
        355                 360                 365

Ile Gly Leu Pro Ser Asp Ile Lys Ser Val Lys Val Ala Trp Gln Thr
    370                 375                 380

Lys Glu Tyr Asn Leu Val Arg Asn Asn Val
385                 390
```

(2) INFORMATION FOR SEQ ID NO:5:

(i) SEQUENCE CHARACTERISTICS:
        (A) LENGTH: 8174 base pairs
        (B) TYPE: nucleic acid
        (C) STRANDEDNESS: unknown
        (D) TOPOLOGY: unknown (ii) MOLECULE TYPE: DNA (genomic)

(iv) ANTI-SENSE: NO (xi) SEQUENCE DESCRIPTION: SEQ ID NO:5:

```
GAATTCCATC GTGGCAAGGG CAGCCTGAAT GGATGATGTA ACCTGGGGTC CTTTCAATGG      60

AGGGCCAGAC TCCTGGGTCT AGGGGATGAG GGAGGGGAGG ATCGGGTTAG CTGGGACCCA     120

GGTGAAAGGG GCTGGGGGCC CACATTCCTG AGTCTCAGAG AGAAGGATCT GGGGTCTCAA     180

GCACCTGAGT CGGAGGGAGG AGGGGTGCTG GGCTCCTGGA AAAACCACCT CTTGGACCAT     240

CTATGCAGAT CACGCAGAAC AAGAGAAATT TCTGCGCCCC ATCTGAATTT CTAAGTTTGG     300

GGGGAGGGCG TGATCTGACA CTGAGGTTCC TTGATCCTCA GCAAGGCGGC AATTGCTGTA     360

TGAAAGAAGC GACCGCATCT GAGACACAAG TATCCTGCCT TGGAAGCCTC TCACCTGGCC     420

GTGGGCCAAC CTCAACCTCA TCTGTCCCTG CTCAGATGCT CAGACCCTGG ACATCCCAGC     480

CTCCTCCTCC CTGATGCAAT CCTGGTGTTT CTTTCACCAG AGAAGCCATC CCAGGCCCAG     540

GCAGGTGCTC CTGAAATAAC CTGGGGGGAG GGGTGGCTGA AAGTCCCTGA CTGGAGTTGG     600

CAGCCAAGCC AGGCCCTGGA GTGGGCACCC AGAGGGAAGA CAGGTTGGCT AATTTCCTGG     660

AGCCCCTAAG GGTGCAAGGG TAGGCCTTCT GTGTCTGAGG GAGGAGGGCT GGGGCTCTGG     720

ACTCCTGGGT CTGAGGGAGG AGGGGTGGGG GGCCTGGACT CCTGGGTCTG AGGGAGGAGG     780
```

```
GTCTGGGCCT GTACTCCTGG ATCTGAGGGA GGAGGGGCTG GGGAACTTGG GCTCCTGGGT    840

CTGAGGGAGG AGGGAGCTTT GGTCTGGACT CCTGGGTCTG AGGGAGTAGG GGCTAGGGAT    900

CTGGACTCGT GGGTGTGAGG AAGGAGGGGC TGGGGTCCTG GACTCCTGGG TCTGAGGAAG    960

GAGGGGCAGG GGGCTTGGAC TCCTGGGTCT GAGGAAGGAG GGGCCGGGAG CCTGGACTCC   1020

TAAGTCTGAG GGAGGAGGGT CTGGGGGCCT GGACTGCTGG GTGTGAGCAG AAGGGTCTGG   1080

GTGCTGGGAG TCCCGAGCCT GGGGAGATGA TGGTTAAACT TCTGGGAATC AAGTCAAACT   1140

CCTGAGTCTT TGACATTGAT GTATCTTGAA TGGGAGGGTC AGTCTGTGGG GAAGGATTAC   1200

CCAGGTGCCG AGGCAAGAGA CTGAAGGCAC AAACTGTTTC AGTATAATAA AGAAAATAGT   1260

TAGAATAAGA ATAGTTATCA TACAAATTAG ATATAGAGAT GATCATGGAC AGTATCAATC   1320

ATTAGTGTAA ACATTATTAA TCATTAGCTA TTACTTTTAT TCTTTGTTGT ATAACTAATA   1380

TAACCAGGAA ACAACCGGTG GGTATAGGGT CAGGTACTGA AGGGACATTG TGAGAAGTGA   1440

CCTAGAAGGC AAGAGGTGAG CCTTCTGTCA CACCGGCATA AGGGCCTCTT GAGGGCTCCT   1500

TGGTCAAGCG GGAACGCCAG TGTCTGGGAA GGCACCCGTT ACTCAGCAGA CCACGAAAGG   1560

GAATCTCCTT TTCTTGGAGG AGTCAGGGAA CACTCTGCTC CACCAGCTTC TTGTGGGAGG   1620

CTGGGTATTA TCTAGGCCTG CCCGCAGTCA TCCTGCTGTG CTGTGCTTCA ATGGTCACGC   1680

TCCTTGTCCT CTTGCATTTT CCTCCCGTAC TCCTGGTTCC TCTTTGAAGT TCGTAGTAGA   1740

TAGCGGTAGA AGAAATAGTG AAAGCCTTTT TTTTTTTTTT TTTGAGGCGG AGTCTCGCTC   1800

TGTCCCCCAG GCTGGAGTGC AGTGGCGTGA TCTCGGCTCA CTGCAATCTC CGCCTCCTGG   1860

GTTCACACCA TTCTCCTGCC TCACCCTCCC AAATAGCTAG GACTACAGGC GCCCTCCACC   1920

ACGCGCCCGG ATAATTTTTT GTATTTTTAG TAGAGACAGG GTTTCACCGT GTTAGCCAGG   1980

ATGGCCTCCA CCTCCTGACC TTGTGATCCG CCCGCCTCAG CCTCCCAAAG TGCTGGGATT   2040

ACAGGCGTGA GCCACCGCGC CCGCCCGAAA TAGTGAAAGT CTTAAAGTCT TTGATCTTTC   2100

TTATAAGTGC AGAGAAGAAA ACGCTGACAT ATGCTGCCTT CTCTTTCTGC TTCGGCTGCC   2160

TAAAAGGGAA GGGCCCCCTG TCCCATGATC ACGTGACTTG CTTGACCTTA TCAGTCATTT   2220

GGACGACTCA CCCTCCTTAT CCTGCCCCCC CTTGTCTTGT ATACAATAAA TATCAGCGCG   2280

CCCAGCCATT CGGGGCCACT ACCGGTCTCT GCGTCTTGAT GGTAGTGGTC CCCCGGGCCC   2340

AGCTGTTTTC TCTTTATCTC TTTGTCTTGT GTCTTTATTT CTTACAATCT CTCCTCTCCT   2400

CACAGGGGAA GAACACCCAC CCGCAAAGCC CCGTAGGGCT GGACCCTACG TTAGCCTGCC   2460

CTGCTCGGGG TTGGCGATGC TGGAGGTGGG CCTTGGACCA GAGAAAATGC TTTAATTAGG   2520

TGACAAGCGG GCAGAGGCCT TTGTCTCTGG CGCCGGCAGC CACGGCCCCC GCTGACGGCG   2580

TGGGAAACAG ACCCTGTTCC ACTCCGGTCT CCAGCCTTGG AATGGTTGCC TTCGTGCAGT   2640

GCAGGTCTGG AAAGTAGCAG TTTGGCACGG GACCCTAGAA TTCCCAAAA GGAGTGACTA    2700

GGGGCTGGGA TTCTGGAATT TGAGTGTGGA CGGTGAGGCG GGGGGTGTGG GAGATCGGAG   2760

ACCCTGGTGG GCGCGGGAGC ACCTGCAGGC TGGAGGCCCT CGCGCGCTCC GGCGGCAGCC   2820

TGGCAAACAG GTTCTCCATC CCCCAGGAGG ACGCGGCAGA GGGCGGACGA TCGCTCCACT   2880

CGCCGGGACC AGGTGCGGGG GCCCTGCCCA GCCGCTGGGG CGTGGCCAGG CTCGAAGCAC   2940

CCAGGTGTCG GGGGCCGACT CTAAGCCCTG GCACCGGAAG AGAGAGGGCG GCGGATTGGA   3000

CCTCCCGGCT CCAGCATTGC AACTGGGCGC TCCGTCTCCT GGTCCACGCA ATGATGCTGC   3060

GGCTGCTCAG AAGCCAGGTA GCCTGCCCTG GGTGAAGCCT TCGCGCAGGT CAATGACGGG   3120

GCGGAGGGGC AGGGCGCGGT CCCCTGCATC CCCGATCTGG GGAGCGGTGG GCCCAGGGGC   3180
```

```
CATCGCCTTA GCCCCTGGCG CTGGGGCTCG GCGCCAAGTG ACGGGCGGGG CTCCACCTTC    3240
CAGCCATCCG CCCGGCCCGG GAGGGCGGAC GCTGCGAGAC TCCCGGCCGC GCCCTCTCCT    3300
TCCTCTCCTC CCCAAGCCCT CGCTGCCAGT CCGGACAGGC TGCGCGGAGG GGAGGGCTGC    3360
CGGGCCGGAT AGCCGGACGC CTGGCGTTCC AGGGGCGGCC GGATGTGGCC TGCCTTTGCG    3420
GAGGGTGCGC TCCGGCCACG AAAAGCGGAC TGTGGATCTG CCACCTGCAA GCAGCTCGGG    3480
TAAGTGGGGA CTGCCCCACT CAGTTGTTCC TGGGACCCAG GAACAACTCC TTCAGAACCA    3540
GGAGGTGCAC CCCCAACCTC TTCTCCAGGT CTTCCTAAGG CCCTAGGAAT CTCCGCCACC    3600
TCCCCAGCCA TTACTCCTCC AGGAACCAAG ATGCTCCTTC CGCTCCTGAC CCTCCAGCCT    3660
CTCTTGTTTT ACTTGAACTA TCGTTTCCCA TCACCACCTC TGTGGTGGAT TTTGCGCCTC    3720
ACAGACAGGT ACTCCTGAGA AACAGGCTGG TGGAAGAGTC CAGTATCAGC GGAACTTACA    3780
GGAGGGGAGA CTCGAGATTC CTTCAGGAAA GGTGTAGGAA CCTGGACCAC TTTCTTTTTT    3840
TTTTTTTTTT TTTTTTTAAG ACAGGGTCCC TCTCTGTCGC GCAAGCTGGA GTGCAGTCAG    3900
CGGTGCTATC GCGGCTCATT GTGAGCTCCG GGGATCCTCC CGCCTTAGCA TCCGGTGTAG    3960
CTGAGACCAC AGACATGTGC CACCATGCCA AGCTAATTTT ATTTATTTTT TTTTGGAGAC    4020
GGAGTTTCAC TCTTGTTGCC CAGGCTGGAG TGTAATGGCA TGATCTCAGC TCACCGCAAC    4080
TCCCGCCCCC CGGGTTCAGG CGATTCTCCT GCCTCAGCCT CCCGAGTGGC TGGGATTACA    4140
GGCATGCGCC ACCATGCCCG GCTAATTTTG TATTTTAAGT AGAGACAGGG TTTCTCCACG    4200
TTGGTCAGGC TGGTCTCGAA CTCCCAACCT CAGGTGATCC ACCCACCTTG GCCTCCCAAA    4260
GTGCTGGGAT TACAGGTGTG AGCCACCGCG CCTGGCCCAT GCCAAGCTAA TTTTAAAATT    4320
TTTTTGTAAG AGTGCTCTGT TGCCCAGGCT GATCTTGAAC TCCTGGGCTC AAGGGATCCT    4380
CCCATCTCAG CCTCCCAATA TGCTGGGATT ACAGGTGTGA GCCACAGTGC CCAGCCAAAC    4440
CATGGCTATC TTGAAAACCA CTTGTCTTCC AGTCCCCATG CCCCGAAATT CCAAGGCTCT    4500
CATCCCTGAA ACCTAGGACT CAGGCTCTCC CTACCTCAGC CCCAGGAGTC TAAACCTTTA    4560
ACTTCCTCTT TCCCTGGGAC TAAGGAGTGC TGCACCCCAG GCGCCTCCCT TACCCCACAT    4620
CCCTCCTCAG CCTCCCCTCC TCAGCCTCAG TGCATTTGCT AATTCGCCTT TCCTCCCCTG    4680
CAGCCATGTG GCTCCGGAGC CATCGTCAGC TCTGCCTGGC CTTCCTGCTA GTCTGTGTCC    4740
TCTCTGTAAT CTTCTTCCTC CATATCCATC AAGACAGCTT TCCACATGGC CTAGGCCTGT    4800
CGATCCTGTG TCCAGACCGC CGCCTGGTGA CACCCCAGT GGCCATCTTC TGCCTGCCGG     4860
GTACTGCGAT GGGCCCCAAC GCCTCCTCTT CCTGTCCCCA GCACCCTGCT TCCCTCTCCG    4920
GCACCTGGAC TGTCTACCCC AATGGCCGGT TTGGTAATCA GATGGGACAG TATGCCACGC    4980
TGCTGGCTCT GGCCCAGCTC AACGGCCGCC GGGCCTTTAT CCTGCCTGCC ATGCATGCCG    5040
CCCTGGCCCC GGTATTCCGC ATCACCCTGC CCGTGCTGGC CCCAGAAGTG GACAGCCGCA    5100
CGCCGTGGCG GGAGCTGCAG CTTCACGACT GGATGTCGGA GGAGTACGCG GACTTGAGAG    5160
ATCCTTTCCT GAAGCTCTCT GGCTTCCCCT GCTCTTGGAC TTTCTTCCAC CATCTCCGGG    5220
AACAGATCCG CAGAGAGTTC ACCCTGCACG ACCACCTTCG GGAAGAGGCG CAGAGTGTGC    5280
TGGGTCAGCT CCGCCTGGGC CGCACAGGGG ACCGCCGCG CACCTTTGTC GGCGTCCACG     5340
TGCGCCGTGG GGACTATCTG CAGGTTATGC CTCAGCGCTG GAAGGGTGTG GTGGGCGACA    5400
GCGCCTACCT CCGGCAGGCC ATGGACTGGT TCCGGGCACG GCACGAAGCC CCCGTTTTCG    5460
TGGTCACCAG CAACGGCATG GAGTGGTGTA AAGAAAACAT CGACACCTCC CAGGGCGATG    5520
TGACGTTTGC TGGCGATGGA CAGGAGGCTA CACCGTGGAA AGACTTTGCC CTGCTCACAC    5580
```

```
AGTGCAACCA CACCATTATG ACCATTGGCA CCTTCGGCTT CTGGGCTGCC TACCTGGCTG      5640

GCGGAGACAC TGTCTACCTG GCCAACTTCA CCCTGCCAGA CTCTGAGTTC CTGAAGATCT      5700

TTAAGCCGGA GGCGGCCTTC CTGCCCGAGT GGGTGGGCAT TAATGCAGAC TTGTCTCCAC      5760

TCTGGACATT GGCTAAGCCT TGAGAGCCAG GGAGACTTTC TGAAGTAGCC TGATCTTTCT      5820

AGAGCCAGCA GTACGTGGCT TCAGAGGCCT GGCATCTTCT GGAGAAGCTT GTGGTGTTCC      5880

TGAAGCAAAT GGGTGCCCGT ATCCAGAGTG ATTCTAGTTG GGAGAGTTGG AGAGAAGGGG      5940

GACGTTTCTG GAACTGTCTG AATATTCTAG AACTAGCAAA ACATCTTTTC CTGATGGCTG      6000

GCAGGCAGTT CTAGAAGCCA CAGTGCCCAC CTGCTCTTCC CAGCCCATAT CTACAGTACT      6060

TCCAGATGGC TGCCCCCAGG AATGGGAAC TCTCCCTCTG GTCTACTCTA AAGAGGGGT        6120

TACTTCTCCC CTGGGTCCTC CAAAGACTGA AGGAGCATAT GATTGCTCCA GAGCAAGCAT      6180

TCACCAAGTC CCCTTCTGTG TTTCTGGAGT GATTCTAGAG GGAGACTTGT TCTAGAGAGG      6240

ACCAGGTTTG ATGCCTGTGA AGAACCCTGC AGGGCCCTTA TGGACAGGAT GGGGTTCTGG      6300

AAATCCAGAT AACTAAGGTG AAGAATCTTT TTAGTTTTTT TTTTTTTTTT TTGGAGACAG      6360

GGTCTCGCTC TGTTGCCCAG GCTGGAGTGC AGTGGCGTGA TCTTGGCTCA CTGCAACTTC      6420

CGCCTCCTGT GTTCAAGCGA TTCTCCTGTC TCAGCCTCCT GAGTAGATGG GACTACAGGC      6480

ACAGGCCATT ATGCCTGGCT AATTTTTGTA TTTTTAGTAG AGACAGGGTT TCACCATGTT      6540

GGCCGGGATG GTCTCGATCT CCTGACCTTG TCATCCACCT GTCTTGGCCT CCCAAAGTGC      6600

TGGGATTACT GGCATGAGCC ACTGTGCCCA GCCCGGATAT TTTTTTTTAA TTATTTATTT      6660

ATTTATTTAT TTATTGAGAC GGAGTCTTGC TCTGTAGCCC AGGCCAGAGT GCAGTGGCGC      6720

GATCTCAGCT CACTGCAAGC TCTGCCTCCC GGGTTCATGC CATTCTGCCT CAGCCTCCTG      6780

AGTAGCTGGG ACTACAGGCG CCCGCCACCA CGCCCGGCTA ATTTTTTTTG TATTTTTAGT      6840

AGAGACGGGG TTTCATCGTG TTAACCAGGA TGGTCTCGAT CTCCTGACCT CGTGATCTGC      6900

CCACCTCGGC CTCCCACAGT GCTGGGATTA CCGGCGTGAG CCACCATGCC TGGCCCGGAT      6960

AATTTTTTTT AATTTTTGTA GAGACGAGGT CTTGTGATAT TGCCCAGGCT GTTCTTCAAC      7020

TCCTGGGCTC AAGCAGTCCT CCCACCTTGG CCTCCCAGAA TGCTGGGTTT ATAGATGTGA      7080

GCCAGCACAC CGGGCCAAGT GAAGAATCTA ATGAATGTGC AACCTAATTG TAGCATCTAA      7140

TGAATGTTCC ACCATTGCTG GAAAAATTGA GATGGAAAAC AAACCATCTC TAGTTGGCCA      7200

GCGTCTTGCT CTGTTCACAG TCTCTGGAAA AGCTGGGGTA GTTGGTGAGC AGAGCGGGAC      7260

TCTGTCCAAC AAGCCCCACA GCCCCTCAAA GACTTTTTTT TGTTTGTTTT GAGCAGACAG      7320

GCTAAAATGT GAACGTGGGG TGAGGGATCA CTGCCAAAAT GGTACAGCTT CTGGAGCAGA      7380

ACTTTCCAGG GATCCAGGGA CACTTTTTTT TAAAGCTCAT AAACTGCCAA GAGCTCCATA      7440

TATTGGGTGT GAGTTCAGGT TGCCTCTCAC AATGAAGGAA GTTGGTCTTT GTCTGCAGGT      7500

GGGCTGCTGA GGGTCTGGGA TCTGTTTTCT GGAAGTGTGC AGGTATAAAC ACACCCTCTG      7560

TGCTTGTGAC AAACTGGCAG GTACCGTGCT CATTGCTAAC CACTGTCTGT CCCTGAACTC      7620

CCAGAACCAC TACATCTGGC TTTGGGCAGG TCTGAGATAA AACGATCTAA AGGTAGGCAG      7680

ACCCTGGACC CAGCCTCAGA TCCAGGCAGG AGCACGAGGT CTGGCCAAGG TGGACGGGGT      7740

TGTCGAGATC TCAGGAGCCC CTTGCTGTTT TTTGGAGGGT GAAAGAAGAA ACCTTAAACA      7800

TAGTCAGCTC TGATCACATC CCCTGTCTAC TCATCCAGAC CCCATGCCTG TAGGCTTATC      7860

AGGGAGTTAC AGTTACAATT GTTACAGTAC TGTTCCCAAC TCAGCTGCCA CGGGTGAGAG      7920

AGCAGGAGGT ATGAATTAAA AGTCTACAGC ACTAACCCGT GTCTCTGTAG CTTTTTTGGA      7980
```

-continued

```
GCCAGAGCCA CTGTGTATGT GTGTGTGGGT TTGTGTGTGT GTGTGTGTGT GTGTGTGTGT         8040

AAGAGAGTGG AGGAAAAGGT GGGGTACTTC TGAAGACTTT TATTTTTTTT TAATTAATTT         8100

ATTTTTTTTC AGAGATCGAG TCTTGCTCTG TGGCCCAGGC TGGAGTGCAG TAGTGTGATC         8160

TCGGCCCACT GCAA                                                          8174
```

(2) INFORMATION FOR SEQ ID NO:6:

(i) SEQUENCE CHARACTERISTICS:
        (A) LENGTH: 365 amino acids
        (B) TYPE: amino acid
        (D) TOPOLOGY: unknown (ii) MOLECULE TYPE: protein (xi) SEQUENCE DESCRIPTION: SEQ ID NO:6:

```
Met Trp Leu Arg Ser His Arg Gln Leu Cys Leu Ala Phe Leu Leu Val
1               5                   10                  15

Cys Val Leu Ser Val Ile Phe Phe Leu His Ile His Gln Asp Ser Phe
            20                  25                  30

Pro His Gly Leu Gly Leu Ser Ile Leu Cys Pro Asp Arg Arg Leu Val
        35                  40                  45

Thr Pro Pro Val Ala Ile Phe Cys Leu Pro Gly Thr Ala Met Gly Pro
    50                  55                  60

Asn Ala Ser Ser Ser Cys Pro Gln His Pro Ala Ser Leu Ser Gly Thr
65                  70                  75                  80

Trp Thr Val Tyr Pro Asn Gly Arg Phe Gly Asn Gln Met Gly Gln Tyr
                85                  90                  95

Ala Thr Leu Leu Ala Leu Ala Gln Leu Asn Gly Arg Arg Ala Phe Ile
            100                 105                 110

Leu Pro Ala Met His Ala Ala Leu Ala Pro Val Phe Arg Ile Thr Leu
        115                 120                 125

Pro Val Leu Ala Pro Glu Val Asp Ser Arg Thr Pro Trp Arg Glu Leu
    130                 135                 140

Gln Leu His Asp Trp Met Ser Glu Glu Tyr Ala Asp Leu Arg Asp Pro
145                 150                 155                 160

Phe Leu Lys Leu Ser Gly Phe Pro Cys Ser Trp Thr Phe Phe His His
                165                 170                 175

Leu Arg Glu Gln Ile Arg Arg Glu Phe Thr Leu His Asp His Leu Arg
            180                 185                 190

Glu Glu Ala Gln Ser Val Leu Gly Gln Leu Arg Leu Gly Arg Thr Gly
        195                 200                 205

Asp Arg Pro Arg Thr Phe Val Gly Val His Val Arg Arg Gly Asp Tyr
    210                 215                 220

Leu Gln Val Met Pro Gln Arg Trp Lys Gly Val Val Gly Asp Ser Ala
225                 230                 235                 240

Tyr Leu Arg Gln Ala Met Asp Trp Phe Arg Ala Arg His Glu Ala Pro
                245                 250                 255

Val Phe Val Val Thr Ser Asn Gly Met Glu Trp Cys Lys Glu Asn Ile
            260                 265                 270

Asp Thr Ser Gln Gly Asp Val Thr Phe Ala Gly Asp Gly Gln Glu Ala
        275                 280                 285

Thr Pro Trp Lys Asp Phe Ala Leu Leu Thr Gln Cys Asn His Thr Ile
    290                 295                 300

Met Thr Ile Gly Thr Phe Gly Phe Trp Ala Ala Tyr Leu Ala Gly Gly
305                 310                 315                 320
```

```
        Asp Thr Val Tyr Leu Ala Asn Phe Thr Leu Pro Asp Ser Glu Phe Leu
                        325                 330                 335

Lys Ile Phe Lys Pro Glu Ala Ala Phe Leu Pro Glu Trp Val Gly Ile
                        340                 345                 350

Asn Ala Asp Leu Ser Pro Leu Trp Thr Leu Ala Lys Pro
                        355                 360         365

(2) INFORMATION FOR SEQ ID NO:7:

(i) SEQUENCE CHARACTERISTICS:
        (A) LENGTH: 3647 base pairs
        (B) TYPE: nucleic acid
        (C) STRANDEDNESS: unknown
        (D) TOPOLOGY: unknown (ii) MOLECULE TYPE: DNA (genomic)

(iv) ANTI-SENSE: NO (xi) SEQUENCE DESCRIPTION: SEQ ID NO:7:

CTGCAGAGAG CGCCACCCGG AAGCCACTTT TATAGAAGCT TTTACACACA ATGCTTGATT        60

TTTTTTTTTT TTTTCCGAGA CGGAGTCTCG CTTTGTCGCC CAGGCTGGAG TGCAGTGGCG       120

CGATCTGGGC TCACTGCAAG CTCCGCCTCC TGGGTTGACG CCATTCTCCT GCCTCAGCTT       180

CCCGAGTAGC TGGGACTACA GGCGCCCGCC ACCAAGCCTG GCTAATTTTT TTTTATTTTT       240

AGTGGAGACA GAGTTTCACC GTGTTAGCCA GGATGGTCTC GATCTCCTGA CCTCGGGATC       300

CGCCCGCCTC GGCCTCCCAA AGTGCTGGGA GTATAGGCGT GAGCCACCGC GCCTGGCCTA       360

TACTTGATTT TTAATGAAAA CATTCTTAAA TTCATATGGC TAACGCAAAT TTATTTTCTG       420

TAGGCATAAC ATCAAAAACA CCTGGCAGGA CTGCCCCATT CCCAGCACTG TCTAGTTCTC       480

CCCTAGTATC AGTGGGACTC CACTGATGCA CAGCTGTGAT CTACTAAAAC TTCTCTCAAA       540

ACTTTCTCCT CTCCTTAGGT CAGCAGCCCC GCCCCTGATC TATTTGGAAA TCCCCTGAAT       600

AAAAGTTGAA TATCATAAAC CAAAGCGAAC ACCCAGAAAT TCAAATTCAA CCCGTAGGTA       660

AAAAATTTCT CAAGTGACTG TAGACGTAGA TGTCTCCAGT GTCGCCTAAT AAGGTAGAAG       720

AGGCCAGTGC GATACTGTCT TTACACCCTT AACTTGGGTG CTAGAATATT TATCTTCGTC       780

ATCATTTTAT CATCCAAACT ATTTTGCATA ACTTTCATGG GTGCAGAAAA TGTTTTTTAA       840

GTGCTTGGTA AAATTAATAG TGATATTCAT TCATTCATCT CACTGAACAG GCAATAAATT       900

CCTTGACGAC AAGGGCCTTG GGGGGGGCCA CATCTTCATC TTTGGTTTAT GAGTCCTGTG       960

CGTCTTGGTA CAAGCAATAC TACTATGAGC CGGCAAGTCA GACTTATTTG GTAGGGGACC      1020

AAAGGAAAGA ACATGTTTTG ATTGCTAAGA AAACATTTTG TTCTCTATCC TTTACTGGGC      1080

TGGCAGGCAA AGGAAATGTT CTTATGAGCA CTCACATTGA AAACTTAAGT TCTTCACCAA      1140

ATGCAGAGAC TCTGAAGGCC ACGCCGCTGC GGGCTGCCTC CACAATTCGA CCGTCTCGGC      1200

GGGCCACGAG ATCCTGGCCA CGGATGCGGT GGCCGCGCCT CTGCTCGCAC GTTCCCCCGG      1260

CCTCTGGACT CCCTCCCTCC CTCAATCCCT CCCTCCGGCG GGCGTCGCTG GCGGGTGGCT      1320

AGGCCCAACG GCAGGAAGCC GACGCTATCC TCCGTTCCGC GGCGCCGGGT CCGCCTTCCG      1380

TCTGTTCTAG GGCCTGCTCC TGCGCGGCAG CTGCTTTAGA AGGTCTCGAG CCTCCTGTAC      1440

CTTCCCAGGG ATGAACCGGG CCTTCCCTCT GGAAGGCGAG GGTTCGGGCC ACAGTGAGCG      1500

AGGGCCAGGG CGGTGGGCGC GCGCAGAGGG AAACCGGATC AGTTGAGAGA GAATCAAGAG      1560

TAGCGGATGA GGCGCTTGTG GGGCGCGGCC CGGAAGCCCT CGGGCGCGGG CTGGGAGAAG      1620

GAGTGGGCGG AGGCGCCGCA GGAGGCTCCC GGGGCCTGGT CGGGCCGGCT GGGCCCCGGG      1680
```

| CGCAGTGGAA GAAAGGGACG GGCGGTGCCC GGTTGGGCGT CCTGGCCAGC TCACCTTGCC | 1740 |
| CTGGCGGCTC GCCCCGCCCG GCACTTGGGA GGAGCAGGGC AGGGCCCGCG GCCTTTGCAT | 1800 |
| TCTGGGACCG CCCCCTTCCA TTCCCGGGCC AGCGGCGAGC GGCAGCGACG GCTGGAGCCG | 1860 |
| CAGCTACAGC ATGAGAGCCG GTGCCGCTCC TCCACGCCTG CGGACGCGTG GCGAGCGGAG | 1920 |
| GCAGCGCTGC CTGTTCGCGC CATGGGGGCA CCGTGGGGCT CGCCGACGGC GGCGGCGGGC | 1980 |
| GGGCGGCGCG GGTGGCGCCG AGGCCGGGGG CTGCCATGGA CCGTCTGTGT GCTGGCGGCC | 2040 |
| GCCGGCTTGA CGTGTACGGC GCTGATCACC TACGCTTGCT GGGGGCAGCT GCCGCCGCTG | 2100 |
| CCCTGGGCGT CGCCAACCCC GTCGCGACCG GTGGGCGTGC TGCTGTGGTG GGAGCCCTTC | 2160 |
| GGGGGGCGCG ATAGCGCCCC GAGGCCGCCC CCTGACTGCC CGCTGCGCTT CAACATCAGC | 2220 |
| GGCTGCCGCC TGCTCACCGA CCGCGCGTCC TACGAGAGG CTCAGGCCGT GCTTTTCCAC | 2280 |
| CACCGCGACC TCGTGAAGGG GCCCCCCGAC TGGCCCCCGC CCTGGGGCAT CCAGGCGCAC | 2340 |
| ACTGCCGAGG AGGTGGATCT GCGCGTGTTG GACTACGAGG AGGCAGCGGC GGCGGCAGAA | 2400 |
| GCCCTGGCGA CCTCCAGCCC CAGGCCCCCG GGCCAGCGCT GGGTTTGGAT GAACTTCGAG | 2460 |
| TCGCCCTCGC ACTCCCCGGG GCTGCGAAGC CTGGCAAGTA ACCTCTTCAA CTGGACGCTC | 2520 |
| TCCTACCGGG CGGACTCGGA CGTCTTTGTG CCTTATGGCT ACCTCTACCC AGAAGCCAC | 2580 |
| CCCGGCGACC CGCCCTCAGG CCTGGCCCCG CCACTGTCCA GGAAACAGGG GCTGGTGGCA | 2640 |
| TGGGTGGTGA GCCACTGGGA CGACCGCCAG GCCCGGGTCC GCTACTACCA CCAACTGAGC | 2700 |
| CAACATGTGA CCGTGGACGT GTTCGGCCGG GGCGGGCCGG GGCAGCCGGT GCCCGAAATT | 2760 |
| GGGCTCCTGC ACACAGTGGC CCGCTACAAG TTCTACCTGG CTTTCGAGAA CTCGCAGCAC | 2820 |
| CTGGATTATA TCACCGAGAA GCTCTGGCGC AACGCGTTGC TCGCTGGGGC GGTGCCGGTG | 2880 |
| GTGCTGGGCC CAGACCGTGC CAACTACGAG GCGTTTGTGC CCCGCGGCGC CTTCATCCAC | 2940 |
| GTGGACGACT TCCCAAGTGC CTCCTCCCTG GCCTCGTACC TGCTTTTCCT CGACCGCAAC | 3000 |
| CCCGCGGTCT ATCGCCGCTA CTTCCACTGG CGCCGGAGCT ACGCTGTCCA CATCACCTCC | 3060 |
| TTCTGGGACG AGCCTTGGTG CCGGGTGTGC CAGGCTGTAC AGAGGGCTGG GGACCGGCCC | 3120 |
| AAGAGCATAC GGAACTTGGC CAGCTGGTTC GAGCGGTGAA GCCGCGCTCC CCTGGAAGCG | 3180 |
| ACCCAGGGGA GCCCAAGTTG TCAGCTTTTT GATCCTCTAC TGTGCATCTC CTTGACTGCC | 3240 |
| GCATCATGGG AGTAAGTTCT TCAAACACCC ATTTTTGCTC TATGGGAAAA AAACGATTTA | 3300 |
| CCAATTAATA TTACTCAGCA CAGAGATGGG GGCCCGGTTT CCATATTTTT TGCACAGCTA | 3360 |
| GCAATTGGGC TCCCTTTGCT GCTGATGGGC ATCATTGTTT AGGGGTGAAG GAGGGGGTTC | 3420 |
| TTCCTCACCT TGTAACCAGT GCAGAAATGA AATAGCTTAG CGGCAAGAAG CCGTTGAGGC | 3480 |
| GGTTTCCTGA ATTTCCCCAT CTGCCACAGG CCATATTTGT GGCCCGTGCA GCTTCCAAAT | 3540 |
| CTCATACACA ACTGTTCCCG ATTCACGTTT TTCTGGACCA AGGTGAAGCA AATTTGTGGT | 3600 |
| TGTAGAAGGA GCCTTGTTGG TGGAGAGTGG AAGGACTGTG GCTGCAG | 3647 |

(2) INFORMATION FOR SEQ ID NO:8:

(i) SEQUENCE CHARACTERISTICS:
        (A) LENGTH: 405 amino acids
        (B) TYPE: amino acid
        (D) TOPOLOGY: unknown (ii) MOLECULE TYPE: protein (xi) SEQUENCE DESCRIPTION: SEQ ID NO:8:

Met Gly Ala Pro Trp Gly Ser Pro Thr Ala Ala Gly Gly Arg Arg
1               5                   10                  15

Gly Trp Arg Arg Gly Arg Gly Leu Pro Trp Thr Val Cys Val Leu Ala
                20                  25                  30

Ala Ala Gly Leu Thr Cys Thr Ala Leu Ile Thr Tyr Ala Cys Trp Gly
            35                  40                  45

Gln Leu Pro Pro Leu Pro Trp Ala Ser Pro Thr Pro Ser Arg Pro Val
 50                  55                  60

Gly Val Leu Leu Trp Trp Glu Pro Phe Gly Arg Asp Ser Ala Pro
 65                  70                  75                  80

Arg Pro Pro Pro Asp Cys Pro Leu Arg Phe Asn Ile Ser Gly Cys Arg
                85                  90                  95

Leu Leu Thr Asp Arg Ala Ser Tyr Gly Glu Ala Gln Ala Val Leu Phe
                100                 105                 110

His His Arg Asp Leu Val Lys Gly Pro Pro Asp Trp Pro Pro Pro Trp
                115                 120                 125

Gly Ile Gln Ala His Thr Ala Glu Glu Val Asp Leu Arg Val Leu Asp
130                 135                 140

Tyr Glu Glu Ala Ala Ala Ala Ala Glu Ala Leu Ala Thr Ser Ser Pro
145                 150                 155                 160

Arg Pro Pro Gly Gln Arg Trp Val Trp Met Asn Phe Glu Ser Pro Ser
                165                 170                 175

His Ser Pro Gly Leu Arg Ser Leu Ala Ser Asn Leu Phe Asn Trp Thr
                180                 185                 190

Leu Ser Tyr Arg Ala Asp Ser Asp Val Phe Val Pro Tyr Gly Tyr Leu
                195                 200                 205

Tyr Pro Arg Ser His Pro Gly Asp Pro Pro Ser Gly Leu Ala Pro Pro
 210                 215                 220

Leu Ser Arg Lys Gln Gly Leu Val Ala Trp Val Val Ser His Trp Asp
225                 230                 235                 240

Glu Arg Gln Ala Arg Val Arg Tyr Tyr His Gln Leu Ser Gln His Val
                245                 250                 255

Thr Val Asp Val Phe Gly Arg Gly Gly Pro Gly Gln Pro Val Pro Glu
                260                 265                 270

Ile Gly Leu Leu His Thr Val Ala Arg Tyr Lys Phe Tyr Leu Ala Phe
                275                 280                 285

Glu Asn Ser Gln His Leu Asp Tyr Ile Thr Glu Lys Leu Trp Arg Asn
 290                 295                 300

Ala Leu Leu Ala Gly Ala Val Pro Val Val Leu Gly Pro Asp Arg Ala
305                 310                 315                 320

Asn Tyr Glu Arg Phe Val Pro Arg Gly Ala Phe Ile His Val Asp Asp
                325                 330                 335

Phe Pro Ser Ala Ser Ser Leu Ala Ser Tyr Leu Leu Phe Leu Asp Arg
                340                 345                 350

Asn Pro Ala Val Tyr Arg Tyr Phe His Trp Arg Arg Ser Tyr Ala
                355                 360                 365

Val His Ile Thr Ser Phe Trp Asp Glu Pro Trp Cys Arg Val Cys Gln
 370                 375                 380

Ala Val Gln Arg Ala Gly Asp Arg Pro Lys Ser Ile Arg Asn Leu Ala
385                 390                 395                 400

Ser Trp Phe Glu Arg
                405

(2) INFORMATION FOR SEQ ID NO:9:

(i) SEQUENCE CHARACTERISTICS:

(A) LENGTH: 1488 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:9:

```
ATGGGGGCAC CGTGGGGCTC GCCGACGGCG GCGGCGGGCG GCGGCGCGG GTGGCGCCGA      60

GGCCCGGGGC TGCCATGGAC CGTCTGTGTG CTGGCGGCCG CCGGCTTGAC GTGTACGGCG     120

CTGATCACCT ACGCTTGCTG GGGGCAGCTG CCGCCGCTGC CCTGGGCGTC GCCAACCCCG     180

TCGCGACCGG TGGGCGTGCT GCTGTGGTGG GAGCCCTTCG GGGGGCGCGA TAGCGCCCCG     240

AGGCCGCCCC CTGACTGCTG CTGGGGGCAG CTGCCGCCGC TGCCCTGGGC GTCGCCAACC     300

CCGTCGCGAC CGGTGGGCGT GCTGCTGTGG TGGGAGCCCT TCGGGGGGCG CGATAGCGCC     360

CCGAGGCCGC CCCCTGACTG CCCGCTGCGC TTCAACATCA GCGGCTGCCG CCTGCTCACC     420

GACCGCGCGT CCTACGGAGA GGCTCAGGCC GTGCTTTTCC ACCACCGCGA CCTCGTGAAG     480

GGGCCCCCCG ACTGGCCCCC GCCCTGGGGC ATCCAGGCGC ACACTGCCGA GCCGCTGCGC     540

TTCAACATCA GCGGCTGCCG CCTGCTCACC GACCGCGCGT CCTACGGAGA GGCTCAGGCC     600

GTGCTTTTCC ACCACCGCGA CCTCGTGAAG GGGCCCCCCG ACTGGCCCCC GCCCTGGGGC     660

ATCCAGGCGC ACACTGCCGA GGAGGTGGAT CTGCGCGTGT GGACTACGA GGAGGCAGCG      720

GCGGCGGCAG AAGCCCTGGC GACCTCCAGC CCCAGGCCCC CGGGCCAGCG CTGGGTTTGG     780

ATGAACTTCG AGTCGCCCTC GCACTCCCCG GGGCTGCGAA GCCTGGCAAG TAACCTCTTC     840

AACTGGACGC TCTCCTACCG GGCGGACTCG GACGTCTTTG TGCCTTATGG CTACCTCTAC     900

CCCAGAAGCC ACCCCGGCGA CCCGCCCTCA GGCCTGGCCC CGCCACTGTC CAGGAAACAG     960

GGGCTGGTGG CATGGGTGGT GAGCCACTGG GACGAGCGCC AGGCCCGGGT CCGCTACTAC    1020

CACCAACTGA GCCAACATGT GACCGTGGAC GTGTTCGGCC GGGGCGGGCC GGGGCAGCCG    1080

GTGCCCGAAA TTGGGCTCCT GCACACAGTG GCCCGCTACA AGTTCTACCT GGCTTTCGAG    1140

AACTCGCAGC ACCTGGATTA TATCACCGAG AAGCTCTGGC GCAACGCGTT GCTCGCTGGG    1200

GCGGTGCCGG TGGTGCTGGG CCCAGACCGT GCCAACTACG AGCGCTTTGT GCCCCGCGGC    1260

GCCTTCATCC ACGTGGACGA CTTCCCAAGT GCCTCCTCCC TGGCCTCGTA CCTGCTTTTC    1320

CTCGACCGCA ACCCCGCGGT CTATCGCCGC TACTTCCACT GGCGCCGGAG CTACGCTGTC    1380

CACATCACCT CCTTCTGGGA CGAGCCTTGG TGCCGGGTGT GCCAGGCTGT ACAGAGGGCT    1440

GGGGACCGGC CAAGAGCAT ACGGAACTTG GCCAGCTGGT TCGAGCGG                  1488
```

(2) INFORMATION FOR SEQ ID NO:10:

(i) SEQUENCE CHARACTERISTICS:
        (A) LENGTH: 1316 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:10:

```
TTTATGACAA GCTGTGTCAT AAATTATAAC AGCTTCTCTC AGGACACTGT GGCCAGGAAG      60

TGGGTGATCT TCCTTAATGA CCCTCACTCC TCTCTCCTCT CTTCCCAGCT ACTCTGACCC     120

ATGGATCCCC TGGGCCCAGC CAAGCCACAG TGGCTGTGGC GCCGCTGTCT GGCCGGGCTG     180

CTGTTTCAGC TGCTGGTGGC TGTGTGTTTC TTCTCCTACC TGCGTGTGTC CCGAGACGAT     240
```

-continued

```
GCCACTGGAT CCCCTAGGCC AGGGCTTATG GCAGTGGAAC CTGTCACCGG GGCTCCCAAT      300

GGGTCCCGCT GCCAGGACAG CATGGCGACC CCTGCCCACC CCACCCTACT GATCCTGCTG      360

TGGACGTGGC CTTTTAACAC ACCCGTGGCT CTGCCCCGCT GCTCAGAGAT GGTGCCCGGC      420

GCGGCCGACT GCAACATCAC TGCCGACTCC AGTGTGTACC CACAGGCAGA CGCGGTCATC      480

GTGCACCACT GGGATATCAT GTACAACCCC AGTGCCAACC TCCCGCCCCC CACCAGGCCG      540

CAGGGGCAGC GCTGGATCTG GTTCAGCATG GAGTCCCCCA GCAACTGCCG GCACCTGGAA      600

GCCCTGGACG GATACTTCAA TCTCACCATG TCCTACCGCA GCGACTCCGA CATCTTCACG      660

CCCTACGGCT GGCTGGAGCC GTGGTCCGGC CAGCCTGCCC ACCCACCGCT CAACCTCTCG      720

GCCAAGACCG AGCTGGTGGC CTGGGCGGTG TCCAACTGGA AGCCGGACTC GGCCAGGGTG      780

CGCTACTACC AGAGCCTGCA GGCTCATCTC AAGGTGGACG TGTACGGACG CTCCCACAAG      840

CCCCTGCCCA AGGGGACCAT GATGGAGACG CTGTCCCGGT ACAAGTTCTA TCTGGCCTTC      900

GAGAACTCCT TGCACCCCGA CTACATCACC GAGAAGCTGT GGAGGAACGC CCTGGAGGCC      960

TGGGCCGTGC CCGTGGTGCT GGGCCCCAGC AGAAGCAACT ACGAGAGGTT CCTGCCGCCC     1020

GACGCCTTCA TCCACGTGGA TGACTTCCAG AGCCCCAAGG ACCTGGCCCG GTACCTGCAG     1080

GAGCTGGACA AGGACCACGC CCGCTACCTG AGCTACTTTC GCTGGCGGGA GACGCTGCGG     1140

CCTCGCTCCT TCAGCTGGGC ACTGGCTTTC TGCAAGGCCT GCTGGAAGCT GCAGCAGGAA     1200

TCCAGGTACC AGACGGTGCG CAGCATAGCG GCTTGGTTCA CCTGAGAGGC CGGCATGGGG     1260

CCTGGGCTGC CAGGGACCTC ACTTTCCCAG GGCCTCACCT ACCTAGGGTC TCTAGA         1316
```

(2) INFORMATION FOR SEQ ID NO:11:

(i) SEQUENCE CHARACTERISTICS:
        (A) LENGTH: 374 amino acids
        (B) TYPE: amino acid
        (D) TOPOLOGY: unknown (ii) MOLECULE TYPE: protein (xi) SEQUENCE DESCRIPTION: SEQ ID NO:11:

```
Met Asp Pro Leu Gly Pro Ala Lys Pro Gln Trp Leu Trp Arg Arg Cys
1               5                   10                  15

Leu Ala Gly Leu Leu Phe Gln Leu Leu Val Ala Val Cys Phe Phe Ser
            20                  25                  30

Tyr Leu Arg Val Ser Arg Asp Asp Ala Thr Gly Ser Pro Arg Pro Gly
        35                  40                  45

Leu Met Ala Val Glu Pro Val Thr Gly Ala Pro Asn Gly Ser Arg Cys
    50                  55                  60

Gln Asp Ser Met Ala Thr Pro Ala His Pro Thr Leu Leu Ile Leu Leu
65                  70                  75                  80

Trp Thr Trp Pro Phe Asn Thr Pro Val Ala Leu Pro Arg Cys Ser Glu
                85                  90                  95

Met Val Pro Gly Ala Ala Asp Cys Asn Ile Thr Ala Asp Ser Ser Val
            100                 105                 110

Tyr Pro Gln Ala Asp Ala Val Ile Val His His Trp Asp Ile Met Tyr
        115                 120                 125

Asn Pro Ser Ala Asn Leu Pro Pro Thr Arg Pro Gln Gly Gln Arg
    130                 135                 140

Trp Ile Trp Phe Ser Met Glu Ser Pro Ser Asn Cys Arg His Leu Glu
145                 150                 155                 160

Ala Leu Asp Gly Tyr Phe Asn Leu Thr Met Ser Tyr Arg Ser Asp Ser
                165                 170                 175
```

```
Asp Ile Phe Thr Pro Tyr Gly Trp Leu Glu Pro Trp Ser Gly Gln Pro
            180                 185                 190

Ala His Pro Pro Leu Asn Leu Ser Ala Lys Thr Glu Leu Val Ala Trp
            195                 200                 205

Ala Val Ser Asn Trp Lys Pro Asp Ser Ala Arg Val Arg Tyr Tyr Gln
            210                 215                 220

Ser Leu Gln Ala His Leu Lys Val Asp Val Tyr Gly Arg Ser His Lys
225                 230                 235                 240

Pro Leu Pro Lys Gly Thr Met Met Glu Thr Leu Ser Arg Tyr Lys Phe
                245                 250                 255

Tyr Leu Ala Phe Glu Asn Ser Leu His Pro Asp Tyr Ile Thr Glu Lys
            260                 265                 270

Leu Trp Arg Asn Ala Leu Glu Ala Trp Ala Val Pro Val Val Leu Gly
            275                 280                 285

Pro Ser Arg Ser Asn Tyr Glu Arg Phe Leu Pro Pro Asp Ala Phe Ile
            290                 295                 300

His Val Asp Asp Phe Gln Ser Pro Lys Asp Leu Ala Arg Tyr Leu Gln
305                 310                 315                 320

Glu Leu Asp Lys Asp His Ala Arg Tyr Leu Ser Tyr Phe Arg Trp Arg
                325                 330                 335

Glu Thr Leu Arg Pro Arg Ser Phe Ser Trp Ala Leu Ala Phe Cys Lys
            340                 345                 350

Ala Cys Trp Lys Leu Gln Gln Glu Ser Arg Tyr Gln Thr Val Arg Ser
            355                 360                 365

Ile Ala Ala Trp Phe Thr
370

(2) INFORMATION FOR SEQ ID NO:12:

(i) SEQUENCE CHARACTERISTICS:
        (A) LENGTH: 1086 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:12:

ATGGATCCCC TGGGTGCAGC CAAGCCACAA TGGCCATGGC GCCGCTGTCT GGCCGCACTG        60
CTATTTCAGC TGCTGGTGGC TGTGTGTTTC TTCTCCTACC TGCGTGTGTC CCGAGACGAT       120
GCCACTGGAT CCCCTAGGGC TCCCAGTGGG TCCTCCCGAC AGGACACCAC TCCCACCCGC       180
CCCACCCTCC TGATCCTGCT ATGGACATGG CCTTTCCACA TCCCTGTGGC TCTGTCCCGC       240
TGTTCAGAGA TGGTGCCCGG CACAGCCGAC TGCCACATCA CTGCCGACCG CAAGGTGTAC       300
CCACAGGCAG ACACGGTCAT CGTGCACCAC TGGGATATCA TGTCCAACCC TAAGTCACGC       360
CTCCCACCTT CCCCGAGGCC GCAGGGGCAG CGCTGGATCT GGTTCAACTT GGAGCCACCC       420
CCTAACTGCC AGCACCTGGA AGCCCTGGAC AGATACTTCA ATCTCACCAT GTCCTACCGC       480
AGCGACTCCG ACATCTTCAC GCCCTACGGC TGGCTGGAGC CGTGGTCCGG CCAGCCTGCC       540
CACCCACCGC TCAACCTCTC GGCCAAGACC GAGCTGGTGG CCTGGGCGGT GTCCAACTGG       600
AAGCCGGACT CAGCCAGGGT GCGCTACTAC CAGAGCCTGC AGGCTCATCT CAAGGTGGAC       660
GTGTACGGAC GCTCCCACAA GCCCCTGCCC AAGGGGACCA TGATGGAGAC GCTGTCCCGG       720
TACAAGTTCT ACCTGGCCTT CGAGAACTCC TTGCACCCCG ACTACATCAC CGAGAAGCTG       780
TGGAGGAACG CCCTGGAGGC CTGGGCCGTG CCCGTGGTGC TGGGCCCCAG CAGAAGCAAC       840
```

```
TACGAGAGGT TCCTGCCACC CGACGCCTTC ATCCACGTGG ACGACTTCCA GAGCCCCAAG      900

GACCTGGCCC GGTACCTGCA GGAGCTGGAC AAGGACCACG CCCGCTACCT GAGCTACTTT      960

CGCTGGCGGG AGACGCTGCG GCCTCGCTCC TTCAGCTGGG CACTGGATTT CTGCAAGGCC     1020

TGCTGGAAAC TGCAGCAGGA ATCCAGGTAC CAGACGGTGC GCAGCATAGC GGCTTGGTTC     1080

ACCTGA                                                                1086
```

(2) INFORMATION FOR SEQ ID NO:13:

(i) SEQUENCE CHARACTERISTICS:
        (A) LENGTH: 1654 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:13:

```
TTTTCTCATC TGTGAAACAG GAATAATAAC AGCTCTTCTC AGGACTCATG GCCTGGAGCT       60

TTGGTAAGCA GGAGATTGTC ATCAATGACC CTCACTCCTC TCTCCCCACT TCCCAGAGAC      120

TCTGACCCAT GGATCCCCTG GGCCCGGCCA AGCCACAGTG GTCGTGGCGC TGCTGTCTGA      180

CCACGCTGCT GTTTCAGCTG CTGATGGCTG TGTGTTTCTT CTCCTATCTG CGTGTGTCTC      240

AAGACGATCC CACTGTGTAC CCTAATGGGT CCCGCTTCCC AGACAGCACA GGGACCCCCG      300

CCCACTCCAT CCCCCTGATC CTGCTGTGGA CGTGGCCTTT TAACAAACCC ATAGCTCTGC      360

CCCGCTGCTC AGAGATGGTG CCTGGCACGG CTGACTGCAA CATCACTGCC GACCGCAAGG      420

TGTATCCACA GGCAGACGCG GTCATCGTGC ACCACCGAGA GGTCATGTAC AACCCCAGTG      480

CCCAGCTCCC ACGCTCCCCG AGGCGGCAGG GGCAGCGATG GATCTGGTTC AGCATGGAGT      540

CCCCAAGCCA CTGCTGGCAG CTGAAAGCCA TGGACGGATA CTTCAATCTC ACCATGTCCT      600

ACCGCAGCGA CTCCGACATC TTCACGCCCT ACGGCTGGCT GGAGCCGTGG TCCGGCCAGC      660

CTGCCCACCC ACCGCTCAAC CTCTCGGCCA AGACCGAGCT GGTGGCCTGG GCAGTGTCCA      720

ACTGGGGGCC AAACTCCGCC AGGGTGCGCT ACTACCAGAG CCTGCAGGCC CATCTCAAGG      780

TGGACGTGTA CGGACGCTCC CACAAGCCCC TGCCCCAGGG AACCATGATG GAGACGCTGT      840

CCCGGTACAA GTTCTATCTG GCCTTCGAGA ACTCCTTGCA CCCCGACTAC ATCACCGAGA      900

AGCTGTGGAG GAACGCCCTG GAGGCCTGGG CCGTGCCCGT GGTGCTGGGC CCAGCAGAA      960

GCAACTACGA GAGGTTCCTG CCACCCGACG CCTTCATCCA CGTGGACGAC TTCCAGAGCC     1020

CCAAGGACCT GGCCCGGTAC CTGCAGGAGC TGGACAAGGA CCACGCCCGC TACCTGAGCT     1080

ACTTTCGCTG GCGGGAGACG CTGCGGCCTC GCTCCTTCAG CTGGGCACTC GCTTTCTGCA     1140

AGGCCTGCTG GAAACTGCAG GAGGAATCCA GGTACCAGAC ACGCGGCATA GCGGCTTGGT     1200

TCACCTGAGA GGCTGGTGTG GGGCCTGGGC TGCCAGGAAC CTCATTTTCC TGGGGCCTCA     1260

CCTGAGTGGG GGCCTCATCT ACCTAAGGAC TCGTTTGCCT GAAGCTTCAC CTGCCTGAGG     1320

ACTCACCTGC CTGGGACGGT CACCTGTTGC AGCTTCACCT GCCTGGGGAT TCACCTACCT     1380

GGGTCCTCAC TTTCCTGGGG CCTCACCTGC TGGAGTCTTC GGTGGCCAGG TATGTCCCTT     1440

ACCTGGGATT TCACATGCTG GCTTCCAGGA GCGTCCCCTG CGGAAGCCTG GCCTGCTGGG     1500

GATGTCTCCT GGGGACTTTG CCTACTGGGG ACCTCGGCTG TTGGGGACTT TACCTGCTGG     1560

GACCTGCTCC CAGAGACCTT CCACACTGAA TCTCACCTGC TAGGAGCCTC ACCTGCTGGG     1620

GACCTCACCC TGGAGGCACT GGGCCCTGGG AACT                                 1654
```

(2) INFORMATION FOR SEQ ID NO:14:

(i) SEQUENCE CHARACTERISTICS:
        (A) LENGTH: 359 amino acids
        (B) TYPE: amino acid
        (D) TOPOLOGY: unknown (ii) MOLECULE TYPE: protein (xi) SEQUENCE DESCRIPTION: SEQ ID NO:14:

```
Met Asp Pro Leu Gly Pro Ala Lys Pro Gln Trp Ser Trp Arg Cys Cys
1               5                   10                  15

Leu Thr Thr Leu Leu Phe Gln Leu Leu Met Ala Val Cys Phe Phe Ser
                20                  25                  30

Tyr Leu Arg Val Ser Gln Asp Asp Pro Thr Val Tyr Pro Asn Gly Ser
            35                  40                  45

Arg Phe Pro Asp Ser Thr Gly Thr Pro Ala His Ser Ile Pro Leu Ile
        50                  55                  60

Leu Leu Trp Thr Trp Pro Phe Asn Lys Pro Ile Ala Leu Pro Arg Cys
65                  70                  75                  80

Ser Glu Met Val Pro Gly Thr Ala Asp Cys Asn Ile Thr Ala Asp Arg
                85                  90                  95

Lys Val Tyr Pro Gln Ala Asp Ala Val Ile Val His His Arg Glu Val
            100                 105                 110

Met Tyr Asn Pro Ser Ala Gln Leu Pro Arg Ser Pro Arg Arg Gln Gly
        115                 120                 125

Gln Arg Trp Ile Trp Phe Ser Met Glu Ser Pro Ser His Cys Trp Gln
130                 135                 140

Leu Lys Ala Met Asp Gly Tyr Phe Asn Leu Thr Met Ser Tyr Arg Ser
145                 150                 155                 160

Asp Ser Asp Ile Phe Thr Pro Tyr Gly Trp Leu Glu Pro Trp Ser Gly
                165                 170                 175

Gln Pro Ala His Pro Pro Leu Asn Leu Ser Ala Lys Thr Glu Leu Val
            180                 185                 190

Ala Trp Ala Val Ser Asn Trp Gly Pro Asn Ser Ala Arg Val Arg Tyr
        195                 200                 205

Tyr Gln Ser Leu Gln Ala His Leu Lys Val Asp Val Tyr Gly Arg Ser
210                 215                 220

His Lys Pro Leu Pro Gln Gly Thr Met Met Glu Thr Leu Ser Arg Tyr
225                 230                 235                 240

Lys Phe Tyr Leu Ala Phe Glu Asn Ser Leu His Pro Asp Tyr Ile Thr
                245                 250                 255

Glu Lys Leu Trp Arg Asn Ala Leu Glu Ala Trp Ala Val Pro Val Val
            260                 265                 270

Leu Gly Pro Ser Arg Ser Asn Tyr Glu Arg Phe Leu Pro Pro Asp Ala
        275                 280                 285

Phe Ile His Val Asp Asp Phe Gln Ser Pro Lys Asp Leu Ala Arg Tyr
290                 295                 300

Leu Gln Glu Leu Asp Lys Asp His Ala Arg Tyr Leu Ser Tyr Phe Arg
305                 310                 315                 320

Trp Arg Glu Thr Leu Arg Pro Arg Ser Phe Ser Trp Ala Leu Ala Phe
                325                 330                 335

Cys Lys Ala Cys Trp Lys Leu Gln Glu Glu Ser Arg Tyr Gln Thr Arg
            340                 345                 350

Gly Ile Ala Ala Trp Phe Thr
```

METHODS AND PRODUCTS FOR THE SYNTHESIS OF OLIGOSACCHARIDE STRUCTURES ON GLYCOPROTEINS, GLYCOLIPIDS, OR AS FREE MOLECULES, AND FOR THE ISOLATION OF CLONED GENETIC SEQUENCES THAT DETERMINE THESE STRUCTURES

This is a Division of application Ser. No. 08/393,246 filed on Feb. 23, 1995, now U.S. Pat. No. 5,595,900, which is a Continuation of application Ser. No. 08/220,433, filed Mar. 30, 1994, abandoned, which is a Division of application Ser. No. 07/914,281, filed Jul. 20, 1992, now U.S. Pat. No. 5,324,663, which is a Continuation-in-Part of application Ser. No. 07/715,900, filed Jun. 19, 1991, abandoned, which is a Continuation-in-Part of application Ser. No. 07/627,621, filed Dec. 12, 1990, abandoned, which is a Continuation-in-Part of application Ser. No. 07/479,858, filed Feb. 14, 1990, abandoned.

BACKGROUND OF THE INVENTION

1. Field of the Invention

The present invention relates to methods and products for the synthesis of oligosaccharide or polysaccharide structures, on glycoproteins, glycolipids, or as free molecules.

2. Discussion of the Background

Carbohydrates are an important class of biological compounds which are remarkable for their structural diversity. This diversity is not random but rather consists of specific sets of oligosaccharide structures that exhibit precise tissue-specific and developmental expression patterns. In cells carbohydrates function as structural components where they regulate viscosity, store energy, or are key components of cell surfaces. Numerous site specific intercellular interactions involve cell surface carbohydrates. For example, union of sperm and egg as well as the implantation of fertilized egg are both mediated by cell surface carbohydrates. Likewise, a number of proteins that function as cell adhesion molecules, including GMP-140, Endothelial Leukocyte Adhesion Molecule-1 (ELAM-1), and lymphocyte adhesion molecules like Mel-14, exhibit structural features that mimic lectins, and are now known to bind specific cell surface carbohydrate structures (Feizi, *Trends Biochem. Sci.* (1991) 16:84–86). Glycosylated proteins as tumor-associated antigens are now being used to identify the presence of numerous carcinomas. Even isolated oligosaccharides have been found to exhibit biological activity on their own.

Specific galactose oligosaccharides are known to inhibit the agglutination of uropathogenic caliform bacteria with red blood cells (U.S. Pat. No. 4,521,592). Other oligosaccharides have been shown to possess potent antithrombic activity by increasing the levels of plasminogen activator (U.S. Pat. No. 4,801,583). This same biological activity has been used, by binding oligosaccharides, in conjunction with an amino glycoprotein, in medical instruments to provide medical surfaces which have anticoagulation effects (U.S. Pat. No. 4,810,784). Still other oligosaccharides have found utility as gram positive antibiotics and disinfectants (U.S. Pat. Nos. 4,851,338 and 4,665,060). Further, oligosaccharides have been used as bacteria receptor sites in the diagnosis and identification of specific bacteria (U.S. Pat. Nos. 4,657,849 and 4,762,824).

It is also well recognized that oligosaccharides have an influence on the protein or lipid to which they are conjugated (Rademacher et al, *Ann. Rev. Biochem.*, (1988) 57:785). Specific oligosaccharides have been shown to influence proteins' stability, rate of in vivo clearance from blood stream, rate of proteolysis, thermal stability and solubility. Changes in the oligosaccharide portion of cell surface carbohydrates have been noted in cells which have become cancerous. Other oligosaccharide changes have been detected during cell differentiation (Toone et al, *Tetrahedron Report* (1989) 45(17):5365–5422). As such, the significance of oligosaccharides to biological function cannot be understated.

The fundamental role of these materials in molecular biology has made them the object of considerable research, in particulars considerable efforts have been made in organic synthesis to synthesize these materials. Although synthetic approaches to making carbohydrates are quite developed, this technique suffers notable difficulties which relate to the selective protection and deprotection steps required in the available synthetic pathways. These difficulties, combined with difficulties associated with isolating and purifying carbohydrates, and determining their structures, has made it essentially impossible for synthetic organic chemistry to economically produce valuable carbohydrates.

Enzyme-mediated catalytic synthesis would offer dramatic advantages over the classical synthetic organic pathways, producing very high yields of carbohydrates (e.g., oligosaccharides and/or polysaccharides) economically, under mild conditions in aqueous solution, and without generating notable amounts of undesired side products. Such enzymes, which include glycosyltransferases, are however difficult to isolate, especially from eukaryotic, e.g., mammalian sources, because these proteins are only found in low concentrations, and are membrane-bound.

As of 1987, standard molecular cloning approaches which require amino acid sequence information or anti-glycosyltransferase antibodies, had been successfully used to isolate just two eukaryotic, e.g., mammalian glycosyltransferase cDNAs, corresponding to $\beta(1,4)$ galactosyltransferase (in 1986) and $\alpha(2,6)$sialyltransferase (in 1987). In light of the above-noted considerable value of carbohydrates, there is accordingly a strongly felt need for an improved method for isolation of additional glycosyltransferase genes and cDNAs and for their use in carbohydrate synthesis.

SUMMARY OF THE INVENTION

Accordingly, it is an object of this invention to provide a method for readily isolating eukaryotic, e.g., mammalian glycosyltransferase genes and cDNAs.

It is another object of this invention to provide a method to modify these isolated genes and cDNAs to obtain correspondingly modified glycosyltransferases.

It is another object of this invention to provide these unmodified and modified isolated genes and cDNAs, and to use them, for example, in modifying cell surface oligosaccharide structure via gene transfer approaches or via in vitro glycosylation reactions.

The inventor has now discovered a gene transfer approach which satisfies all of the above-noted objects of this invention, and other objects which will be seen from the description of the invention given hereinbelow. The present methodology takes advantage of existing information about substrate and acceptor properties of glycosyltransferases and makes use of the numerous antibody and lectin reagents that are specific to the cell surface-expressed oligosaccharide products of these enzymes.

BRIEF DESCRIPTION OF THE FIGURES

Figure 3N:
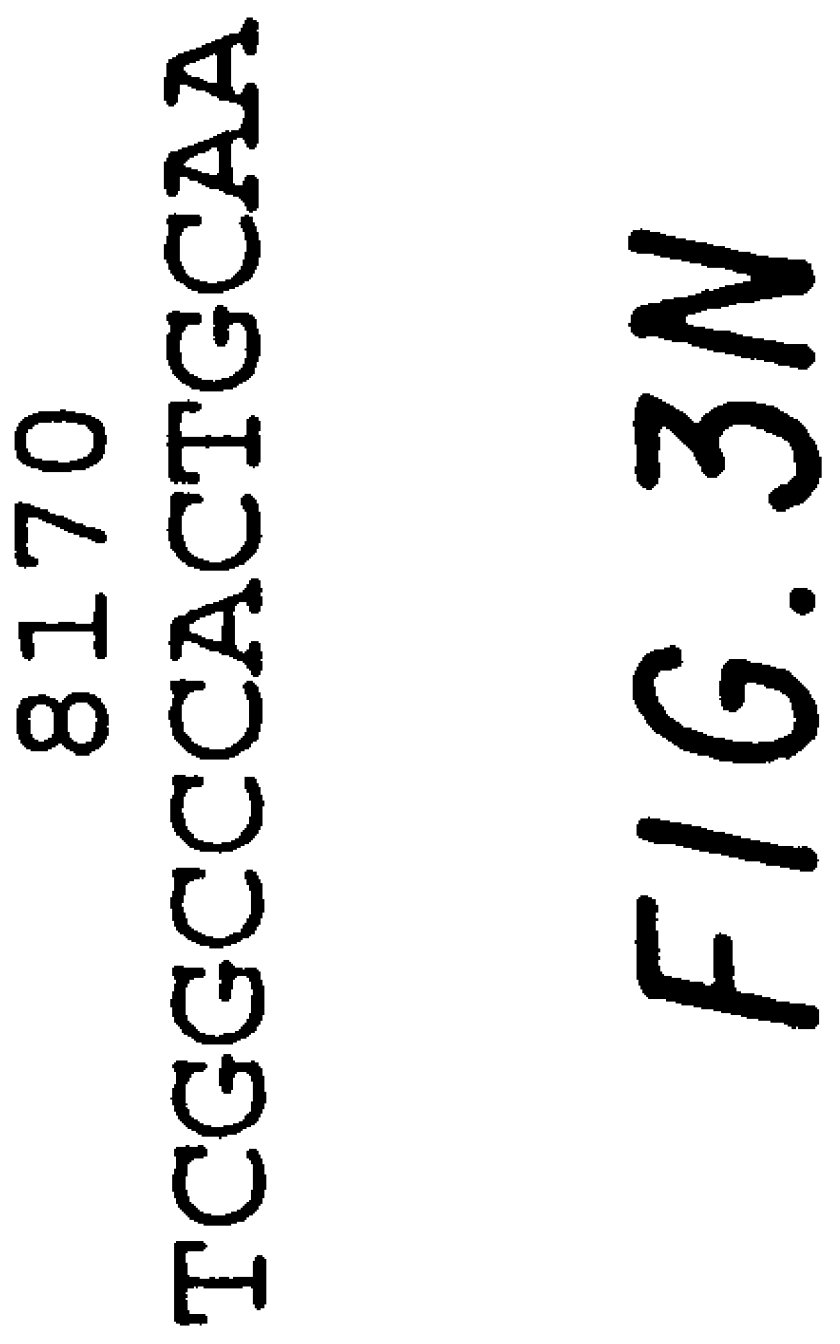

FIGS. 1, 2, 3, 4, 5, 6, and 7 provide six DNA sequences provided by the invention, encloding glycosyltransferases.

FIG. 1 shows the DNA sequence encoding a protein capable of functioning as a GDP-Fuc:[β-D-Gal(1,4/1,3)-D-GlcNac(/Glc)-α-(1,3/1,4)-fucosyltransferase (Lewis fucosyltransferase, Fuc-TIII) (SEQ ID NO:1) and the amino acid sequence of the encoded protein (Fuc-TIII)(SEQ ID NO:2).

FIG. 2 shows the DNA sequence encoding a mouse UDP-Gal:β-D-Gal-(1,4)-D-GlcNac α(1,3)-galactosyltransferase (SEQ ID NO:3) and the encoded protein (SEQ ID NO:4).

FIG. 3 shows the DNA sequence encoding a human GDP-Fuc:β-D-galactoside α(1,2)-fucosyltransferase (SEQ ID NO:5) and the amino acid sequence of the encoded protein (SEQ ID NO:6).

FIGS. 4 and 5 provide DNA sequences (SEQ ID NO:7 and SEQ ID NO:9, respectively) encoding a GDP-Fuc:[β-D-Gal(1,4)]-D-GlcNacα(1,3)-fucosyltransferase (Fuc-TIV) and the encoded protein (Fuc-TIV) (SEQ ID NO:8). FIG. 5 also shows the amino acid sequence of the Lewis fucosyltransferase (Fuc-TIII) (SEQ ID NO:2).

FIG. 6 provides a DNA sequence (SEQ ID NO:10) encoding a GDP-Fuc: [β-D-Gal(1,4)]-D-GlcNAcα(1,3)-fucosyltransferase (Fuc-TV) (numbered upper nucleotide strand) and its corresponding protein sequence (Fuc TV) (SEQ ID NO:11), together with the DNA sequence of the Lewis blood group fucosyltransferase (Fuc-TIII) (unnumbered lower sequence). Amino acid differences with the Lewis fucosyltransferase are indicated by inclusion of Lewis amino acids below the Lewis DNA sequence (SEQ ID NO:12). The transmembrane domain of the fucosyltransferase is underlined.

FIG. 7 provides a DNA sequence of the coding portion of the genomic DNA insert in pCDNAl-α(1,3)Fuc-TVI (SEQ ID NO:13), and parts of the 5' and 3' regions of that gene. DNA sequence comparison between the GDP-Fuc:[β-D-Gal (1,4)]-D-GlcNAcα(1,3)-fucosyltransferase (Fuc-TVI) encoded by the genomic DNA fragment in pCDNAl-α(1,3) Fuc-TVI (labeled α(1,3)FT DNA) and the Lewis blood group fucosyltransferase (Fuc-TIII) (labeled Lewis DNA) (SEQ ID NO:12) is also shown in FIG. 7. Positions of DNA sequence identity are denoted by a vertical line (|) between identical nucleotides at similar positions. Positions where the sequences are out of register are denoted by (.). The derived protein sequence of Fuc-TVI, in single letter code, and labeled α(1,3)FT AA, is indicated above its DNA sequence (SEQ ID NO:14).

DETAILED DESCRIPTION OF THE PREFERRED EMBODIMENTS

Figure 8:
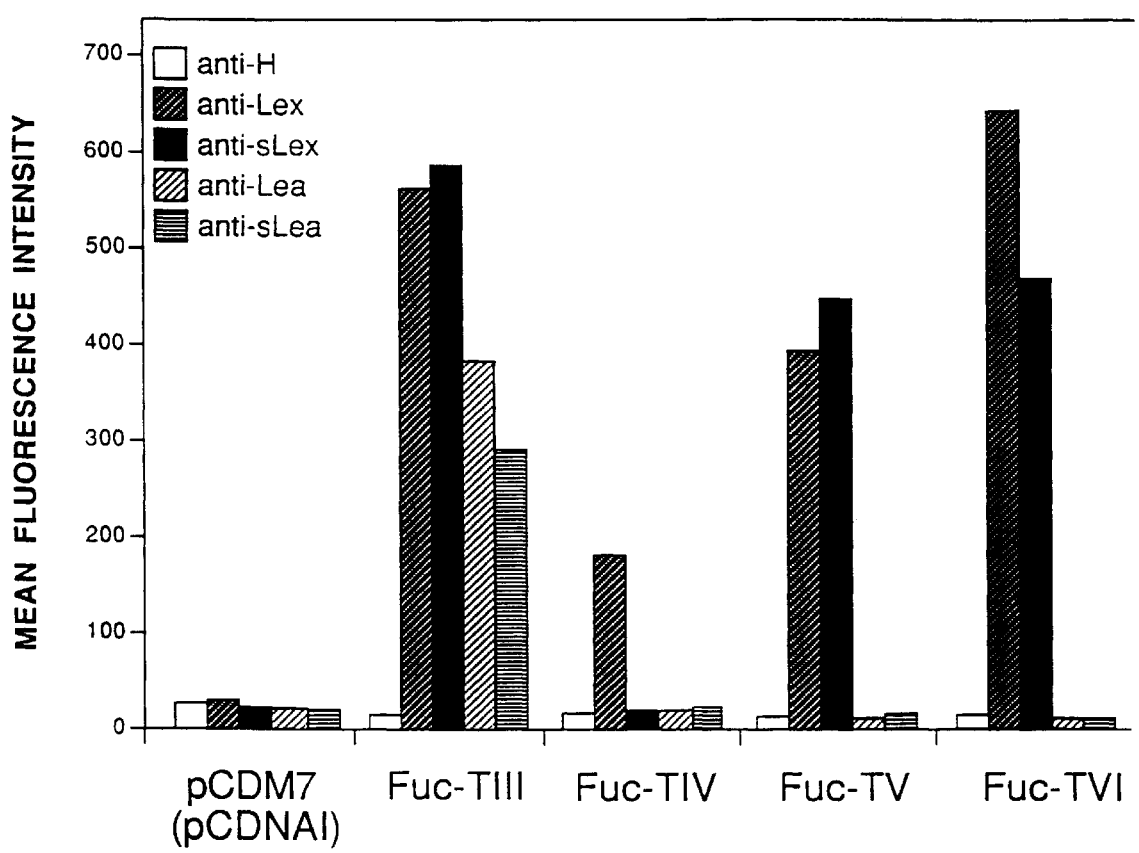
FIG. 8 presents flow cytometry profile histograms of COS-1 cells transfected with different α(1,3) fucosyltransferase gene expression vectors, or with control vectors, and subjected to analysis with monoclonal antibodies directed against cell surface oligosaccharide determinants. COS-1 cells were transfected either with plasmid pCDM7 (pCDM7), with plasmid pCDNAI(pCDNAI), with pCDM7 containing DNA sequences encoding the α(1,3/1, 4)fucosyltransferase depicted in FIG. 1 (the Lewis fucosyltransferase, also known as Fuc-TIII, SEQ ID NO:2), or with pCDNAI containing DNA sequences encoding the α(1,3)fucosyltransferase depicted in FIG. 4 (Fuc-TIV, SEQ ID NO:8), the α(1,3)fucosyltransferase depicted in FIG. 6 (Fuc-TV, SEQ ID NO: 11), or the α(1,3)fucosyltransferase depicted in FIG. 7 (Fuc-TV, SEQ ID NO:14). Three days after transfection, the cells were harvested, stained with monoclonal antibodies (shown at the top left within the figure) directed against the H (anti-H), Lewis x (anti-Lex), sialyl Lewis x (anti-sLex), Lewis a (anti-Lea), or sialyl Lewis a (sLea) oligosaccharide determinants, and then stained with a fluorescein-conjugated second antibody. The cells were then subjected to analysis by flow cytometry. The histograms represent the mean fluorescent intensities of the antigen-positive cells in each transfectant population (approximately 25% to 30% of the cells are transfected and express the positive cell surface markers). Methods for these analyses have been described in detail in Lowe et al, *J. Biol. Chem.*, (1991), 266:17467–17477, Weston et al, *J. Biol. Chem.*, (1992), 267:4152–4160, Lowe et al, *Cell*, (1990), 63:475–484, and Ernst et al, *J. Biol. Chem.*, (1989), 264:3436–3447.

Generally, the present invention provides a method for isolating a gene and/or a cDNA from a cell, by using a post-translational characteristic of the cell. The cell from which this gene and/or cDNA may be isolated may be either a cell from a unicellular or a multicellular organism.

In the context of the present invention, a post-translational characteristic of a certain cell is defined by the ability of that cell to modify a protein or a lipid by an enzymatic process that covalently attaches to this protein or lipid one or more monosaccharides, or an enzymatic process that specifically removes such substituents from a protein or lipid molecule.

In one embodiment, the method comprises the following four basic steps:

(i) identifying for use as a genetic donor, a eukaryotic (e.g. mammalian) cell possessing a post-translational characteristic of interest i.e. a particular membrane-bound oligosaccharide or polysaccharide (i.e. a glycoprotein or glycolipid), soluble oligosaccharide or polysaccharide, or a particular enzymatic activity (vide infra);

(ii) creating a genetic library of either cDNA or genomic DNA from the genetic material of the donor eukaryotic (e.g. mammalian) cell;

(iii) identifying a specific eukaryotic host suitable as a recipient for gene transfer, and transforming this eukaryotic, (e.g. mammalian), host cells with this genetic library; and (iv) screening the transformed host cells for host cells possessing the post-translational characteristic of interest.

The host cell which now possesses this post-translational characteristic contains genetic information related to the post-translational characteristic of interest. Using the techniques set forth below this genetic information (gene) can then be retrieved from the transformed host cell and used by standard approaches i.e., Axel et al (U.S. Pat. No. 4,634,665) or Gilbert et al (U.S. Pat. No. 4,411,994) to produce large quantities of the gene product, i.e., the glycosyltransferase, responsible for the post-translational characteristic.

In step (i) above the donor eukaryotic (e.g. mammalian) cell is chosen on the basis of detecting a specific enzymatic activity in an extract of the cell or detecting a membrane-bound or soluble oligosaccharide or polysaccharide of the cell.

Thus in one embodiment the enzymatic activity which is detected in the cell extract can be enzymatic activity attributable to an animal enzyme which post-translationally modifies proteins, lipids, or oligosaccharides by glycosylation or glycosyl modification. This enzymatic activity may be detected by using a substrate specific for one of these enzymes. Such substrates are known.

In another embodiment, in step (i) above a cell is chosen on the basis of detection of a specific cellular membrane-bound oligosaccharide and/or polysaccharide.

In another embodiment, the cell in step (i) is chosen on the basis of detecting the presence of a soluble oligosacharride or polysaccharide in an extract of the cell, or released by the cell in soluble form.

The present invention provides a novel gene transfer approach designated to isolate genes from an organism without requiring that amino acid sequence information be obtained about the gene product or that an antibody specific to the gene product be available. For example, if a gene encoding a particular enzyme is sought, a series of cultured cell lines or tissues are screened by known and standard methods to identify one or more cell lines or tissues containing an expressible gene of interest by detecting in an extract of the cell or tissue specific enzymatic activity (corresponding to the enzyme of interest and thus the cell contains and/or expresses a gene for the enzyme sought). If an oligosaccharide or polysaccharide membrane component of the cell is of interest, a cell line or tissue possessing such a membrane characteristic is isolated. If a soluble oligosaccharide or polysaccharide is of interest, a cell line or tissue possessing a soluble oligosaccharide or polysaccharide detectable in an extract thereof is isolated.

Once such a cell line or tissue has been identified, a genetic library based on this isolated cell is created. This genetic library may be either cDNA or genomic DNA. In a preferred embodiment, if the isolated cell is known to be susceptible to enhancement of its post-translational characteristic of interest by being contacted with a particular reagent, this reagent is used to obtain an enhancement of the mRNA signal in this cell, and/or the gene itself, which consequently produces amplified in mRNA copies and thus ultimately cDNA copies, corresponding to that particular gene, or amplified gene segments. Both the cDNA and the genomic DNA genetic libraries may otherwise be obtained using known techniques. Once the genetic library is obtained, it is used to transform host cells using known techniques (e.g., by calcium phosphate precipitation, liposomal transfection, DEAE dextran transfection, microinjection, etc.).

Host cells useful in the present invention are preferably susceptible to lectin or antibody detection of the desired post-translational characteristic; that is, susceptible to lectin or antibody detection of membrane-bound oligosaccharide, polysaccharide, or of glycoprotein or glycolipid produced in the transformed host cell. However, screening of host cells not susceptible to such lectin or antibody detection may be achieved through screening for enzyme activity in accordance with the invention.

(A) Host (e.g. mammalian) cells should be eukaryotic cells to allow and preserve the catalytic function of the enzyme (the glycosyltransferase). (B) The host cell should not express significant levels of glycosyltransferase activity analogous to the desired one, or the cognate product. With glycosyltransferase-related genes, successful transformation of a host cell can be determined by detecting corresponding enzymatic activity in an extract of the cell. (C) In another characteristic, the host cell should be capable of synthesizing the appropriate sugar nucleotide substrate and transport it into Golgi (where glycosyltransferase catalytic domains exist and function). Virtually all wild type animal cells possess this function. (D) The host cell should possess the ability to synthesize the appropriate acceptor substrate (oligosaccharide, lipid, or protein) that the desired glycosyltransferase requires, and the cell must display the structure on the cell surface or release it into the cellular environment/media. (E) The host cell should allow or provide for expression of transfected sequences that encode or otherwise determine expression of the desired glycosyltransferase. This is inherent in eukaryotic (e.g. mammal) to eukaryotic (e.g. mammal) genomic DNA transfer, or in vector systems chosen for cDNA expression system, using known technology. (F) The host cell should allow for rescue of the transfected sequences that encode or otherwise determine expression of the relevant glycosyltransferase.

Wild-type eukaryotic (e.g. mammalian) cells possess these characteristics generally. Any particular wild-type cell of interest which does not possess criteria (B) or (D) set forth above, may be mutated, using standard techniques, to obtain a mutant cell possessing either of these criteria. If an enzyme assay-based selection method is used, then the criteria (C) and (D) set forth above are not necessary.

Once the host cells have been transformed, the population is screened for host cells containing the genetic material of interest. This is achieved by determining whether the host cell possesses the post-translational characteristic of interest, i.e., by detecting enzymatic activity in an extract of the transformed host cell, detecting membrane-bound oligosaccharide or polysaccharide on the cell, or detecting soluble oligosaccharide or polysaccharide in an extract of or secreted by the cell. The host cells which test positive are isolated, and the gene of interest can be retrieved from these transformed cells.

If the host cells are transformed by genomic DNA transfection, the gene rescue may be carried out as follows:
(a) molecular cloning by hybridization, via tagging of transfected genomic sequences by species-specific repetitive sequences; or
(b) tagging of transfected genomic sequences by in vitro or in vivo ligation to marker sequences.

If cDNA is used to transform the host cells, the gene/cDNA rescue may be carried out as follows:
(a) episomal rescue via Hirt procedure, or
(b) integrated copy rescue via plasmid tag.

Further detail with regard to gene rescue is provided in the accompanying examples.

Example of appropriate donor and host cells include the following:

(I) Human Blood Group H α(1,2)fucosyl-transferase—(Ernst et al, *J. Biol. Chem.* 264:3436–3447, 1989; Ralan et al, *J. Biol. Chem.* 264:11158–11167, 1989; Larsen et al, *Proc. Natl. Acad. Sci. USA*, 87:6674–6678, 1990).
  A.) L cell host-mouse species.
  B.) Does not express α(1,2)fucosyltransferase activity. Does not express Fucα(1,2)Gal structures on cell surface.
  C.) Does synthesize GDP-fucose, the sugar nucleotide substrate of α(1,2)fucosyltransferase.
  D.) Does synthesize Galβ(1,4)GlcNAc-R molecules that are acceptor substrates for the enzyme, and expresses them at cell surface.
  E.) Mouse cells are known to be able to express human genes.
  F.) Mouse cells do not contain DNA sequences similar to human Alu repetitive DNA sequences. These Alu sequences (species-specific repetitive sequences) were used to identify and ultimately rescue the human gene from the mouse transfectant cell line.

(II) Mouse α(1,3)galactosyltransferase—Larsen et al, *Proc. Natl. Acad. Sci. USA,* 86: 8227–8231, 1989.
  A.) Kidney cell line expressing SV40 virus large T antigen—COS-1 cell line, monkey species.
  B.) Does not express α(1,3)galactosyltransferase activity. Does not express Galα(1,3)Gal structures on cell surface.

C.) Does synthesize UDP-galactose, substrate of α(1, 3)galactosyltransferase.

D.) Does synthesize Galβ(1,4)GlcNAc-R molecules that are acceptor substrates for the enzyme, and expresses them at cell surface.

E.) cDNA/COS-1 cell expression system for cDNA libraries—standard technology.

F.) cDNA/COS-1 cell expression system for cDNA libraries—standard technology.

(III) Human Lewis Blood Group α(1,3/1,4)fucosyltransferase—J. F. Kukowska-Latallo et al, *Genes and Development,* vol. 4, (1990), pp. 1288–1303.

A.) Kidney cell line expressing SV40 large T antigen COS-1 cell line, monkey.

B.) Does not express significant levels of α(1,3) fucosyltransferase activity. Does not express cell surface Galβ(1,4)[Fucα(1,3)]GlcNAc-R structure.

C.) Does synthesize GDP-fucose, substrate of α(1,3) fucosyltransferase.

D.) Does synthesize Galβ(1,4)GlcNAc-R molecules that are acceptor substrates for the enzyme, and expresses them at cell surface.

E.) CDM 7/COS-1 cell expression system for cDNA libraries—standard technology.

F.) CDM 7/COS-1 cell expression system for cDNA libraries—standard technology.

In the latter stages of selection for this gene, criteria C and D were not necessary because pools of cDNA clones were screened by transfecting them into COS-1 cells, and then directly assaying extracts prepared from the transfected cells for α(1,3)fucosyltransferase activity.

In one of its embodiments, the present invention provides a method for isolating a gene encoding a glycosyltransferase, and the gene thus isolated. This glycosyltransferase may be a fucosyltransferase, a sialyltransferase, a N-acetylglucosaminyltransferase, a galactosyltransferase, a N-acetylgalactosaminyltransferase, a mannosyltransferase, a sulfotransferase, a glucosyltransferase, an acetylase, or another glycosyltransferase.

Individual glycosyltransferases are known to be particularly related to different types of sugars transferred by the enzyme (Beyer et al, "Glycosyltransferases and Their Use in Assessing Oligosaccharide Structure and Structure-Function Relationships" *Adv. Enzymology* (1982) 52: 23–175—hereby incorporated by reference). Thus a particular kind of sugar linkage found on an oligosaccharide, glycoprotein, or glycolipid in or on a cell is associated with a particular glycosyltransferase. Methods are known for identifying such linkages (see Beyer et al, supra), and can be used in accordance with the present invention to isolate the gene encoding the corresponding glycosyltransferase.

Sialyltransferases, one of the glycosyltransferase provided by the present invention, are associated with the following sialic acid linkages: (1) Siaα2→6Gal; (2) Siaα2→3Gal; (3) Siaα2→6GalNac; (4) Siaα2→6GlcNAc; (5) Siaα2→8Sia; (6) Siaα2→4Gal; and (7) Siaα2→4GlcNAc.

Fucosyltransferases, another type of glycosyltransferases provided by the present invention, are associated with the following linkages: (1) Fucα(1→2)Galβ-; (2) Galβ(1→3)[Fucα(1→4)]GlcNAcβ-; (3) Galβ(1→4)[Fucα(1→3)]GlcNAcβ-; (4) Galβ(1→4)(Fucα(1→3)]Glc; (5) -GlcNAcβ(1→4)[Fucα(1→6)]GlcNAcβ1→Asn; (6) -GlcNAcβ(1→4)[Fucα(1→3)GlcNAcβ1→Asn; (7) Fucα(1→6)Galβ-; (8) Fucα(1→3)Galβ-; (a) Glcβ1→3Fucα1→O-Thr and Fucα1→O-Thr/Ser; (10) Fucα1→Ceramide; and (11) Fucα1→3Fuc.

N-Acetylglucosaminyltransferases, also provided by the invention, are associated with the following linkages: (1) GlcNAcβ1→4GlcNAc; (2) GlcNAcβ1→Asn; (3) GlcNAcβ1→2Man; (4) GlcNAcβ1→4Man; (5) GlcNAcβ1→6Man; (6) GlcNAcβ1→3Man; (7) GlcNAcα1→3Man; (8) GlcNAcβ1→3Gal; (9) GlcNAcβ1→4Gal; (10) GlcNAcβ1→6Gal; (11) GlcNAcα1→4Gal; (12) GlcNAcα1→4GlcNAc; (13) GlcNAcβ1→6GalNAc; (14) GlcNAcβ1→3GalNAc; (15) GlcNAcβ1→4GlcUA; (16) GlcNAcα1→4GlcUA; (17) GlcNAcα1→4IdUA.

Galactosyltransferases, also provided by the invention, are associated with the following linkages: (1) Galβ1→4Glc; (2) Galβ1→4GlcNAc; (3) Galβ1→3GlcNAc; (4) Galβ1→6GlcNAc; (5) Galβ1→3GalNAc; (6) Galβ1→6GalNAc; (7) Galα1→3GalNAc; (8) Galα1→3Gal; (9) Galα1→4Gal; (10) Galβ1→3Gal; (11) Galβ1→4Gal; (12) Galβ1→6Gal; (13) Galβ1→4xylose; (14) Galβ1→1'-sphingosine; (15) Galβ1→1'-ceramide; (16) Galβ1→3 diglyceride; (17) Galβ1→-O-hydroxylysine; and (18) Gal-S-cysteine.

N-Acetylgalactosaminyltransferases also provided by the invention are associated with the following linkages: (1) (GalNAcα1→3)[(Fucα1→2)]Galβ-; (2) GalNAcα1→Ser/Thr; (3) GalNAcβ1→4Gal; (4) GalNAcβ1→3Gal; (5) GalNAcα1→3GalNAc; (6) (GalNAcβ1→4GlcUAβ1→3)$_n$; (7) (GalNAcβ1→4IdUAα1→3-)$_n$; (8) -Manβ→GalNAc→GlcNAc→Asn.

Other glycosyltransferases, also provided by the invention, are associated with the following linkages:

To GalNAc

Galβ1–3GalNAc

Galβ1–4GalNAc

Galα1–3GalNAc

GlcNAcβ1–3GalNAc

GlcNAcβ1–6GalNAc

GalNAcα1–3GalNAc

Siaα2–3GalNAc

Siaα2–6GalNAc

To Gal

Galβ1–3Gal

Galα1–3Gal

Fucα1–2Gal

GlcNAcβ1–3Gal

GlcNAcβ1–4Gal

GlcNAcβ1–6Gal

GlcNAcα1–4Gal

GalNAcα1–3Gal

GalNAcβ1–3Gal

GalNAcβ1–4Gal

Siaα2–3Gal

Siaα2–6Gal

To Glc

Manα1–6Glc

Manα1–4Glc

To GlcNAc
Galβ1–4GlcNAc
Galβ1–3GlcNAc
Fucα1–3GlcNAc
Fucα1–4GlcNAc
Glcα1–4GlcNAc
GlcNAcα1–4GlcNAc
Siaα2–4GlcNAc
To Sia
Siaα2–8Sia
To Protein
GalNAcα1-O-Ser/Thr Still other glycosyltransferases provided by the invention include: β1,3GlcNAc-β1,3glucuronyltransferase, glucuronic acid-β1,4-N-acetylglucosaminyltransferase, asparagine N-acetylglucasaminyltransferase, serine β-xylosyltransferase, xylose β1,4-galactosyltransferase, galactose β1,3-galactosyltransferase, galactose β1,3-glucuronyltransferase, glucuronic acid β1,4-N-acetylgalactosaminyltransferase, N-acetylgalactosamine β1,3-glucuronyltransferase, N-acetylgalactosamine-4-sulfotransferase, N-acetylgalactosamine-6-sulfotransferase, asparagine-βN-acetylglucosaminyltransferase, serine/threonine-αN-acetylgalactosaminyltransferase, N-acetylglucosamine-β1,4-galactosaminyltransferase, galactose-β1,3-N-acetylglucosaminyltransferase, N-acetylglucosamine-6-sulfotransferase, galactose-6-sulfotransferase, glucuronic acid-α1,4-N-acetylglucosaminyltransferase, N-acetylglucosamine β1,4-glucuronyltransferase, heparin-N-acetyl-glucosamine-N-acetyltransferase, galactose-1,6-N-acetylgalactosyltransferase, heparin-N-acetylglucosamine sulfotransferase, N-acetylglucosamine-α1,4-glucoronyl epimerase, N-acetylglucosamine-6-sulfotransferase, N-acetylglucosamine-N-sulfotransferase, glucuronyl-α1,4-N-acetylglucosaminyltransferase, Iduronyl-2-sulfotransferase, glucuronyl-β1,4-N-acetylgalactosaminyltransferase, and N-acetylgalactosamine-α1,3-glucuronyl epimerase.

These enzymes are associated with the following linkages and oligosaccharide structures in connective tissue polysaccharides (Roden, L. "Structure and Metabolism of Connective Tissue Proteoglycans," in The Biochemistry of Glyc2cograteoproteins and Proteoglycans, Wm. Lennarz, ed. pp. 267–371 Plenum Press, New York, incorporated herewith by reference, in particular the tables on pages 269, 270 and 271 thereof).

The above-noted glycosyltransferase genes and/or cDNAs are obtained as cloned molecules, or are transferred to host cell lines, in accordance with the invention by using the post-translational property manifest in the cognate and appropriate above-noted characteristic linkages, to isolate a cell from which the gene or cDNA library is then created, and from which the gene or cDNA encoding the glycosyltransferase is isolated.

Additional enzymes comprising members of the mannosyltransferase family include α(1,2) mannosyltransferases, α(1,3) mannosyltransferases, α(1,6) mannosyltransferases, and β(1,4) mannosyltransferases, associated with the construction of the linkages formed in asparagine-linked oligosaccharides, as exemplified below (and as reviewed in Kornfeld, F., and Kornfeld, S. (1985)) "Assembly of asparagine-linked oligosaccharides" *Annu. Rev. Biochem.* 54, pp. 631–664.)

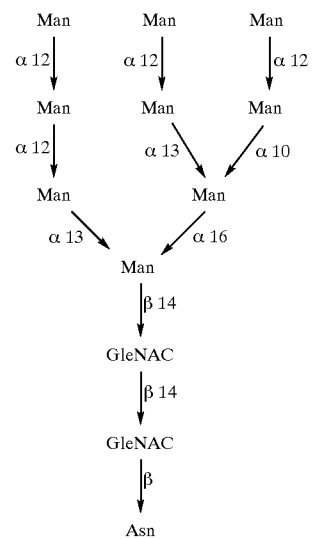

Others include ceramide glucosyltransferase and ceramide galactosyltransferase, oligosaccharyltransferase, and O-acetylases that O-acetylate N-acetylneuraminic acid (sialic acid).

| Abbreviations: | |
|---|---|
| Sia; sialic acid | IdUA: L-iduronic acid |
| Gal; D-galactose | GlcUA; D-glucuronic acid |
| GalNac; D-N-acetylgalactosamine | Xyl; D-xylose |
| Glc; D-glucose | Ser; serine |
| GlcNAc; D-N-acetylglucosamine | Thr; Threonine |
| Fuc; L-fucose | Asn; asparagine--. |
| Man; D-mannose | |

In another embodiment, the present invention provides a method for obtaining a soluble or a solid-phase oligosaccharide, polysaccharide, lipid, or protein. This method comprises contacting an oligosaccharide or polysaccharide precursor with a fused protein. The enzyme used, provided by the present invention, is either an unglycosylated glycosyl transferase or a fused protein which comprises two moieties: as the first moiety, at least the catalytically functional domain of a glycosyltransferase (vide infra); and, as a second moiety, either a proteinaceous spacer attached to the solid support or a proteinaceous component comprising an affinity ligand. The enzyme of the invention transforms the precursor into the desired oligosaccharide, polysaccharide, glycolipid, or glycoprotein which is thereby obtained.

A notable advantage of the invention is that it may provide, in one embodiment, non-glycosylated glycosyltransferases. It is thought to be generally true that many (if not all) naturally occurring glycosyltransferases are glycoproteins. When they are used to produce oligosaccharides or polysaccharides from oligosaccharide/polysaccharide precursors, the enzymes themselves may be susceptible to glycosylation. This (undesired) activity may consume starting material and may result in premature loss of enzyme activity. The non-glycosylated glycosyltransferases of the present invention do not suffer these salient disadvantages. They may be obtained as non-glycosylated enzyme either because they are obtained as a product produced in a microorganism deficient in the relevant glycosylation mechanism, or in an animal cell in which glycosylation of the glycosyltransferase has been suppressed. Suppression of the glycosylation of the glycosyltransferase in an animal cell is obtained by mutating the isolated glycosyltransferase gene using known techniques to eliminate the glycosyation sites on the glycosyltransferase.

The non-glycosylated glycosyltransferase of the present invention can be a non-glycosylated protein corresponding at least to the catalytically functional domain of the glycosyltransferase (vide infra) and up to a non-glycosylated protein corresponding to the whole gene encoding the glycosyltransferase.

In another embodiment, the present invention provides a fused protein comprising two moieties as set forth above: as a first moiety, at least the catalytically functional domain of a glycosyltransferase; and, as a second moiety, either a proteinaceous spacer capable of being attached to a solid support or a proteinaceous component comprising an affinity ligand.

Glycosyltransferases are known to possess three domains which correspond to three different areas of the gene encoding the enzyme. The area of the gene found at the 3'-end of the gene is known to encode the catalytically functional domain (Lowe, *Seminars in Cell Biology*, (1991) 2:289–307 hereby incorporated by reference). The fused protein of the present invention contains at least this catalytically functional domain, but it can contain up to the whole protein sequence. The protein is produced fused to the second moiety using known techniques.

The second moiety can be used either to anchor the catalytically functional domain onto a solid support, or permit its recovery by exploiting the presence of a specific affinity ligand on the second moiety. For the second moiety, the IgG binding domain of Staph. protein A can be used. Such a fusion protein can be bound to an IgG-containing solid phase matrix, such as IgG-Sepharose. A number of other alternative proteins can be fused to the catalytically active segments of the glycosyltransferase to effect binding to a solid matrix. Such proteins, and their respective matrix-associated receptors include streptavidin-biotin, IgG heavy chain-protein A, and virtually any other known protein or peptide segment for which an antibody exists or can be made.

In another embodiment, the present invention provides a method for producing a recombinant glycoprotein, glycolipid or free oligosaccharide using, e.g., either an enzyme obtained in accordance with the present invention or a recombinant organism obtained in accordance with the present invention. For example, specific post-translational glycosylation capability can be added to a host cell by the following steps: first the desired gene or cDNA which has been isolated is introduced into a cell by using standard transformation or transfection techniques in a manner to obtain an organism capable of expression of the transfected cloned gene product; the host cell acquires the post-translational capability determined by the transfected gene, where the cell did not express this capability prior to transfection. Alternatively, the approach set forth above is performed, but instead of using a single cloned gene that determines post-translational capabilities, use is made of uncloned gene segments (high molecular weight genomic DNA, for example) or a library of cloned genomic DNA fragments or cDNA molecules. Transfected cells generated in this manner are then subjected to selection methods based upon detection of a newly-acquired desired post-translational capability, to isolate clonal cell lines expressing this capability.

In another embodiment, enzymes obtained in accordance with the present invention can be used in an in vitro reaction to modify cell-surface oligosaccharide molecules. For example, the inventor has purified the blood group A UDP-GalNAc transferase and its substrate UDP-GalNAc to convert in vitro blood group H oligosaccharide determinants on mouse cells to blood group A determinants (Ernst et al, *J. Biol. Chem.* (1989) 264:3436–3447). An analogous scheme can be employed using enzymes obtained in accordance with the present invention, alone, or in conjunction with other available glycosyltransferases and glycohydrolases, to modify existing cell surface oligosaccharide molecules on dead or viable, functional eukaryotic or prokaryotic cells, in such a manner as to render their cell surface oligosaccharide structures relevant for a desired characteristic.

Such a host cell possessing added specific post-translational glycosylation capability is used in accordance with known recombinant technology to obtain a glycoprotein, glycolipid, or free oligosaccharide. This cell being characterized by possessing both the post-translational glycosylation capability as well as the capability of producing the recombinant glycoprotein, glycolipid, or free oligosaccharide.

These latter embodiments can be used, for example, to add novel oligosaccharide molecules to the surface of specific kinds of mammalian cells (cells with specific or general immune function, for example) for the purpose of targeting them to particular tissues or other locations in the body, for a therapeutic or diagnostic use. In particular, such modified cells could then be targeted to tissues expressing lectin-like cell adhesion molecules that specifically recognize particular oligosaccharide structures that have been added to the surface of the modified cells.

In another embodiment, the present invention provides a method for suppression of glycosylation activity in a cell. In this embodiment, specific post-translational glycosylation capability is deleted from a host cell. This result can be achieved by introducing a specific cloned reagent into a cell by standard transformation or transfection techniques, after in vitro modifications that (i) inactivate the gene and (ii) insert with it or adjacent to it one or more genetically selectable markers. Introduction of this modified inactive gene effectively replaces the endogenous functional gene via homologous recombination, using standard techniques.

If necessary, two or more rounds of this process can be performed to inactivate both wild type genes in a diploid (or higher ploidy) organism. The end result is a cell line with (two) non-functional genes not now capable of determining the post-translational capability whose elimination was desired. Alternatively, the gene obtained in accordance with the present invention is introduced to a cell by transformation or transfection, in a state in which it is expressed in an anti-sense orientation, using standard techniques. This eliminates expression of its cognate wild type gene, via standard anti-sense expression methods. Treatment of the cell with anti-sense synthetic oligonucleotides, whose sequence(s) is (are) derived from the gene obtained in accordance with the present invention, can also be used to eliminate expression of the cognate wild type gene, again via standard methods.

Alternatively, the gene obtained in accordance with the present invention is introduced into a cell by transformation or transfection, such that the expression of a new post-translational modification prevents or eliminates expression of an undesired one. This approach turns on the observation that the actions of some glycosyltransferases on common acceptor substrates are mutually exclusive, i.e., α(1,2) fucosylation can prevent α(2,3)siaylation and vice versa, or α(1,3)galactosylation can prevent α(2,3)siaylation, and vice versa.

Addition or deletion of cellular post-translational capabilities (including glycosylation) allows, for example, the generation of host cell lines that can be used to produce lipids, proteins, or free oligosaccharides of diagnostic or therapeutic utility, whose specific post-translational modifications, including glycosylation, affect their function. For example, recombinant proteins such as tissue plasminogen activator or erythropoietin normally exists as glycoproteins. Should specific oligosaccharide structures on these glycoproteins be shown to have beneficial effects on their biosynthesis, serum half life, receptor interaction, or other function, the reagents and processes provided by the present invention can be used to construct hosts that yield recombinant proteins with the specific, and functionally optimal, oligosaccharide structures.

This embodiment can be used, for example, to delete specific oligosaccharide molecules from the surface of specific kinds of mammalian cells (cells with specific or general immune function, for example) for the purpose of preventing targeting to their normal, physiologic tissues or other locations in the body, and thus allow them to be targeted to other non-physiologic targets for therapeutic or diagnostic use. In particular, such modified cells can be shunted away from tissues where they normally act, to tissues expressing lectin-like cell adhesion molecules with specificities for other kinds of cells.

In another embodiment, the present invention provides gene products in heretofore unavailable amounts. These gene products, glycosyltransferase enzymes, can be used in enzymatic reactors to produce glycoproteins, glycolipids, oligosaccharides or polysaccharides of interest. In this embodiment, cloned glycosyltransferase gene segments can be used with standard recombinant protein expression systems to generate large amounts of the enzyme encoded by the gene. These enzymes can be used in bioreactors in in vitro, large scale, synthesis of oligosaccharides or glycolipids, or for glycosidic modification of proteins and glycoproteins.

Acceptor oligosaccharides in such a scheme can be derived from any of the following:

(a) commercially available mono-, di- or higher order saccharides prepared from natural sources, or by chemical synthesis;

(b) di- or higher order oligosaccharides produced in vitro by other recombinant enzymes generated by this process; or (c) di- or higher order oligosaccharides produced by or purified from cell lines whose post-translational capabilities have been engineered as described above.

In this embodiment, two in vitro bioreactor-type approaches can be used. In one embodiment, an oligosaccharide acceptor and nucleotide sugar substrate are introduced into the reactor containing a solid phase matrix to which is bound catalytically active glycosyltransferase. This matrix can be generated using the fusion protein noted above which comprises a catalytically active moiety, as a soluble segment of the glycosyltransferase, fused to a protein segment that can be used to bind the fusion protein to a solid phase matrix. A specific example of such a fusion protein is a catalytically active segment of the mouse α(1,3) galactosyltransferase, fused to a segment of the IgG binding domain of Staph. protein A (Larsen et al, *Proc. Natl. Acad. Sci. (USA)*, 86, 8227–8231, 1989).

Acceptor and nucleotide sugar substrates are incubated in such a reactor, at an appropriate temperature, pH, and other known conditions, for a length of time sufficient to yield a desired amount of oligosaccharide or polysaccharide product. The product is then harvested by using known techniques.

In the variation, the nucleotide sugar substrate and soluble glycosyltransferase catalytic domain-containing fusion protein is introduced into a reactor containing the oligosaccharide acceptor molecule covalently attached (i.e., immobilized) to a solid phase matrix. Attachment is carried out using known techniques in such a manner as to make available to the reaction medium the portion of the oligosaccharide acceptor molecule that will be enzymatically modified.

The present invention provides a method for generating animal cell lines with specific capabilities for post-translational modification of proteins produced by them, as well as a method to isolate cloned genes, cloned complementary cDNAs, and their mRNAs, that determine the expression or biosynthesis of the enzymes responsible for post-translational modification of eukaryotic (e.g. animal, such as mammalian) proteins, especially (but not limited to) those post-translational processes that construct eukaryotic (e.g. animal, such as mammalian) glycoconjugates, without the need to first isolate the protein products of these genes. This includes cloned genes, cloned complementary cDNAs, and their mRNAs, that encode eukaryotic (e.g. animal, such as mammalian) enzymes that post-translationally modify proteins by glycosylation and sulfation, as well as phosphorylation, methylation, fatty acylation, and removal of glycosyl modification (glycohydrolases).

The uses of the present invention thus include the following:

(i.) Construction of animal cell lines with specific post-translational capabilities (for the production of diagnostics and therapeutics).

This method can be used to construct animal cell lines that are suitable host cells for the production of diagnostic or therapeutic material whose usefulness or efficacy depends upon specific post-translational modifications. For example, the biological effectiveness of most therapeutic proteins or peptides, recombinant or otherwise, often depends critically upon the oligosaccharide structure(s) that are covalently attached to them. The structure of these oligosaccharides is primarily a function of the number and kind of glycosyltransferase enzymes that are found in the cell used to produce these therapeutic products.

Animal cells and yeasts are competent to perform these glycosylation reactions; however, not all glycosyltransferase enzymes are produced by every animal cell or yeast, and therefore, some oligosaccharide structures are not produced by them. The converse is also true, namely, that the producing cell may express some glycosyltransferases that create oligosaccharide structures which prevent effective bioactivity. The present invention provides for the creation or elimination of specific glycosyltransferases capabilities in producing cells, so that therapeutic effectiveness of products made by the cells may be optimized.

The old methods used for this process include an empirical approach to identify a cell line most appropriate for the production of the recombinant or natural product. This is generally not optimal since cell lines with suitable post-translation modification capabilities may not exist naturally, or may not be especially suited to high level production of an appropriately modified product. Alternatively, unwanted post-translational modifications present on a therapeutic material produced by an empirically identified animal cell line can be removed chemically or enzymatically, a process that may be costly or inefficient, or both.

The advantages of the present methods over the older methods include the ability to construct cell lines with specific post-translational modification capabilities; properly constructed, these cell lines eliminate any need for chemical or enzymatic treatment of a therapeutic or diagnostic material to remove unwanted post-translational modifications. Moreover, cell lines with inappropriate post-translational modification capabilities, but that are otherwise excellent cells for production, may be modified to achieve correct post-translational modification of the product.

This method allows the construction of animal cell lines with post-translational modification capabilities precisely tailored to the specific needs of a particular diagnostic or therapeutic product produced by animal cells.

(ii.) Isolation of reagents suitable for efficient enzymatic synthesis and production of oligosaccharides (in enzyme reactors, for example).

Oligosaccharides can have therapeutic utility as immunomodulatory reagents in the field of organ transplantation. In particular, soluble and solid-phase oligosaccharides may find use as therapeutic agents with which to block or ameliorate antibody-mediated organ transplant rejection in cases involving incompatibility due to differences in the major blood group antigen systems of the organ donor and the recipient. Similarly, soluble oligosaccharides can find use as therapeutic agents that function by blocking attachment of bacterial, viral, or parasitic pathogens to glycoconjugate receptors found on the surface of the animal tissues that these pathogens invade.

Moreover, glycoconjugates have been implicated in modulating adhesive events between cells and between cells and their environment during developmental and differentiation processes. These events included binding of spermatozoa to eggs, and the initial events that mediate attachment of fertilized ova to the uterine wall at the beginning of implantation. These observations show, for example, the possibility that contraceptive uses for (biologically "natural") oligosaccharide molecules exist.

Currently, oligosaccharides of defined structure are produced by chemical synthesis (a procedure that is inefficient and costly) or by isolation from natural sources (using costly and inefficient procedures that often require the processing of large quantities of animal or plant material, and the purification of the desired oligosaccharide from other contaminating oligosaccharides).

The present invention provides a mechanism for the isolation of cloned glycosyltransferase genetic sequences, which in turn can be used to economically synthesize abundant quantities of purified glycosyltransferase enzymes. These can be used to construct enzyme bioreactors (enzymes in solution or immobilized on a solid phase matrix) capable of enzymatic synthesis of these structures.

This is more efficient than approaches involving the chemical synthesis of oligosaccharides or their purification from natural sources, for a variety of reasons. One, the only chemicals necessary are the enzyme substrates; most of these are easily obtained or synthesized. Two, enzymatic synthesis produces only the desired product and the nucleotide monophosphate or nucleotide diphosphate product of substrate hydrolysis. These latter two chemicals are found as the natural by-products of these reactions in animal cells, are essentially non-toxic, and may be easily separated from the oligosaccharide synthetic product.

By contrast, chemical synthetic procedures typically generate numerous products of side reactions which must be removed, and which may be toxic as well. Similarly, purification of oligosaccharides from natural sources requires the removal of other contaminating oligosaccharides present in the natural material.

Three, enzymatic catalysis is extraordinarily efficient; virtually complete conversion of substrate to product can be achieved. By contrast, chemical synthesis of these structures is a multi-step process; yields at each step may be much much less than 100%, and the cumulative efficiency of current chemical synthesis procedures does not approach the efficiency possible with enzymatic synthesis. Similarly, purification of oligosaccharides from natural materials can entail significant losses inherent to the purification procedures required to separate the desired oligosaccharide from contaminating, irrelevant and/or undesirable oligosaccharides, with inefficient isolation of the desired oligosaccharide.

Although glycosyltransferases for synthetic use may be purified from animal tissues, these purifications are themselves inefficient, primarily because the enzymes are typically present in very low abundance. The present invention provides two mechanisms that provide for the abundant production of these enzymes.

First, this can be done through the construction and selection of animal cells that produce relatively large quantities of the enzymes. Alternatively, this invention provides a mechanism to isolate cloned cDNAs encoding these enzymes, or to construct synthetic genes that encode these enzymes via information derived from such cloned cDNAs or genes. These cloned nucleic acid sequences can then be used with standard recombinant DNA technologies to produce large quantities of glycosyltransferases.

(iii.) Isolation of reagents suitable for producing recombinant glycosyltransferases to be used directly as research reagents, or to be used to generate anti-glycosyltransferase antibodies for research applications.

The present invention provides two mechanisms for producing large quantities of these enzymes (see (ii.) above— i.e., specially constructed animal cells, or via natural or synthetic genes encoding these enzymes) which may be used as research tools with which to study the structures and functions of oligosaccharides and glycoproteins. Likewise, the enzymes produced by this method, or the nucleic acid sequence and derived protein sequence provided by this method, may be used to generate antibodies to these enzymes (via immunization with synthetic peptides whose sequences are derived from the cloned enzyme cDNAs or genes, or by direct immunization with the recombinant enzymes). These antibodies can also be used as research reagents to study the biosynthesis and processing of these enzymes, and can be used as an aid in their purification for all the uses described in this disclosure.

(iv.) Antibodies to glycosyltransferases as diagnostic reagents.

Some of these glycosyltransferases have been implicated as tumor markers in body fluids. The enzymes have typically been assayed in these fluids by activity assays, which may be subject to non-specificity due to competing glycosyltransferase activity. These assays may also be insensitive since it is possible that inactive enzymes might be useful as tumor markers but would not be detected by enzyme activity assays.

The present invention provides a mechanism for generating antibodies to these enzymes (monoclonal and polyclonal antibodies against synthetic peptides constructed from information derived from cloned glycosyltransferase cDNAs or genes, against enzymes produced by recombinant glycosyltransferases, or against enzymes produced by animal cells constructed by this method). Anti-glycosyltransferase antibodies specific for particular glycosyltransferases can be produced by this means, and can be used to detect and quantitate glycosyltransferases in body fluids with specificity and sensitivity exceeding enzyme activity assays.

(v.) Engineering of glycosyltransferase substrate specificity to generate novel glycoconjugate structures on secreted or cell-associated glycoconjugates.

The present invention provides reagents (cloned glycosyltransferase genes or cDNAs) and genetic selection methods that, when used with appropriate known mutagenesis schemes, allow the generation of mutant glycosyltransferases that generate glycosidic linkages different from that generated by the wild-type enzyme. These novel linkages may or may not be naturally occurring, and find utility as moieties that enhance bioactivity of the molecules to which they are attached. Alternatively, mutagenesis and selection approaches can be used to generate mutant enzymes that act in a dominant negative fashion. The dominant negative mutants so generated can be used to inactivate endogenous glycosyltransferase activities when the product(s) of such an enzyme are not desired.

This invention allows the isolation of glycosyltransferase genes (as well as genes that direct the synthesis of enzymes that perform the post-translational modifications) by methods designed to identify the surface-expressed product of the enzyme, and without the need to purify the enzyme as is required of standard molecular cloning procedures (i.e., without any information about the primary structure of the enzyme, and without antibodies directed against the enzyme).

A consequence of one implementation of this method is the generation of cells with specific capabilities for glycosylation. One version of the detailed implementation of this method is described in the following publications by the inventor, *J. Biol. Chem.* (1989) 264(6): 3436–3447 and *J. Biol. Chem.* (1989) 264(19): 11158–11167, both of which are herein incorporated by reference.

In outline, this version of the method entails the generation of cultured animal cell lines with specific abilities to construct desired glycoconjugate structures, by introducing exogenous genetic material into cells that do not express the desired glycosyltransferase or its product, using genetic material from cells that do express the desired enzyme. A positive selection procedure is then employed to identify transfected cells that express the enzyme product on the surface of the cell. The transfected genetic sequences responsible for this new phenotype are then isolated by standard procedures involving gene library construction and nucleic hybridization. This method allows the isolation of the genetic material determining expression of the glycosyltransferase without the need to purify the enzyme.

Although detection and isolation of these sequences by hybridization procedures involving a dispersed and repetitive human DNA sequence (Alu) is used to illustrate isolation of the gene, other methods may be used to "tag" transfected sequences, including but not limited to the ligation to the transfected DNA of DNA markers that allow identification and isolation of the desired genes by nucleic acid hybridization or genetic selection (supF or G418 resistance "Neo" sequences, for example) procedures. Three methods for the selection of transfected cells with the appropriate phenotype, flow cytometry, "resetting", and "panning", are described in Examples I, II, and III. Although an antibody specific for the enzyme product was used in the examples, other non-antibody reagents that specifically recognize surface expressed enzyme products may also be employed, including plant and animal lectins.

The enzymes provided by the present invention are imbued with certain unique characteristics, as compared to the corresponding native enzyme. Naturally-derived glycosyltransferases have been purified, with certain claims being made to the homogeneity of the product obtained. Nonetheless, such claims of homogeneity have been made based upon analyses of the preparations by SDS-polyacrylamide gel electrophoresis methods. In the older literature (i.e., pre-(1982) the homogeneous enzyme was identified in the gel by Coomassie blue staining, or other staining methods, that are notably less sensitive than contemporary silver staining approaches. It is thus almost certain that such preparations were less than homogeneous.

In more contemporary literature, three glycosyltransferases have been analyzed by silver staining methods (i.e., rat sialyl-T, GlcNAc-T-I and GlcNAc-T-II). These appear to be virtually free of contaminant proteins. Nonetheless the small amounts of final pure proteins obtained using these purification procedures were analyzed using the sensitive silver staining method, which is not sufficiently sensitive to detect levels of contaminants of roughly 5 to 10 wt. %, in the small amounts of pure protein available. Thus, prior to the present invention, glycosyltransferases having a level of purity of at least 95 wt. %, preferably at least 98 wt. % were not available. The present recombinant glycosyltransferases which are obtained using cloned glycosyltransferase DNA sequences, in large amounts, in soluble form, or fused to an affinity-purifiable protein segment, can be obtained in a truly, heretofore unavailable, homogeneous state.

The proteins provided by the present invention, as noted above, may also be distinguished from heretofore available proteins by the fact that they can be made in a non-glycosylated form. Many, if not all naturally-derived glycosyltransferases are glycoproteins, that is, they contain themselves one or more N-linked and/or O-linked oligosaccharide structures. These structures can themselves be glycosylated by the enzyme itself in an enzymatic reactor, for example, and this represents a competing acceptor substrate which could reduce the efficiency of the reaction and contribute to premature enzymatic activity loss. This "autoglycosylation" phenoma has the potential of either inactivating or reducing the catalytic efficiency of the enzyme and/or bioreactor.

Cloned glycosyltransferases provide a way to circumvent this problem. Firstly, expression of cloned glycosyltransferases in a bacteria host, such as *E. coli,* that is incapable of glycosylating these enzymes, will yield large amounts of non-glycosylated glycosyltransferases. These recombinant proteins can be used in a bioreactor, and since they are not themselves glycosylated, may be superior in performance to the naturally derived, glycosylated enzymes for the reasons noted above.

Alternatively, if it is necessary to express these enzymes in an eukaryotic cell host that is capable of glycosylating the recombinant enzyme, standard site-directed mutagenesis approaches can be used to eliminate from the recombinant protein the amino acid signals that allow animal cells to glycosylate the enzymes. These known signals include certain asparagine residues, falling within the N-X-T or N-X-S motif that allows asparagine-linked glycosylation, and also includes some serine and threonine residues that are substrates for O-linked glycosylation.

Standard mutagenesis methods can be used to alter the DNA sequence encoding the glycosyltransferase to either delete the codon that encodes these N, S or T residues, or change the respective codon to a codon that determines an amino acid with similar physical properties, but that is incapable of supporting N-linked or O-linked glycosylation.

The present invention also provides unique mutant recombinant glycosyltransferases. Isolation and expression of glycosyltransferase genes and cDNAs offers the opportunity to generate mutant glycosyltransferases with properties superior to the fixed properties inherent in the naturally occurring enzymes. Standard techniques based upon site-directed, or random mutagenesis, can be used to obtain mutant glycosyltransferases with some of the illustrative properties:

(1) Minimal catalytic domain: progressive deletion of amino acids from the glycosyltransferase protein can be achieved, and the resulting mutant glycosyltransferases can be tested for activity. Based upon known functions for different parts of these molecules, it can be predicted that a catalytically active mutant glycosyltransferase can be produced that is (a) soluble (lacks transmembrane segment on natural glycosyltransferases that render them insoluble and thus unsuitable for bioreactors), and (b) much smaller than the natural glycosyltransferase (which retains transmembrane segment and the "stem" region, neither of which are necessary for catalytic activity).

On a protein mass basis, small catalytically-active domains derived from mutated glycosyltransferase genes or cDNAs represent more catalytic activity than the larger, naturally occurring glycosyltransferases that carry along non-catalytically active transmembrane and/or stem region protein "baggage." Thus, the recombinant mutant-derived catalytic domain is much more efficient for use in vitro synthesis of oligosaccharides, and by a reactor for example. Approaches to amplification of mRNA for glycosyltransferases:

The cell line used as a source of genetic material (mRNA for cDNA library construction, or genomic DNA for genomic library construction or genomic DNA transfection) for gene transfer to isolate a glycosyltransferase gene can be manipulated to optimize this process. Selection can be applied to this cell line to enhance steady state levels of the glycosyltransferase mRNA, and/or amplify its respective gene so that multiple copies of it exist in this donor cell. This can be done by subjecting the cell line (either after or without chemical, radiation, or other mutagenesis method) to a selection procedure that selects a variant of the cell that expresses higher amounts of the glycosyltransferase oligosaccharide product, at the surface of the cell, for example. This type of approach is illustrated in Example II.

Increased numbers of the oligosaccharide product molecules correlate with increased numbers of the cognate glycosyltransferase(s) enzyme molecules within the cell, and with an increase in steady state levels of the glycosyltransferase mRNA. Higher levels of this glycosyltransferase mRNA means that more copies of the respective cDNA will be present in a cDNA library prepared from the high-expression variant cell line, and thus will increase the likelihood of rescuing these glycosyltransferase cDNAs from the library. In some cases, higher levels of the specific mRNA can be associated with an increase in the number of copies of the cognate glycosyltransferase gene. Since such an amplified glycosyltransferase gene is more abundant in the cell's genome than other irrelevant genes, and more abundant than in a parental, non-selected cell line, it is easier to isolate by genomic DNA library or genomic DNA transfection approaches.

It can be shown by transfection studies that expression of some oncogenes can increase expression of some glycosyltransferases. Thus a cell line can be modified by transfection with one or more oncogenes, using standard transfection methods, and readily available vectors containing oncogenes, and resultant transfected clones can be assayed for increased glycosyltransferase levels. Such clones can also be identified or selected for by FACS or lectin selection methods outlined in Examples I, II, and III below. These clones can then be used for cDNA library preparation as noted above.

A number of chemical reagents have been shown to induce expression of, or increase expression of, glycosyltransferases, in cell lines. This may be associated with in vitro differentiation of the cell line, and such agents include retinoic acid, as well as dimethylsulphoxide-induced differentiation of human and mouse hematopoietic precursors, with concomittant increases in the expression of some glycosyltransferases. This occurs because of an increase in the steady state level of mRNA for the glycosyltransferase in question, and can be used to enhance the ability to isolate a cognate cloned cDNA using the cDNA library-mediated transfection approach (as shown in Example II, below).

An alternative approach for the isolation of genes or cloned cDNAs that encode animal glycosyltransferases (or other post-translational modification enzymes), by detecting the enzyme product at the cell surface, and without the need to purify the enzyme, is as follows: cDNA libraries are constructed in a plasmid or phage vector that will express the cloned cDNAs in a mammalian or yeast host, using mRNA prepared from cells or tissue that expressed the desired enzyme. This cDNA library is then screened for the desired cDNA by introducing the library into a host cell line that does not express significant amounts of the enzyme, nor its surface-expressed product, but that does have the necessary enzyme substrate molecules, and which is capable of displaying the enzyme's oligosaccharide product on its surface. The host cells which have taken up the cDNA library are subjected to selection for cells that contain the desired cDNA and thus express the new corresponding oligosaccharide product, using flow cytometry, resetting, or panning, and a reagent specific for the enzyme's oligosaccharide product. Cloned cDNAs that direct the expression of the desired enzyme may then be isolated from the selected cells by standard methods.

This approach may be used with the following techniques:

1. Stable transfection into animal cells, selection, followed by rescue of the desired clone cDNA by nucleic acid hybridization procedures, or by the COS cell fusion technique, depending on the vector used.

2. Transient transfection into COS or WOP cells, selection, followed by rescue of the desired clone cDNAs, by the method of Seed, *Proc. Nat'l. Acad. Sci. (USA)* (1987) 84:3365–3369, or similar methods that make use of cDNA cloning vectors that replicate as episomes in mammalian cells (i.e. Margolskee et al, *Mol. Cell. Biol.,* (1988) 8:2837–2847.

3. Transformation of yeast cells, selection, followed by rescue of the desired cloned cDNA by nucleic acid hybridization procedures.

In addition, the mammalian cDNA expression libraries may also be screened by the sib selection method, using an enzyme assay to detect pools of cDNA molecules that contain cloned cDNAs encoding the relevant glycosyltransferase (or other enzyme involved in post-translational modification). Specifically, a cDNA library is constructed in a mammalian expression vector (plasmid or phage), using mRNA prepared from a cell that expresses the appropriate glycosyltransferase.

This library is then screened by first dividing it into pools of bacteria cells containing clones, each pool representing some fraction of the library, but the pools in aggregate representing the entire library. A portion of each pool is stored, and the remainder (containing sibs of the stored clones) is processed for cDNA-vector DNA molecules (i.e. plasmid or phage DNAs). The DNA prepared from each pool is separately introduced into one of the appropriate host cells described above (see 1, 2, and 3), and, after allowing for an appropriate expression time, extracts are prepared from the transfected or transformed host cells and these extracts are assayed for the appropriate glycosyltransferase activity.

The smallest pool that is thus found to contain plasmids directing the synthesis of the appropriate enzyme is retrieved from storage and subdivided. Again, a representative portion of these pools is stored, and the remainder (again containing sibs of the stored clones) of each is processed for plasmid DNA, transfection or transformation, expression, extract preparation, and enzyme assay. This process is repeated until single clones are isolated that direct expression of the relevant glycosyltransferase. Thus, this process does not rely upon surface expression of the enzyme product to isolate the appropriate cloned cDNA or gene. A version of this approach is presented in Example III.

The procedure used in the present invention need not be restricted by the genetic complement of the host; the gene transfer aspect of this invention allows expression of genes not normally expressed or even present in the recipient cell. Although the present text specifically illustrates application to glycosyltransferases, it may be applied to the enzymes and genes that control other forms of post-translational modification, including sulfation, phosphorylation, methylation, fatty acylation, and removal of glycosyl modification (glycohydrolases).

The method described to this point involves isolation of glycosyltransferase genes or cDNAs by selection for a dominant glycosylation trait. The transient expression system described for use in COS or WOP cells can also be used to identify and clone cDNAs homologous to glycosyltransferase transcripts already present in the COS or WOP host. Specifically, cloned cDNAs transcribed in the "antisense" orientation may eliminate expression of the cognate glycosyltransferase in the COS or WOP host, resulting in a recessive glycosylation trait. These DNA sequences can then be isolated by selection for surface expression of the oligosaccharide linkage recognized by the glycosyltransferase whose expression was eliminated, again by the procedures described below (flow cytometry, "resetting", and "panning"), as detailed in Examples I, II, and III. Alternatively, the sib selection approach might be used to identify cloned cDNA molecules that decrease or eliminate the expression of an endogenous glycosyltransferase, as determined by enzyme assays.

The DNA sequences and corresponding glycosyltransferases of the present invention are summarized in Table 1.

TABLE 1

A. Fuc-TIII (Lewis enzyme), SEQ ID NO: 1 (DNA) and SEQ ID NO: 2 (protein)
   DNA     at least nucleotide positions 199 through 1158 of SEQ ID NO: 1, and up to the whole of SEQ ID NO: 1
   Protein at least amino acid positions 43 to 361 of SEQ ID NO: 2, and up to the whole of SEQ ID NO: 2
B. Murine α(1,3)galactosyltransferase, SEQ ID NO: 3 (DNA) and SEQ ID NO: 4 (protein)
   DNA     at least nucleotide positions 463 through 1461 of SEQ ID NO: 3, and up to the whole of SEQ ID NO: 3
   Protein at least amino acid positions 63 to 394 of SEQ ID NO: 4, and up to the whole of SEQ ID NO: 4
C. Human H α(1,2)fucosyltransferase, SEQ ID NO: 5 (DNA) and SEQ ID NO: 6 (protein)
   DNA     at least nucleotide positions 4782 through 5783 of SEQ ID NO: 5, and up to the whole of SEQ ID NO: 5
   Protein at least amino acid positions 33 to 3365 of SEQ ID NO: 6, and up to the whole of SEQ ID NO: 6
D. Fuc-TIV, SEQ ID NO: 7 (DNA) and SEQ ID NO: 8 (protein)
   DNA     at least nucleotide positions 2089 through 3159 of SEQ ID NO: 7, and up to the whole of SEQ ID NO: 7
   Protein at least amino acid positions 50 to 405 of SEQ ID NO: 8, and up to the whole of SEQ ID NO: 8
E. Fuc-TV, SEQ ID NO: 10 (DNA) and SEQ ID NO: 11 (protein)
   DNA     at least nucleotide positions 247 through 1111 of SEQ ID NO: 10, and up to the whole of SEQ ID NO: 10
   Protein at least amino acid positions 43 to 374 of SEQ ID NO: 11, and up to the whole of SEQ ID NO: 11
F. Fuc-TVI, SEQ ID NO: 13 (DNA) and SEQ ID NO: 14 (protein)
   DNA     at least nucleotide positions 255 through 1208 of SEQ ID NO: 13, and up to the whole of SEQ ID NO: 13
   Protein at least amino acid positions 43 to 359 of SEQ ID NO: 14, and up to the whole of SEQ ID NO: 14

SEQ ID NO:1 encodes a protein sequence termed Fuc-TIII capable of functioning as a GDP-Fuc:[β-D-Gal(1,4/1,3)]-D-GlcNAc(/Glc) α(1,3/1,4)-fucosyltransferase. This protein is an enzyme that can be used to construct the oligosaccharide "ligand" for Endothelial Leukocyte Adhesion Molecule-1(ELAM-1) that is disclosed in Applicant's co-pending U.S. patent application Ser. No. 07/603,018, filed Oct. 25, 1990, which is hereby incorporated by reference. This ligand is the sialyl-Lewis x molecule. Also, this enzyme, when expressed by the cloned DNA sequence described here, functions within mammalian cells to generate de novo expression of specific cell surface glycoconjugate structures on those cells. These structures are recognized by antibodies against the following cell surface glycoconjugate structures (See FIG. 8 and Table 2).

TABLE 2

| | |
|---|---|
| SSEA-1 or Lewis x | Galβ(1,4)[Fucα(1,3)]GlcNAc |
| sialyl-Lewis x | NeuAcα(2,3)Galβ(1,4)[Fucα(1,3)]GlcNAc |
| Lewis a | Galβ(1,3)[Fucα(1,4)]GlcNAc |
| sialyl-Lewis a | NeuAcα(2,3)Galβ(1,3)[Fucα(1,4)]GlcNAc. |

In the above DNA sequence; (I), the sequence corresponding from amino acid position 43 to amino acid position 361 is functional, but a larger sequence of up to the whole sequence shown can be used.

This enzyme, when expressed by the cloned DNA sequence described here, functions in the enzymatic manner indicated in its name, when assayed in extracts prepared from cells that express the DNA sequence (See Table 4). The oligosaccharide product of this enzyme represents fucose linked in alpha 1,3 configuration to neutral or α(2,3) sialylated "type II" acceptors, or fucose linked in alpha 1,4 configuration to neutral or α(2,3) sialylated "type I" acceptors as shown below:

| | |
|---|---|
| SSEA-1 or Lewis x | Galβ(1,4)[Fucα(1,3)]GlcNAc |
| sialyl-Lewis x | NeuAcα(2,3)Galβ(1,4)[Fucα(1,3)]GlcNAc |
| Lewis y | Fucα(1,2)Galβ(1,4)[Fucα(1,3)]GlcNAc |
| Lewis a | Galβ(1,3)[Fucα(1,4)]GlcNAc |
| sialyl-Lewis a | NeuAcα(2,3)Galβ(1,3)[Fucα(1,4)GlcNAc |
| Lewis b | Fucα(1,2)Galβ(1,3)[Fucα(1,4)]GlcNAc. |

Throughout the remainder of this text, these products will be referred to as sub-terminal α(1,3) and α(1,4) fucose residues.

The catalytic domain of this enzyme has also been localized by expression studies. The enzymatic properties of the enzyme encoded by this cDNA, and chromosomal localization studies, indicate that this cDNA is the product of the human Lewis blood group locus.

This DNA sequence and the corresponding protein have the following uses:

(i.) Construction of animal cell lines with specific capabilities with respect to post-translational modification of the oligosaccharides on cell-surface, intracellular, or secreted proteins or lipids by sub-terminal α(1,3) and α(1,4) fucose residues that represent the products of this enzyme (for the production of diagnostics and therapeutics).

Specifically, the present cloned DNA sequence can be introduced by standard technologies into a mammalian cell line that does not normally express the cognate enzyme or its product (sub-terminal α(1,3) and α(1,4) fucose residues on oligosaccharides), and transcribed in that cell in the "sense" direction, to yield a cell line capable of expressing sub-terminal α(1,3) and α(1,4) fucose residues on oligosaccharides on cell-surface, intracellular, or secreted glycoproteins or lipids.

Alternatively, this cloned DNA sequence may be introduced by standard technologies into a mammalian cell line that does express the cognate enzyme and its product (sub-terminal α(1,3) and α(1,4) fucose residues), and transcribed in that cell in the "anti-sense" direction, to yield a cell line incapable of expressing sub-terminal α(1,3) and α(1,4) fucose residues on cell-surface, intracellular, or secreted glyco-proteins or lipids.

Alternatively, the endogenous GDP-Fuc: [β-D-Gal(1,4/1,3)]-D-GlcNAc(/Glc)α(1,3/1,4)-fucosyltransferase gene(s), in a mammalian cell expressing the cognate enzyme(s), can be inactivated with the DNA sequence described here by homologous recombination techniques, or by "anti-sense" gene expression or oligonucleotide approaches based upon the DNA sequence described herein, or by dominant negative mutant fucosyltransferase sequences that inactivate endogenous GDP-Fuc:[β-D-Gal(1,4/1,3)]-D-GlcNAc(/Glc) α(1,3/1,4)-fucosyltransferase(s) and that may be derived via mutagenesis and genetic selection schemes, in conjunction with the sequence information in this text.

This method can be used to construct animal cell lines that are suitable host cells for the production of diagnostic or therapeutic materials whose usefulness or efficacy depends upon the specific post-translational modification determined by this cloned DNA sequence and its cognate enzyme. For example, it is known that the biological effectiveness of many therapeutic proteins or peptides, recombinant or otherwise, may depend critically upon the oligosaccharide structure(s) that are covalently attached to them. The structure of these oligosaccharides is primarily a function of the number and kind of glycosyltransferase enzymes that are found in the cell used to produce these therapeutic products.

Animal cells and yeasts are competent to perform these glycosylation reactions; however, not all glycosyltransferase enzymes are produced by every animal cell or yeast, and therefore, some oligosaccharide structures (including subterminal α(1,3) and α(1,4) fucose residues generated by the enzyme encoded by the DNA sequence described here) are not produced by them.

The converse is also true, namely, that producing cells may express a glycosyltransferase analagous to, or identical to, the GDP-Fuc:[β-D-Gal(1,4/1,3)]-D-GlcNAc(/Glc)α(1,3/1,4)-Fucosyltransferase encoded by the DNA sequence described here. It is likely that sub-terminal α(1,3) and α(1,4) fucose residues alter the bioactivity (for better or for worse) of natural or recombinant therapeutic or diagnostic agents (glycoproteins or glycolipids) produced by mammalian or other eukaryotic hosts. Eukaryotic host cells that are used to produce these recombinant agents can be altered with the DNA sequence information and related information described in this invention, to add subterminal α(1,3) and α(1,4) fucose residues to the oligosaccharides on recombinant product by expressing all or part of the cloned sequences described here in the desired host. Alternatively, sub-terminal α(1,3) and α(1,4) fucose residues may be eliminated from the product produced in these host cells by the use of transfected "anti-sense" vector constructs, recombination-based gene inactivation, "anti-sense" oligonucleotide approaches, or dominant negative mutant fucosyltransferases, outlined above.

The old "methods" used for this process include an empirical approach to identify a cell line that does or does not express this particular enzyme or an enzyme that functions in a similar or identical manner, for the production of the appropriately modified recombinant or natural product. This is not always optimal since cell lines with this particular post-translation modification capabilities may not exist naturally, or may not be especially suited to high level production of an appropriately modified product. Alternatively, unwanted sub-terminal α(1,3) and α(1,4) fucose residues present on a therapeutic material produced by an empirically identified animal cell line must be removed chemically or enzymatically, a process that may be costly or inefficient.

The advantages of using the cloned, functional DNA sequence described here in conjunction with the technologies outlined above, relative to these older methods, include the ability to construct lines that specifically lack the capability to generate sub-terminal α(1,3) and α(1,4) fucose residues on the oligosaccharides of glycoproteins and glycolipids; properly constructed, these cell lines will eliminate any need for chemical or enzymatic treatment of a therapeutic or diagnostic material to remove unwanted sub-terminal α(1,3) and α(1,4) fucose residues. Moreover, in the event that sub-terminal α(1,3) and α(1,4) fucose residues are found to be desirable for a particular diagnostic or therapeutic product produced by animal cells, cell lines may be engineered with the cloned DNA sequence described here to generate these residues.

(ii.) Isolation of reagents suitable for efficient enzymatic synthesis and production of oligosaccharides (in enzyme reactors, for example).

Oligosaccharides have therapeutic utility as immunomodulatory reagents in the field of organ transplantation. In particular, soluble and solid-phase oligosaccarides find use as therapeutic agents with which to block or ameliorate antibody-mediated organ transplant rejection in cases involving incompatibility due to differences in the major blood group antigen systems of the organ donor and the recipient, including the Lewis blood group system. Likewise, soluble oligosaccharides may find use as therapeutic agents that function by blocking attachment of bacterial, viral, or parasitic pathogens to glycoconjugate "receptors" found on the surface of the animal tissues that these pathogens invade.

For example there is evidence that portions of the Lewis blood group oligosaccharide antigen (containing subterminal $\alpha(1,3)$ and $\alpha(1,4)$ fucose residues) serve as "receptors" for some forms of uropathogenic bacteria. Moreover, glycoconjugates, including subterminal $\alpha(1,3)$ and $\alpha(1,4)$ fucose residues, have been implicated in modulating adhesive events between cells, like leukocyte-ELAM-1 interactions, and between cells and their environment during developmental and differentiation processes. These events include binding of spermatozoa to eggs, and the initial events that mediate attachment of fertilized ova to the uterine wall at the beginning of implantation. These observations suggest, for example, the possibility that contraceptive uses for (biologically "natural") oligosaccharide molecules might exist. Oligosaccharide molecules constructed by this enzyme can disrupt leukocyte-ELAM interactions and thus function as anti-inflammatory agents.

Currently, oligosaccharides containing subterminal $\alpha(1,3)$ and $\alpha(1,4)$ fucose residues are produced by chemical synthesis (a procedure that is inefficient and costly or both) or by isolation from natural sources (using costly and inefficient procedures that often require the processing of large quantities of animal or plant material, and the purification of the desired oligosaccharide from other contaminating oligosaccharides).

The invention described here provides a mechanism to synthesize abundant quantities of purified GDP-Fuc:[β-D-Gal(1,4/1,3)3-D-GlcNAc(/Glc)$\alpha$(1,3/1,4)-Fucosyltransferase, Fuc-TIII. This can be used to construct an enzyme bioreactor (enzyme in solution or immobilized on a solid phase matrix, for example via the protein-A moiety fused to the catalytic domain of the enzyme (as described in Kukowska-Latallo et al, Genes Devel., (1990) 4:1288–1303) capable of enzymatic synthesis of structures containing sub-terminal $\alpha(1,3)$ and $\alpha(1,4)$ fucose residues.

This is more efficient than approaches involving chemical synthesis of structures containing sub-terminal $\alpha(1,3)$ and $\alpha(1,4)$ fucose residues or their purification from natural sources, for a variety of reasons. One, the only chemicals necessary are the enzyme substrates and co-factors; these are easily obtained or synthesized. Two, enzymatic synthesis of such structures will produce only the desired product and the nucleotide diphosphate product of substrate hydrolysis. This latter chemical is found as the natural by-product of these reactions in animal cells, is relatively non-toxic, and may be easily separated from the oligosaccharide synthetic product. By contrast, chemical synthetic procedures typically generate numerous products of side reactions which must be removed, and which may be toxic as well. Similarly, purification of oligosaccharides from natural sources requires the removal of other contaminating oligosaccharides present in the natural material.

Three, enzymatic catalysis is extraordinarily efficient; nearly or totally complete conversion of substrate to product might be achieved. By contrast, chemical synthesis of subterminal $\alpha(1,3)$ and $\alpha(1,4)$ fucose residues on oligosaccharides is a multi-step process; yields at each step may be much less than 100%, and the cumulative efficiency of current chemical synthesis procedures does not approach the efficiency possible with enzymatic synthesis. Similarly, purification of oligosaccharides with sub-terminal $\alpha(1,3)$ and $\alpha(1,4)$ fucose residues from natural materials can entail significant losses inherent to the purification procedures required to separate the desired oligosaccharide from contaminating, irrelevant oligosaccharides, with inefficient isolation of the desired oligosaccharide.

Although the GDP-Fuc: [β-D-Gal(1,4/1,3) ]-D-GlcNAC (/Glc) $\alpha$(1,3/1,4)-fucosyltransferase encoded by the DNA sequence described here may be isolated from animal tissues for synthetic use, these purifications are themselves inefficient, primarily because the enzyme is typically present in very low abundance.

This invention provides two mechanisms that provide for the abundant production of this enzyme. First, this may be done through the construction and selection of animal cells that produce relatively large quantities of the enzymes. Alternatively, this cloned nucleic acid sequence may be used with standard recombinant DNA technologies to produce large quantities of the fucosyltransferase in yeasts or in prokaryotic hosts. Furthermore, the sequence encoding this enzyme may be modified via standard molecular cloning schemes or mutagenesis to yield a recombinant fucosyltransferase with novel properties that make it more desirable than the wild-type enzyme.

For example, modifications can be made to the enzyme that make it more stable, or more suitable for immobilization in a bioreactor.

(iii.) Isolation of reagents suitable for producing recombinant GDP-Fuc:[β-D-Gal(1,4/1,3)]-D-GlcNac(/Glc) $\alpha$(1,3/1,4)-fucosyltransferase to be used directly as a research reagent, or to be used to generate antibodies against the GDP-Fuc:[β-D-Gal(1,4/1,3)]-D-GlcNAc(/Glc) $\alpha$(1,3/1,4)-fucosyltransferase, for research applications.

This invention provides two mechanisms for producing large quantities of this enzyme (see ii. above—i.e., specially constructed animal cells, or via natural or synthetic genes encoding these enzymes) which may be used as a research tool with which to study the structures and functions of oligosaccharides and glycoproteins. Likewise, the enzyme produced by this method, or the nucleic acid sequence and derived protein sequence provided by this method, may be used to generate antibodies to this enzyme (via immunization with synthetic peptides whose sequences are derived from the cloned gene(s) or cDNA(s), or by immunization with the recombinant enzyme itself). These antibodies might also be used as research reagents to study the biosynthesis and processing of these enzymes, and can be used as an aid in their purification for all the uses described in this text.

(iv.) Antibodies to glycosyltransferases as diagnostic reagents.

Aberrant expression of GDP-Fuc:(β-D-Gal(1,4/1,3)]-D-GlcNac(/Glc) $\alpha$(1,3/1,4)-fucosyltransferase has been associated with malignancy in humans, suggesting that this enzyme might serve as a tumor marker for early detection of malignancy involving a number of human tissues. Enzyme tumor markers have typically been assayed in body fluids by activity assays, which may be subject to non-specificity due to competing or similar glycosyltransferase activity. These assays may also be insensitive since it is possible that inactive enzymes might be useful as tumor markers but would not be detected by enzyme activity assays.

This invention provides a mechanism for generating antibodies to this enzyme (monoclonal and polyclonal antibodies against synthetic peptides constructed from information derived from cloned DNA sequence encoding GDP-Fuc:

[β-D-Gal(1,4/1,3)]-D-GlcNac(/Glc) α(1,3/1,4)-fucosyltransferase, or against the recombinant enzyme produced by eukaryotic or prokaryotic hosts). Antibodies specific for this GDP-Fuc:[β-D-Gal(1,4/1,3)]-D-GlcNac(/Glc) α(1,3/1,4)-fucosyltransferase produced could be used to detect and quantitate this glycosyltransferase in body fluids, with specificity and sensitivity exceeding enzyme activity assays, and with the possibility of serving as a tumor marker for early detection of malignancy.

(v.) Recombinant enzyme for use in screening natural and synthetic compounds for fucosyltransferase inhibitors or inactivators.

A number of studies have noted an association between increased numbers of cell surface sub-terminal α(1,3) and α(1,4) fucose residues on oligosaccharides of a cell and the ability of that cell to metastasize in a malignant fashion. If there is a causal relationship, then drugs that inhibit the enzyme encoded by the sequence in this text could be active as anti-tumor agents. Likewise, numerous recent studies have implicated sialylated and neutral oligosaccharides containing subterminal α(1,3) and α(1,4) fucose linkages in mediating adhesion of leukocytes to the selectin adhesion molecules (ELAM-1; GMP-140; Mel14/LAM-1) during inflammation. These studies suggest that molecules capable of preventing synthesis of α(1,3) and α(1,4) fucose linkages on leukocytes may thus function to diminish or even eliminate the ability of leukocytes to synthesize and display subterminal α(1,3) and α(1,4) fucose linkages, and would thus represent anti-inflammatory pharmaceutical agents. The reagents described in this text are useful for screening to isolate compounds or identify compounds that exhibit anti-fucosyltransferase activity, since the cloned sequence may be used with standard techniques to produce relatively large amounts of pure fucosyltransferase. This further aids in screening since the effects of potential inhibitors will be tested on a pure enzyme, without the confounding effects that may occur in whole cell extracts or with partially purified enzyme.

(vi.) Engineering of glycosyltransferase substrate specificity to generate novel glycoconjugate structures on secreted or cell-associated glycoconjugates.

This invention provides a reagent a) cloned GDP-Fuc:[β-D-Gal(1,4/1,3)]-D-GlcNac(/Glc) α(1,3/1,4)-Fucosyltransferase cDNA) and the genetic selection method used to isolate it, that, when used with appropriate mutagenesis schemes, may allow the generation of mutant GDP-Fuc:[β-D-Gal(1,4/1,3)]-D-GlcNac(/Glc) α(1,3/1,4)-Fucosyltransferases that generate glycosidic linkages different from that generated by the wild-type enzyme. These novel linkages may or may not be naturally occurring, and might find utility as moieties that enhance bioactivity of the molecules to which they are attached.

Alternatively, mutagenesis and selection approaches may be used to generate mutant GDP-Fuc:[β-D-Gal(1,4/1,3)]-D-GlcNac(/Glc) α(1,3/1,4)-Fucosyltransferases that act in a dominant negative fashion. The dominant negative mutants so generated can be used to inactivate endogenous glycosyltransferase activities when the product(s) of such an enzyme are not desired. Mutant GDP-Fuc:[β-D-Gal(1,4/1,3)]-D-GlcNac(/Glc) α(1,3/1,4)-Fucosyltransferases can also be generated, for example, that function as fucosidases that hydrolyze various sugar linkages (fucose, mannose, or others) from oligosaccharides in vitro and in vivo.

(vii.) Genotyping individuals for the Lewis locus.

DNA sequence polymorphisms within or linked to the gene corresponding to this cloned cDNA may be used to genotype individuals for the Lewis locus. This can find utility with respect to organ transplantation procedures, or as a measure of susceptibility to infections caused by pathogens that may use blood group structures as receptors for invasion (as in urinary tract infections, for example).

SEQ ID NO:3 encodes a mouse UDP-Gal:β-D-Gal(1,4)-D-GlcNAc α(1,3)-galactosyltransferase. SEQ ID NO:5 encodes a human GDP-Fuc:β-D-galactoside α(1,2)-fucosyltransferase. The uses for each of these proteins are generally the same as those discussed herein for the enzyme of SEQ ID NO:1.

Specific application of the enzyme encoded by SEQ ID NO:5 include enzymatic fucosylation of chain-terminating galactose residues on lactoseamine or neolacto type β-D-galactoside to α-2-L-fucose residues. Such modification can be performed in vitro using the purified α(1,2)FT, or its derivatives and its substrate GDP-fucose, using asialoglycans terminating with β-D-galactoside residues. Such asialoglycans exist naturally, and can also be constructed from glycans with terminal galactose moieties substituted with sialic acid by in vitro digestion with neuraminidase. Likewise, such fucosylation can be expected to occur when glycans are expressed in mammalian cells that have been transfected with the α(1,2)FT cDNA or gene segment. Such α(1,2) fucosylated glycans may have increased solubility properties, may have prolonged plasma half lifes (by virtue of the fact that the terminal galactose residues that normally mediate glycoprotein clearance by the asialoglycoprotein receptor of the liver are now covered up by fucose residues), differentiate from natural glycoforms, and may enhance bioactivity.

Molecular mechanisms used by cells to regulate the precise tissue-specific and developmental expression patterns of oligosaccharide structures are poorly understood. Such patterns however are probably determined largely by the coordinate regulation of expression of cognate glycosyltransferases. Since many of these enzymes recognize identical nucleotide sugar substrates or oligosaccharide acceptor substrates, it can be expected that they exhibit substantial primary protein and nucleic acid sequence similarities that would facilitate isolation of related glycosyltransferase genes by cross hybridization strategies.

Molecular cloning efforts by the inventor have allowed the isolation of several cloned glycosyltransferase cDNAs discussed above. Comparisons of the primary sequences of these enzymes reveals that they maintain virtually identical predicted structural topologies.

With the exception of one pair of distinct glycosyltransferases, however, there appear to be no substantial primary sequence similarities between these enzymes, even though many of them exhibit nucleotide sugar substrate or oligosaccharide acceptor substrate requirements that are virtually identical. The exceptional pair, a murine α1,3 galactosyltransferase sequence, or its human pseudogene homologue, and a human α1,3N-acetylgalactosaminide transferase share substantial primary protein and nucleic acid sequence similarity, even though these enzymes use different nucleotide sugar substrates and exhibit distinct oligosaccharide acceptor substrate requirements.

Taken together, these observations indicate that some glycosyltransferases may be structurally related, but such relationships cannot necessarily be predicted from knowledge of nucleotide sugar or oligosaccharide acceptor substrate requirements.

As noted above, the gene transfer procedure of the invention has been used by the inventor to isolate a cloned cDNA that encodes the human Lewis blood group fucosyltransferase. This enzyme is an exceptional glycosyltransferase in that it can catalyze two distinct transglycosylation reactions. Sequence comparisons of this enzyme with the blood group H α(1,2)fucosyltransferase indicates that these two fucosyltransferases maintain distinct primary sequences despite the fact that they use the identical nucleotide sugar substrate GDP-fucose, and can each utilize oligosaccharide acceptor molecules that terminate with unsubstituted type I or type II disaccharide moieties.

Biochemical and genetic data indicate that the human genome contains one or more structural genes that encode fucosyltransferases competent to construct surface localized SSEA-1 determinants. These enzymes are thought to be polypeptides distinct from the Lewis fucosyltransferase because they exhibit different acceptor substrate specificities and differential sensitivities to divalent cation and N-ethylmaleimide inactivation. Moreover, their expression is determined by loci distinct from the Lewis blood group fucosyltransferase locus, and they display tissue specific patterns that are distinct from the Lewis locus patterns.

Because these enzymes exhibit properties that are very similar to the Lewis blood group fucosyltransferase, the inventor recognized that it was possible that these enzymes and their corresponding genes might be sufficiently related at the primary sequence level to be able to isolate them by crosshybridization approaches. In another embodiment, the invention therefore provides a method for isolating a gene encoding a glycosyltransferase by cross-hybridization. The cross-hybridization techniques which can be used in accordance with the invention are generally known. See, e.g., Lauer et al. Cell (1980) 20:119–130, Fritsch et al, Cell (1980) 19:959–972, Haynes et al, J. Biol. Chem. (1980) 255:6355–6367, and Proudfoot et al, Proc. Nat. Acad. Sci. (USA) (1979) 76:5425–5439, all of which are hereby incorporated by reference.

As noted above, oligosaccharides constructed by animal cells are remarkable for their structural diversity. This diversity is not random but rather consists of specific sets of oligosaccharide structures that exhibit precise tissue-specific and developmental expression patterns. Molecular mechanisms used by cells to regulate these expression patterns are poorly understood. It can be expected, however, that such patterns are determined largely by the coordinate regulation of expression of the glycosyltransferases that determine these patterns. Recent molecular cloning efforts have allowed the isolation of several cloned glycosyltransferase cDNAs. Comparisons of the primary sequences of these enzymes have revealed that they maintain virtually identical predicted structural topologies. With the exception of one pair of distinct glycosyltransferases, however, there appear to be no substantial primary sequence similarities between these enzymes, even though many of them exhibit nucleotide sugar substrate or oligosaccharide acceptor substrate requirements that are virtually identical. The exceptional pair, a murine α1,3galactosyltransferase sequence, or its human pseudogene homologue, and a human α1,3N-acetylgalactosaminide transferase share substantial primary protein and nucleic acid sequence similarity, even though these enzymes use different nucleotide sugar substrates and exhibit distinct oligosaccharide acceptor substrate requirements. Taken together, these observations suggest that some glycosyltransferases may be structurally related, but such relationships cannot necessarily be predicted from knowledge of nucleotide sugar or oaigosaccharide acceptor substrate requirements. The inventor has recently used a mammalian gene transfer procedure to isolate a cloned cDNA that encodes the human Lewis blood group fucosyltransferase (Kukowska-Latallo et al, Genes Devel., 4:1288–1303, 1990). This enzyme is an exceptional glycosyltransferase in that it can catalyze two distinct transglycosylation reactions. Sequence comparisons of this enzyme with the blood group H α(1,2)fucosyltransferase (Larsen et al, Proc. Natl. Acad. Sci. USA, 87:6674–6678, 1990) indicates that these two fucosyltransferases maintain distinct primary sequences despite the fact that they use the identical nucleotide sugar substrate GDP-fucose, and can each utilize oiigosaccharide acceptor molecules that terminate with unsubstituted type I or type II disaccharide moieties (Kukowska-Latallo et al, Genes Devel., 4:1288–1303, 1990; Larsen et al, Proc. Natl. Acad. Sci. USA, 87:6674–6678, 1990). Biochemical and genetic data indicate that the human genome contains one or more structural genes that encode fucosyltransferases competent to construct surface localized SSEA-1 determinants (Kukowska-Latallo et al, Genes Devel., 4:1288–1303, 1990; Potvin et al, J. Biol. Chem., 265:1615–1622, 1990). These enzymes are thought to be polypeptides distinct from the Lewis fucosyltransferase because they exhibit different acceptor substrate specificities and differential sensitivities to divalent cation and N-ethylmaleimide inactivation (Potvin et al, J. Biol. Chem., 265:1615–1622, 1990). Moreover, their expression is determined by loci distinct from the Lewis blood group fucosyltransferase locus, and they display tissue specific patterns that are distinct from the Lewis locus patterns (Watkins, Adv. Hum. Genet., 10:1–116, 1980). Because these enzymes exhibit properties that are very similar to the Lewis blood group fucosyltransferase, the inventor considered it possible that enzymes and their corresponding genes might be sufficiently related at the primary sequence level to be able to isolate them by cross-hybridization approaches. The inventor has now achieved the isolation of several such cross-hybridizing human genes, an analysis of their structures, their expression in COS-1 cells after DEAE-dextran-mediated transfection, and analysis of their acceptor substrate properties.

Thus, in another embodiment, the invention provides DNA sequence SEQ ID NO:7 (set forth in FIG. 4) that encodes a protein sequence capable of functioning as a GDP-Fuc:[β-D-Gal(1,4)]-D-GlcNAc α(1,3)-Fucosyltransferase, Fuc-TIV. This enzyme, when expressed by the cloned DNA sequence SEQ ID NO:7 functions within mammalian cells to generate de novo expression of specific cell surface glycoconjugate structures of those cells.

Figure 5A:
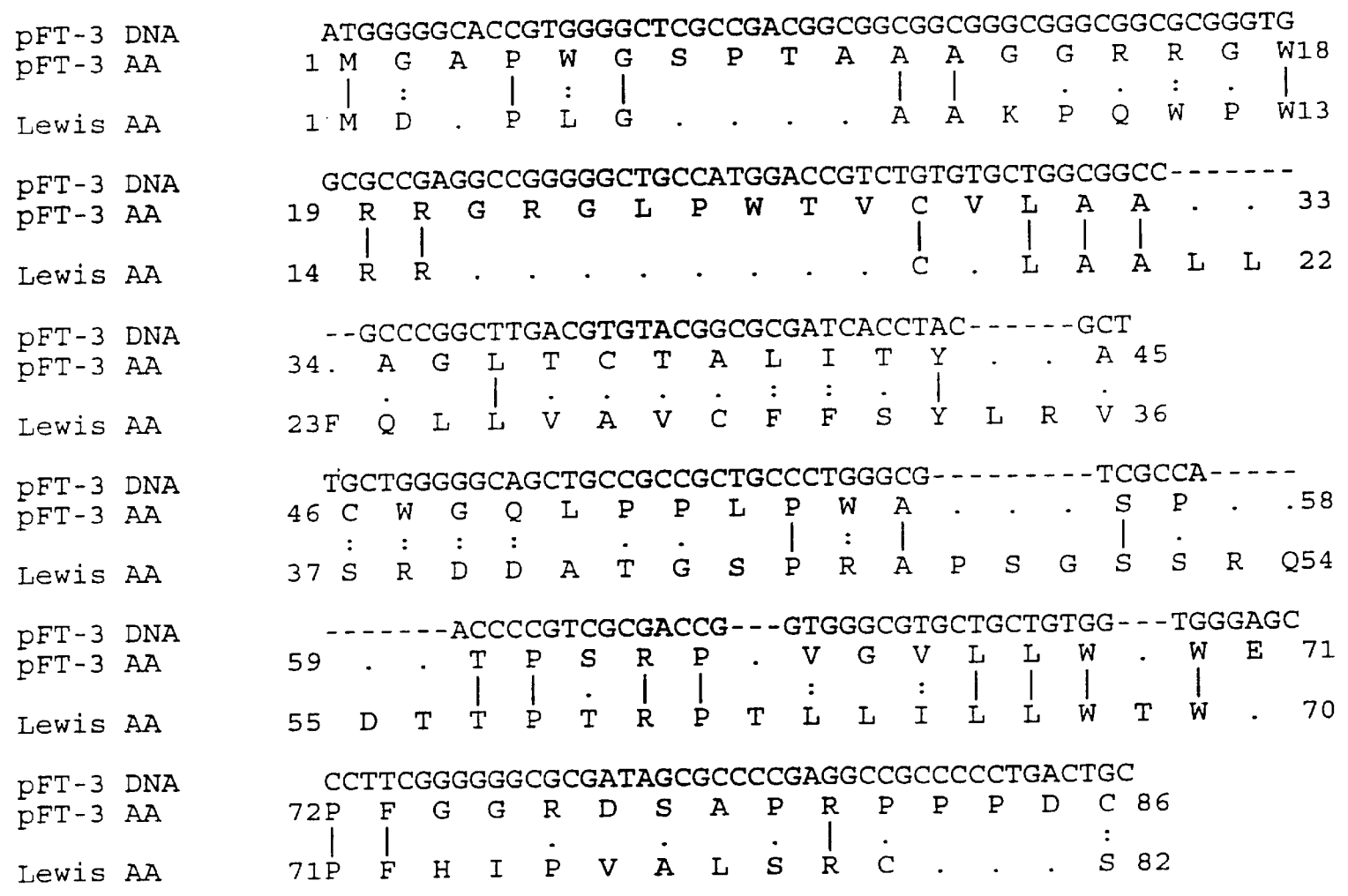

Present DNA sequence SEQ ID NO:9 (set forth in FIG. 5 wherein it is indentified as pFT-3 DNA) is comprised within DNA sequence SEQ ID NO:7. Namely, sequence SEQ ID NO:9 is found beginning at nucleotide position 1942 (the codon at nucleotide position 1942–1944) in sequence SEQ ID NO:7.

The DNA sequence and corresponding peptide provided in this embodiment of the invention must correspond at least to the segment from nucleotide position 2089 to 3159, preferably positions 1942 to 3156, of Sequence SEQ ID NO;7 set forth in FIG. 4. These DNA sequences, can have further DNA sequence attached optionally to each end. These pendent DNA sequences can be of any length and up to a length corresponding to that set forth in FIG. 4.

In a preferred embodiment, this embodiment of the invention provides DNA sequences, and their corresponding proteins, corresponding at least to the sequence between nucleotide positions 2089 to 3159, preferably positions 1942 to 3156, SEQ ID NO:7 and having attached to each end, optionally, further DNA sequences corresponding to those set forth in FIG. 4. In this case, the pendent DNA sequences and corresponding proteins, can be of any length and up to the length set forth in FIG. 4.

These glycoconjugate structures, constructed in part by this enzyme, are recognized by an antibody against the stage specific embryonic antigen I (SSEA-1 or Lewis x; structure Galβ(1,4)[Fuc α(1,3)]GlcNAc), and by an antibody against the VIM-2 determinant NeuAcα(2,3)Galβ(1,4)GlcNAcβ-(1,3)Galβ(1,4)[Fucα(1,3)]GlcNAc. This enzyme when expressed by DNA SEQ ID NO:7 functions in the enzymatic manner implied in its name, when assayed in extracts prepared from cells that express the DNA sequence, as illustrated in FIG. 8 and Table 2.

The oligosaccharide products of this enzyme represents fucose linked in alpha 1,3 configuration to the GlcNac residue of a "type II", lactos[amine] acceptor. Throughout the remainder of this disclosure, these products will be referred to as subterminal α(1,3) fucose residues.

The isolation of three specific such cross-hybridizing human genes (SEQ ID NO:7, SEQ ID NO:10, SEQ ID NO:13), an analysis of their structure, their expression in COS-1 cells after DEAE-dextran-mediated transfection, and analysis of their acceptor substrate properties is described in the examples below, (Examples IV, V, and VI), and summarized in FIGS. 8 and Table 2. SEQ ID NO:10 (Fuc-TV) encodes a specific protein sequence capable of functioning as a GDP-Fuc:[β-D-Gal(1,4)]-D-GlcNAc α(1,3) fucosyltransferase. This enzyme, when expressed by the cloned DNA sequence described, functions within mammalian cells to generate de novo expression of specific cell surface glycoconjugate structures on those cells. These structures are recognized by an antibody against the stage specific embryonic antigen I (SSEA-1 or Lewis x; structure Galβ(1,4)(Fucα(1,3))GlcNAc), and by an antibody against the sialyl-Lewis x determinant NeuAcα(2,3)Galβ(1,4)[Fucα(1,3)]GlcNAc. This enzyme, when expressed by the cloned DNA sequence described, also functions in the enzymatic manner implied in its name, when assayed in extracts prepared from cells that express the DNA sequence. The oligosaccharide products of this enzyme represent fucose linked in alpha 1,3 configuration to the GlcNac residue of a "type II" lactos[amine] acceptor. Throughout the remainder of this disclosure, these products will be referred to as subterminal α(1,3) fucose residues. The location of the catalytic domain of this enzyme has been shown experimentally to encompass amino acids 43 to 374 of SEQ: ID NO:11.

The DNA and encoded protein of SEQ ID NO:13 and SEQ ID NO:14 (Fuc-TVI) may be used as follows:

i. Construction of animal cell lines with specific capabilities with respect to post-translational modification of the oligosaccharides on cell-surface, intracellular, or secreted proteins or lipids by sub-terminal α-(1,3) fucose residues that represent the products of this enzyme (for the production of diagnostics and therapeutics by the biotechnology industry).

Specifically, the cloned DNA sequence described here may be introduced by standard technologies into a mammalian cell line that does not normally express the cognate enzyme or its product (sub-terminal α(1,3)fucose residues on oligosaccharides), and transcribed in that cell in the "sense" direction, to yield a cell line capable of expressing sub-terminal α(1,3) fucose residues residues on oligosaccharides on cell-surface, intracellular, or secreted proteins or lipids. Alternatively, this cloned DNA sequence may be introduced by standard technologies into a mammalian cell line that does express the cognate enzyme and its product (subterminal α(1,3) fucose residues), and transcribed in that cell in the "antisense" direction, to yield a cell line incapable of expressing sub-terminal α(1,3) and fucose residues on cell-surface, intracellular, or secreted proteins or lipids.

Alternatively, the endogenous GDP-Fuc: [β-D-Gal(1,4)]-D-GlcNAc α(1,3)-Fucosyltransferase gene(s), in a mammalian cell expressing the cognate enzyme(s), might be inactivated with the DNA sequence described here by homologous recombination techniques, or by "antisense" oligonucleotide approaches based upon the DNA sequence described herein, or by dominant negative mutant fucosyltransferase sequences that inactivate endogenous GDP-Fuc:[β-D-Gal(1,4)]-D-GlcNAc α(1,3)-Fucosyltransferase(s) and that may be derived via mutagenesis and genetic selection schemes, in conjunction with the sequence information in this Disclosure.

This method could be used to construct animal cell lines that will be suitable host cells for the production of diagnostic or therapeutic materials whose usefulness or efficacy depends upon the specific post-translational modification determined by this cloned DNA sequence and its cognate enzyme. For example, it is known that that the biological effectiveness of many therapeutic proteins or peptides, recombinant or otherwise, may depend critically upon the oligosaccharide structure(s) that are covalently attached to them. The structure of these oligosaccharides is primarily a function of the number and kind of glycosyltransferase enzymes that are found in the cell used to produce these therapeutic products. Animal cells and yeasts are competent to perform these glycosylation reactions; however, not all glycosyltransferase enzymes are produced by every animal cell or yeast, and therefore, some oligosaccharide structures (including sub-terminal α(1,3) fucose residues generated by the enzyme encoded by the DNA sequence described here) are not produced by them. The converse is also true, namely, that producing cells may express a glycosyltransferase analogous to, or identical to, the GDP-Fuc:[β-D-Gal(1,4)]-D-GlcNAc α(1,3)-Fucosyltransferase encoded by the DNA sequence described here. It is likely that sub-terminal α(1,3) fucose residues may alter the bioactivity (for better or for worse) of natural or recombinant therapeutic or diagnostic agents (glycoproteins or glycolipids) produced by mammalian or other eukaryotic hosts. Eukaryotic host cells that the biotechnology industry uses to produce tthese recombinant agents may be altered with the DNA sequence information and related information described in this invention, to add sub-terminal α(1,3) fucose residues to the oligosaccharides on recombinant product by expressing all or part of the cloned sequences described here in the desired host. Alternatively, sub-terminal α(1,3) fucose residues may be eliminated from the product produced in these host cells by the use of transfected "anti-sense" vector constructs, recombination-based gene inactivation, 'anti-sense' oligonucleotide approaches, or dominant negative mutant fucosyltransferases, outlined above.

The old 'methods' used for this process include an empirical approach to identify a cell line that does or does not express this particular enzyme or an enzyme that functions in a similar or identical manner, for the production of the appropriately modified recombinant or natural product. This is not always optimal since cell lines with this particular post-translation modification capabilities may not exist naturally, or may not be especially suited to high level production of an appropriately modified product. Alternatively, unwanted sub-terminal α(1,3)fucose residues present on a therapeutic material produced by an empirically identified animal cell line must be removed chemically or enzymatically, a process that may be costly or inefficient. The advantages of using the cloned, functional DNA sequence described here in conjunction with the technologies outlined above, relative to these older methods, include the ability to construct lines that specifically lack the capability to generate sub-terminal α(1,3)fucose residues on the oligosaccharides of glycoproteins and glycolipids; properly constructed, these cell lines will eliminate any need for chemical or enzymatic treatment of a therapeutic or diagnostic material to remove unwanted sub-terminal α(1,3) fucose residues. Moreover, in the event that sub-terminal α(1,3)fucose residues residues are found to be desirable for a particular diagnostic or therapeutic product produced by animal cells, cell lines may be engineered with the cloned DNA sequence described here to generate these residues.

ii. Isolation of reagents suitable for efficient enzymatic synthesis and production of oligosaccharides (in enzyme reactors, for example).

Oligosaccharides may have therapeutic utility as immunomodulatory reagents in the field of organ transplantation. In particular, soluble and solid-phase oligosaccharides may find use as therapeutic agents with which to block or ameliorate antibody-mediated organ transplant rejection in cases involving incompatibility due to differences in the major blood group antigen systems of the organ donor and the recipient, including the Lews blood group system. Likewise, soluble oligosaccharides may find use as therapeutic agents that function by blocking attachment of bacterial, viral, or parasitic pathogens to glycoconjugate "receptors" found on the surface of the animal tissues that these pathogens invade. For example there is evidence that portions of the Lewis blood group oligosaccharide antigen (containing sub-terminal α(1,3)fucose residues) serve as "receptors" for some forms of uropathogenic bacteria. Moreover, glycoconjugates, including sub-terminal α(1,3) fucose residues, have been implicated in modulating adhesive events between cells, and between cells and their environment during developmental and differentiation processes. These events included binding of spermatozoa to eggs, and the initial events that mediate attachment of fertilized ova to the uterine wall at the beginning of implanatation. These observations suggest, for example, the possibility that contraceptive uses for (biologically "natural") oligosaccharide molecules might exist. In addition, specific glycoconjugates containing sub-terminal α(1,3)fucose residues have been implicated as ligands for the LECCAM/Selectin family of adhesion molecules, that play important roles in mediating adhesion between cells of the immune system, and some tumor cells, and the surfaces of the endothelial cells that line the vascular tree. Thus, the cloned fucosyltransferase sequence described here may be used to construct oligosaccharide-type molecules, with pharmaceutical properties possessing anti-inflammatory and anti-tumor metastatic functions.

Currently, oligosaccharides containing sub-terminal α(1, 3) fucose residues are produced by chemical synthesis (a procedure that is inefficient and costly) or by isolation from natural sources (using costly and inefficient procedures that often require the processing of large quantities of animal or plant material, and the purification of the desired oligosaccharide from other contaminating oligosaccharides). The invention described here provides a mechanism to synthesize abundant quantities of purified GDP-Fuc:[β-D-Gal(1, 4)]-D-GlcNAc α(1,3)-Fucosyltransferase. This could be used to construct an enzyme bioreactor (enzyme in solution or immobilized on a solid phase matrix, for example via the protein-A moiety fused to the catalytic domain of the enzyme, as described in previous manuscripts published by the Inventor John Lowe) capable of enzymatic synthesis of structures containing sub-terminal α(1,3) fucose residues. This may be more efficient than approaches involving chemical synthesis of structures containing sub-terminal α(1,3) fucose residues or their purification from natural sources, for a variety of reasons. One, the only chemicals necessary would be the enzyme substrates; these are easily obtained or synthesized. Two, enzymatic synthesis of such structures will produce only the desired product and the nucleotide diphosphate product of substrate hydrolysis. This latter chemical is found as the natural byproducts of these reactions in animal cells, is relatively non-toxic, and may be easily separated from the oligosaccharide synthetic product. By contrast, chemical synthetic procedures typically generate numerous products of side reactions which must be removed, and which may be toxic as well. Similarly, purification of oligosaccharides from natural sources requires the removal of other contaminating oligosaccharides present in the natural material. Three, enzymatic catalysis is extraordinarily efficient; essentially complete conversion of substrate to product might be achieved. By contrast, chemical synthesis of sub-terminal α(1,3) fucose residues on oligosaccharides is a multi-step process; yields at each step may be much less than 100%, and the cumulative efficiency of current chemical synthesis procedures does not approach the efficiency possible with enzymatic synthesis. Similarly, purification of oligosaccharides with subterminal α(1,3) fucose residues from natural materials can entail significant losses inherent to the purification procedures required to separate the desired oligosaccharide from contaminating, irrelevant oligosaccharides, with inefficient isolation of the desired oligosaccharide. Although the GDP-Fuc:[β-D-Gal (1,4)]-D-GlcNAc α(1,3)-Fucosyltransferase encoded by the DNA sequence described here may be partially purified from animal tissues for synthetic use, these purifications are themselves inefficient, primarily because the enzyme is typically present in very low abundance. This invention provides two mechanisms that may provide for the abundant production of this enzyme. First, this may be done through the construction and selection of animal cells that produce relatively large quantities of the enzymes. Alternatively, this cloned nucleic acid sequence may then be used with standard recombinant DNA technologies to produce large quantities of glycosyltransferases in yeasts or in prokaryotic hosts. Furthermore, the sequence encoding this enzyme may be modified via standard molecular cloning schemes or mutagenesis to yield a recombinant fucosyltransferase with novel properties that make it more desireable than the wild-type enzyme. For example, the modifications might be made to the enzyme that make it more stable, or more suitable for immobilization in a bioreactor.

iii. Isolation of reagents suitable for producing recombinant GDP-Fuc:[β-D-Gal(1,4)]-D-GlcNAc α(1,3)-Fucosyltransferase to be used directly as a research reagent, or to be used to generate antibodies against the GDP-Fuc:[β-D-Gal(1,4)]-D-GlcNAc α(1,3)-Fucosyltransferase, for research applications.

This invention provides two mechanisms for producing large quantities of this enzyme (see ii. above—i.e. specially constructed animal cells, or via natural or synthetic genes encoding these enzymes) which may be used as a research tool with which to study the structures and functions of oligosaccharides and glycoproteins. Likewise, the enzyme produced by this method, or the nucleic acid sequence and derived protein sequence provided by this method, may be used to generate antibodies to this enzyme (via synthetic peptides). These antibodies might also be used as research reagents to study the biosynthesis and processing of these enzymes, and might be used as an aid in their purification for all the uses described in this disclosure.

iv. Antibodies to glycosyltransferases as diagnostic reagents.

Aberrant expression of GDP-Fuc:[β-D-Gal(1,4)]-D-GlcNAc α(1,3)-Fucosyltransferase has been associated with malignancy in humans, suggesting that this enzyme might serve as a tumor marker for early detection of malignancy involving a number of human tissues. Enzyme tumor markers have typically been assayed in body fluids by activity assays, which may be subject to non-specificity due to competing glycosyltransferase activity. These assays may also be insensitive since it is possible that inactive enzymes might be useful as tumor markers but would not be detected by enzyme activity assays. This invention provides a mechanism for generating antibodies to this enzyme (monoclonal and polyclonal antibodies against synthetic peptides constructed from information derived from cloned DNA sequence encoding GDP-Fuc:[β-D-Gal(1,4)]-D-GlcNAc α(1,3)-Fucosyltransferase, or against the recombinant enzyme produced by eukaryotic or prokaryotic hosts). Antibodies specific for this GDP-Fuc:[β-D-Gal(1,4)]-D-GlcNAc α(1,3)-Fucosyltransferase so produced could be used to detect and quantitate this glycosyltransferase in body fluids, with specificity and sensitivity exceeding enzyme activity assays, and with the possibility of serving as a tumor marker for early detection of malignancy.

v. Recombinant enzyme for use in screening natural and synthetic compounds for fucosyltransferase inhibitors or inactivators.

A number of studies have noted an association between increased numbers of cell surface sub-terminal α(1,3) fucose residues on oligosaccharides of a cell and the ability of that cell to metastasize in a malignant fashion. If there is a causal relationship here, then it may be possible that drugs that inhibit the enzyme encoded by the sequence in this disclosure might be active as anti-tumor agents. Likewise, numerous recent studies have implicated sialylated and neutral oligosaccharides containing subterminal α(1,3) and α(1,4) fucose linkages in mediating adhesion of leukocytes to the selectin adhesion molecules (ELAM-1; GMP-140; Mel14/LAM-1) during inflammation. These studies suggest that molecules capable of preventing synthesis of α(1,3) and α(1,4) fucose linkages on leukocytes may thus function to diminish or even eliminate the ability of leukocytes to synthesize and display subterminal α(1,3) and α(1,4) fucose linkages, and would thus represent anti-inflammatory pharmaceutical agents. The reagents described in this disclosure may prove useful for screening to isolate or identify compounds that exhibit anti-fucosyltransferase activity, since the cloned sequence may be used with standard techniques to produce relatively large amounts of pure fucosyltransferase. This will aid in screening since the effects of potential inhibitors will be tested on a pure enzyme, without the confounding effects that may occur in whole cell extracts or with partially purified enzyme.

vi. Engineering of glycosyltransferase substrate specificity to generate novel glycoconjugate structures on secreted or cell-associated glycoconjugates.

This invention provides a reagent (a cloned GDP-Fuc:[β-D-Gal(1,4)]-D-GlcNAc α(1,3)-Fucosyltransferase gene segment), that, when used with appropriate mutagenesis and genetic selection schemes, may allow the generation of mutant GDP-Fuc:[β-D-Gal(1,4)]-D-GlcNAc α(1,3)-Fucosyltransferases that generate glycosidic linkages different from that generated by the wild-type enzyme. These novel linkages may or may not be naturally occuring, and could find utility as moieties that enhance the bioactivity of the molecules to which they are attached. Directed mutagenesis procedure may also be considered since this enzyme maintains primary sequence similarity to other α(1,3)-Fucosyltransferases, yet exhibits a distinct set of acceptor substrate utilization properties. Alternatively, mutagenesis and selection approaches may be used to generate mutant GDP-Fuc:[β-D-Gal(1,4)]-D-GlcNAc α(1,3)-Fucosyltransferases that act in a dominant negative fashion. The dominant negative mutants so generated might be used to inactivate endogenous glycosyltransferase activities when the product(s) of such an enzyme are not desired. Mutant GDP-Fuc:[β-D-Gal(1,4)]-D-GlcNAc α(1,3)-Fucosyltransferases might also be generated, for example, that function as fucosidases that hydrolyze various sugar linkages (fucose, mannose, or others) from oligosaccharides in vitro and in vivo.

vii. Genotyping individuals at this fucosyltransferase locus.

Absence of a fucosyltransferase similar or identical to the one encoded by the DNA sequence detailed here has been found in several families. Should such absence be associated with a detrimental phenotype, DNA sequence polymorphisms within or linked to the gene corresponding to this cloned gene segment may be used to genotype individuals at this locus, for the purpose of genetic counseling. Likewise, the molecular basis for any such detrimental phenotypes might be elucidated via the study of the gene segment described here, should it be causally-related to such phenotypes.

Other features of this invention will become apparent in the course of the following description of exemplary embodiments which are given for illustration of the invention and are not intended to be limiting thereof.

EXAMPLES

Example I. Cloning and Expression of a DNA Sequence Encoding α(1,2)Fucosyltransferase (DNA SEQ ID NO:5, protein SEQ ID NO:6

Mouse L Cells as a Host for Human (α-1,2) Fucosyltransferase Gene Transfer—Mouse L cells were tested as a host for gene transfer. These cells have been widely used for this purpose. Genomic DNA may be introduced into L cells with high efficiency, and these cells allow the use of several metabolic and antibiotic resistance schemes for selecting stable incorporation of exogenous DNA sequences.

L cells were examined for surface expression of the H Fuc α(1,2)Gal linkage, using a monoclonal antibody that recognizes type II H structures and fluorescence-activated cell sorting. Cells stained with this anti-H antibody exhibit a FACS profile virtually identical to the profile generated by cells stained with a control mouse IgM monoclonal antibody, and to profiles generated by cells stained only with FITC-conjugated second antibody. These results indicate that L cells do not express surface-localized Fuc α(1,2)Gal linkages that are detectable with the anti-H-antibody.

The inventor assayed L cell extracts to confirm that this absence of surface-expressed H determinants was due to a deficiency of (α-1,2)fucosyltransferase activity. Phenyl-β-D-galactoside was used as the acceptor for assay of (α-1, 2)fucosyltransferase. This compound is a specific acceptor for (α-1,2)fucosyltransferases; it is used efficiently by these enzymes, yet does not function as an acceptor for fucosyltransferases that generate (α-1,3), (α-1,4), or (α-1,6) linkages. L cell extracts contained no detectable (α-1,2) fucosyltransferase activity, even in assays that contained increased amounts of extract, or that were subjected to prolonged incubation. Mixing experiments with A431 cell extracts showed that inhibitors were not responsible for an apparent lack of detectable enzyme activity.

The inventor also examined L cells for surface expression of glyconjugates possessing N-acetyllactosamine (Galβ(1, 4)GlcNAc) end groups. These would represent potential acceptor molecules for a complementing human (α-1,2) fucosyltransferase activity and would allow the resulting surface-expressed Fucα(1,2)Gal linkages to be detected with anti-H antibody. The agglutinin from Erythrina cristagalli (ECA) was used for this analysis. This lectin exhibits high affinity for oligosaccharides possessing one or more unsubstituted N-acetyllactosamine end groups. L cells were stained with purified, FITC-labeled ECA, or with FITC-labeled ECA that had been preincubated with the hapten N-acetyllactosamine and were subjected to FACS analysis. The results indicated that significant amounts of ECA bind to these cells, and that the binding is effectively inhibited by the hapten N-acetyllactosamine. These results are consistent with the expectation that L cells synthesize oligosaccharides containing N-acetyllactosamine moieties and suggest that some of these glycoconjugates remain unmodified and are expressed at the cell surface.

The inventor also tested L cells for the ability to synthesize the fucosyltransferase substrate GDP-fucose. These analyses identified both GDP-[$^3$H]fucose and GDP-[$^3$H]mannose in aqueous extracts prepared from cells labeled with [2-$^3$H]mannose. The subcellular location of GDP-[$^3$H]fucose in these cells cannot be determined from these experiments. Effective Golgi fucosyltransferase activity would presumably require the presence of substrate concentrations of GDP-fucose within the lumen of the Golgi. Since these cells have not been selected to the defective in fucose metabolism, it seemed likely that they would be competent to transport this cytoplasmically synthesized compound into the Golgi lumen. This was confirmed by demonstrating that these cells are able to incorporate radio-labeled fucose into membrane glycoconjugates; most of this may represent fucose in α(1,6) linkage to the asparagine-linked N-acetylglucosamine of some N-linked oligosaccharides.

Taken together, these studies show that L cells are competent to display surface-localized H Fucα(1,2)Gal linkages, after introduction and expression of human DNA sequences determining (α-1,2)fucosyltransferase activity.

Human A431 Cells as a Donor for (α-1,2) Fucosyltransferase DNA Sequences—The human A431 cell line was investigated as a source of DNA for gene transfer since these cells express type I and II blood group H structures. Extracts prepared from A431 cells are found to contain (α-1,2)fucosyltransferase activity when assayed using phenyl-β-D-galactoside. The radiolabeled product elaborated by A431 extracts cochromatographed with authentic [$^{14}$C] fucosylated phenyl-β-D-galactoside produced by human serum H (α-1,2)fucosyltransferase. Digestion of the A431 product with α-L-fucosidase generated L-fucose in quantitative yield. These results indicate that A431 cells contain one or more functional (α-1,2) fucosyltransferase genes and thus represent an appropriate source of human DNA for gene transfer.

Isolation of a Mouse Transfectant That Expresses Surface Molecules Recognized by a Monoclonal Anti-H Antibody—To isolate mouse cells containing DNA sequences that determine expression of a human (α-1,2)fucosyltransferase, monolayer cultures of L cells were cotransfected with 30:1 ratio of high molecular weight genomic DNA prepared from A431 cells and pSV2-neo plasmid DNA. Cotransfection with pSV2-neo followed by growth of the transfected cells in media containing G418 allows selection of transfectants that have stably incorporated exogenous DNA sequences. With this procedure the inventor generated a population of cells representing approximately 60,000 independent G418-resistant transfectants. This method typically incorporates approximately 1000 kb of transfected sequences into the genome of a recipient cell. Since the size of the human genome is approximately 3×10$^6$ kb, the inventor estimated that approximately 20 copies of the haploid human genome were represented within this "library" of primary transfectants.

Transfectants were selected for H antigen expression by a combination of panning and sterile cell sorting. A pool of cells representing the entire population of transfected cells was reacted with a mouse IgM monoclonal antibody that recognizes type II H structures. Transfectants with bound anti-H antibody were subjected to an initial selection by panning on sterile dishes coated with goat anti-mouse IgM. At this stage, the inventor found this procedure to be more effective than selection by flow cytometry because it allowed larger numbers of transfectants to be rapidly and easily processed. Transfectants selected by panning were returned to culture to be amplified for subsequent rounds of selection. The FACS profile of cells present after this first selection revealed no obvious peak of cells that had bound the anti-H antibody. However, analysis of the FACS histogram indicated that approximately 0.13% of the cells stained more brightly than cells stained with the control antibody. Cells representing the brightest 3–5% of the total population were aseptically collected, returned to culture for 14 days, and then reselected by the same procedure. After three selections, FACS analysis revealed the presence of a distinct population of cells that were brightly stained with the anti-H antibody. These cells were collected and returned to culture. For heuristic reasons, transfectants were also subjected to selection by panning, in parallel with the FACS selections. The inventor found that the panning procedure more efficiently enriched for populations of cells that bound the anti-H antibody. This is perhaps because the IgM anti-H antibody induced agglutination of H-positive transfectants and interfered with selection by FACS.

Therefore, all subsequent selections were performed by the panning procedure. After three additional rounds of panning (representing a total of seven rounds of selection), more than 90% of the cells within the selected population stained brightly with anti-H antibody. Clonal isolates from this population were generated, and individual subclones were analyzed for H antigen expression by FACS. Most clones gave rise to phenotypically mixed populations of cells consisting of H-expressing and non-expressing transfectants. The reasons for this apparent phenotypic instability are not known. One clone that exhibited a stable, bright H antigen-positive phenotype was selected for further analysis (clone mH1-12). The phenotype of clone mH1-12 has remained stable for more than 9 months in the absence of selection of H expression.

The inventor wished to rule out the possibility that a murine (α-1,2)fucosyltransferase gene might be active in rare variants in the L cell population or that the transfection procedure itself might activate this gene and that the selection process might enrich for these undesired events. Therefore, in a parallel control experiment, L cells were transfected with high molecular weight genomic DNA prepared from L cells, using pSV2-neo as the selectable marker. These transfectants were then subjected to selection for H antigen expression, exactly as described above. The inventor was unable to detect or isolate H-expressing cells from a population of independent transfectants (at least 40,000) that together has integrated the equivalent of more than 15 copies of the haploid murine genome.

The Primary Transfectant Expresses Cell Surface Type II Blood Group H Antigen and ($\alpha$-1,2)Fucosyltransferase Activity—Clone mH1-12 was selected with a monoclonal anti-H antibody that recognizes type II blood group H structures (Fuc$\alpha$(1,2)Gal$\beta$(1,4)GlcNAc-R). Binding of this antibody to mH1-12 cells is blocked when the antibody is preincubated with the type II H hapten 2'-fucosyllactose (Fuc$\alpha$(1,2)Gal$\beta$(1,4)Glc). By contrast, preincubation of the anti-H antibody with L-fucose, or with N-acetyllactosamine or lactose, at identical concentrations, does not inhibit binding of the antibody to mH1-12 cells. When a different monoclonal anti-H antibody (BE2) previously shown to be specific for type II H structures was used in these experiments, the inventor also observed inhibition of binding with 2'-fucosyllactose, but not with the other haptens. These studies indicate that mH1-12 cells express cell surface glycoconjugates with terminal Fuc$\alpha$(1,2)Gal linkages.

Additional evidence for the presence of this linkage was obtained by using the linkage-specific blood group A ($\alpha$-1,3)GalNAc transferase purified from human plasma. This glycosyltransferase has an absolute requirement for blood group H acceptors containing fucosyl $\alpha$(1,2)galactoside as the terminal nonreducing group. It catalyzes the addition of N-acetylgalactosamine in $\alpha$-1,3 linkage to the galactose moiety of this structure to construct blood group A-reactive molecules of the form GalNAc$\alpha$(1,3)[Fuc$\alpha$(1,2)]Gal. Generation of blood group A-reactive determinants on the surface of mH1-12 cells by the action of blood group A glycosyltransferase would provide confirmation of the presence of terminal Fuc$\alpha$(1,2)Gal linkages inferred by the results of the type II H hapten inhibition study.

Formalin-fixed mH1-12 cells were incubated with preparations of the blood group A ($\alpha$-1,3)GalNAc transferase and its nucleotide sugar substrate (UDPGalNAc, 1 mM, approximately 20-fold above $K_m$ for UDP-GalNAc) in a buffer supporting activity of this enzyme. The cells were then probed for the presence of newly synthesized, surface-localized blood group A determinants by indirect immunofluorescence using a monoclonal anti-A antibody.

After a 4-h incubation with the A ($\alpha$-1,3)GalNAc transferase and its substrate, blood group A determinants were detectable on the surface of the cells. No staining with anti-A antibody was observed in control reactions done in the absence of either UDP-GalNAc or group A transferase. L cells showed no binding of anti-H or anti-A under any of these conditions.

The inventor also stained A enzyme-treated cells with anti-H antibody to test for loss of surface expressed H structures. These should be "masked" with N-acetylgalactosamine molecules that are attached by the A enzyme to the galactose of the Fuc$\alpha$(1,2)Gal linkage. After a 4-h incubation with both A enzyme and its substrate, the staining generated by the anti-H antibody was only slightly diminished. However, after the conversion reaction was allowed to proceed for 24 h, essentially complete elimination of cell surface H reactivity was seen. This is coincident with continued expression of strong A reactivity. Cells treated for 24 h with a control reaction mixture containing the A enzyme but without substrate exhibited strong anti-H staining. This indicates that loss of H reactivity seen after the 24-h reaction was not due to destruction of H structures by glycohydrolase or protease activities contaminating the group A enzyme preparation. Loss of H reactivity after prolonged incubation thus represents "masking" of H structures by the A enzyme-catalyzed attachment of $\alpha$-1,3-linked N-acetylgalactosamine. These data indicate that mH1-12 cells express cell surface glycoconjugates terminating with authentic H Fuc$\alpha$(1,2)Gal linkages.

Assays of extracts prepared from mH1-12 cells confirmed that these cells express $\alpha$-(1,2)fucosyltransferase activity. $\alpha$-Fucosidase digestion of the fucosylated product of these reactions confirmed the $\alpha$ anomeric linkage of the attached fucose.

Analysis of the Human DNA Sequences in the Primary Transfectant—Southern blot analysis was used to determine if the mH1-12 cell line contains human DNA sequences. The BLUR8 Alu sequence was used to detect human sequences. With the hybridization and washing conditions used, the human Alu probe did not cross-hybridize with mouse sequences, but was able to detect the equivalent of a few copies of an Alu sequence that had been added to mouse L cell DNA (10 $\mu$g). By comparison, the A431 DNA sample (3 ng) displayed a diffuse yet relatively intense hybridization signal expected for the highly repetitive interspersed Alu sequences. Under these conditions, the inventor was able to detect significant amounts of human sequences in the genome of mH1-12 cells (500 ng). This analysis indicates that, as expected, the genome of mH1-12 cells contains roughly 1000 kb of human DNA.

Isolation of Multiple Secondary Transfectants That Express Cell Surface Type II H Antigen and ($\alpha$-1,2) Fucosyltransferase Activity—The inventor wished to be able to identify within the large number of human sequences in the genome of mH1-12 cells specific human sequences that mediate expression of its H-positive phenotype. To reduce the amount of extraneous human DNA, the inventor used DNA prepared from the mH1-12 cell line to generate "secondary" transfectant "libraries," and screened these libraries for transfectants that expressed the H structure. The inventor expected that H-expressing secondary transfectants so identified would each have a small number of human DNA restriction fragments identifiable within their genomes. The inventor sought to isolate several independent secondary transfectants since it was anticipated that human sequences linked to H-determining gene(s) should be a subset of these human fragments, identifiable as characteristic restriction fragments of identical sizes in each independently derived H-expressing secondary transfectant.

Genomic DNA prepared from mH1-12 cells was con-transfected with pSV2-neo into L cells. Four different secondary libraries were generated in this way (Table 3).

TABLE 3

Estimated frequencies of H antigen-positive transfectants in six independent libraries Frequencies are expressed as one independent H-expressing transfectant isolated/number of plates of transfectants screened. For libraries screened by cell sorting or panning, this is a minimum estimate since these immunoselection procedures do not allow discrimination between H-expressing sibs and independently derived H-positive transfectants; at least one independent H-expressing transfectant was present in each of these libraries. For the primary library mH1, and secondary libraries mHs1, mHs3, mHs4, and mHs5, each plate contained approximately 2000 independent transfectants, as determined from transfection efficiency estimates (see "Experimental Procedures"). For the mHs2 secondary library,

TABLE 3-continued

Estimated frequencies of H antigen-positive transfectants in six independent libraries inspection of the plates prior to screening indicated that approximately 50 colonies were present on each plate. Clones s2-1 and s2-2 were isolated with the rosette procedure from two separate plates. Clone s2-3 was isolated by panning a population of cells representing approximately 650 independent transfectant colonies.

| Library name | Source of transfected DNA | Added selection plasmid | Fraction of transfectants expressing H determinants |
| --- | --- | --- | --- |
| mH1 (primary) | A431 Cells | pSV2-neo | ≥1/30 dishes |
| mHs1 (secondary) | mH1-12 | pSV2-neo | ≥1/30 dishes |
| mHs3 (secondary) | mH1-12 | pSV2-neo | ≥1/10 dishes |
| mHs4 (secondary) | mH1-12 | pSV2-neo | ≥1/10 dishes |
| mHs5 (secondary) | mH1-12 | pSV2-neo | ≥1/10 dishes |
| mHs2 (secondary) | mH1-12 | None | ≥1/~650 colonies ≥1/~50 colonies (rosette s2-1) ≥1/~50 colonies (rosette s2-2) |

Each library was independently screened for H-expressing transfectants using the panning procedure. Prior to the third round of panning, FACS analysis indicated that each of these libraries contained H antigen-positive cells (1–60% of the cells bound anti-H antibody). Sequential selection by panning was continued until 50–90% of the cells exhibited the H-positive phenotype. Clonal cell lines (S1–11 and S3–6) were then established from populations derived from the mHsl and mHs2 libraries; more than 95% of the cells in these lines exhibited bright staining with anti-H antibody. Libraries mHs4 and mHs5 were not subjected to the cell cloning procedure but were instead subjected to additional selections by panning. After a total of 11 rounds of selection, approximately 95% (selected from mHs4 library) and 50% (selected from mHs5 library) of these cells exhibited H antigen expression.

The calcium phosphate transfection procedure the inventor used for constructing the mH1-12 cell line occasionally results in physical linkage of selectable plasmid sequences with the transfected genomic DNA sequences that determine the desired phenotype. Linkage of pSV2-neo sequences to human DNA sequences determining the H-positive phenotype in the mH1-12 primary transfectant would simplify identification of H-expressing secondary transfectants and would facilitate isolation of the relevant transfected sequences by molecular cloning procedures. As a test of such linkage, the inventor generated a secondary library, mHs2, by transfecting L cells with DNA prepared from the mH1-12 primary transfectant. The transfection was done without the addition of exogenous pSV2-neo DNA. This procedure yielded approximately 50 independent G418 transfectants on each of fifteen 10-cm dishes. This represents a 40-fold reduction in the number of G418-resistant colonies obtained, relative to the numbers generated when secondary libraries were generated with the addition of pSV2-neo DNA (~2000 G418 resistant cells/dish).

This mHs2 library was initially screened with an in situ rosette procedure for rapid identification of transfectant colonies that bound anti-H antibody (see "Experimental Procedures" below). Culture dishes containing approximately 50 colonies each were screened with this method 16 days after transfection and prior to any other manipulations. A single rosette-positive colony was identified on two of the 15 dishes tested. These two independent H-positive colonies were isolated with cloning rings and an H-expressing cell line (s2-1 and s2-2) was established from each. An additional, independent, clonal H-expressing transfectant (s2-3) was isolated by harvesting the colonies on the other 13 dishes and subjecting these cells to selection by panning and then cell cloning.

Cotransfection of unlinked single-copy markers occurs at a frequency less than 1%. The frequencies of coexpression of G418 resistance and the H phenotype the inventor observed in the mHs2 library (Table 3) are consistent with the possibility that the two markers are linked in the primary transfectant. Alternatively, these frequencies could be explained by cotransfection of unlinked markers present in multiple copies in the primary transfectant. In any event, the frequencies of H-expressing transfectants observed in the primary and secondary libraries (Table 3) indicate that the H-positive phenotype expressed by these transfectants is determined by a single transfected locus.

The anti-H reactive surface molecules on a representative H-expressing secondary transfectant (clone s2-2) were shown to be authentic H Fucα(1,2)Gal linkages, using analyses identical to those used for the H antigen-positive primary transfectant mH1-12. Extracts prepared from s2-2 cells were found to contain (α-1,2)fucosyltransferase activity. (α-1,2)Fucosyltransferase activity was also found in extracts prepared from each of the other H-expressing secondary transfectants.

Independent H-Expressing Secondary Transfectants Have Common Restriction Fragments Containing Human DNA Sequences—The inventor anticipated that the genome of each H-positive secondary transfectant would contain a relatively small amount of human DNA and that this DNA would include human sequences controlling expression of the (α-1,2)fucosyltransferase found in each. In principle, one or more characteristic restriction fragment(s) generated by these sequences should be identifiable in every transfectant. Conversely, irrelevant human sequences should exhibit a random restriction pattern in the secondary transfectants. The inventor therefore isolated genomic DNA from each transfectant, digested these DNAs with various restriction enzymes, and subjected these digests to Southern blot analysis. Restriction fragments containing human DNA sequences were detected with the BLUR8 Alu probe. A number of DNA restriction fragments are present in each clonal secondary transfectant; the aggregate amount of human genomic DNA present in these cells is estimated to be between 25 and 55 kb. The genome of each clonal secondary transfectant contains a characteristic pair of human DNA EcoRI restriction fragments with sizes of 2.7 and 3.4 kb. These fragments are also evident in pools of cells selected by panning from libraries mHs4 and mHs5. Similar analyses indicate that the genome of each H-expressing secondary transfectant contains common 1.5 and 1.9 kb PstI fragments and a common 2.8-kb PvuII human DNA restriction fragment. These observations imply that DNA sequences within or linked to these characteristic human restriction fragments are associated with expression of the cell surface H Fucα (1,2)Gal linkages used to select these transfectants, and are thus implicated in the expression of the (α-1,2) fucosyltransferase found in these cells.

To further confirm that the common human DNA sequences in the transfectants direct (α1,2) fucosyltransferase expression in these cells, molecular cloning procedures were used to isolate these fragments and then test their function in a mammalian transient expression system. The two human DNA EcoRI fragments previously found to be associated with expression of the H phenotype in the H-expressing secondary transfectants were isolated from mini genomic libraries prepared in a lambda phage vector, using the secondary transfectant s2-2 (see "Experimental Procedures"). To determine if these fragments contained sufficient genetic information to direct synthesis of (a1,2)fucosyltransferase, these were first individually subcloned into the mammalian expression cosmid vector pWE15. This vector contains the SV40 origin of replication, enabling it to replicate efficiently as an episome in COS-1 cells. The resulting plasmids contained either the 3.4 kb EcoRI (plasmid pH3.4) or the 2.7 kb EcoRI fragment (plasmid pH2.7). These plasmids were then individually introduced into COS-1 cells by DEAE-dextran transfection (see "Experimental Procedures") and the transfected cells were subsequently assayed for ($\alpha$1,2)fucosyltransferase activity. The inventor found no detectable ($\alpha$1,2) fucosyltransferase activity in mock transfected COS-1 cells or in COS-1 cells transfect with pH2.7. However, COS-1 cells transfected with plasmid pH3.4 expressed significant amounts of ($\alpha$1,2)fucosyltransferase activity. $\alpha$-Fucosidase digestion of the fucosylated phenyl-$\beta$-D galactoside product generated by this extract confirmed the alpha anomeric configuration of the attached fucose (see "Experimental Procedures").

The pH-activity profile of this ($\alpha$1,2)fucosyltransferase mirrors the profiles determined for the ($\alpha$1,2) fucosyltransferases found in fractionated human serum, in A431 cells, and in the H-expressing mouse transfectants. Likewise, the apparent Michaelis constants exhibited by the recombinant enzyme expressed in COS-1 cells (GDP-fucose $K_m$=17.5 $\mu$M; phenyl-$\beta$-D-galactoside $K_m$=4.4 mM) are essentially the same as those determined by the inventor for the ($\alpha$1,2)fucosyltransferases in fractionated human serum, and in each of the cell lines he analyzed. Considered together, these results are consistent with the proposal that human DNA sequences within the 3.4 kb EcoRI fragment encode an ($\alpha$1,2)fucosyltransferase, and that these sequences encompass part or all of the human blood group H ($\alpha$1,2)fucosyltransferase gene. The 3.4 kb EcoRI fragment in pH3.4, the 2.7 kb EcoRI fragment in pH2.7, and DNA sequence adjacent to the 3.4 kb fragment, were sequenced to provide SEQ ID NO:5.

To characterize the nature of these cloned human genomic DNA sequences, the inventor first isolated various restriction fragments from the insert in plasmid pH3.4 and tested these for their ability to identify transcripts in the H-expressing, stable transfectants, and in a human cell line (A431) that also expresses H determinants and a cognate ($\alpha$1,2)fucosyltransferase. He found that a 1.2 kb HinfI restriction fragment from the insert in pH3.4 identifies a single, relatively non-abundant 3.6 kb transcript in A431 cells. This probe also detects transcripts in the H-expressing mouse L cell transfectants, but not in the non-transfected parental L cells.

A cloned cDNA that directs expression of cell surface H structures and an ($\alpha$1,2)fucosyltransferase. The inventor used the 1.2 kb HinfI fragment and colony hybridization to isolate two hybridization positive cDNA clones from an A431 cell cDNA library. To test the cloned cDNAs for their ability to determine expression of surface-localized H antigen and a cognate ($\alpha$1,2)fucosyltransferase activity, a plasmid was constructed (pCDM7-$\alpha$(1,2)FT, see "Experimental Procedures") that consisted of the largest cDNA insert cloned into the mammalian expression vector pCDM7, in the sense orientation with respect to the vector's enhancer-promoter sequences. Flow cytometry analysis of COS-1 cells transfected with PCDM7-$\alpha$(1,2)FT indicates that this cDNA determines expression of cell surface H molecules. Moreover, CoS-1 cells transfected with pCDM7-$\alpha$-(1,2)FT, but not cells transfected with pCDM7, express substantial quantities of an ($\alpha$1,2)fucosyltransferase activity. The inventer determined the apparent Michaelis constant exhibited by this ($\alpha$1,2)fucosyltransferase for an artificial acceptor (phenyl-$\beta$-D-galactoside) that is specific for this enzyme and that can discriminate between the human H and Se ($\alpha$1,2) fucosyltransferases. This apparent Km (2.4 mM) is nearly identical to the apparent Km the inventor (3.1 mM,) and others (4.6 mM, 6.4 mM, 1.4 mM) have determined for the blood group H ($\alpha$1,2)fucosyltransferase. Moreover, this apparent $K_m$ is also very similar to the one exhibited by the ($\alpha$1,2)fucosyltransferase in extracts prepared from COS-1 cells transfected with pH3.4 (4.4 mM). This apparent Km is distinct from the one exhibited by an ($\alpha$1,2) fucosyltransferase found in human milk enzyme (15.1 mM), that is though to represent the ($\alpha$1,2)fucosyltransferase encoded by the Se locus. These data demonstrate that the cDNA in plasmid pCDM7-$\alpha$(1,2)FT determines expression of an ($\alpha$1,2)fucosyltransferase whose kinetic properties reflect those exhibited by the human H blood group ($\alpha$1,2) fucosyltransferase.

The cDNA sequence predicts a Type II transmembrane glycoprotein. The cDNA insert in pCDM7-$\alpha$(1,2)FT is 3373 bases pairs long. Its corresponding transcript is 3.6 kb in length, suggesting that this cDNA is virtually full-length. Two potential initiator codons are found within its first 175 nucleotides. Only the second of these, however, is embedded within a sequence contest associated with mammalian translation initiation. The methionine codon initiates a long open reading frame that predicts a protein of 365 amino acids (SEQ ID NO:6), with a calculated Mr of 41,249 Da. This open reading frame is colinear with the open reading frame found in the 3.4 kb EcoRI fragment in pH3.4. Hydropathy analysis of the predicted protein sequence indicates that it is a Type II transmembrane protein, as noted for several other cloned glycosyltransferases. This topology predicts an 8 residue $NH_2$-terminal cytosolic domain, a 17 residue hydrophobic transmembrane domain flanked by basic amino acids, and a 340 amino acid COOH-terminal domain that is presumably Golgi-resident and catalytically functional. Two potential N-glycosylation sites are found in this latter domain suggesting that this sequence, like other glycosyltransferases, may exist as a glycoprotein. No significant similarities were found between this sequence and other sequences in protein or DNA databases (Protein Identification Resource, Release 21.0, and Genbank, Release 60.0), with the exception of a 642 bp sequence within the 3'-untranslated segment of the cDNA that is similar to the human Alu consensus sequence. Moreover, the inventor identified no significant sequence similarities between this cDNA sequence or its predicted protein sequence, and those of other cloned glycosyltransferase cDNAs.

The protein encoded by the cDNA is an ($\alpha$1.2) fucosyltransferase. The results of the expression experiments present above, when considered together with the domain structure predicted by the cDNA sequence, are consistent with the presumption that it encodes an ($\alpha$1,2) fucosyltransferase. Nonetheless, the inventor wished to directly confirm this, and thus exclude the possibility that it instead encodes a molecule that trans-determines this enzyme activity. The inventor therefore fused the putative catalytic domain of the predicted protein to a secreted form of the IgG-binding domain of *Staph. aureus* protein A (see Experimental Procedures) in the mammalian expression vector pPROTA, to yield the vector pPROTA-α(1,2)FT$_c$. By analogy to similar constructs the inventor has prepared with other cloned glycosyltransferases (detailed infra), he expected that if the cDNA sequence actually encodes an (α1,2)fucosyltransferase, then plasmid pPROTA-α(1,2)FT$_c$ would generate a secreted, soluble, and affinity purifiable (α1,2)fucosyltransferase. Indeed, conditioned media prepared from a plate of COS-1 cells transfected with pPROTA-α(1,2)FT$_c$ contained a total of 5,790 units of (α1,2) fucosyltransferase activity, whereas a total of 1,485 units were found to be cell-associated. Moreover, virtually 100% of the released (α1,2)fucosyltransferase activity was specifically retained by IgG-Sepharose, and most could be recovered after exhaustive washing of this matrix. By contrast, the inventor found that most of the activity in COS-1 cells transfected with pCDM7-α(1,2)FT was cell-associated (3450 units), with only trace amounts of activity in the conditioned media prepared from these cells (~80 units). Virtually none of this latter activity bound to either matrix. Extracts prepared from COS-1 cells transfected with vector pCDM7 or vector PPROTA did not contain any detectable cell-associated or released (α1,2) fucosyltransferase activity. These data demonstrate that the cDNA insert in pCDM7-α(1,2)FT encodes an (α1,2) fucosyltransferase, and that information sufficient to generate a catalytically active (α1,2)fucosyltransferase is encompassed with the 333 amino acids distal to the putative transmembrane segment.

Experimental Procedures for Example I, "Cloning and Expression of a DNA Sequence Encoding (α1, 2)Fucosyltransferase"

The term "L cells" used throughout the text refers to the mouse Laprt$^-$tk$^-$ cell line.

Lactose, N-acetyllactosamine, 2'-fucosyllactose (Fucα(1, 2) Galβ(1,4)Glc), UDP-GalNAc, phenyl-β-D-galactoside, and Ficoll 400 were obtained from Sigma. L-Fucose was from Pfanstiehl Labs (Waukegan, Ill.). UDP[1-$^3$H]N-acetylgalactosamine (8.7 Ci/mmol) and D-[U-$^{14}$C]mannose (239 mCi/mmol) were from DuPont-New England Nuclear. D-[2-$^3$H]mannose (16.3 Ci/mmol), L-[6-$^3$H]fucose (72 Ci/mmol), L-[1-$^{14}$C]fucose (58.7 mCi/mmol), GDP[U-$^{14}$C]-β-L-fucose (268 mCi/mmol), and [α-$^{32}$P dCTP (3000 Ci/mmol) were from Amersham Corp. Nonradioactive GDP-fucose was kindly provided by Dr. Eric Holmes (Seattle). FITC-ECA was obtained from E-Y Labs (San Mateo, Calif.). Plasmid pSV2-neo was obtained from Dr. David Chaplin (Washington University, St. Louis). Restriction enzymes (New England Biolabs or Boehringer Mannheim) were used according to the manufacturer's instructions.

Antisera

Monoclonal anti-H, anti-A, and anti-B antibodies (mouse IgM) were purchased from Chembiomed, Ltd. (Alberta, Canada). Monoclonal anti-H antibody BE2 was prepared from BE2 hybridoma cell culture supernatants (see below). Anti-mouse IgM and FITC-labeled antimouse IgM (both antigen-affinity purified, goat) were from Sigma.

Cell Lines and Culture

Mouse Laprt$^-$tk$^-$ cells were obtained from Dr. David Chaplin. Human A431 cells were from Dr. Brian Whiteley and Dr. Luis Glaser (Washington University, St. Louis). BE2 cells were obtained from the American Type Culture Collection. Cells were grown in Dulbecco's modified Eagle's medium (GIBCO) supplemented with 10% fetal calf serum (Hyclone, Logan, Utah). Transfected cells were grown in media containing G418 (GIBCO) at 400 μg/ml (active drug).

Preparation of Genomic DNA

High molecular weight genomic DNA was prepared from cultured cells by standard methods. Samples of genomic DNA were electrophoresed through 0.3% agarose gels buffered in Tris-acetate-EDTA to confirm their integrity and to estimate the average size of the molecules in the preparations.

Transfections

The calcium phosphate precipitation method was used to transfect mouse L cells with human genomic DNA. Cells (5×10$^5$/100-mm dish) were incubated overnight with DNA precipitates 20–30 μg of genomic DNA and 1 μg of pSV2-neo). No exogenous pSV2-neo DNA was included in transfections that generated the mHs2 secondary library. The cells were fed fresh media the following day and were placed under G418 selection the next day. Transfection efficiencies were estimated by harvesting transfected cells 1 day after addition of DNA and plating duplicate serial dilutions of the cell suspensions. One set of dilutions was grown under G418 selection, and the other was grown in the absence of antibiotic to allow the derived transfection efficiencies to be corrected for plating efficiency. After 2 weeks of growth, colonies were counted after staining with 0.2% methylene blue in 50% methanol. Approximately 2000 independent transfectants were typically obtained by transfecting 5×10$^5$ cells on a 100-mm dish.

Immunologic Selection of H-expressing Transfectants

Transfectants were removed from culture dishes by incubating them with PBS containing 3 mM EDTA. Detached cells were washed and resuspended in staining medium (10 mM Hepes, pH 7.4, 0.1% sodium azide, 2% fetal calf serum in Dulbecco's modified Eagle's medium). The cells were kept at 4° C. throughout the panning or cell sorting procedures. Cell cloning was done by plating cells at low density, allowing individual cells to form colonies, and isolating individual colonies with cloning cylinders.

Panning—Bacteriological culture dishes (Falcon 1007, 60 mm) were prepared for panning. Goat antimouse IgM was coupled to the dishes by incubating them overnight at 4° C. with 4 ml of antibody solution diluted to 10 μg/ml in 50 mM Tris, pH 9.5. The antibody solution was aspirated, and the dishes were washed twice with PBS. The dishes were then blocked by incubating them at room temperature for at least 1 h with PBS containing 1 mg/ml bovine serum albumin. Dishes were then used immediately or were stored indefinitely at 4° C. The dishes were washed three times with PBS prior to use.

Cells to be panned were resuspended at a concentration of 10$^7$/ml, in staining media containing anti-H antibody at 10 μg/ml. The cells were incubated for 30 min at 4° C., and unbound antibody was removed by pelleting the cells through 10 ml of PBS containing 1 mM EDTA, 0.1% sodium azide, and 2% Ficoll 400. After centrifugation, the supernatant was carefully aspirated, and the cells were resuspended at 10$^6$/ml, in staining media. Three-ml aliquots of this cell suspension were applied to 60-mm panning dishes coated with goat anti-mouse IgM. The dishes were then incubated for 1 h at 4° C., and were then rinsed 5 times with serum-free Dulbecco's modified Eagle's medium to remove nonadherent cells. Fresh, serum-replete media was added to the dishes, and they were returned to the tissue culture incubator. The next day, adherent cells were removed with trypsin-EDTA and were replated on standard tissue culture dishes. These cells were grown for 10–18 days prior to the subsequent selection.

Cell Sorting—Transfectants were prepared for FACS analysis by incubating them for 30 min at 4° C. with monoclonal IgM anti-H antibody (10 μg/ml in staining media) or with a control monoclonal IgM anti-B antibody (10 μg/ml) in staining media). The cells were then washed in ice-cold staining media, and incubated for 30 min at 4° C. in staining media containing fluorescein-conjugated goat anti-mouse IgM at 40 μg/ml. The cells were washed, resuspended in staining media, and subjected to analysis by the FACS (Coulter Electronics model Epics C). Samples were gated on forward and 90° light scatter to eliminate dead cells from analysis. H-expressing cells were collected aseptically into staining media and then returned to culture for 10–18 days before additional selections.

Rosette Procedure—A resetting method was used to identify colonies of transfectants that bound anti-H antibody. This was done on 100-mm dishes containing isolated colonies comprised of approximately 100–300 cells. Plates of colonies were first rinsed twice with PBS and were then incubated for 1 h at 4° C. with 4 ml of mouse IgM monoclonal anti-H antibody at 10 μg/ml in PBS, 2% fetal calf serum, 0.1% sodium azide. The plates were then rinsed three times with PBS, and were incubated for 30 min at 4° C. with 4 ml of human erythrocytes conjugated with goat anti-mouse IgM. (Goat anti-mouse IgM was coupled to human blood group O red cells with chromic chloride. After conjugation, the red cells were washed with PBS, diluted to a 0.2% v/v suspension in PBS, 2% fetal calf serum, 0.1% sodium azide, and were used immediately.) Afterwards, the suspension of erythrocytes was carefully aspirated, and the plates were gently rinsed with PBS and examined on a light box. Colonies that had bound anti-H antibody were macroscopically visible as "rosettes" consisting of red cells adherent to the colonies.

Purification of Blood Group A (α-1.3)GalNAc Transferase

Group A transferase was isolated from human blood group A plasma by affinity chromatography on Sepharose 4B (Sigma lot no. 104F0334). Column fractions containing the peak of enzyme activity were pooled, mouse serum albumin (Behring Diagnostics >98%) was added to a 1% concentration, and aliquots were stored at −80° C. until use. The activity of the final preparation was determined by a standard radiochemical method. One enzyme unit is defined as one nmol of GalNAc transferred to 2'-fucosyllactose acceptor/h.

Paper Chromatography

Descending paper chromatography was performed using Whatman No. 3 mm or Whatmann No. 1 in the following solvent systems: Solvent A, ethyl acetate/pyridine/water (10:4:3); Solvent B pyridine/water/ethyl acetate (10:11:5:36), upper phase. The dried chromatograms were cut into 1-cm strips and radiolabeled compounds were eluted with water. Radioactivity in an aliquot of each eluate was determined by scintillation counting.

Analysis of L Cell GDP-Fucose Content

To identify GDP-fucose in mouse L cells, cells ($2.5 \times 10^6$) were labeled for 3 days with 250 μCi of D-[2-$^3$H]mannose in 30 ml of complete media. Cells were harvested and extracted with 60% ethanol for 5 min in a boiling water bath. The aqueous extract containing nucleotide sugars was concentrated under vacuum and resuspended in a small volume of water. Unlabeled GDP-mannose (270 nmol) and GDP-fucose (130 nmol) were added as internal standards, as the mixture was subjected to gel filtration chromatography on a Sephadex G-25 column (0.9×42-cm) equilibrated in 50 mM ammonium acetate. The eluate was monitored at 268 nm; fractions containing GDP-fucose and GDP-mannose were pooled, concentrated under vacuum, and resuspended in 200 μl of water. This was subjected to fractionation by HPLC on a weak anion exchange column (AX300, 4 mm×24 cm, Pierce Chemical Co.). The sample was applied to the HPLC column equilibrated in 100 mM triethylamine acetate, pH 7.0, and was eluted with a linear gradient from 100 to 300 mM triethylamine acetate, pH 7.0 in 50 min at a flow rate of 2 ml/min. The eluant was monitored at 268 nm, and fractions (0.5 ml) were collected for scintillation counting and subsequent analysis. The unlabeled nucleotide sugar internal standards were identified by their characteristic elution times (GDP-fucose, 35.5 min. approximately 800 cpms; GDP-mannose, 33.0 min. approximately 1000 cpms). The radioactive peaks corresponding to the fractions coeluting with unlabeled GDP-fucose and GDP-mannose were subjected to hydrolysis with 0.1 N HCl for 45 min at 100° C. These were then fractionated by descending paper chromatography on Whatman No. 3MM in solvent B for 20 h, in parallel with L-[$^{14}$C]fucose and D-[$^{14}$C] mannose standards. In each case, approximately 30% of the counts hydrolyzed were recovered as the appropriate monosaccharide.

Analysis of Fucose-Labeled Glycopeptides

Radiolabeled glycopeptides were prepared and analyzed. Mouse L cells ($2 \times 10^6$) were labeled for 3 days with 200 μCi of L-[6-$^3$H]fucose in 20 ml of complete media. Cells were harvested and extracted with chloroform, and then water, and the pellet remaining after the final extraction was subjected to exhaustive digestion with Pronase (Behring Diagnostics). This was then desalted by gel filtration chromatography on Sephadex G-25-80. This material was concentrated under vacuum, and an aliquot was hydrolyzed in 0.1 N HCl at 100° C. for 45 min. The hydrolysate was then subjected to descending paper chromatography on Whatman No. 3MM in solvent B for 20 h, in parallel with an L-[$^{14}$C]fucose standard. Approximately 26% of the counts present in the macromolecular material were released and cochromatographed with the radiolabelled fucose standard.

Assay of GDP-L-Fucose:β-D-Galactoside 2-α-L-Fucosyltransferase

Cultured cells were washed with PBS, pelleted by centrifugation, and resuspended in a small volume of 25 mM sodium phosphate, pH 6.1, containing 0.5% Triton X-100. Volumes were adjusted to achieve a protein concentration of approximately 5 mg/ml (BCA method, Pierce Chemical Co.). Extracts were typically assayed immediately after preparation. The standard assay contained 5–20 μl of enzyme solution (typically 30–100 μg of cell extract protein or 15 μl of serum) in 40 μl of 25 mM potassium phosphate, 0.1% Triton X-100, 3 μM GDP-[$^{14}$C]fucose, 25 mM phenyl-β-D-galactoside, and 5 mM ATP. The pH of the reaction mixture was adjusted to a final measured pH of 6.1. Assays were terminated after an appropriate period of time by the addition of 20 μl of ethanol. The mixture was then centrifuged at 15,000×g for 5 min. The supernatant was collected, spotted on Whatman No. 1, and subjected to fractionation by descending paper chromatography for 4 h in Solvent A. Radioactivity was then determined as described above. In all cases, parallel reactions were done in the absence of added phenyl-β-D-galactoside acceptor to allow correction for endogenous acceptor molecules. No products of endogenous acceptor molecules cochromatographing with fucosylated phenyl-β-D-galactoside were identified in any samples.

α-Fucosidase Digestion

[$^{14}$C]Fucosylphenyl-β-B-galactoside (approximately 10,000 cpm) was isolated from fucosyltransferase assays by paper chromatography, concentrated from the water eluate under vacuum, and resuspended in 5 μl of water. This was digested with 0.025 units of bovine kidney α-L-fucosidase (EC 3.2.1.51) in a final volume of 20 μl containing 5 mM sodium citrate, pH 6.0, at 37° C. for 1 h. This mixture was then fractionated by descending paper chromatography on Whatman No. 1 in Solvent A for 4 h. Products of the digestions were identified by comparison to parallel separations of authentic L-[$^{14}$C]fucose, and purified [$^{14}$C] fucosylphenyl-β-D-galactoside synthesized by human plasma H (α-1,2)fucosyltransferase.

Indirect Immunofluorescence

Immunofluoroscence was performed on cells plated on 8-well tissue culture chamber slides (Lab-Tek). Cells were plated at a density of 5×10$^4$/well 24 h prior to analysis. Anti-H and anti-A primary antibodies were diluted in PBS containing bovine serum albumin at 2 mg/ml, to a final concentration of 10 μg/ml. Cell-bound primary antibodies were detected with FITC-conjugated goat anti-mouse IgM, diluted to 40 μg/ml in PBS containing 2 mg/ml bovine serum albumin.

Hapten Inhibition—Plated cells were washed twice with PBS, and were incubated for 30 min at 4° C. with 100 μl of diluted anti-H antibody, or with 100 μl of diluted antibody containing different oligosaccharide haptens, each at a concentration of 20 mM. The chambers were then washed twice, and 100 μl of FITC-conjugated goat anti-mouse IgM was added. After 30 min at 4° C., the chambers were washed three times with PBS, and the cells were fixed at room temperature for 10 min in 3.7% formaldehyde in PBS. The cells were washed twice with PBS, the chambers were removed, and the slide was mounted in PBS containing 25% glycerol. Cells were examined by fluorescence microscopy using a Zeiss Axiophot photomicroscope equipped with fluorescence epiillumination.

Labeling of Intact Cells with Human Blood Group A (α-1,3)GalNac Transferase—Cells plated in culture slide chambers were washed twice with 150 mM NaCl and were then fixed for 10 min at room temperature in 3.7% formaldehyde in 150 mM NaCl. The cells were washed three times with 150 mM NaCl and were then incubated with 100 μl of complete transferase reaction mixture or a control mixture. The complete transferase mixture consisted of 150 mM NaCl, 15 mM MnCl$_2$, 50 mM sodium cacodylate, pH 6.8, 0.2% bovine serum albumin, 1 mM UDP-GalNAc, and 1.14 units of human blood group A (α-1,3)GalNAc transferase. Control mixtures consisted of identical components except for the omission of either UDP-GalNAc or blood group A (α-1,3)GalNAc transferase. Incubations were performed at 37° C. and were terminated after either 4 or 24 h by washing the chambers twice with PBS. The cells were then analyzed by indirect immunofluorescence using mouse monoclonal anti-A or anti-H antibodies, as described above for the hapten inhibition studies.

Southern Blotting

Genomic DNA was digested to completion with restriction enzymes (8 units/μg DNA, overnight digestion). The restriction fragments were fractionated by electrophoresis through 0.6% agarose gels buffered in Tris-borate-EDTA. The DNA fragments were then transferred to nylon membranes (Hybond-N, Amersham Corp.), according to the standard Southern blotting method. Blots were prehybridized at 39° C. for at least 2 h in 50% formamide, 5 SSC (1×SSC is 150 mM NaCl, 15 mM sodium citrate, pH 7.0, 1×PE is 50 mM Tris, pH 7.5, 0.1% sodium pyrophosphate, 1% sodium dodecyl sulfate, 0.2% polyvinylpyrrolidone (M$_r$40,000), 0.2% Ficoll (M$_r$400,000), and 5 mM EDTA), and 150 μg/ml denatured salmon sperm DNA. Hybridizations were done in the same solution at 39° C. for at least 16 h. Blots were washed four times at room temperature in 2×SSC, 0.1% sodium dodecyl sulfate, and then once for 30 min at 65° C. in 0.75×SSC, 0.5% sodium dodecyl sulfate. The BLUR8 probe consisted of a 300-base pair BamHI segment isolated from the BLUR8 plasmid. This fragment was subjected to two cycles of gel purification prior to labeling to ensure that it was free from contaminating plasmid sequences. Probes were labeled with [α$^{32}$p]dCTP to a specific activity of at least 5×10$^8$ cpm/μg using the random priming method.

Paper Chromatography

Descending paper chromatography was performed using Whatman No. 40 in ethyl acetate/pyridine/water (10:4:3; Solvent A) or using Whatman No. 3MM in 95% ethanol/1M ammonium acetate (7:3; Solvent B). $^{14}$C-Labelled compounds were located by autoradiography of dried chromatograms. Alternatively, the dried chromatograms were cut into 1 cm strips and the radiolabelled compounds were eluted with water. An aliquot of each eluate was mixed with scintillation cocktail and radioactivity was determined in a scintillation counter.

Preparation of Radiolabelled Standards

[$^{14}$C]Fucose-1-phosphate was prepared by enzymatic cleavage of GDP-[$^{14}$C]fucose (1 nmol) with snake venom phosphodiesterase (EC 3.1.4.1, 1 μl, 0.003 units, Boehringer-Mannheim) in 20 μl of 100 mM Tris-HCI, pH 8 at 37° C. for 1 h. The reaction was then fractionated by descending paper chromatography on Whatman No. 3MM using Solvent B for 20 h in parallel with GDP-[$^{14}$C]fucose and [$^{14}$C]fucose. [$^{14}$C Fucose-1-phosphate ($R_{fucose}$=0.45) was then eluted from the chromatogram with water and concentrated under vacuum. [$^{14}$C]Fucosylphenyl-β-D-galactoside was generated from GDP-[$^{14}$C]fucose (3 μM) and phenyl-β-D-galactoside (25 mM) by the action of (α1, 2)fucosyltransferase activity in human serum, using the reaction conditions described below for assay of α(1,2) fucosyltransferase. The products of this reaction were fractionated by descending paper chromatography on Whatman No. 40 for 4 h in Solvent A. [$^{14}$C] Fucosylphenyl-β-D-galactoside was identified by autoradiography of the dried chromatogram and was then eluted from the paper with water and concentrated under vacuum. Alternatively, [$^{14}$C] fucosylphenyl-β-D-galactoside was isolated from fucosyltransferase assay mixtures using the Sep-Pak procedure described below.

Cell Lines and Cell Culture

COS-1 cells were obtained from the American Type Culture Collection and were grown in Dulbecco's modified Eagle's medium containing 10% fetal calf serum.

Protein Determinations

Protein concentrations were determined by the BCA method (Pierce Chemical Co.) according to the manufacturer's instructions. Bovine serum albumin was used as the standard.

Preparation of Cell Extracts

Cells were washed with PBS, removed from culture dishes with a rubber policeman, and pelleted by centrifugation. Cell pellets were resuspended in 2 volumes of cold 1% Triton X-100 (Surfactamps X-100, Pierce Chemical Co.) and sonicated for 15 seconds using a Branson sonicator equipped with a micro tip at 50% power. These extracts were either assayed immediately, or were stored at −20° C. until use. Under these conditions, enzyme activity in the frozen extracts was stable for several weeks, but deteriorated rapidly on repeated freezethawing. Tissues from C3H mice were isolated, minced with a razor blade, suspended in 2 volumes of 1% Triton X-100 and sonicated as described above, centrifuged at 1500×g for 5 min and the supernatants were collected. Mouse intestinal mucosa extracts were prepared by everting the small intestine onto a thin polypropylene rod, scraping the mucosa cells into phosphate buffered saline, and collecting the cells by centrifugation at 1500×g. Extracts were then prepared as described above.

Partial Purification of Mouse Intestinal ($\alpha$1,2) Fucosyltransferase

Preliminary experiments indicated that extracts prepared from mouse intestinal mucosa contained large amounts of an activity that hydrolyzed GDP-fucose in an acceptor-independent manner. Since substrate hydrolysis interfered with accurate determination of ($\alpha$1,2)fucosyltransferase activity, intestinal extracts were fractionated by anion exchange chromatography to separate GDP-fucose hydrolysis activity from ($\alpha$1,2)fucosyltransferase activity. All procedures were performed at 40° C. Two ml of the Triton-solubilized extract was made 10 mM in Tris-HCl, pH 7.6, and treated for 5 min with 2 ml (bed volume) of DEAE-cellulose (DE52, Whatman) previously equilibrated with 10 mM Tris-HCl, pH 7.6. The enzyme solution was filtered, made 10 mM in sodium phosphate buffer and the pH was adjusted to 6.1. Approximately 47% of the enzyme activity present in the initial extracts was recovered after the DEAE-cellulose fractionation procedure. A second treatment with DEAE-cellulose resulted in substantial loss of enzyme activity with no significant reduction in GDP-fucose hydrolysis activity (data not shown). When used under standard fucosyltransferase assay conditions, but in the absence of added acceptor, this preparation hydrolyzed less than 2% of the GDP-fucose initially present in the reaction.

Ammonium Sulfate Fractionation of Serum

Serum was prepared from freshly drawn blood obtained from a non-Secretor individual. The blood was clotted in a glass tube at 37° C. for 1 h and was immediately fractionated by ammonium sulfate precipitation exactly as described. The 20%–40% ammonium sulfate fraction was dialyzed against 2 changes of 4 liters of water (8 h each) at 4° C. Assay of ($\alpha$1,2)fucosyltransferase was done immediately. Alternatively, the fractionated serum was aliquoted and stored at −20° C. until use.

Ion Exchange Chromatography of Human Milk ($\alpha$1,2)Fucosyltransferase ($\alpha$1,2)Fucosyltransferase was isolated from human milk by published procedures. Briefly, 300 ml of milk from a Se-positive donor was defatted by centrifugation and was extensively dialyzed against 20 mM sodium cacodylate, pH 6.0. This was applied to a column (2.6×115 cm) of sulfopropyl-Sephadex equilibrated in 20 mM cacodylate, pH 6.0. The column was then washed with 1 liter of 20 mM cacodylate, pH 6.0, and was eluted with a linear gradient made from 1.5 liter each of 20 mM cacodylate, pH 6.0, and 500 mM NaCl in 20 mM cacodylate, pH 6.0. Fractions (13 ml) were collected and assayed for ($\alpha$1,2)fucosyltransferase activity using phenyl-$\beta$-D-galactoside acceptor as described below. Fractions 130–144 contained ($\alpha$1,2) fucosyltransferase activity. These were combined, concentrated to 1 ml by ultrafiltration in an Amicon stirred cell fitted with a YM5 membrane (MW cutoff=5,000), and were then equilibrated against cold deionized water. The concentrated enzyme was aliquoted and stored at −80° C.

Synthesis and Characterization of GDP-$\beta$-L-fucose and GDP-$\alpha$-L-fucose GDP-$\beta$-L-fucose was synthesized and purified by modifications of the method of Nunez et al. (Nunez et al, Can. J. Chem., 59, 2086–2095, 1981). The modified method described here eliminates the need to separate the anomeric 1-fucopyranosyl phosphates by differential crystallization prior to subsequent synthetic steps. Separation of anomeric products is effected by HPLC subsequent to the last synthetic procedure.

Pyridine and tetrahydrofuran (Aldrich) used in the synthesis were boiled under reflux over calcium hydride, distilled and stored over 4 Å molecular sieves. All evaporations were performed under reduced pressure on a rotary evaporator, with a bath temperature below 35° C. L-Fucose was acetylated exactly as described in Nunez et al (Can. J. Chem., 59, 2086–2095, 1981). The resulting mixture of 2,3,4-tri-O-acetyl-$\alpha$- and $\beta$-L-fucopyranoses (2.7 g, 9.27 mmol) was phosphorylated using o-phenylene phosphochloridate. The crude reaction product containing a mixture of anomeric 1-fucopyranosyl phosphates was fractionated on a Dowex-1 column ($HCO_3^-$, 20–50 mesh, 1.5×23 cm) pre-equilibrated in water. After application of the anomeric mixture, the column was washed with water (500 ml) and eluted with 400 mM triethylammonium bicarbonate buffer, pH 7.5 (250 ml). The triethylammonium bicarbonate eluant was evaporated to a thick syrup under reduced pressure. The syrup was dissolved in water and evaporated to dryness. This partially purified anomeric mixture of 1-fucopyranosyl phosphates (bis-triethylammonium salt, crude yield 70%) was used for the synthesis of GDP-$\beta$-L-fucose. The anomeric 1-fucopyranosyl phosphates (200 mg) were first repeatedly dissolved in dry pyridine and then evaporated to dryness in vacuo. Guanosine 5'-phosphomorpholidate (400 mg) was then added to the dried anomeric 1-fucopyranosyl phosphates. This mixture was subjected to repeated resuspension in dry pyridine and evaporation to dryness in vacuo. The reaction mixture was then suspended in dry pyridine (15 ml) and was incubated at room temperature. The formation of GDP-$\beta$-L-fucose was monitored daily by high performance liquid chromatography (HPLC) on a weak anion exchange column (AX 300, 4.6 mm×22 cm, Pierce Chemical Co.). An aliquot (10 $\mu$l) from the reaction mixture was evaporated to dryness, dissolved in water and mixed with GDP-[$^{14}$C]fucose (2000 cpm). The sample was then applied to the HPLC column equilibrated in water, and was eluted with a linear gradient from 100% water to 250 mM triethylammonium acetate, pH 7.0, in 60 min at a flow rate of 2 ml/min. The eluant was monitored at 268 nm, and 0.5 ml fractions were collected for scintillation counting to identify the co-injected GDP-[$^{14}$C]fucose. Three peaks absorbing at 268 nm eluted at approximately 180 mM triethylammonium acetate. The retention time of the first peak (38.5 min) was identical to the retention time of GDP-$\alpha$-L-fucose (see below). The second peak eluted at 40.6 min and coeluted with the GDP-$\beta$-L-[$^{14}$C]fucose standard. A third small peak eluting at 42.4 min was not identified. The reaction was judged to be essentially complete after 5 days. The proportion of α to β anomer in the final reaction mixture was found to be approximately 2:3. The reaction was then evaporated to dryness and dissolved in water. GDP-β-L-fucose was purified from this solution on a preparative Hydropore AX column (21.4 mm×25 cm, Rainin Instruments Co.). Aliquots of the aqueous solution were applied to the column equilibrated in water, and the sample was eluted with a linear gradient of 100% water to 200 mM triethylammonium acetate, pH 7.0, in 45 min, at a flow rate of 10 ml/min. The eluant was monitored at 268 nm. GDP-α-L-fucose eluted at 36.2 min. GDP-β-L-fucose eluted at 38.5 min. The GDP-β-L-fucose peak was collected and evaporated to dryness under reduced pressure. Ammonium acetate was removed by repeated co-evaporation with water. The compound that co-eluted with GDP-[$^{14}$C]fucose, and that we tentatively identified as GDP-β-L-fucose, was subjected to negative ion fast atom bombardment mass spectrum analysis (xenon), using a VG mass spectrometer (model 7B-250S). The results (m/z [M-H]$^-$ 588) were consistent with this identification. The compound was then analyzed by proton decoupled $^{13}$C NMR spectroscopy to confirm the anomeric configuration of the fucose, and to further establish the identity of the compound as GDP-β-L-fucose. Proton decoupled $^{13}$C NMR spectra were obtained on a Bruker WM 360, operating at 909.5 MHz and a sweep width of 221 ppm with 32K data points. Probe temperature was 38±° C. Resonances are reported in ppm relative to tetramethylsilane. This analysis yielded the following spectral data: $^{13}$C NMR (40 μM in D$_2$O, pH 7.0); guanine: δ140.27 (C1 and C8), 156.46 (C2), 154.38 (C4), 118.85 (C5), 161.46 (C6); ribosyl moiety: 89.36 (C1), 76.06 (C2), 73.6 (C3), 86.4 (C4), 67.8 (C5); fucosyl moiety: 100.9 (C1), 75.09 (C2), 73.94 (C3), 73.71 (C4), 73.02 (C5), 17.35 (C6). The distinction between anomeric forms of GDP-L-fucose is based upon the chemical shift of anomeric C(1) of the fucose ring. The C(1) resonance of the fucose ring in the β-anomer is shifted downfield (100.9 ppm) relative to the resonance of the anomeric C(1) in the α anomer (98.31 ppm, see below). The values obtained for this compound are essentially identical to those reported by Nunez et al. for GDP-β-L-fucose. The resonances attributable to the C atoms of the guanine, ribose and fucose ring are also in agreement with the literature values.

GDP-α-L-fucose was synthesized in a manner similar to that described for the preparation of GDP-β-L-fucose, except that the dicyclohexylammonium salt of (α-L-(-)-fucose-1-phosphate (Sigma) was used instead of the anomeric mixture of 1-fucopyranosyl phosphates. Analysis and purification of GDP-α-L-fucose was performed by HPLC using the same conditions described for GDP-β-L-fucose. The purified compound, tentatively identified as GDP-α-L-fucose, was subjected to analysis by negative ion fast atom bombardment mass spectroscopy. The results (m/z [M-H]$^-$ 588) were consistent with this assignment. The subsequent analysis of the compound by $^{13}$C NMR spectroscopy yielded the following spectral data: $^{13}$C NMR (50 μM in D$_2$O, pH 6.97); guanine: δ140.27 (C1 & C8), 156.46 (C2), 154.41 (C4), 118.84 (C5), 161.46 (C6); ribosyl moiety: 89.35 (C1), 76.04 (C2), 71.98 (C3), 86.4 (C4), 67.8 (C5); fucosyl moiety: 98.31 (C1), 70.36 (C2), 72.99 (C3), 74.3 (C4), 70.36 (C5), 17.88 (C6). The C(1) resonance of the fucose ring in this compound (98.31 ppm) is consistent with an α anomeric configuration, as reported by Nunez et al. The resonances attributable to the C atoms of the guanine and the ribose ring are also in agreement with the literature values reported for these atoms in GDP-β-L-fucose. GDP-β-L-fucose was found to be inactive as a substrate for (α1,2) fucosyltransferase.

Assay of GDP-L-fucose:β-D-galactoside:2-α-L-fucosyltransferase

Fucosyltransferase assays were performed by a modification of the procedure reported by Chester et al. (Chester et al, Eur. J. Biochem., 69: 583–593, 1976). The standard assay contained GDP-[$^{14}$C]fucose (3 μM), phenyl-β-D-galactoside (25 mM), ATP (5 mM) and the enzyme solution (1–10 μl) in 20 μl of 25 mM sodium phosphate buffer, pH 6.1. Based upon preliminary assays, amounts of added enzyme activities were adjusted to ensure that reactions were linear throughout the period of incubation (4 h for fractionated serum, 2 h for each of the other enzyme preparations). Under these conditions, less than 15% of the substrate was consumed during the incubation period. For the determination of pH optima, assays were buffered with 25 mM sodium acetate, sodium phosphate, or Tris-HCl, using concentrated solutions of these buffers previously adjusted to various pH values. The final pH value of each reaction was determined with a micro pH probe. In assays to determine the apparent Km values for GDP-fucose, GDP-[$^{14}$C]fucose was diluted with unlabeled GDP-fucose to a final specific activity of 26.3 mCi/mmol. The concentration of GDP-fucose in this stock solution was calculated from the UV absorbance at 254 nm of an aliquot diluted in water. The molar extinction coefficient of GDP (ϵ=13800 at 254 nm, pH 7.0) was used for this calculation since the extinction coefficient of GDP-fucose is not known. This stock was then used to yield variable GDP-fucose concentrations (3–300 μM) in the assays. The concentration of phenyl-β-D-galactoside in these assays was 25 mM, for all but the milk-derived enzyme. This was assayed in the presence of 75 mM phenyl-β-D-galactoside since the apparent Km exhibited by this enzyme for this acceptor is 15.1 mM. In assays to determine apparent Km values for phenyl-β-D-galactoside, the concentration of the acceptor was varied from 0.5 to 100 mM. GDP-[$^{14}$C]fucose was present in these assays at a concentration of 3 μM. The relatively low specific activity of commercially available GDP-[$^{14}$C] fucose, and its cost, necessitated the use of a substrate concentration well below its $K_m$ in these experiments. All assays were performed at 37° C. Assays were terminated after an appropriate period of time by addition of 20 μl of ethanol, followed by dilution with 1 ml of water. The mixture was then centrifuged at 15,000×g for 5 min. The supernatant contained virtually 100% of the radiolabelled product; this was collected, and an aliquot was used for separation and quantitation of the fucosylated product using the hydrophobic interaction chromatography method described below. All assays were performed in duplicate or triplicate and included parallel incubations done in the absence of acceptor. The values obtained in the absence of exogenous acceptor were subtracted to correct for the presence of endogenous acceptor molecules. This background acceptor "activity" was always less than 3% of the radioactivity incorporated into the phenyl-β-D-galactoside acceptor. Apparent Michaelis constants were derived from Lineweaver-Burke plots of acceptor concentration-rate determinations. Intercepts were calculated by the least squares estimation method.

A separation procedure based upon hydrophobic interaction chromatography was developed for rapid processing of large numbers of samples. This procedure effects separation of [$^{14}$C]fucosylphenyl-β-D-galactoside product from GDP-[$^{14}$C]fucose on disposable C-18 Sep-Pak cartridges (Waters-Millipore). The bottom of the Sep-Pak cartridge is mounted in one hole of a two-holed rubber stopper, and a 5 ml syringe is attached to the top of the cartridge. The other hole in the stopper is attached to a vacuum source (approximately 350 mm of Hg). The mounted Sep-Pak cartridge is prepared by washing with 5 ml of acetonitrile, followed by 5 ml of water. This is done by separately pipetting each wash solution into the attached syringe barrel and drawing it through the cartridge under the vacuum created when the rubber stopper (with attached vacuum line) is pressed onto the top of a 20 ml plastic scintillation vial. The contents of the syringe are aspirated through the cartridge into the vial. The fucosyltransferase reaction sample is then loaded into the syringe and aspirated through the cartridge into a fresh scintillation vial. The [$^{14}$C]fucosylphenyl-$\beta$-D-galactoside is retained on the Sep-Pak cartridge. The cartridge is then washed sequentially by aspiration with three 2 ml portions of water, collecting each wash into a new scintillation vial. The [$^{14}$C]fucosylphenyl-$\beta$-D-galactoside product is then eluted by aspiration with three 2 ml portions of 50% acetonitrile. Scintillation cocktail (10 ml, Biosafe II, Research Products International) is added to each vial to obtain a clear solution and the radioactivity in each is determined by scintillation counting. Radioactivity eluting in fractions 1–4 represents GDP-[$^{14}$C]fucose, fucose-1-phosphate, and [$^{14}$C]fucose present either as a contaminant in the substrate as obtained from the manufacturer (approximately 1%), or that is formed by substrate or product hydrolysis. Fractions 5–7 represent [$^{14}$C]fucosylphenyl-$\beta$-D-galactoside. The recovery of radioactivity with this procedure exceeds 97%. Reconstruction experiments showed that recovery of pure [$^{14}$C]fucosylphenyl-$\beta$-D-galactoside is essentially 100%. Separation and recovery are independent of pH and enzyme source, and are tolerant of detergents (Triton X-100 and Lubrol-PX) at concentrations up to 2%. Product separation by this method requires approximately one minute per sample. Sep-Pak cartridges have been reused indefinitely with no deterioration in performance.

The Sep-Pak method does not separate GDP-[$^{14}$C]fucose from [$^{14}$C]fucose-1-phosphate and thus cannot detect nucleotide pyrophosphatase activity that may consume GDP-fucose while generating fucose-1-phosphate and/or fucose. ATP (5 mM) was therefore included in all assays to inhibit nucleotide pyrophosphatase activity. Effective inhibition of pyrophosphatase activity was confirmed by descending paper chromatography analysis of mock fucosyltransferase assays using each enzyme preparation. Each enzyme source was incubated for 1 to 4 h at 37° C. in 20 $\mu$l of standard assay cocktail, but in the absence of phenyl-$\beta$-D-galactoside. After the reactions were terminated, an aliquot of each was spotted on Whatman No. 3MM, fractionated by descending paper chromatography for 20 h in solvent B, and radioactivity was determined as described above. Authentic GDP-[$^{14}$C]fucose, [$^{14}$C]fucose-1-phosphate, and L-[$^{14}$C]fucose standards were chromatographed in parallel. This system separates GDP-fucose, fucose-1-phosphate, and fucose. It therefore allows quantitation of the amount of GDP-[$^{14}$C]fucose remaining at the end of the incubation, and thus provides an estimate of pyrophosphatase activity. Under the standard assay conditions, more than 97% of the GDP-[$^{14}$C]fucose initially present in each mock reaction remained unhydrolyzed and available for transglycosylation.

Each enzyme preparation was also tested for $\alpha$-fucosidase activity that could hydrolyze the [$^{14}$C]fucosylphenyl-$\beta$-D-galactoside product and prevent accurate determination of ($\alpha$1,2)fucosyltransferase activity. Enzyme preparations were incubated with purified [$^{14}$C]fucosylphenyl-$\beta$-D-galactoside (7000 cpm, 10 pmol) in fucosyltransferase assay buffer, but in the absence of added GDP-[$^{14}$C]fucose or phenyl-$\beta$-D-galactoside. These reactions were incubated at 37° C. for various times, and were then fractionated by the Sep-Pak method to determine the amount of remaining [$^{14}$C]fucosylphenyl-$\beta$-D-galactoside. Fractionated human serum and mouse intestinal mucosa extracts each contained significant $\alpha$-fucosidase activity. However, inclusion of 10 mM L-fucose in the reaction cocktail effectively inhibited fucosidase activity in these enzyme preparations. Therefore 10 mM L-fucose was included when assaying these enzyme sources. Significant amounts of a-fucosidase activity were not detected in any of the other cell extracts; product hydrolysis never exceeded 1%/h under the standard assay conditions. Reconstruction experiments with these extracts showed that L-fucose at a concentration of 10 mM does not alter the activity of ($\alpha$1,2)fucosyltransferase.

In aggregate, these experiments showed that, under the conditions used to assay fractionated human serum, human milk, and mouse intestinal mucosa, or crude cell extracts, the quantity of [$^{14}$C]fucosylphenyl-$\beta$-D-galactoside product determined reflected true enzymatic activity, because both product hydrolysis and acceptor-independent hydrolysis of the GDP-fucose substrate were negligible.

Digestion of [$^{14}$C]Fucosylphenyl-$\beta$-D-galactoside with $\alpha$-Fucosidase

[$^{14}$C]Fucosylphenyl-$\beta$-D-galactoside (approximately 10,000 cpm) was digested with 0.025 units of bovine kidney $\alpha$-L-fucosidase (EC 3.2.1.51, Sigma) in a final volume of 20 $\mu$l containing 5 mM sodium citrate pH 6.0, at 37° C. for 1 h. This mixture was then fractionated by descending paper chromatography on Whatman No. 40 in Solvent A for 4 h. The products of the digestion were identified by comparison to parallel separations of L-[$^{14}$C]fucose and [$^{14}$C] fucosylphenyl-$\beta$-D-galactoside standards.

Isolation of Human DNA Restriction Fragments from Transfectant Clone s2-2

High molecular weight genomic DNA was isolated from the H-expressing secondary transfectant s2-2, digested to completion with EcoRI, and fractionated through a 1% agarose gel buffered in tris-borate-EDTA. The region of the gel containing the 2.7 kb and the 3.4 kb human EcoRI fragments was divided into 3 mm slices and the DNA in these was isolated by electroelution. Aliquots of the size-fractionated DNA were analyzed by Southern blotting with a radiolabelled Alu probe (BLUR8), using hybridization and wash conditions described above. Fractions containing either the 2.7 kb or the 3.4 kb fragment were used separately to prepare phage libraries in lambda gtll. These libraries were screened with a radiolabelled BLUR8 probe. Positive phages isolated from a tertiary screen were used to prepared phage DNA, and phages containing either the 2.7 kb EcoRI fragment or the 3.4 kb EcoRI fragment were identified by Southern blotting. The 3.4 kb or the 2.7 kb inserts were released from the phage arms by EcoRI digestion, purified by agarose gel electrophoresis and electroelution, and individually subcloned between the EcoRI sites in pWE15.

COS-1 Cell Transfection

Plasmid DNAs were transfected into COS-1 cells by the DEAE-dextran procedure. Seventy two hours after transfection, cells were harvested, extracts were prepared as described above, and extracts were subjected to assays for ($\alpha$1,2)fucosyltransferase activity, for GDP-fucose hydrolysis activity, and for $\alpha$-fucosidase activity.

Isolation of Human $\alpha$(1.2)FT cDNA Clones $1.8 \times 10^6$ recombinant clones from an A431 cell cDNA mammalian expression library were screened by colony hybridization, using a $^{32}$P-labeled 1.2 kb HinfI fragment of pH3.4 as a probe. Filters were hybridized for 18 hours at 42° C. in a hybridization solution described above, washed, and subjected to autoradiography. Two hybridization-positive colonies were obtained and isolated via two additional rounds of hybridization and colony purification. Preliminary sequence analysis of the inserts in both hybridization-positive cDNA clones indicated that they each were in the anti-sense orientation with respect to the pCDM7 expression vector promoter sequences. The largest insert was therefore re-cloned into pCDM7 in the sense orientation for expression studies, and the resulting plasmid was designated pCDM7-α(1,2)FT.

Flow Cytometry Analysis

COS-1 cells were transfected with plasmid DNAs using the DEAE-dextran procedure described above. Transfected cells were harvested after a 72 hour expression period and stained either with mouse IgM anti-H monoclonal antibody (Chembiomed; 10 μg/ml) or with a mouse IgM anti-Lewis a monoclonal antibody (Chembiomed; 10 μg/ml). Cells were then stained with fluorescein-conjugated goat anti-mouse IgM antibody (Sigma; 40 μg/ml) and subjected to analysis by flow cytometry.

Northern and Southern Blotting

A431 poly(A)-plus RNA (10 μg/lane) was subjected to Northern blot analysis. Genomic DNA (10 μg/lane) was subjected to Southern blot analysis. Blots were probed with $^{32}$P-labeled 1.2 kb HinfI fragment of pH3.4.

DNA Sequence Analysis

The insert in pCDM7-α(1,2)FT was sequenced by the method of Sanger using T7 DNA polymerase (Pharmacia) and 20-mer oligonucleotide primers synthesized according to the sequence of the cDNA insert. Sequence analyses and data base searches were performed using the Microgenie Package (Beckman) and the Sequence Analysis Software Package of the University of Wisconsin Genetics Computer Group.

Assay of α(1.2)fucosyltransferase Activity

Cell extracts, conditioned medium from transfected COS-1 cells, and IgG-Sepharose-bound enzyme were prepared and assayed for α(1,2)fucosyltransferase activity by the methods described above. One unit of α(1,2) fucosyltransferase activity is defined as 1 pmol product formed per hour. The apparent Michaelis constant for the acceptor phenyl-β-D-galactoside was determined exactly as described above.

Construction and Analysis of a Protein A-α(1,2)FT Fusion Vector

A 3196 bp StuI/XhoI segment of the cDNA insert containing the putative catalytic domain and 3'-untranslated sequences was isolated from pCDM7-α(1,2)FT. This fragment was blunt-ended using Klenow enzyme and ligated to phosphorylated and annealed oligonucleotides (CGGAATTCCCCACATGGCCTAGG, CCTAGGCCATGTGGGGAATTCCG) designed to reconstruct the coding sequence between the putative transmembrane segment proximal to the StuI site, corresponding to amino acids 33 through 365 of SEQ ID NO:6. The ligated fragment was gel purified, digested with EcoRI and then gel purified again. This EcoRI linkered fragment was ligated into the unique EcoRI site of pPROTA. One plasmid, designated pPROTA-α(1,2)FT,, containing a single insert in the correct orientation, was analyzed by DNA sequencing to confirm the sequence across the vector, linker and insert junctions. Plasmids pPROTA-α(1,2)FTC, PPROTA, pCDM7-α(1,2)FT, or pCDM7 were transfected into COS-1 cells. Following a 72 hour expression period, α(1,2)FT activities in the media, associated with cells, bound to a Sepharose IgG matrix, or to a control Sepharose matrix, were quantitated.

Example II

Cloning and expression of a DNA Sequence Encoding a UDP-Gal:β-D-Gal(1.4)-D-GlcNAc α(1.3) galactosyltransferase (DNA SEQ ID NO:3, Protein SEQ ID NO:4)

A Gene Transfer Approach to Isolate Cloned, Functional, β-D-galactosyl-1,4-N-acetyl-D-glucosaminide α-1,3-galactosyltransferase cDNAs. Tissue- and cell-specific expression of surface-localized terminal Gal(α1–3)Gal linkages is associated with expression of cognate (α1–3)GTs that catalyze a transglycosylation reaction between UDP-Gal and N-acetyllactosamine. COS-1 cells construct surface-expressed polylactosamine molecules that can function as an acceptor substrate for (α1–3)GT but do not express this enzyme or its surface-localized product (see below). The inventor therefore expected that cloned cDNAs encoding an (α1–3)GT would, if expressed in COS-1 cells, generate the surface-localized oligosaccharide product of that enzyme [terminal Gal(α1–3)Gal linkages]. Moreover, these particular transfectants could be isolated by virtue of adherence to plates coated with a lectin (GS I-B$_4$) that specifically binds terminal Gal(α1–3)Gal linkages. A standard transient expression system was used for this approach since it provides for the rescue of transfected cDNAs that determine the expression of cell surface molecules on COS-1 cells and allows the facile construction of large cDNA libraries in a mammalian expression vector.

Isolation of a Cloned cDNA That Determines Expression of GS I-B$_4$ Binding Activity in Transfected COS-1 Cells. Mouse F9 teratocarcinoma cells express an (α1–3)GT, and this enzyme activity increases concomitant with retinoic acid-induced differentiation of these cells. The inventor therefore prepared a cDNA expression library from retinoic acid-differentiated F9 cells and screened this library for cDNAs that determine expression of GS I-B$_4$ binding activity in transfected COS-1 cells. One plasmid (pCDM7-αGT) was isolated that, when transfected into COS-1 cells, determined expression of surface molecules that directed specific adherence of cells to culture dishes coated with GS I-B$_4$. Fluorescence-activated cell sorting analysis confirmed these observations. COS-1 cells transfected with pCDM7-αGT, but not cells transfected with pCDM7, stained brightly with fluorescein isothiocyanate-conjugated GS I-B$_4$. This staining could be inhibited with raffinose, a hapten for this lectin. These observations indicate that pCDM7-αGT determines de novo expression of surface-localized molecules recognized by GS I-B$_4$ and thus expression of terminal Gal(α1–3) Gal linkages on cell surface oligosaccharides.

cDNA Sequence Analysis Predicts a Protein with a Transmembrane Topology. The cDNA insert in pCDM7-αGT (SEQ ID NO:3), FIG. 2, is 1500 base pairs long and contains a single long open reading frame in the sense orientation with respect to pCDM7 promoter sequences. Three methionine codons are found within the first 15 codons of this reading frame; the inventor assigned the most proximal of these as the initiator codon, based on Kozak's rules for mammalian translation initiation. This reading frame predicts a protein of 394 amino acids in length (SEQ ID NO:4), FIG. 2, with a molecular mass of 46,472 Da. Hydropathy analysis indicates that this protein has features of a type II transmembrane molecule that is topologically identical to that predicted for two other mammalian glycosyltransferases. This topology predicts a 41-amino-acid, cytoplasmically oriented, $NH_2$-terminal segment; a single transmembrane domain consisting of a 19-amino-acid hydrophobic segment flanked by basic residues; and a large (presumably catalytic) COOH-terminal domain that would ultimately be targeted to the lumen of the Golgi. Two potential N-glycosylation sites are present, indicating that this protein, like other glycosyltransferases, may be synthesized as a glycoprotein. This cDNA sequence contains a long 5' untranslated region, with ATG codons at −90 and −251, suggesting that translational control mechanisms may participate in the regulation of expression of this sequence. This is reminiscent of another mammalian glycosyltransferase whose transcript also contains upstream ATG codons. The putative $NH_2$-terminal end of this protein lacks a characteristic cleavable signal sequence that may exist in one form of a murine β-1,4-galactosyltransferase.

Searches of the currently available protein and nucleic acid data bases (Protein Identification Resource, Release 21.0 and GenBank, Release 60.0) identified no sequences with significant similarity to the (α1–3)GT DNA sequence, including the sequences of a murine β-1,4-galactosyltransferase and a rat α-2,6-sialyltransferase.

Expression of a Catalytically-Active, Secreted Protein A-(α1–3)GT Fusion Protein. The inventor wished to confirm that this cDNA encodes an (α1–3)GT and to simultaneously exclude the formal possibility that it instead encodes a trans-acting molecule that induces (α1–3)GT activity by interaction with an endogenous gene, transcript, or protein. Therefore, sequences corresponding to the putative catalytic domain of this protein (residues 63–394 of SEQ ID NO:4) were fused in-frame to a secretable form of the IgG binding domain of *Staphylococcus aureus* protein A in the mammalian expression vector pPROTA yielding the vector pPROTA-α$GT_c$. This vector was then tested for its ability to express a catalytically active, secreted and soluble protein A-(α1–3)GT fusion protein.

COS-1 cells transfected with the pCDM7 vector or with the pPROTA vector generated no detectable cell-associated or released (α1–3)GT activity. By contrast, extracts prepared from COS-1 cells transfected with pCDM7-αGT or with the pPROTA-αGT, vector contained 4574 and 20,500 total units, respectively, of (α1–3)GT activity. Moreover, conditioned media prepared from cells transfected with pCDM7-αGT or pPROTA-αGT, contained soluble (α1–3)GT activity amounting to 4,155 units or 50,438 units, respectively. Importantly, the released activity generated by pPROTA-αGT, could be specifically bound to a IgG-Sepharose matrix, whereas the released activity generated by pCDM7-αGT did not interact with this affinity adsorbent. These results indicate that this cloned cDNA encodes an (α1–3) GT, show that information sufficient to generate a catalytically active (α1–3)GT resides within the 332 amino acids distal to the putative transmembrane segment, and show that the catalytic domain can be affinity purified in an enzymatically active state as a portion of a bipartite fusion protein.

Determination of the Structure of the Trisaccharide Product of the (α1–3)GT. Exoglycosidase digestion was used to confirm the α-anomeric linkage predicted for the oligosaccharide product generated by the recombinant enzyme. Radiolabeled trisaccharide product was prepared from UDP-[$^{14}$C]Gal and N-acetyllactosamine by using the IgG-Sepharose-bound enzyme activity generated by pPROTA-α$GT_c$. Digestion of the HPLC-purified trisaccharide product with a galactosidase resulted in quantitative release of [$^{14}$C]Gal, whereas the trisaccharide was completely resistant to β-galactosidase digestion.

To confirm that carbon 3 of the galactose in the N-acetyllactosamine acceptor is involved in the glycosidic linkage formed by the recombinant enzyme, the inventor prepared a [$^3$H]Gal-labeled N-acetyllactosamine acceptor and incubated it with IgG-Sepharose-bound protein A-(α1–3)GT activity and 1 mM UDP-Gal under the standard (α1–3)GT reaction conditions. The trisaccharide product of this reaction was purified and subjected to methylation analysis. Radioactive 2,4,6-trimethylgalactose was identified. Together, these results indicate that the recombinant enzyme can utilize UDP-Gal and N-acetyllactosamine as substrates to construct a trisaccharide product with the structure Gal(α1–3)Gal(β1–4)-GlcNAc.

Northern Blot Analysis. The (α1–3)GT cDNA hybridizes to a single 3.6-kilobase transcript in F9 teratocarcinoma cells. The inventor's DNA sequence analysis of another cloned (α1–3)GT cDNA isolated by colony hybridization indicates that the insert in pCDM7-αGT represents the 5' end of this transcript. The remaining 2.1 kilobases of this transcript consist of 3' untranslated sequence not rescued by the expression cloning procedure.

The specific activity of (α1–3)GT in retinoic acid-differentiated F9 teratocarcinoma cells is approximately 4-fold higher than that in untreated F9 cells. Northern blot analysis indicates that steady-state levels of the (α1–3)GT transcript also increase concomitant with retinoic acid-induced differentiation of F9 teratocarcinoma cells. These results are similar to those reported in F9 cells with β-1,4-galactosyltransferase and suggest that the dynamic changes in cell surface oligosaccharide structures known to accompany in vitro differentiation of this cell line are associated with significant changes in glycosyltransferase gene expression.

Experimental Procedures for Example II, "Cloning and expression of a DNA sequence encoding a UDP-Gal:β-D-Gal(1,4)-D-GlcNAc α(1,3)galactosyltransferase".

Construction of an F9 Cell cDNA Library. A cDNA library was prepared from poly(A)$^+$ RNA isolated from retinoic acid-differentiated mouse F9 teratocarcinoma cells by using the procedure of Seed and Arruffo, and the mammalian expression vector pCDM7. pCDM7 is a progenitor of the vector pCDM8; pCDM7 lacks the polyoma sequences present in pCDM8, but is otherwise virtually identical. The library contained 3×10$^6$ independent recombinants.

Isolation of a Mouse (α1–3)GT cDNA Clone. Plasmid DNA was prepared from an amplified portion of the library and was transfected in to COS-1 cells by using the DEAE-dextran procedure. Forty samples of 5×10$^5$ COS-1 cells (in 100-mm dishes) were transfected with 50 μg of plasmid DNA each. After a 72-hr expression period, the transfected COS-1 cell monolayers were harvested and panned on dishes coated with *Griffonia simplicifolia* isolectin I $B_4$ (GS I-$B_4$). Lectin panning dishes were prepared by using 10 μg of GS I-B4 per ml in phosphate-buffered saline (PBS) containing 0.1 mM Ca$^{2+}$ and 0.1 mM Mn$^{2+}$. Plasmid DNA molecules were rescued from adherent cells and were transformed into the *Escherichia coli* host MC1061/P3. Plasmid DNA was prepared from these transformants and was subjected to an additional screening by the same procedure. Sib selection was subsequently used to screen for plasmids that determined expression of GS I-$B_4$ binding activity in COS-1 cells. *E. coli* transformants containing plasmid molecules rescued from the second screening were plated to yield 16 pools containing between 100 and 5000 colonies each. Plasmid DNAs were prepared from replica plates and were transfected separately into COS-1 cells, and the transfectants were screened by panning on GS I-B$_4$-coated dishes. These experiments indicated that approximately 1 out of 1000 colonies contained cloned cDNAs determining the GS I-B$_4$-binding phenotype. One "active" ~1000-colony pool was subdivided into several smaller pools, and these were each tested for GS I-B$_4$-binding activity. Three subsequent rounds of sib selection with sequentially smaller, active pools identified a single plasmid (pCDM7-αGT) that directed expression of GS I-B$_4$-binding activity in COS-1 cells.

Flow Cytometry

COS-1 cells transfected with plasmid DNAs were harvested 48–72-hr after transfection. These were stained with either fluorescein isothiocyanate-conjugated GS I-B$_4$ at 10 μg per ml in staining media or with fluorescein isothiocyanate- conjugated GS I-B$_4$ that had been previously incubated with 50 mM raffinose. Cells were then subjected to analysis by fluorescence- activated cell sorting as described above.

Northern Blotting and DNA Sequence Analysis

Northern blots were hybridized with radiolabeled pCDM7-αGT cDMA insert at 42° C. in hybridization solution. DNA sequencing was performed with the chain termination method by using oligodeoxynucleotides synthesized according to the sequence within the cDNA insert. Sequence data base searches and analyses were performed with the Sequence Analysis Software Package published by the University of Wisconsin Genetics Computer Group.

Assay of (α1–3)GT and Product Characterization

Extracts were prepared from transfected COS-1 cells. Cell extracts, conditioned medium from transfected cells, or IgG-Sepharose-bound enzyme was assayed for (α1–3)GT. One unit of (α1–3)GT activity is defined as 1 pmol of Gal transferred to N-acetyllactosamine acceptor per hour.

HPLC-purified, radiolabeled oligosaccharide reaction products were subjected to digestion with either α-galactosidase (Sigma, 20 mU) or β-galactosidase (Sigma, 1 mU) for 1 hr at 37° C. in buffers recommended by the manufacturer. Reaction products were then fractionated by HPLC. Methylation analysis of reaction product(s) was carried out according to standard procedures.

Construction and Analysis of the Protein A-(α1–3)GT Fusion Vector

A 1050-base-pair segment of the (α1–3)GT cDNA containing the putative catalytic domain was excised from pCDM7-αGT by digestion with EcoRI. This was cloned into the EcoRI site of pPROTA by using a double-stranded linker (5'-ACGGAATTCCGT-3') to maintain the correct reading frame, yielding plasmid pPROTA-αGT$_c$.

Plasmids pPROTA-αGT$_c$, pCDM7-αGT, and PPROTA were separately transfected into COS-1 cells. After a 72-hr expression period, the media were harvested and subjected to low-speed (300×g for 8 min) and high-speed (100,000×g for 1 hr) centrifugations. Supernatants were then adjusted to 0.05% Tween 20 and were incubated batchwise with 100 μl of preequilibrated IgG-Sepharose or Sepharose 6B overnight at 4° C. The matrices were then thoroughly washed and used directly in (α1–3)GT assays.

Example III
Isolation of a cloned human cDNA that encodes a GDP-Fuc:β-D-Gal (1.4/1.3)-D-GlcNac(/Glc)-α(1.3/1,4)-fucosyltransferase. (DNA SEQ ID NO:1, Protein SEQ ID NO:2)

In one embodiment, the present invention provides a gene transfer system that allows isolating cloned cDNAs encoding functional α(1,3)fucosyltransferase [α(1,3)FT] or α(1,4) fucosyltransferase [α(1,4)FT] molecules or that otherwise determine α(1,3)FT or α(1,4)FT expression, without the need to first purify the enzyme. This system instead exploits existing reagents that allow detection of the cell surface-expressed oligosaccharide product of these enzymes, and that provide for specific assay of their enzymatic activity.

This approach requires a recipient host cell with specific properties that allow selection of the appropriate cloned cDNA molecules. The host must not express α(1,3)FTs, nor cognate surface Gal β(1,4)[Fucα(1,3)]GlcNAc linkages (SSEA-1 structures). However, this host must synthesize the appropriate substrates for surface display of SSEA-1 molecules. These substrates include the nucleotide sugar GDP-fucose, and surface-expressed glycoconjugate molecules that may serve as oligosaccharide acceptors for the transglycosylation reaction. Each of these properties are fulfilled by COS-1 cells.

Fluorescence-activated cell sorter (FACS) analysis indicated that COS-1 cells do not express surface-localized SSEA-1 determinants. Enzyme analyses performed with COS-1 extracts confirmed that absence of SSEA-1 expression was due to a deficiency of α(1,3)FT activity. The inventor expected that COS-1 cells would contain substrate levels of GDP-fucose within their Golgi, since with the exception of certain lectin-resistant mutant cells lines, virtually all mammalian cells synthesize GDP-fucose and translocate it into the Golgi lumen. COS-1 cells also construct surface-expressed glycoconjugates containing unsubstituted polylactosamine moieties that represent potential oligosaccharide acceptors for α(1,3)FT activity determined by a transfected cDNA. The inventor confirmed that these substrates are available for use in the construction of surface-expressed, terminal fucose linkages by demonstrating expression of a different terminally-linked fucose linkage (H Fucα(1,2)Gal) on COS-1 cells after transfection with a cloned human gene fragment that the inventor had previously shown to determine expression of an α(1,2)FT. The inventor therefore observed that COS-1 cells could construct surface-expressed SSEA-1 molecules following transfection with α(1,3)FT-determining cDNAs.

Isolation of a Cloned cDNA That Determines Expression of an α(1,3)FT and Surface-Localized SSEA-1 Structures The human A431 cell line has been shown to express cell surface Lewis blood group a and b structures that represent the products of an α(1,4)FT. Enzyme assays performed with A431 extracts confirmed that cells also express a corresponding α(1,3)FT activity. A cDNA library was therefore constructed with A431 cell MRNA in the mammalian expression vector pCDM7 and was transfected into COS-1 cells. The transfected cells were screened by the procedure of Seed using a monoclonal antibody specific for SSEA-1 determinants.

In order to follow enrichment for an α(1,3)FT-determining cDNA during the selection procedure, an assay was employed in which 2'-fucosyllactose was used as an acceptor substrate. This acceptor can discriminate between the Lewis α(1,3/1,4)FT and nonallelic human α(1,3)FTs, since it is used efficiently by the former enzyme but not by the latter. With this assay, the inventor was unable to detect any enzyme activity in COS-1 cells transfected with the A431 cDNA library, or in cells transfected with amplified plasmid DNA isolated from the initial selection. However, amplified plasmid DNA obtained from the second selection was found to direct a low level of enzyme activity when transfected into COS-1 cells. A modest increment in enzyme activity was obtained after a third selection by panning. At this stage, "sib selection" was employed to identify and isolate a cloned α(1,3)FT cDNA. Pools of clones isolated from the third panning selection were tested for their ability to generate α(1,3)FT activity in transfected COS-1 cells. From these experiments, it was estimated that approximately one in 500 clones represented a plasmid that determined α(1,3)FT expression. One "active" pool of approximately 400 clones was further subdivided and the resulting pools were tested for their ability to generate enzyme activity in transfected cells. One clone (pCDM7-α(1,3/1,4)FT) in an active 16 clone pool was found to direct very high level expression of the α(1,3)FT. FACS analysis was used to confirm that this plasmid also directs surface expression of SSEA-1 (Lewis x) determinants (FIG. 8). COS-1 cells transfected with this plasmid stain brightly with anti-SSEA-1 antibody, but not with a control IgM anti-H antibody, whereas cells transfected with pCDM7 vector alone exhibit background staining with both antibodies. Identical results were obtained in experiments where the transfected cells were stained with an anti-Lewis a antibody (FIG. 8).

Deduced Protein Sequence of the Cloned cDNA Predicts a Transmembrane Topology

The cDNA insert in pCDM7-α(1,3/1,4)FT (SEQ ID NO:1) is 2022 nucleotides in length, and consists of a 72 bp 5' untranslated region, a continuous open reading frame of 1083 bp, and a 3' untranslated region of 867 bp that is terminated by a poly(A) tail.

This cloned cDNA hybridizes to a single prominent 2.3 kb transcript in A431 cells showing that this insert is essentially full-length. The nature of an additional faint 7.5 kb transcript is at present undefined. The initiation codon at the beginning of the long open reading frame is embedded within a sequence similar to the Kozak consensus initiation sequence and is preceded by two in-frame stop codons. There is also a single additional ATG upstream from the assigned initiator. This ATG also fits the Kozak consensus sequence, but initiates a very short in-frame sequence. The long open reading frame predicts a 361 amino acid protein (SEQ ID NO:2) of Mr 42,069 Da. Sequence comparisons with the latest DNA and protein sequence databases (Protein Identification Resource, Release 21.0, and GenBank, Release 60.0) identified no sequences with significant similarity to this sequence, except for a segment within the 3' untranslated region that is similar to human Alu sequences. The 3' untranslated region also contains 20 degenerate copies of a 16 nucleotide sequence of unknown functional significance.

Comparisons between the sequence predicted by the insert in pCDM7-α(1,3/1,4)FT and four different cloned mammalian glycosyltransferases revealed no obvious primary sequence similarities. While these latter enzymes also share no extensive primary sequence similarities, they exhibit an analogous overall structural organization. Specifically, these enzymes are representative of Type II transmembrane proteins, each composed of a short, $NH_2$-terminal cytoplasmic domain, a single transmembrane segment, and a larger, COOH-terminal catalytic domain that ultimately inhibits the Golgi lumen. Inspection and hydropathy analysis of the predicted protein sequence suggested that this protein maintains a similar structural organization. There is a single hydrophobic segment near the amino terminus that is comprised of 19 amino acids and is flanked by basic residues. This putative signal-anchor sequence would place 327 amino acids within the Golgi lumen, while leaving 15 residues within the cytosolic compartment.

The Protein Encoded by pCDM7-α(1,3/1,4)FT is a Fucosyltransferase

Expression data and the predicted topological similarity of this sequence to other glycosyltransferases, show that this cDNA encodes an α(1,3)FT. Nonetheless, these data are also formally consistent with the possibility that this cDNA sequence instead encodes a molecule that trans-determines α(1,3)FT activity by interaction with an endogenous gene, transcript, or protein. To demonstrate that enzymatic activity is directly associated with this molecule, the putative catalytic domain of the predicted polypeptide (residues 43–361 of SEQ ID NO:2) was fused to a secreted form of the IgG binding domain of *Staphulococcus aureus* protein A in the mammalian expression vector pPROTA, to generate the vector pPROTA-α(1,3/1,4-Ft),. Since this fusion protein would lack the putative transmembrane anchoring segment of the fucosyltransferase, the inventor expected it would be synthesized as a secreted molecule that could be affinity-purified on an IgG-containing matrix and subsequently tested for α(1,3)FT activity. COS-1 cells transfected with the control vectors pCDM7 or PROTA generated no detectable cell-associated or released enzyme activity. However, conditioned media prepared from COS-1 cells transfected with pPROTA-α(1,3/1,4)FT$_c$ or with pCDM7-α(1,3/1,4)FT, contained significant quantities of α(1,3)FT activity. Significantly, virtually 100% of the released activity generated by pPROTA-α(1,3/1,4)FT$_c$ was specifically retained by the IgG-Sepharose matrix, and approximately 24% of this activity could be recovered from the matrix after exhaustive washing. By contrast, the released activity generated by pCDM7-α(1,3/1,4)FT did not interact with the affinity adsorbent. These results indicate that the protein encoded by this cloned cDNA encodes a fucosyltransferase, demonstrate that information sufficient to generate α(1,3)FT activity resides within the enzyme's COOH-terminal 319 amino acids, and show that this approach can be used to affinity purify the catalytic domain in an enzymatically active state as a portion of a bipartite fusion protein.

The Fucosyltransferase is a Glycosylated Transmembrane Protein

In order to confirm the transmembrane topology predicted for the enzyme, fucosyltransferase cRNA was prepared and was subjected to analyses by a series of in vitro translation experiments. The $^{35}$S-methionine-labelled primary translation product generated in these experiments migrated with a molecular weight of approximately 37,500 Da. The discrepancy between this observed molecular weight and the predicted one (42,069 DA) may be reconciled by the observation that membrane-spanning proteins often migrate in an anomalously rapid manner through SDS-polyacrylamide gels, relative to soluble protein molecular weight markers. When this radiolabelled protein was generated by in vitro translation in the presence of canine pancreatic microsomes, it migrated with an Mr of approximately 42,000 Da. The ~6,000 Da increase in molecular mass observed when the translations were performed in the presence of microsomes suggests that two core glycosylation structures are added by microsomal oligosaccharyltransferase to the two potential asparagine-linked glycosylation sites during cotranslational translocation across the microsomal membrane. This product also co-sedimented with the microsomes, suggesting that the protein had become cotranslationally inserted within, or translocated across, the microsomal membrane. When this raiolabelled, microsome-associated protein was subjected to limit digestion with endoglycosidase H, its molecular mass was reduced to a one essentially identical to that of the primary translation product. Partial endoglycosidase H digestion generated an additional band of intermediate size, that likely consists of molecules that contain a single residual core glycosylation unit. These results indicate that the addition of core oligosaccharide structures is responsible for the increase in size of the protein observed in the co-translation experiments. These observations indicate that the two potential N-glycosylation sites found within the predicted fucosyltranserase amino acid sequence are glycosylated during translocation across the microsomal membrane.

Additional support for the predicted transmembrane topology of the fucosyltransferase was provided by the results of protease protection experiments. Co-translation in the presence of microsomes yields a 42,000 Da polypeptide that is resistant to digestion with protease. The protease-digested product migrates slightly faster than the undigested, microsome-associated polypeptide; this difference is most likely accounted for by removal of some or all of the 15 $NH_2$-terminal amino acids predicted to be displayed on the exterior of the microsomes. Addition of microsomes after translation yielded a protease-sensitive, nonglycosylated radiolabelled product, indicating that membrane insertion of the protein is a cotranslational, but not post-translation, event. A small amount of a ~34KDa polypeptide that is protease-sensitive and glycosylated can also be identified in these experiments. The precise nature of this protein is unknown, but it appears in a proteinase K concentration-dependent manner. The inventor therefore suspected that it represents a proteolytic fragment of the intact protein generated when the integrity of some microsomal vesicles is disrupted. In aggregate, these experiments indicate that the bulk of this polypeptide can be sequestered within the microsomal lumen by a cotranslational translocation process, ultimately yielding a product that is N-glycosylated. These results are consistent with the type II transmembrane topology predicted by the fucosyltransferase sequence.

The Fucosyltransferase Can Construct Two Distinct Glycosidic Linkages

It is believed that, in general, each glycosyltransferase is competent to perform a single transglycosylation reaction, that in turn generates a single glycosidic linkage. However, genetic and biochemical studies indicate that the human Lewis blood group locus may determine expression of a single fucosyltransferase capable of generating subterminal Fuc$\alpha$(1,3) and Fuc$\alpha$(1,4) linkages on several type I and type II acceptor substrates. In particular, the Lewis enzyme is thought to be the only human fucosyltransferase capable of using the acceptor 2'-fucosyllactose. Since plasmid pCDM7-$\alpha$(1,3/1,4)FT was isolated with an enrichment scheme involving an enzymatic assay based upon this acceptor substrate, it therefore seemed likely that its cDNA insert encodes the Lewis enzyme. To confirm this, the inventor performed a series of analyses to determine the acceptor specificities of the recombinant enzyme.

Extracts of COS-1 cells transfected with pCDM7-$\alpha$(1,3/1,4)FT were tested for their ability to catalyze transglycosylations between GDP-[$^{14}$C] fucose and the type I acceptor lacto-N-biose I, or the type II acceptors lactose and N-acetyllactosamine. There are only two possible classes of monofucosylated products that can be formed from each of these acceptors by known human fucosytransferases. These are H-active products containing a Fuc$\alpha$(1,2) linkage on the terminal Gal of these molecules, or Lewis x- or Lewis a-active products containing fucose linked in alpha anomeric configuration to the subterminal monosaccharide of these acceptors via either the monosaccharide's C4 hydroxyl (type I acceptor) or its C3 hydroxyl (type II acceptors). The inventor therefore fractionated the reaction products with a descending paper chromatography method that could distinguish between the two classes of reaction products possible with each acceptor, and thus allow determination of enzyme specificity.

The inventor found that lactose was utilized by the recombinant enzyme to form a radiolabelled compound with the chromatographic mobility characteristic of the Lewis x trisaccharide 3-fucosyllactose, and distinct from the other possible product, the type II H trisaccharide. Likewise, these extracts also generated 3-fucosyl-N-acetyllactosamine when N-acetyllactosamine was used as an acceptor. Radiolabelled fucose was quantitatively released from each product upon digestion with $\alpha$-fucosidase, indicating that the enzyme attaches fucose to these acceptor substrates in alpha anomeric configuration. These results are consistent with the flow cytometry observations indicating that pCDM7-$\alpha$(1,3/1,4)FT determines expression of the Gal$\beta$(1,4)[Fuc$\alpha$1,3] GlcNAc linkage representing the SSEA-1 determinant.

Moreover, the radiolabelled product of the type I acceptor lacto-N-biose I chromatographed with a mobility distinct from the H active standard 2'-fucosyllacto-N-biose I and consistent with its identity as the Lewis a trisaccharide 4-fucosyllacto-N-biose I. This product was also susceptible to digestion with $\alpha$-fucosidase. Identical results were obtained for all three disaccharide acceptors when affinity-purified protein A-fucosyltransferase was used in these experiments. Taken together, these results indicate that the recombinant fucosyltransferase can construct both Fuc$\alpha$(1,3) and Fuc$\alpha$(1,4) glycosidic linkages on type II and type I disaccharide acceptors, respectively.

In a complementary set of analyses, type I and type II blood group H trisaccharides were tested as acceptors for the enzyme encoded by the fucosyltransferase cDNA. Radiolabelled type I and type II H molecules were prepared by fucosylating their disaccharide precursors at the C2 hydroxyl of their terminal galactose residues, using cell extracts containing the blood group H $\alpha$(1,2)-FT and GDP [$^{14}$C]fucose. These HPLC-purified radiolabelled type I and type II H acceptors were then each used in reactions containing unlabelled GDP-fucose and affinity-purified fucosyltransferase activity generated by pPROTA-$\alpha$(1,3/1,4)FT$_c$. HPLC analysis of these reactions identified new radiolabelled compounds withchromatographic mobilities predicted for the Lewis b tetrasaccharide and the Lewis y tetrasaccharide, generated with the type I or type II acceptors, respectively. Virtually identical results were obtained with extracts prepared from COS-1 cells transfected with pCDM7-$\alpha$(1,3/1,4)FT. Results of these experiments and similar ones, are summarized in Table 2.

In a third series of experiments, the inventor demonstrated that this enzyme can operate on "type I" or "type II" acceptors whose terminal galactose residues are substituted with sialic acid in $\alpha$(2,3) linkage, to generate the sialyl Lewis x and sialyl Lewis a tetrasaccharide determinants. Flow cytometry analysis of COS-1 cells transfected with pCDM7-$\alpha$(1,3/1,4)FT and stained with a monoclonal anti-sialyl Lewis x antibody indicates that this plasmid can determine surface expression of the sialyl Lewis x antigen (FIG. 8), that is the product of $\alpha$(1,3)FT action on "type II" acceptors whose terminal galactose residues are substituted with sialic acid in $\alpha$(2,3) linkage. Likewise, COS-1 cells transfected with pCDM7-$\alpha$(1,3/1,4)FT and stained with a monoclonal anti-sialyl Lewis a antibody indicates that this plasmid can determine surface expression of the sialyl Lewis a antigen (FIG. 8), that is the product of $\alpha$(1,4)FT action on type I acceptors whose terminal galactose residues are substituted with sialic acid in α(2,3) linkage. These analyses indicate that the fucosyltransferase encoded by pCDM7-α(1,3/1,4)FT is able to construct two distinct glycosidic linkages on the subterminal Glc or GlcNAc of type I and type II acceptors, and that this does not depend upon the α(1,2)fucosylation or α(2,3)sialylation status of the terminal galactose on these acceptors. These properties mirror those reported for the fucosyltransferase activities determined by human Lewis blood group locus, and confirm that a single fucosyltransferase can catalyze the formation of two distinct glycosidic linkages.

The Fucosyltransferase cDNA Identifies Human Genomic Sequences Syntenic to the Human Lewis Blood Group Locus Genetic data indicate that the human Lewis blood group is determined by a locus on chromosome 19. The fucosyltransferase cDNA was therefore used for Southern blot analysis of a pair of human-mouse somatic cell hybrids that differ only by the presence or absence of human chromosome 19. The results indicate that at high stringency, the fucosyltransferase cDNA identifies cross-hybridizing sequences located on chromosome 19. Taken together with the enzymatic analyses, these data strongly suggest that this cloned cDNA represents the product of the human Lewis blood group locus.

Experimental Procedures for Example III, "Isolation of a cloned human cDNA that encodes a GDP-Fuc:β-D-Gal (1,4/1,3)-D-GlcNAc(/Glc)-α(1,3/1,4)-fucosyltransferase".

cDNA Library Construction

A cDNA library was prepared from poly(A)-plus RNA isolated from human A431 cells, using standard procedures and the mammalian expression vector pCDM7. pCDM7 lacks polyoma sequences present in the vector pCDM8, but is otherwise virtually identical. The library contained 2.6× $10^6$ independent recombinants.

Cell Lines

Mouse 3T3-human hybrid cell lines KLEJ-47 and KLEJ-47/P-1 were obtained from Dr. Howard Green (Harvard University, Boston). Mouse 3T3 cells were from Dr. Vishva Dixit (University of Michigan, Ann Arbor). The origins of all other cell lines, and conditions for cell growth are as previously described in the literature.

Preparation of Panning Dishes

Panning dishes were prepared by first coating them with goat anti-mouse IgM, and then with monoclonal anti-SSEA-1 antibody (ascites generously provided by D. Solter, diluted 1:1000).

cDNA Library Screening

The A431 library was screened as described previously. Plasmid DNA was rescued from transfected COS-1 cells adherent to panning dishes and introduced into the bacterial host MC1061/P3 by transformation. Transformants were grown to saturation in liquid culture under antibiotic selection, aliquots were removed for frozen storage, and the remainder of the culture was used to prepare plasmid DNA. A portion of this plasmid DNA was used for subsequent enrichment by transfection and immunoselection on anti-SSEA-1 panning dishes.

FACS Analysis

Transfected COS-1 cells were stained with the mouse IgM anti-SSEA-1 (anti-Lewis x) monoclonal antibody (1:1000 dilution of ascites) mouse monoclonal IgM anti-H or anti-Lewis a antibodies (Chembiomed, Ltd., Edmonton; 10 μ/ml), a mouse monoclonal IgM anti-sialyl Lewis x antibody (CSLEX, P. Terasaki, 10 μg/ml), or a mouse monoclonal IgG anti-sialyl Lewis a antibody (CSLEA, P. Terasaki, 1:1000 dilution of ascites). Cells were then stained with fluorescein-conjugated goat anti-mouse IgM (Sigma; 40 μg/ml) and subjected to analysis by fluorescence activated cell sorting as described previously in the literature by the inventor.

Northern and Southern Blotting

A431 cell RNA was subjected to Northern blot analysis as previously described. The probe consisted of a 1.7 kb XhoI - XbaI fragment isolated from the 5' end of the cDNA insert in plasmid pCDM7-α(1,3/1,4)FT. This fragment does not contain the portion of this cDNA that exhibits sequence similarity to human Alu sequences. This probe was labelled by nick translation with α[$^{32}$P]dCTP to a specific activity of 6×$10^8$ cpm/μg.

Genomic DNA was prepared and subjected to Southern blotting as described previously. Blots were subjected to a final wash for 30 minutes at 65° C. in O.1X SSC, 0.5% SDS. The probe used was identical to the one used for Northern blot analysis except that it was labelled with the random priming method.

Sequencing

The cDNA insert in plasmid pCDM7-α(1,3/1,4)FT was sequenced by the chain termination method using a double stranded plasmid DNA template and commercial reagents (Pharmacia). Both strands were sequenced using 17-mer or 19-mer oligonucleotide probes synthesized according to the sequence of the cDNA insert. The DNA sequence was assembled and analyzed using the Beckman Microgenie package, and the Sequence Analysis Software Package of the University of Wisconsin Genetics Computer Group.

In Vitro Transcription-Translation

Plasmid pCDM7-α(1,3/1,4)FT DNA was linearized downstream from the cloned cDNA insert by digestion with NotI. Capped RNA transcripts were then generated from this linearized template using a T7 polymerase promoter based in vitro transcription kit (Pharmacia). Transcripts initiate from the T7 promoter proximal to the cDNA cloning site in pCDM7. RNA transcripts produced in vitro were used to program a rabbit reticulocyte lysate in vitro translation system (Promega), in the presence of $^{35}$S-methionine (Amersham), according to the manufacturer's instructions. Membrane-associated radiolabelled in vitro translation products, generated in the presence of canine pancreatic microsomal membranes (Promega) (cotranslation) or generated prior to the addition of microsomes (post-translational microsome addition), were isolated from the bulk of the soluble reaction components by centrifugation through a sucrose cushion (0.5 M sucrose, 10 mM Tris 7.4, 150 mM NaCl; 170,000×g for 60 min). For endoglycosidase H digestions, pellets containing microsome- associated radiolabelled products were first resuspended in 50 mM sodium citrate pH 5.5, were made 0.2% in SDS, and were heated to 100° C. for 4 minutes. Aliquots of this material were then diluted with an equal volume of water and subjected to digestion with either 10 mU or 5 mU of endoglycosidase H for 20 hrs at 37° C., in the presence of 0.1% BSA, 0.5% Triton X-100, 0.5 mM PMSF, 40 μg/ml Bestatin, 10 μg/ml α$_2$ macroglobulin, and 30 μg/ml of E-64. Alternatively, the pellets were resuspended in ice cold in vitro translation buffer containing 5 mM $CaCl_2$, and were subjected to incubation with 150 μg/ml proteinase K, on ice for 1 hour, in the presence or absence of 1% Triton X-100. The various radiolabelled in vitro translation products were then denatured and reduced by heating to 100° C. for 4 minutes in 62.5 mM Tris pH 6.8, 100 mM dithiothreitol, 2% SDS, 10% glycerol, and 0.02% bromphenol blue. Samples were then fractionated through SDS polyacrylamide gels, and the gels were subjected to autoradiography.

Fucosyltransferase Assays

Cultured cells were washed in PBS, harvested by scraping with a rubber policeman, washed again in PBS, and pelleted by centrifugation. Cell extracts were prepared by resuspending cell pellets in 1% Triton X-100 such that the final protein concentration in the extracts was approximately 5 mg/ml (BCA method, Pierce Chemical Co.).

Fucosyltransferase assays were performed in 50 mM MOPS pH 6.5, 25 mM $MnCl_2$ 10 mM L-fucose, 5 mM ATP, 3 mM GDP-[$^{14}$C]fucose (specific activity of 600,000 cpm/nmol; 35,000 cpm per assay), 2.5 mM acceptor (e.g. 2'-fucosyllactose, N-acetyllactosamine, lactose or lacto-N-biose I), and up to 10 μl of cell extract, in a final volume of 20 μl. When determining α(1,3)FT specific activities achieved during the sib selection process, and in the analysis of the protein A-fucosyltransferase fusion protein experiments, the amount of added cell extract and incubation times were adjusted to yield (linear) reaction rates reflecting accurate specific activities. Reactions were incubated at 37° C. for 2 or 6 hours, and then terminated by the addition of 20 μl of ethanol, followed by dilution with 500 μl of $H_2O$. The terminated, diluted reactions were then centrifuged at 15,000×g for 5 min. Fifty μl of each reaction supernatant was counted to determine total radioactivity, and 200 μl of each was fractionated by Dowex-1 chromatography. The neutral radiolabelled material eluting from the column was then counted directly as a measure of product formation. Enzyme specific activity is defined as pmol of fucose transferred from GDP-fucose to acceptor per mg cell extract protein per hour. Neutral products were also further analyzed as described below by descending paper chromatography and by HPLC to confirm their identity. Parallel reactions were done in the absence of added acceptor to allow correction for transfer to endogenous acceptor molecules and for substrate and product hydrolysis. These control experiments indicated that less than 2.6% of the radioactivity in GDP-[$^{14}$C]fucose was found as a neutral product in the absence of added acceptor, and that virtually all of this material represented [$^{14}$C] fucose.

In instances where radiolabelled, H type I and H type II molecules were used as acceptors, nonradiolabelled GDP-fucose was included instead of GDP-[$^{14}$C fucose, and reactions were allowed to proceed for 16 hours. Residual unreacted neutral radiolabelled acceptor substrate, and neutral radiolabelled product were isolated by Dowex-1 chromatography and then analyzed by HPLC.

Preparation of Radiolabelled H Type I and H Type II Acceptors

Cell extracts containing a human α(1,2)FT activity were used to synthesize radiolabelled type I H or type II H acceptor molecules. The cell extracts were prepared from mH1–12 cells, a mouse L cell transfectant containing a human DNA segment that encodes a human α(1,2)FT. These extracts contain no detectable α(1,3)FT activity or α(1,4)FT activity. Lacto-N-biose I (20 mM), or N-acetyllactosamine (20 mM), were incubated with 100 μg of mH1–12 extract protein in 40 μl of 25 mM sodium cacodylate pH 6.2 containing 3 μM GDP-[$^{14}$C]fucose, for 16 hours at 37° C. Reactions were terminated by the addition of 40 μl of ethanol followed by dilution with 200 μl of water. Precipitated protein was removed by centrifugation at 12,000×g for 5 minutes, and the neutral radiolabelled reaction products in the supernatant were isolated by Dowex-1 chromatography. The type I H trisaccharide molecules (lacto-N-biose I reaction) or type II H trisaccharide molecules (N-acetyllactosamine reaction) comprising the majority of the respective neutral radiolabelled materials were then purified by HPLC as described below.

Product Analysis by HPLC and Descending Parer Chromatography

Neutral radiolabelled reaction products generated by affinity-purified protein A-fucosyltransferase fusion protein, or by pCDM7-α(1,3/1,4FT)-programmed COS-1 extracts, type I or type II disaccharide acceptors, and GDP-[$^{14}$C] fucose (see above, Fucosyltransferase Assays) were fractionated by descending paper chromatography or by HPLC chromatography to determine their structures. Samples analyzed by HPLC were dissolved in 70% acetonitrile and applied to a Dynamax 60A (primary amine column, Rainin Instruments, 4.14 mm×25 cm) equilibrated in acetonitrile:water (70:30). Compounds were eluted with a linear gradient of acetonitrile:water (70:30 to 40:60), in 1 hour, at a flow rate of 1 ml per minutee. The eluant was monitored with a Beckman Instruments on-line radioisotope detector.

Samples analyzed by descending paper chromatography were dissolved in water and fractionated through Whatman No. 40 in phenol/isopropanol/formic acid/water (85:5:10:100, lower layer). After chromatography (FIG. 6; 40 hours in panel A or 48 hours in panel B), air-dried chromatograms were cut into 1 cm strips and the radiolabelled compounds were eluted into 2 ml of water. The radioactivity in each eluate was determined by scintillation counting after mixing with 10 ml of scintillation cocktail. HPLC-purified $^{14}$C-labelled type I and type II H-active trisaccharide standards were prepared as described above for the preparation of $^{14}$C-labelled type I and type II H-active acceptor trisaccharides.

α-L-Fucosidase Digestion

Neutral, HPLC-purified, radiolabelled fucosyltransferase products were subjected to α-L-fucosidase digestion to confirm the alpha anomeric configuration of the attached fucose. (1,3)($^{14}$C]fucosyl-N-acetyllactosamine, (1,3) [$^{14}$C] fucosyl-2'-fucosyllactose, (1,3)[$^{14}$C]fucosyllactose, and (1,4) [$^{14}$C]fucosyllacto-N-biose I were purified by HPLC, and aliquots of each (10,000 to 20,000 cpms) were digested with 100 mU of a-L-fucosidase (E.C. 3.2.1.51, Boehringer-Mannheim) in 70 μl of 100 mM Na citrate pH 5.5, at 37° C. for 22 hrs. The reactions were desalted by Dowex column chromatography and subjected to HPLC analysis using conditions described above. The products of the digestion were identified by comparison to parallel separations of L-[$^{14}$C]fucose and [$^{14}$C]fucose-labelled acceptors. In each case, quantitative release of L-[$^{14}$C]fucose was achieved by α-L-fucosidase digestion.

pPROTA-α(1,3/1,4)FT, Construction and Analysis

A 1344-bp SmaI-BamHI segment of the cDNA insert containing the putative fucosyltransferase catalytic domain was isolated from pCDM7-α(1,3/1,4)FT. This fragment was blunt-ended with the Klenow fragment of DNA polymerase I, and the ends were ligated to kinased double stranded linkers (5' CGGAATTCCG 3'). The ligated fragment was gel purified, digested with EcoRI, and gel purified again. This fragment was inserted at the unique EcoRI site of PPROTA. One plasmid (pPROTA-α(1,3/1,4)FT$_c$) containing a single insert in the appropriate orientation was analyzed by DNA sequencing to confirm the predicted sequence across the junctions between the vector, linker, and insert.

Plasmids pPROTA-α(1,3/1,4)FT$_c$, pCDM7-α(1,3/1,4)FT, or pPROTA, (50 μg each) were separately introduced into COS-1 cells (500,000 per 100 mm dish) by DEAE-dextranmediated transfection. After a 72-hour expression period, the media (10 ml) was harvested from each plate and subjected to low speed (300×G for 8 min) and high speed (100,000×G for 1 h) centrifugations. The supernatants were then adjusted to 0.05% Tween 20 and were either assayed directly, or were used in IgG-Sepharose binding studies. IgG-Sepharose or Sepharose 6B were preequilibrated as described by the manufacturer (Pharmacia), and then equilibrated in 10% fetal calf serum in Dulbecco's modified Eagle's medium (FCS/DMEM). Aliquots of processed supernatants containing known amounts of enzyme activity prepared from transfected COS-1 cells were incubated batchwise with 100 μl of equilibrated IgG-Sepharose or Sepharose 6B, overnight at 4° C. Supernatants were saved for assay ("Flow thru" activity). The matrices were then washed by centrifugation, 9 times with 1 ml of 50 mM Tris pH 7.5, 1 mg/ml bovine serum albumin, twice with 1 ml of 20 mM Tris pH 7.5, 5 mM CaCl$_2$, 0.05% Tween-20, and once with FCS/DMEM. The matrices were then resuspended in an equal volume of FCS/DMEM. This suspension was used directly for assay of α(1,3)FT activity.

Example IV

Cloning by cross-hybridization, and expression, of a DNA sequence encoding GDP-FuC:β-D-Gal(1,4)-D-GlcNAc α(1,3)fucosyltransferase (Fuc-TIV) (DNA SEQ ID NO:7. Protein SEQ ID NO:8).

The inventor had previously used a mammalian gene transfer procedure to isolate a clone cDNA (SEQ ID NO:1) that encodes the human Lewis blood group fucosyltransferase (SEQ ID NO:2). The inventor was aware of biochemical and genetic data indicating that the human genome contains two or more other structural genes that encode fucosyltransferases competent to construct surface localized Lewis x determinants (Galβ1→4[Fucα(1→3)]GlcNAc-). These other enzyme(s) were thought to be polypeptides distinct from the Lewis fucosyltransferase because they exhibit different acceptor substrate specificities and differential sensitivities to divalent cation and N-ethylmaleimide inactivation. Moreover, their expression is determined by loci distinct from the Lewis blood group fucosyltransferase locus, and they display tissue specific patterns that are different from expression patterns determined by the Lewis locus. Because these enzymes exhibit properties that are very similar to the Lewis blood group fucosyltransferase, the inventor considered it possible that their corresponding genes might be sufficiently related at the primary sequence level to be able to isolate them by cross-hybridization approaches. He considered this even though he and others had previously shown that glycosyltransferase sequences that use the same substrates are not at all related in their primary nucleic acid or amino acid sequences, since he knew that the fucosyltransferases exhibited very similar substrate requirements, and in each case constructed one or more oligosaccharide products identical to those made by the Lewis fucosyltransferase.

In consideration of the possibility that these α(1,3) fucosyltransferases might be encoded by a family of structurally-related genes, he sought to isolate other such members by cross-hybridization methods, using the cloned Lewis fucosyltransferase cDNA. Low stringency Southern blot hybridization experiments indicate that the coding region of the Lewis α(1,3)fucosyltransferase cDNA detects strongly hybridizing human DNA restriction fragments, as well as several weakly hybridizing fragments. Weakly hybridizing fragments were always detected regardless of the restriction enzyme used, suggesting that these represented one or more DNA sequences distinct from the authentic Lewis gene presumably represented by the strongly-hybridizing fragments. To further examine the molecular nature of these sequences, he screened a human lambda phage genomic DNA library at low stringency with the Lewis cDNA probe. A total of 18 phages were isolated from phages representing approximately five human genomic equivalents. Southern blot analysis of 16 of these phages allowed them to be placed into three groups, based upon their restriction patterns and hybridization signal intensity strengths. Six phages representing a class of intermediate hybridization intensity were identified. A 3.6 kb cross-hybridizing PstI restriction fragment was subcloned from a representative phage of this class. To determine the relationship of this fragment to cross-hybridizing fragments detected in human genomic DNA with the Lewis probe, a 400 bp AvaII-PvuII segment of this fragment, that cross-hybridized with the Lewis coding sequence probe, was also used to probe Southern blots at low stringency. For each enzyme used to generate the Southern blots, the AvaII-PvuII probe detected one strongly hybridizing fragment, and one or more weakly hybridizing fragments. Each strongly hybridizing fragment corresponded to one of the weakly hybridizing fragments generated by the same enzyme and detected by the Lewis probe. Likewise, the strongly hybridizing fragments detected with the Lewis probe correspond to fragments that exhibit weak hybridization to the AvaII-PvuII probe. These results suggested that this probe, and the 3.6 kb fragment from which it was derived, represented the weakly cross-hybridizing DNA sequences detected by the Lewis probe on genomic DNA Southern blots.

Figure 5D:
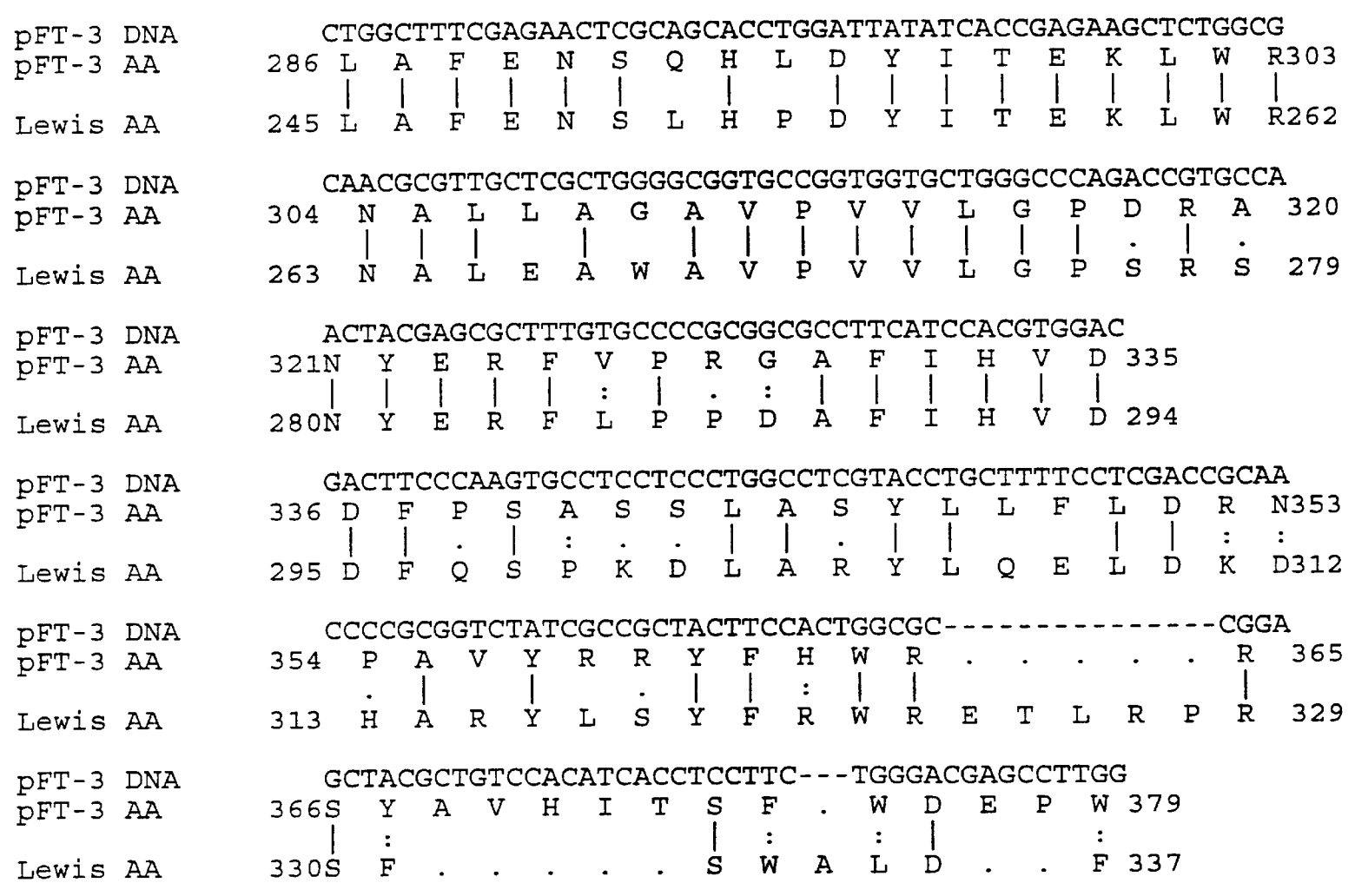

The homologous DNA restriction fragment maintains a single long open reading frame that predicts a polypeptide with similarity to the Lewis blood group α(1,3/1,4) fucosyltransferase cDNA DNA sequence analysis of the 3.6 kb PstI fragment (SEQ ID NO:7) identified a single long open reading frame within its 3' portion corresponding to sequences that cross-hybridized to the Lewis cDNA probe (FIG. 4 and FIG. 5). This reading frame begins with a methionine codon that is found within a sequence context consistent with Kozak's consensus rules for mammalian translation initiation. Moreover, hydropathy analysis of the protein sequence predicted by this reading frame indicates a single hydrophobic segment at its NH$_2$-terminus, suggesting that the predicted polypeptide (SEQ ID NO:8) would maintain the type II transmembrane orientation typical of mammalian glycosyltranferases. The distal portion of this reading frame shares a substantial amount of amino acid sequence identity with the corresponding portion of the Lewis fucosyltransferase (FIG. 5). These sequences share the highest degree of similarity between their COOH-terminal portions, within the catalytic domain of the Lewis fucosyltransferase. Sequence divergence occurs toward the predicted NH$_2$-end, within the "stem" and transmembrane regions of the latter enzyme.

The DNA restriction fragment detects mRNA transcripts in HL-60 myeloid cells

To test the possibility that this segment represents a functional α(1,3)fucosyltransferase gene, a portion of it was used as a probe to identify transcripts in a cell line known to express such enzymes. The HL-60 human cell line was examined since these myeloid lineage cells are known to express one or more α(1,3)fucosyltransferases that are distinct from the Lewis α(1,3)fucosyltransferase. Northern blot analysis of polyadenylated mRNA isolated from these cells, using the 400 bp AvaII-PvuII segment corresponding to a portion of the open reading frame, identified four distinct transcripts. By contrast, no transcripts were detected when the same analysis was preformed using the Lewis cDNA. These results are consistent with the possibility that the fucosyltransferase(s) expressed by HL-60 cells are encoded by the open reading frame in the cloned PstI segment.

The open reading frame in the homoloaous DNA restriciton fracment determines expression of an α(1,3) fucosyltransferase.

To determine it this segment encodes an α(1,3) fucosyltransferase, the 3.6 kb PstI fragment was cloned into a mammalian expression vector and the resulting plasmid (pCDNA1-Fuc-TIV, "Experimental Procedures") was introduced into two types of mammalian host cells by transfection. Transfected cells were then analyzed for vector-dependent cell surface glycoconjugate expression and for fucosyltransferase activity. COS-1 cells and CHO cells were used as hosts for these experiments since neither cell line normally expresses any detectable α(1,3)- and α(1,4) fucosyltransferase activities. Likewise, COS-1 and CHO cells do not normally express detectable amounts of cell surface Galβ1→4[Fucα(1→3)]GlcNAc-(Lewis x, SSEA-1) moieties, or the α2→3 sialylated derivative (NeuAcα2→3Galβ1→4[Fucα(1→3)]GlcNac-, sialyl Lewis x). These cells do, however maintain surface-display of the non-fucosylated neutral and α2→3-sialylated type II oligosaccharides that can function as precursors to such molecules, via the action of the α(1,3)fucosyltransferase encoded by a transfected Lewis cDNA expression vector. COS-1 cells also maintain surface display of the type I precursors to the Lewis a (Galβ1→3[Fucα(1→4)]GlcNAc-) and sialyl Lewis a (NeuNAcα2→3Galβ1→3(Fucα(1→4)] GlcNAc-) moieties. The vector pCDNAI was used since this plasmid efficiently transcribes exogenous, subcloned sequences in mammalian hosts by virtues of the cytomegalovirus immediate early promoter sequences in the vector.

In initial biochemical analyses, extracts prepared from COS-1 cells transfected with plasmid pCDNAI-Fuc-TIV were tested for the presentce of vector-dependent fucosyltransferase activity, using several low molecular weight acceptor substrates. In a standard fucosyltransferase assay ("Experimental Procedures"), extracts prepared from pCDNA1-Fuc-TIV transfected cells, but not from control transfectants, contained a fucosyltransferase activity (296 pmol/mg-h) that utilized the type II disaccharide acceptor N-acetyllactosamine to yield a radiolabeled product with a chromatographic mobility ("Experimental Procedures") characteristic of authentic Galβ1→3[Fucα(1→4)]GlcNAc ($R_{2'\text{-}fucosyl\text{-}N\text{-}acetyllactosamine}$=0.85). However, under these assay conditions, two other neutral type II molecules (2'fucosyllactose, lactose) did not function as efficiently as N-acetyllactosamine as acceptor substrates for the fucosyltransferase in these extracts (17 and 10 pmol/mg-h, respectively, for 2'-fucosyllactose and lactose). Only a trace amount of transfer could be detected using the type I substrate lacto-N-biose I.

Likewise, the inventor did not detect fucose transfer to the sialylated acceptor NeuAcα(2→3)Galβ(1→4)GlcNAc (less than 1 pmol/mg-h), even in extracts that exhibited a relatively large amount of activity toward N-acetyllactosamine (474 pmol/mg-h). By contrast, under these same conditions, extracts containing the Lewis blood group fucosyltransferase utilized both the sialylated acceptor (297 pmol/mg-h) and N-acetyllactosamine (526 pmol/mg-h), to form, respectively, the sialyl Lewis x tetrasaccharide and the Lewis x trisaccharide (see "Experimental Procedures"). Thus, the restricted acceptor preference exhibited by this enzyme in vitro contrasts remarkably with that exhibited by the Lewis α(1,3/1,4)fucosyltransferase, which can efficiently utilize each of the five acceptors tested. These results are summarized in Table 2.

COS-1 cells transfected with pCDNA1-Fuc-TIV were also analyzed by flow cytometry to detect de novo, vector-dependent surface expression of these oligosaccharide products, to allow an assessment of the enzyme's in vivo acceptor substrate requirements. The transfected COS-1 cells exhbited positive staining with a monoclonal antibody directed aginst the Lewis x moiety Galβ1→4[Fucα(1→3)] GlcNAc-) (FIG. 8), whereas cells transfected with the pCDNA1 vector without insert did not express this determinant. However, COS-1 cells transfected with pCDNA1-Fuc-TIV, or with its control plasmid, did not stain with antibodies specific for the sialyl Lewis x antigen (FIG. 8). Likewise, the transfected cells did not exhibit detectable surface expression of Lewis a or sialyl Lewis a molecules (FIG. 8).

Polylactosaminoglycans with terminal α(2→3)-linked sialic acid also exist that maintain a single internal α(1,3)-linked fucose on the N-acetylglucosamine residue of the pneultimate lactosamine repeat. This determinant (NeuAcα2→3Galβ1→4GlcNAcβ1→4[Fucα(1→3)] GlcNAc-) can be detected on the surfaces of myeloid cells by the monoclonal antibody VIM-2, and may be constructed by the action of α(1,3)fucosyltransferase(s) on type II polylactosamine acceptors whose terminal galactose residues are substituted with α(2,3)sialic acid moieties. Neither COS-1 cells transfected with the Lewis α(1,3/1,4) fucosyltransferase, nor COS-1 cells tranfected with plasmid pCDNA1-Fuc-TIV display detectable amounts of this determinant.

Virtually identical results were obtained with COS-1 cells transfected with the plasmid pCDNAI-α(1,3)FTMlu ("Experimental Procedures"). This vector encompasses sequences corresponding to bp-1904 through the end of the open reading frame in FIG. 4. These results provide additional evidence for the hypothesis that the open reading frame displayed in FIG. 4 corresponds to the coding portion of this fucosyltransferase gene.

To further demonstrate that enzymatic activity is directly associated with this protein, the putative catalytic domain of the predicted polypeptide (amino acids 50 to 405 of SEQ ID NO: 8) was fused to a secreted form of the IgG binding domain of Staphylococcus aureus protein A in the mammalian expression vector pPROTA, to generate the vector pPROTA-α(Fuc-TIV)$_c$. Since this fusion protein would lack the putative transmembrane anchoring segment of the fucosyltransferase, the inventor expected it would be synthesized as a secreted molecule that could be affinity-purified on an IgG-containing matrix and subsequently tested for α(1,3)FT activity. COS-1 cells transfected with the control vectors pCDM7 or pPROTA generated no detectable cell-associated or released enzyme activity. However, conditioned media prepared from COS-1 cells transfected with pPROTA-α(Fuc-TIV), contained significant quantities of α(1,3)FT activity when assayed with N-acetyllactosmine.

Virtually 100% of the released activity generated by pPROTA-α(Fuc-TIV), is specifically retained by the IgG-Sepharose matrix. These results indicate that the protein encoded by this cloned DNA segment encodes a fucosyltransferase, and demonstrate that information sufficient to generate α(1,3)FT activity resides within the enzyme's COOH-terminal 356 amino acids.

Biochemical analysis of extracts prepared from a CHO cell line transfected with pCDNA1-Fuc-TIV (CHO-FT3 cells) yielded results similar to those obtained with the transfected COS-1 cells. In the standard fucosyltransferase assay (Experimental Procedures), extracts prepared from the control transfected cell line CHO-V did not contain α(1,3) fucosyltransferase activity when tested with N-acetyllactosamine, 2'-fucosyllactose, lactose, or lacto-N-biose I, or NeuAcα(2→3)Gal(1→4)GlcNAc. By contrast, extracts prepared from the CHO-FT3 line contained an α(1,3)fucosyltransferase activity (59.1 pmol/mg-h) that utilized the type II disaccharide acceptor N-acetyllactosamine to yield a radiolabeled product characteristic of authentic Galβ(1→4) [Fucα(1→3)]GlcNAc ($R_{2'\text{-}fucosyl\text{-}N\text{-}acetyllactosamine}=0.85$) (see "Experimental Procedures"). Under these assay conditions, the CHO-FT3 extracts utilized the type II acceptor molecules 2'-fucosyllactose and lactose with substantially lower efficiency (5.8 pmol/mg-h and 2.0 pmol/mg-h, respectively). Virtually no transfer could be detected when these extracts were tested with the type I substrate lacto-N-biose I (<1 pmol/mg-h) or with the sialyl Lewis x precursor NeuNAcα2→3Galβ1→4GlcNAc (<1 pmol/mg-h). These results confirm those obtained with extracts prepared from the transfected COS-1 cells, and indicate that, to a first approximation, the COS-1 and CHO genetic backgrounds do not strongly influence the enzyme's ability to utilize these five low molecular weight acceptor substrates.

With one striking and important exception, flow cytometry analyses with the CHO-FT3 cells were virtually identical to those obtained with the transfected COS-1 cells. CHO-FT3 cells exhibit uniform, bright staining with anti-Lewis x antibody, but not with antibody directed against the sialyl Lewis x molecule. Control transfected cells do not stain with either antibody. As expected, neither cell line stained with antibodies against the neutral and α2→3-sialylated Lewis a isomers, since CHO cells do not construct type I precursors. However, these cells differed in an important way from the transfected COS-1 cells, in that, like CHO cells transfected with the Lewis α(1,3/1,4) fucosyltransferase cDNA (pCDM7-α(1,3/1,4)FT), these cells expressed substantial amounts of the VIM-2 determinant.

Taken together with the results of the biochemical analyses performed with extracts from the transfected cells and summarized in Table 2, the flow cytometry analyses presented in FIG. 8, the protein A gene fusion experiments, and the DNA sequence analysis indicate that plasmid pCDNA1-Fuc-TIV encodes an α(1,3)fucosyltransferase. Transfection results obtained with plasmid pCDNAI-α(1,3)FTM1u also demonstrate that this enzyme is encoded by the open reading frame displayed in FIG. 4. The results further indicate that this enzyme can utilize type II precursors, but not type I precursors, and suggest that the enzyme cannot efficiently utilize α2→3-sialylated type II glycoconjugates to form the sialyl Lewis x determinant.

Experimental Procedures for Example IV, "Cloning by cross-hybridization and expression, of a DNA sequence encoding GDP-Fuc:β-D-Gal(1,4)1-D-GlcNAc α(1,3)-Fucosyltransferase: (Fuc-TIV)"

Cell Culture

The source and growth conditions of COS-1 cells, CHO transfectants, and A431 cells are as previously described (Ernst et al, *J. Biol. Chem.* (1989) 265:3436–3447; Rajan et al, *J. Biol. Chem.* (1989) 264:11158–11167). The human HL-60 cell line was obtained from Dr. Steve Kunkel (University of Michigan, Ann Arbor). HL-60 cells were grown in 10% fetal calf serum and Dulbeccols Modified Eagle's Medium.

Antibodies

The anti-Lex antibody anti-SSEA-1 Solter et al, *Proc. Nat. Acad. Sci.* (*USA*) (1978) 75:5565–5569) (mouse monoclonal IgM as ascites) was used. Anti-H and anti-Lewis a antibodies (mouse monoclonal IgM, antigen affinity purified) were purchased from Chembiomed Ltd. (Edmonton, Alberta). Anti-sialyl Lewis x antibody CSLEX1 (Fukushima et al, *Cancer Res.* (1984) 44:5279–5285) (mouse monoclonal IgM, HPLC purified) and anti-sialyl Lewis a antibody CSLEA1 (Chia et al, *Cancer Res.* (1985) 45:435–437) (mouse monoclonal IgG3, ammonium sulfate precipitate) were used. Anti-VIM-2 was obtained from Dr. Bruce Macher (San Francisco State University). A pooled mouse IgG antibody preparation (MsIg) was purchased from Coulter. Fluorescein-conjugated goat anti-mouse IgM or IgG antibodies were purchased from Sigma.

Human Genomic Library Construction

High molecular weight human genomic DNA was prepared from peripheral blood leukocytes as described previously (Ernst et al (1989)). Genomic DNA was subjected to partial digestion with the restriction endonuclease Sau3A. The partially digested genomic DNA was size fractionated by ultracentrifugation through a sodium chloride gradient. Fractions enriched for DNA fragments between 8 Kb and 20 Kb were ligated to XhoI digested lambda FIX (Stratagene) phage arms that had been partially filled in with dTTP and dCTP to make the ends compatible with the Sau3A fragments. The ligation mixture was packaged in vitro with commercial packaging extracts (Stratagene), titered on *E. coli* host TAP90 (Patteron et al, *Nucl. Acids Res.* (1987) 15:6298). Approximately $1.0\times10^6$ recombinant lambda phage were screened by plaque hybridization. Plaque lifts were prepared using nitrocellulose filters (Schleicher and Schuell) and were prehybridized at 42° C. for 16 hours in 50% formamide, 5X SSC, 10X Denhart's solution, and 0.1% SDS. Filters were hybridized for 72 hours at 35° C. in prehybridization solution containing 10% dextran sulfate, and 100 micrograms per ml denatured salmon sperm DNA. The probe consisted of a 1.7 Kb XhoI-XbaI fragment isolated from the 5' end of a cDNA insert encoding the Lewis blood group α(1,3/1,4) fucosyltransferase which was labeled with [α-$^{32}$P] dCTP. The filters were rinsed three times for 20 minutes each at room temperature in 2X SSC and then once for 40 minutes at 50° C. and 1X SSC, 0.5% SDS. Filters were then subjected to autoradiography. Eighteen independent hybridization-positive plaques were identified after 2 additional cycles of plaque hybridization. Phage DNAs were prepared from liquid lysates and were subsequently characterized by restriction endonuclease digestions and Southern blot analyses.

DNA Sequence Analysis

Phage DNA was digested with PstI and a 3.8 Kb fragment homologous to the human α(1,3/1,4)fucosyltransferase cDNA was gel purified and ligated into the PstI site of pTZ18R. A representative subclone containing a single insert was designated pFT-3. A 970 bp hybridization-positive AvaII-PstI fragment was isolated from insert in pFT-3 and subcloned into pTZ18R. The DNA sequence of the insert in this plasmid was determined by the dideoxy chain determination method using T7 DNA polymerase (Pharmacia LKB Biotechnology, Inc.) and oligonucleotides synthesized according to flanking plasmid sequences and subsequently according to the insert sequence. This sequence data was used to generate additional synthetic deoxynucleotides which were then used to sequence portions of the insert in pFT-3. Sequence analysis was performed using the sequence analysis software package of the University of Wisconsin Genetics Computer Group.

Southern Blot Analysis

High molecular weight human genomic DNA was prepared from whole peripheral blood. Genomic DNA (10 $\mu$g) was digested with restriction endonucleases, fractionated through a 0.8% agarose gel, and subjected to Southern blot analysis. To aid in the comparison of hybridization patterns obtained with different probes, duplicate blots were prepared from identical sets of restriction digests electrophoresed on a single gel. Southern blots were hybridized with the temperature being maintained at 35° C. Southern blots were probed with the 1.7 Kb XhoI-XbaI fragment of plasmid pCDM7-$\alpha$(1,3/1,4)FT which represents the 5' end of the human cDNA encoding the Lewis $\alpha$(1,3/1,4) fucosyltransferase enzyme. Alternatively, Southern blots were probed with a 400 bp AvaII-PvuII fragment isolated from the insert in pFT-3. Following hybridization, blots were rinsed twice in 2X SSC 0.5% SDS at room temperature for 10 minutes, washed, and then subjected to autoradiography.

Northern Blot Analysis

Total RNA was prepared from cultured cells Poly A+ RNA was then isolated from total RNA by p;ogp dT cellulose column chromatography using commercially supplied columns (Clontech) and procedures supplied by the manufacturer. RNA samples were electrophoresed through 1.0% agarose gels containing formaldehyde and were then transferred to a nylon tembrane (Hybond-N, Amersham). Northern blots were prehybridized for 1 hour at 61° C. in 1X PE (16), 5X SSC, 1% sodium dodecyl sulfate, and 100 $\mu$g/ml sheared salmon sperm DNA. Blots were then hybridized for at least 16 hours at 61° C. in the same hybridization solution. The probe was a radiolabelled 400 bp AvaII-PvuII fragment isolated from the insert in pFT-3. Following hybridization, blots were subjected to three, ten minute room temperature rinses in 2X SSC, and then washed for 30 minutes at 62° C. in 2X SSC, -0.2% SDS.

Transfection and Expression of the Insert in PFT-3

The 3.8 Kb PstI insert in plasmid pFT-3 was excised and cloned into the PstI site in the mammalian expression plasmid pCDNA1 (Invitrogen). One plasmid with a single insert in the sense orientation with respect to the plasmid's CMV promoter enhancer sequences was designated pCDNA1-Fuc-TIV, and was used for subsequent analysis. Construction and radiolabeling of stably transfected CHO cell lines CHO Ade-C cells were transfected with ScaI-linearized pCDM7-Fuc-TIV, co-precipitated in a 10-fold molar excess over EcoRI-linearized pSV2-Neo. A single, clonal, SSEA-1-positive cell line (CHO-FT3) was derived from this population. Cell extracts prepared from CHO-FT3 contained substantial amounts of $\alpha$(1,3)fucosyltransferase activity when assayed with the acceptor N-acetyllactosamine.

FACS Analysis

COS-1 cells transfected with plasmid DNAs were harvested 48–72 hours after transfection, and stained with monoclonal antibodies diluted in staining media. Anti-Lewis a and anti-H antibodies (mouse IgM monoclonal; antigen-affinity purified; Chembiomed, Edmonton) were used at 10 $\mu$g/ml. Anti-SSEA-1 (mouse monoclonal IgM; ascites) was used at a dilution of 1:1000. Anti-sialyl Lewis x (mouse monoclonal IgM; HPLC purified from ascites) was used at 10 $\mu$g/ml. Anti-sialyl Lewis a (mouse monoclonal IgG3; ammonium sulfate precipitate of ascites) was used at a dilution of 1:1000. Control mouse IgG3 antibody (MsIg, Coulter) was used at a concentration of 10 $\mu$g/ml. Anti-VIM-2 antibody (mouse monoclonal IgM; ascites) was used at a dilution of 1:200. Cells were then stained with fluorescein isothiocyanate-conjugated goat anti-mouse IgM or IgG, as appropriate, and were then subjected to analysis on a FACScan (Becton-Dickinson).

Fucosyltransferase Assays

Cell extracts containing 1% Triton X-100 were prepared from transfected COS-1 cells. Fucosyltransferase assays were performed in a total volume of 20 $\mu$l, and contained 50 mM sodium cacodylate, pH 6.2, 5 mM ATP, 10 mM fucose, 20 mM MnCl$_2$, 3 $\mu$M GDP-$^{14}$C-fucose, and 5 $\mu$l (30 $\mu$g protein) of cell extract. Acceptor substrates were added to a final concentration of 20 mM. Reactions were incubated at 37° C. for 1 hour and terminated by addition of 20 $\mu$l ethanol, followed by addition of 600 $\mu$l of distilled water. An aliquot of each reaction (50 $\mu$l) was subjected to scintillation counting to determine total radioactivity in the reaction. Another aliquot (200 $\mu$l) was applied to a column containing 400 $\mu$l of Dowex IX2–400, formate form. The flow through fraction, and 2 $\mu$l of a subsequent water elution, were collected and pooled, and an aliquot was subjected to scintillation counting to quantitate incorporation of radioactive fucose into neutral product. Descending paper chromatography was used to confirm the structure of the product formed with the acceptor N-acetyllactosamine. The neutral product in the Dowex column eluate was concentrated by lyophilization, resuspended in a small volume of water, and fractionated through Whatman No. 40 in phenol/isopropanol/formic acid/water (85:5:10:100, lower layer). After chromatography (40 hours), the air-dried chromatogram was cut into 1 cm strips and the strips eluted into 2 ml of water. Radioactivity in each eluate was determined by scintillation counting after mixing with 10 ml of scintillation cocktail.

An affinity-purified, protein A-Lewis fucosyltransferase fusion protein was used to prepare an authentic, radiolabeled Gal$\beta$(1$\rightarrow$4)[$^{14}$C-Fuc$\alpha$(1$\rightarrow$3)]GlcNAc standard for this analysis. This fusion protein was incubated with 20 mM N-acetyllactosamine, 150 $\mu$m GDP-[($^{14}$C]fucose (sp. act.= 3,800 cpms/nmol), in a standard fucosyltransferase reaction mixture. The neutral, radiolabeled product was purified by amine adsorption HPLC on a Waters Carbohydrate Analysis column, using an isocratic gradient consisting of 70% acetonitrile in water, at a flow rate of 1 ml/min. The product (17 nmol) was subjected to analysis by $^{14}$C NMR (Center for Complex Carbohydrate Research, Athens, Ga.). The sample was exchanged repeatedly in D$_2$O and subjected to NMR analysis at 500 MHz. The proton NMR spectrum was recorded on a Bruker AM500 instrument at 28° C. Chemical shifts are relative to acetate ($\delta$1.908 ppm). The structure of the expected trisaccharide Gal$\beta$(1$\rightarrow$4)[Fuc$\alpha$(1$\rightarrow$3)) GlcNAc, was verified by 500 MHz spectroscopy. The spectrum, recorded in D$_2$O at 28° C., showed H-1 signals for GlcNAC ($\alpha$-anomer) at $\delta\approx$5.102, for Gal at $\delta\approx$4.467 and 4.454 ppm (for the $\alpha$- and $\beta$-anomers, respectively, of the trisaccharide) and for Fuc at $\delta\approx$5.102 ppm. The anomeric signal for the β-anomer of GlcNAc was obscured by the residual HOD peak (δ≈4.72 ppm). The methyl signals of the GlcNAc N-acetyl group and the C6 protons of Fuc were observed at δ≈2.032 and 1.178 ppm, respectively. These chemical shifts match those published for the authentic trisaccharide Galβ(1→4)(Fucα(1→3)]GlcNAc.

α-L-Fucosidase Digestion

The neutral, chromatographically-purified radiolabeled fucosyltransferase product was subjected to a-L-fucosidase digestion to confirm the alpha anomeric configuration of the attached fucose. 3-[$^{14}$C] fucosyl-N-acetyllactosamine was purified by descending paper chromatography as described above, and an aliquot (7000 cpms) was digested with 40 mU of α-L-fucosidase (E.C. 3.2.1.51, Boehringer-Mannheim) in 20 μl of 100 mM Na citrate pH 5.5, at 37° C. for 22 hrs. The reaction was desalted by Dowex column chromatography and subjected to HPLC analysis using conditions described above for preparation of the radiolabeled standard. The product of the digestion was identified by comparison to parallel separations of L-[$^{14}$C] fucose and the 3-[$^{14}$C] fucosyl-N-acetyllactosamine starting material. Quantitative release of L-[$^{14}$C]fucose was achieved by α-L-fucosidase digestion.

Example V
Isolation of a GDP-Fuc:β-D-Gal(1,4)-D-GlcNAc α(1,3) Fucosyltransferase (Fuc-TV. DNA SEQ ID NO:10, Protein SEQ ID NO:11) through cross-hybridization Molecular cloning of a human genomic DNA segment that cross-hybridizes to the Lewis blood group α(1,3/1,4) fucosyl-transferase cDNA: Low stringency Southern blot hybridization experiments have indicated to the inventor that the coding region of the Lewis fucosyltransferase cDNA detects strongly hybridizing restriction fragments, as well as several weakly hybridizing fragments.

The inventor expected that the strongly hybridizing fragments represented one or more genes similar to the Lewis fucosyltransferase cDNA. To further examine the molecular nature of these sequences, as noted above in Example IV, the inventor screened a human lambda phage genomic DNA library at low stringency with the Lewis cDNA probe. A total of 18 phages were isolated from phages representing approximately five human genomic equivalents. Southern blot analysis of 16 of these phages allowed them to be placed into three groups, based upon their restriction patterns and hybridization signal intensity strengths. Several phages representing a class with strong hybridization intensities were identified. Cross-hybridizing restriction fragments isolated from one of these phages was subcloned and sequenced.

The homologous DNA restriction fragment maintains a single long open reading frame that predicts a polypeptide with strong similarity to the Lewis blood group α(1,3/1,4) fucosyltransferase cDNA: DNA sequence analysis of the subcloned fragments identified a single long open reading frame within its 3' portion, beginning at base pair 1 and ending at base pair 1125 (SEQ ID NO:10) (see FIG. 6). This reading frame begins with a methionine codon that is found within a sequence context consistent with Kozak's consensus rules for mammalian translation initiation. A hydropathy analysis of the protein sequence predicted by this reading frame (SEQ ID NO:11) would predict a single hydrophobic segment at its NH$_2$-terminus, suggesting that the predicted polypeptide would maintain the type II transmembrane orientation typical of mammalian glycosyltransferases. Virtually the entire length of this reading frame shares a strikingly high amount of amino acid and nucleic acid sequence identity with the corresponding portion of the Lewis fucosyltransferase cDNA (FIG. 6). This sequence similarity diverges in just a few positions, most notably at base pair 139 within the open reading frame. This 33 base pair insertion, relative to the Lewis cDNA, would create a peptide insertion of 11 amino acids, relative to the Lewis fucosyltransferase. Because of the substantial sequence similarity between these two DNA sequences, and their derived protein sequences, the inventor expected this new cross-hybridizing sequence to represent a single exonic sequence, representing a heretofore undefined gene, that encodes a fucosyltransferase.

The homologous DNA restriction fragment determines expression of an α(1,3)fucosyltransferase: To determine if this segment encodes a functional fucosyltransferase, a 1.94 kb EarI-XbaI fragment containing the entire open reading frame was cloned into a mammalian expression vector, and the resulting plasmid (pCDNA1-Fuc-TV) was introduced into mammalian host cells by transfection. COS-1 cells were used as hosts for these experiments since these cells normally express virtually undetectable α(1,3)- and α(1,4) fucosyltransferase activities. Likewise, COS-1 cells do not normally express detectable amounts of cell surface Galβ1→4(Fucα(1→3))GlcNAc- (Lewis x, SSEA-1) or Galβ1→3[Fucα(1→4)]GlcNAc- (Lewis a) moieties, whereas they do maintain surface-display of non-fucosylated type II and type I oligosaccharide precursors necessary for the construction of such molecules. The vector pCDNAI was used, since this plasmid efficiently transcribes exogenous, subcloned sequences in COS-1 hosts by virtue of the cytomegalovirus immediate early promoter sequences in the vector, and is maintained in these cells as a multicopy episome.

COS-1 cells transfected with pCDNA1-Fuc-TV were first analyzed by flow cytometry to detect de novo, vector-dependent surface expression of these oligosaccharides. A substantial fraction of these transfected cells exhibited bright staining with a monoclonal antibody directed against the Lewis x moiety (Galβ(1→4)[Fucα(1→3)]GlcNAc-) (FIG. 8), whereas cells transfected with the pCDNA1 vector without insert did not express this determinant. By contrast, COS-1 cells transfected with pCDNA1-Fuc-TV, or with its control plasmid, did not stain with antibodies specific for the type I-based Lewis a trisaccharide (FIG. 8).

Taken together, these results are consistent with the results of DNA sequence analysis indicating that this segment encodes an α(1,3)fucosyltransferase competent to utilize neutral type II oligosaccharide precursor, but that the enzyme cannot efficiently utilize type I glycoconjugates and thus does not exhibit strong α(1,4)fucosyltransferase activity.

There is evidence supporting the possibility that one or more human α(1,3)fucosyltransferases exist that can utilize type II acceptors whose terminal galactose residues are substituted with α(2,3)sialic acid moieties. Such enzymes can fucosylate these molecules to form the sialyl-Lewis x determinant (NeuAcα(2→3)Galβ(1→4)[Fucα(1→3)]GlcNAc-). The Lewis fucosyltransferase, for example, is competent to perform this reaction.

It was therefore of interest to determine if the fucosyltransferase apparently encoded by plasmid pCDNA1-Fuc-TV would be capable of constructing sialyl-Lewis X determinants. COS-1 cells maintain surface-expressed glycoconjugates terminating in (NeuAcα(2,3)Galβ(1,4)GlcNAC-; these represent acceptor substrates for sialyl-Lewis construction determined via the action of enzymes encoded by transfected fucosyltransferase expression vectors. COS-1 cells were therefore transfected with plasmid pCDNA1-Fuc-TV, stained with a monoclonal anti-sialyl Lewis x antibody, and subjected to flow cytometry analysis. A significant amount of staining was detected, relative to control cell transfected with the vector alone, or relative to pCDNA1-α(1,3)-Fuc-TV-transfected cells stained with a negative control antibody (anti-H). (FIG. 8).

However, these cells did not stain with an antibody specific for the type I-based, sialyl-Lewis a determinant (NeuAcα(2,3)Galβ(1,3)[Fucα(1,4)]GlcNAc-) (FIG. 8). By contrast, the inventor had previously observed that a substantial fraction of COS-1 cells transfected with the Lewis fucosyltransferase expression plasmid pCDM7-α(1,3/1,4) FT exhibit bright staining with the sialyl-Lewis x and sialyl-Lewis a antibodies, as predicted by biochemical analysis of the acceptor substrate specificity of this enzyme.

The conclusion that plasmid pCDNA1-Fuc-TV encodes an α(1,3)fucosyltransferase was confirmed by biochemical analysis of the acceptor substrate requirements of the enzyme in extracts of COS-1 cells transfected with plasmid pCDNA1-Fuc-TV. As expected, the enzyme in these extracts utilized the type II disaccharide acceptor N-acetyllactosmine, to yield the predicted product Galβ(1→4)[Fucα(1→3)]GlcNAc. The enzyme also efficiently utilized the trisaccharide NeuAcα(2,3)Galβ(1,4)GlcNac to form the sialyl Lewis x tetrasaccharide (Table 2). Under these conditions, other type II molecules, including lactose, and the α(1,2)fucosylated type II acceptor Fucα(1→2)Galβ(1→4)Glc, did function as acceptor substrates for the fucosyltransferase in these extracts, although with substantially lower efficiencies. (Summarized in Table 2).

Interestingly, the type I substrate lacto-N-biose I is also utilized by this enzyme, although again at low efficiency (Table 2). This suggests that the enzyme can also function as an α(1,4)fucosyltransferase, but at a very low efficiency, as also suggested by the absence of α(1,4) structures on flow cytometry analysis. The acceptor preferences exhibited by this enzyme contrast with that exhibited by the Lewis fucosyltransferase, which is able to efficiently utilize each of the four acceptors tested.

To further demonstrate that enzymatic activity is directly associated with this protein, the putative catalytic domain of the predicted polypeptide (amino acids 43 to 374 of SEQ ID NO: 11) was fused to a secreted form of the IgG binding domain of Staphylococcus aureus protein A in the mammalian expression vector pPROTA, to generate the vector pPROTA-Fuc-TV. Since this fusion protein would lack the putative transmembrane anchoring segment of the fucosyltransferase, the inventor expected it would be synthesized as a secreted molecule that could be affinity-purified on an IgG-containinq matrix and subsequently tested for α(1,3)fucosyltransferase activity. COS-1 cells transfected with the control vector pCDM7 or pPROTA generated no detectable cell-associated or released enzyme activity. However, conditioned media prepared from COS-1 cells transfected with pPROTA-Fuc-TV, contained significant quantities of α(1,3)fucosyltransferase activity when assayed with N-acetyllactosmine. Virtually 100% of the released activity generated by pPROTA-Fuc-TV, is specifically retained by the IgG-Sepharose matrix. These results indicate that the protein encoded by this cloned DNA segment encodes a fucosyltransferase, and demonstrate that information sufficient to generate α(1,3)fucosyltransferase activity resides within the enzyme's COOH-terminal 332 amino acids.

Taken together with the results of the flow cytometry analyses and DNA sequence analysis, these experiments indicate that plasmid pCDNA1-Fuc-TV encodes a novel α(1,3)fucosyltransferase.

Experimental Procedures for Example V, "Isolation of a GDP-Fuc-β-D-Gal (1,4)-D-GlcNAc α(1 3)Fucosyltransfedrase (Fuc-TV) through cross-hybridization

Cell Culture

The source and growth conditions of COS-1 cells used are as previously described. See Ernst et al;, *J. Biol. Chem.* (1989) 265:3436–3447 and Rajan et al. *J. Biol. Chem.* (1989) 264:11158–11167.

Antibodies

The anti-Lex antibody anti-SSEA-1 (mouse monoclonal IgM as ascites) was used. Solter et al, *Proc. Nat. Acad. Sci. (USA)* (1978), 75:5565–5569. Anti-H and anti-Lewis a antibodies (mouse monoclonal IgM, antigen affinity purified) were purchased from Chembiomed Ltd. (Edmonton, Alberta). Anti-sialyl Lewis x antibody CSLEX1 (Fukushima et al, *Cancer Res.* (1984) 44:5279–5285) (mouse monoclonal IgM, HPLC purified) and anti-sialyl Lewis a antibody CSLEA1 (Chia et al, *Cancer Res.* (1985) 45:435–437) (mouse monoclonal IgG3, ammonium sulfate precipitate) were used. Fluorescein-conjugated goat anti-mouse IgM or IgG antibodies were purchased from Sigma.

Human Genomic Library Construction

High molecular weight human genomic DNA was prepared from peripheral blood leukocytes. Genomic DNA was subjected to partial digestion with the restriction endonuclease Sau3A. The partially digested genomic DNA was size fractionated by ultracentrifugation through a sodium chloride gradient. Fractions enriched for DNA fragments between 8 Kb and 20 Kb were ligated to XhoI digested lambda FIX (Stratagene) phage arms that had been partially filled in with dTTP and dCTP to make the ends compatible with the Sau3A fragments.

The ligation mixture was packaged in vitro with commercial packaging extracts (Stratagene), tittered on *E. coli* host TAP90. Approximately 1.0×10$^6$ recombinant lambda phage were screened by plaque hybridization. Plaque lifts were prepared using nitrocellulose filters (Schleicher and Schuell) and were prehybridized at 42° C. for 16 hours in 50% formamide, 5X SSC, 10X Denhart's solution, and 0.1% SDS. Filters were hybridized for 72 hours at 35° C. in prehybridization solution containing 10% dextran sulfate, and 100 micrograms per ml denatured salmon sperm DNA. The probe consisted of a 1.7 Kb XhoI-XbaI fragment isolated from the 5' end of a cDNA insert encoding the Lewis blood group α(1,3/1,4) fucosyltransferase, which was labeled with [α-$^{32}$P] dCTP. The filters were rinsed three times for 20 minutes each at room temperature in 2X SSC and then once for 40 minutes at 50° C. and 1X SSC, 0.5% SDS. Filters were then subjected to autoradiography. Eighteen independent hybridization-positive plaques were identified after 2 additional cycles of plaque hybridization. Phage DNAs were prepared from liquid lysates and were subsequently characterized by restriction endonuclease digestions and Southern blot analyses.

DNA Sequence Analysis

Phage DNA was digested with various restriction enzymes, and fragments homologous to the human α(1,3/1,4)fucosyltransferase cDNA were gel purified and ligated into the multicloning site of pTZ18R. Representative subclones were sequenced by the dideoxy chain determination method using T7 DNA polymerase (Pharmacia LKB Biotechnology, Inc.) and oligonucleotides synthesized according to flanking plasmid sequences and subsequently according to the insert sequence. This sequence data was used to generate additional synthetic deoxynucleotides which were then used to sequence remaining portions of the inserts. Sequence analysis was performed using the sequence analysis software package of the University of Wisconsin Genetics Computer Group.

Construction of Plasmid pCDNA1-Fuc-TV

A 1.94 kb EarI-XbaI fragment was isolated from a representative phage taken from a strongly hybridizing class of phages, made blunt with the Klenow fragment of E. coli DNA polymerase I, and cloned into the EcoRV and XbaI sites in the mammalian expression plasmid pCDNA1 (Invitrogen). One plasmid with a single insert in the sense orientation with respect to the plasmid's CMV promoter enhancer sequences was designated pCDNA1-Fuc-TV.

FACS Analysis

COS-1 cells transfected with plasmid DNAs were harvested 48–72 hours after transfection, and stained with monoclonal antibodies diluted in staining media. Anti-Lewis a and anti-H antibodies (mouse IgM monoclonal; antigen-affinity purified; Chembiomed, Edmonton) were used at 10 µg/ml. Anti-SSEA-1 (mouse monoclonal IgM; ascites) was used at a dilution of 1:1000. Anti-sialyl-Lewis x (mouse monoclonal IgM; HPLC purified from ascites) was used at 10 µg/ml. Anti-sialyl Lewis a (mouse monoclonal IgG3; ammonium sulfate precipitate of ascites) was used at a dilution of 1:500. Cells were then stained with fluorescein isothiocyanate-conjugated goat anti-mouse IgM or IgG, as appropriate, and were then subjected to analysis on a FAC-Scan (Becton-Dickinson).

Fucosyltransferase Assays

Cell extracts containing 1% Triton X-100 were prepared from transfected COS-1 cells. Fucosyltransferase assays were performed in a total volume of 20 µl, and contained 25 mM sodium cacodylate, pH6.2, 5 mM ATP, 10 mM L-fucose, 10 mM MnCl$_2$, 3 µM GDP-$^{14}$C-fucose, and 5 µl of cell extract. Acceptor substrates were added to a final concentration of 20 mM. Reactions were incubated at 37° C. for 1 hour and terminated by addition of 20 µl ethanol, followed by addition of 600 µl of distilled water. An aliquot of each reaction (50 µl) was subjected to scintillation counting to determine total radioactivity in the reaction. Another aliquot (200 µl) was applied to a column containing 400 µl of Dowex 1X2–400, formate form. The flow through fraction, and 2 µl of a subsequent water elution, were collected and pooled, and an aliquot was subjected to scintillation counting to quantitate incorporation of radioactive fucose into neutral product.

Example VI

Cloning and expression of a DNA sequence encoding a GDP-Fuc:β-D-Gal(1,4)-D-GlcNAc α(1,3) fucosyltransferase" (Fuc-TVI:DNA SEQ ID NO:13, protein SEQ ID NO:14) through cross hybridization.

Biochemical and genetic studies indicate that the human genome encodes two or more distinct GDP-L-fucose:β-D-Galactoside 3-α-L-Fucosyltransferases (Potvin et al, J. Biol. Chem., 265:1615–1622, 1990; Watkins, Adv. Hum. Genet., 10:1–116, 1980). the inventor has recently described a cloned cDNA that encodes one of these enzymes, that is thought to represent the product of the human Lewis blood group locus (Kukowska-Latallo et al, Genes Devel., 4:1288–1303, 1990) (DNA SEQ ID NO:1 and Protein SEQ ID NO:2). In consideration of the possibility that these GDP-L-fucose:β-D-Galactoside 3-α-L-Fucosyltransferases might be encoded by a family of structurally-related genes, the inventor sough to isolate other such members by cross-hybridization methods, using the cloned Lewis fucosyltransferase cDNA.

Figure 7A:
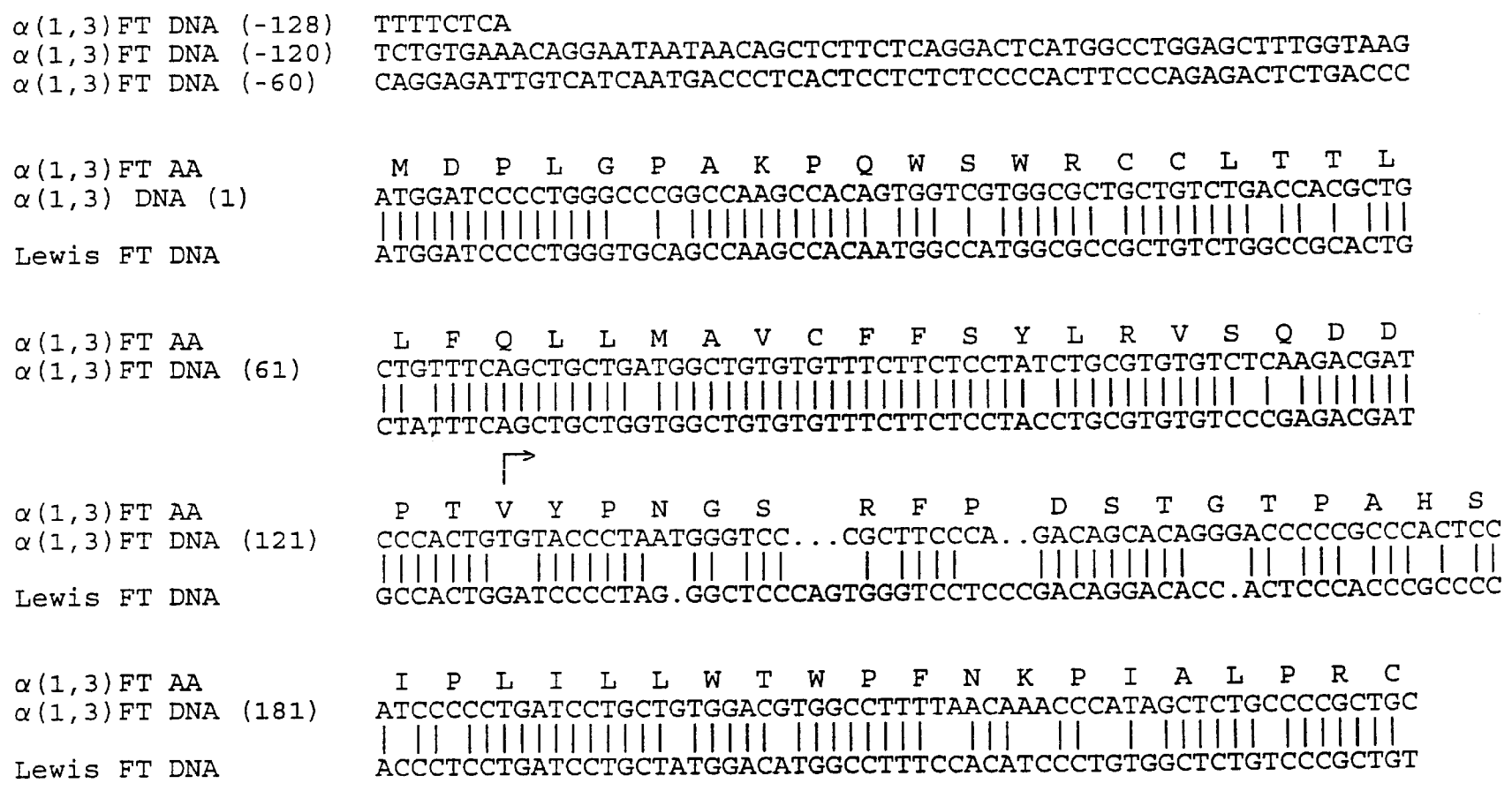

Molecular cloning of a human genomic DNA sectment that crosshybridizes to the Lewis blood group α(1,3/1,4) fucosyltransferase cDNA As noted above in Examples IV and V, low stringency Southern blot hybridization experiments indicate that the coding region of the Lewis fucosyltransferase cDNA detects strongly hybridizing restriction fragments, as well as several weakly hybridizing fragments. To further examine the molecular nature of these sequences, the inventor screened a human lambda phage genomic DNA library at low stringency with the Lewis cDNA probe. A total of 18 phages were isolated from phages representing approximately five human genomic equivalents. Southern blot analysis of 16 of these phages allowed them to be placed into three groups, based upon their restriction patterns and hybridization signal intensity strengths. Several phages representing a class with strong hybridization intensities were identified. Cross-hybridizing restriction fragments isolated from one of these phages was subcloned and sequenced. The homologous DNA restriction fragment maintains a single long open reading frame that predicts a polypentide with strong similarity to the Lewis blood group α(1,3/1,4) fucosyltransferase cDNA DNA sequence analysis of the cross-hybridizing subcloned fragment (SEQ ID NO:13) identified a single long open reading frame, beginning at base pair 1 and ending at base pair 1080 (FIG. 7). This reading frame begins with a methionine codon that is found within a sequence context consistent with Kozak's consensus rules for mammalian translation initiation. A hydropathy analysis of the protein sequence predicted by this reading frame (SEQ ID NO:14) predicts a single hydrophobic segment at its NH$_2$-terminus, suggesting that it represents a 359 amino acid protein (SEQ ID NO:14) that is predicted to maintain the type II transmembrane orientation typical of mammalian glycosyltransferases. Virtually the entire length of this reading frame shares a strikingly high amount of amino acid (not shown) and nucleic acid sequence identity with the corresponding portion of the Lewis fucosyltransferase cDNA (FIG. 7). Because of the substantial sequence similarity between these two DNA sequences, and their derived protein sequences, we expected this new cross-hybridizing sequence to represent a single exonic sequence, representing a heretofore undefined gene, that encodes a fucosyltransferase.

The homologous DNA restriction fragment determines expression of an α(1,3)fucosyltransferase To determine if this segment encodes a functional fucosyltransferase, a 1.2 kb fragment containing the entire open reading frame was generated by the polymerase chain reaction and was cloned into a mammalian expression vector, and the resulting plasmid (pCDNA1-Fuc-TVI) was introduced into mammalian host cells by transfection. COS-1 cells were used as hosts for these experiments since these cells normally express virtually undetectable α(1,3)- and α(1,4)fucosyltransferase activities (Kukowska-Latallo et al, Genes Devel., 4:1288–1303, 1990). Likewise, COS-1 cells do not normally express detectable amounts of cell surface Galβ1→4[Fucα(1→3)]GlcNAc-(Lewis x, SSEA-1) or Galβ1→3[Fucα(1→4)]GlcNAc-(Lewis a) moieties, whereas they do maintain surface-display of non-fucosylated type II and type I oligosaccharide precursors necessary for the construction of such molecules (Kukowska-Latallo et al, *Genes Devel.*, 4:1288–1303, 1990). The vector pCDNA1 was used since this plasmid efficiently transcribes exogenous, subcloned sequences in COS-1 hosts by virtue of the cytomegalovirus immediate early promoter sequences in the vector, and is maintained in these cells as a multicopy episome (Kukowska-Latallo et al, *Genes Devel.*, 4:1288–1303, 1990). COS-1 cells transfected with pCDNA1-Fuc-TVI were first analyzed by flow cytometry to detect de novo, vector-dependent surface expression of these oligosaccharides. A substantial fraction of these transfected cells exhibited bright staining with a monoclonal antibody directed against the Lewis x moiety (Galβ(1→4) [Fucα(1→3)]GlcNAc-) (FIG. 8), whereas cells transfected with the pCDNA1 vector without insert did not express this determinant. By contrast, COS-1 cells transfected with pCDNA1-Fuc-TVI, or with its control plasmid, did not stain with antibodies specific for the type I-based Lewis a trisaccharide (FIG. 8). Taken together, these results are consistent with the results of the DNA sequence analysis indicating that this segment encodes an α(1,3)fucosyltransferase competent to utilize neutral type II oligosaccharide precursor, but that the enzyme cannot utilize type I glycoconjugates and thus does not exhibit α(1,4)fucosyltransferase activity.

There is evidence supporting the possibility that one or more human α(1,3)fucosyltransferases exist that can utilize type II acceptors whose terminal galactose residues are substituted with α(2,3)sialic acid moieties (Potvin et-al, *J. Biol. Chem.*, 265:1615–1622, 1990; Holmes et al, *J. Biol. Chem.*, 261:3737–3743, 1986; Palcic et al, *Carbohyd. Res.*, 190:1–11, 1989). Such enzymes can fucosylate these molecules to form the sialyl-Lewis x determinant (NeuAcα(2→3)Galβ(1→4)[Fucα(1→3)]GlcNAc-). The Lewis fucosyltransferase, for example, is competent to perform this reaction (Palcic et al, *Carbohyd. Res.*, 190:1–11, 1989; Lowe et al, *Cell*, 63:475–484, 1990). It was therefore of interest to determine if the fucosyltransferase apparently encoded by plasmid pCDNA1-α(1,3)Fuc-TVI would be capable of constructing sialyl-Lewis x determinants. COS-1 cells maintain surface-expressed glycoconjugates terminating in (NeuAcα(2,3)Galβ(1,4)GlcNAc- (Lowe et al, *Cell*, 63:475–484, 1990; Fukuda et al, *J. Biol. Chem.*, 263:5314–5318, 1988); these represent acceptor substrates for sialyl-Lewis x construction determined via the action of enzymes encoded by transfected fucosyltransferase expression vectors (Lowe et al, *Cell*, 63:475–484, 1990). COS-1 cells were therefore transfected with plasmid pCDNA1-Fuc-TVI, stained with a monoclonal anti-sialyl Lewis x antibody, and subjected to flow cytometry analysis. A significant amount of staining was detected, relative to control cell transfected with the vector alone, or relative to pCDNA1-Fuc-TVI-transfected cells stained with a negative control antibody (anti-H, FIG. 8). However, these cells did not stain with an antibody specific for the type I-based, sialyl-Lewis a determinant (NeuAcα(2,3)Galβ(1,3)[Fucα(1,4)]GlcNAc-) (FIG. 8). By contrast, the inventor has previously demonstrated that a substantial fraction of COS-1 cells transfected with the Lewis fucosyltransferase expression plasmid pCDM7-α(1,3/1,4)FT exhibit bright staining with the sialyl-Lewis x and sialyl-Lewis a antibodies (Lowe et al, *Cell*, 63:475–484, 1990), as predicted by biochemical analysis of the acceptor substrate specificity of this enzyme (Palcic et al, *Carbohyd. Res.*, 190:1–11, 1989).

The conclusion that plasmid pCDNA1-Fuc-TVI encodes an α(1,3)fucosyltransferase was confirmed by biochemical analysis of the acceptor substrate requirements of the enzyme in extracts of COS-1 cells transfected with plasmid pCDNA1-Fuc-TVI. As expected, the enzyme in these extracts utilized the type II disaccharide acceptor N-acetyllactosmine, to yield the predicted product Galβ (1→4)[Fucα(1→3)]GlcNAc. The enzyme also efficeintly utilized the trisaccharide NeuAcα(2,3)Galβ(1,4)GlcNAc to form the sialyl Lewis X tetrasaccharide (Table 2). Under these conditions, other type II molecules, including lactose, and the α(1,2)fucosylated type II acceptor Fucα(1→2)Galβ (1→4)Glc, did not function as acceptor substrates for the fucosyltransferase in these extracts, with any detectable efficiency. The type I substrate lacto-N-biose I was also not utilized by this enzyme. This suggests that the enzyme can function effectively only as an α(1,3)fucosyltransferase, as also suggested by the flow cytometry analyses. The acceptor preferences exhibited by this enzyme contrast significantly with those exhibited by the Lewis fucosyltransferase, which is able to efficiently utilize each of the four acceptors tested (Kukowska-Latallo et al, *Genes Devel.*, 4:1288–1303, 1990; Mollicone et al, *Eur. J. Biochem.*, 191:169–176, 1990). Taken together with the results of the flow cytometry analyses presented in FIG. 8, and DNA sequence analysis, these biochemical experiments, summarized in Table 2, indicate that plasmid pCDNA1-Fuc-TVI encodes a novel fucosyltransferase with its own distinct acceptor specificity.

Since the protein sequence of Fuc-TVI is so very similar to the sequences of FUC-TV and FUC-TIII, it may be expected that a catalytically active, secreted protein A-Fuc-TVI fusion porotein may be generated by fusing residues 43 through 359 of Fuc-TVI (SEQ ID NO:14) to the protein A segment, in a manner identicial to that used to generate pPROTA-α(1,3/1,4)FT:, and pPROTA-Fuc-TV$_c$.

Experimental Procedures for Example VI "Cloning and expression of a DNA sequence encoding GDP-Fuc-β-D-Gal (1,4)-D-GlcNAc α(1,3) fucosyltransferaseI" (Fuc-TVI; DNA SEQ ID NO:14. protein SEQ ID NO:15) through cross hybridation Cell Culture The source and growth conditions of COS-1 cells are as previously described (Ernst et al, *J. Biol. Chem.*, 265:3436–3447, 1989; Rajan et al, *J. Biol. Chem.*, 264:11158–11167, 1989).

Antibodies

The anti-Lex antibody anti-SSEA-1 (Solter et al, *Proc. Natl. Acad. Sci. USA*, 75:5565–5569, 1978) (mouse monoclonal IgM as ascites) was provided by Dr. Davor Solter (Wistar Institute, Philadelphia). Anti-H and anti-Lewis a antibodies (mouse monoclonal IgM, antigen affinity purified) were purchased from Chembiomed Ltd. (Edmonton, Alberta). Anti-sialyl Lewis x antibody CSLEX1 (Fukushima et al, *Cancer Res.*, 44:5279–5285, 1984) (mouse monoclonal IgM, HPLC purified) and anti-sialyl Lewis a antibody CSLEA1 (Galton et al, *Ninth Int. Convoc. Immuno.*, Amherst, N.Y., pp. 117–125, Karger, Basel; Chia et al, *Cancer Res.*, 45:435–437, 1985) (mouse monoclonal IgG3, ammonium sulfate precipitate) were provided by Dr. P. Terasaki (UCLA, Los Angeles). A pooled mouse IgG antibody preparation (MsIg) was purchased from Coulter. Fluorescein-conjugated goat anti-mouse IgM or IgG antibodies were purchased from Sigma.

Human Genomic Library Construction

High molecular weight human genomic DNA was prepared from peripheral blood leukocytes as described previously (Ernst et al, *J. Biol. Chem.*, 265:3436–3447, 1989). Genomic DNA was subjected to partial digestion with the restriction endonuclease Sau3A. The partially digested genomic DNA was size fractionated by ultracentrifugation through a sodium chloride gradient. Fractions enriched for DNA fragments between 8 Kb and 20 Kb were ligated to XhoI digested lambda FIX (Stratagene) phage arms that had been partially filled in with dTTP and dCTP to make the ends compatible with the Sau3A fragments. The ligation mixture was packaged in vitro with commercial packaging extracts (Stratagene), titered on *E. coli* host TAP90 (Patterson et al, *Nucl. Acids. Res.*, 15:6298, 1987). Approximately $1.0 \times 10^6$ recombinant lambda phage were screened by plaque hybridization. Plaque lifts were prepared using nitrocellulose filters (Schleicher and Schuell) and were prehybridized at 42° C. for 16 hours in 50% formamide, 5X SSC, 10X Denhart's solution, and 0.1% SDS. Filters were hybridized for 72 hours at 35° C. in prehybridization solution containing 10% dextran sulfate, and 100 micrograms per ml denatured salmon sperm DNA. The probe consisted of a 1.7 Kb XhoI-XbaI fragment isolated from the 5' end of a cDNA insert encoding the Lewis blood group α(1,3/1,4) fucosyltransferase (Kukowska-Latallo et al, *Genes Devel.*, 4:1288–1303, 1990), which was labeled (Feinberg et al, *Anal. Biochem.*, 132:6–13, 1983) with [α-$^{32}$P] dCTP. The filters were rinsed three times for 20 minutes each at room temperature in 2X SSC and then once for 40 minutes at 50° C. and 1X SSC, 0.5% SDS. Filters were then subjected to autoradiography. Eighteen independent hybridization-positive plaques were identified after 2 additional cycles of plaque hybridization. Phage DNAs were prepared from liquid lysates (Maniatis et al, *Molecular Cloning: A Laboratory Manual*, Cold Spring Harbor Lab., Cold Spring Harbor, N.Y., 1982) and were subsequently characterized by restriction endonuclease digestions and Southern blot analyses.

DNA Sequence Analysis

Phage DNA was digested with various restriction enzymes, and fragments homologous to the human α(1,3/1,4)fucosyltransferase cDNA were gel purified and ligated into the multicloning site of pTZ18. Representative subclones were sequenced by the dideoxy chain determination method (Sanger et al, *Proc. Natl. Acad. Sci. USA*, 74:5463–5467, 1977) using T7 DNA polymerase (Pharmacia LKB Biotechnology, Inc.) and oligonucleotides synthesized according to flanking plasmid sequences and subsequently according to the insert sequence. This sequence data was used to generate additional synthetic deoxynucleotides which were then used to sequence remaining portions of the inserts. Sequence analysis was performed using the sequence analysis software package of the University of Wisconsin Genetics Computer Group (Devereux et al, *Nucl. Acids. Res.*, 12:387–395, 1984).

Transfection and expression of the insert in pCDNA1-Fuc-TVI

A 1.2 kb fragment was generated by the PCR, using DNA isolated from a representative phage taken from a strongly hybridizing class of phages, and cloned into the HindIII site in the mammalian expression plasmid pCDNA1 (Invitrogen). One plasmid with a single insert in the sense orientation with respect to the plasmid's CMV prmnoter enhancer sequences was designated pCDNA1-Fuc-TVI.

FACS Analysis

COS-1 cells transfected with plasmid DNAs were harvested (Rajan et al, *J. Biol. Chem.*, 264:11158–11167, 1989) 48–72 hours after transfection, and stained with monoclonal antibodies diluted in staining media, as previously described (Kukowska-Latallo et al, *Genes Devel.*, 4:1288–1303, 1990; Ernst et al, *J. Biol. Chem.*, 265:3436–3447, 1989). Anti-Lewis a and anti-H antibodies (mouse IgM monoclonal; antigen-affinity purified; Chembiomed, Edmonton) were used at 10 μg/ml. Anti-SSEA-1 (mouse monoclonal IgM; ascites) was used at a dilution of 1:1000. Anti-sialyl-Lewis x (mouse monoclonal IgM; HPLC purified from ascites) was used at 10 μg/ml. Anti-sialyl lewis a (mouse monoclonal IgG3; ammonium sulfate precipitate of ascites) was used at a dilution of 1:1000. Control mouse IgG3 antibody (MsIg, Coulter) was used at a concentration of 10 μg/ml. Anti-VIM-2 antibody (mouse monoclonal IgM; ascites) was used at a dilution of 1:200. Cells were then stained with fluorescein isothiocyanate-conjugated goat anti-mouse IgM or IgG, as appropriate, and were then subjected to analysis on a FACScan (Becton-Dickinson), as described previously (Kukowska-Latallo et al, *Genes Devel.*, 4:1288–1303, 1990).

Fucosyltransferase Assays

Cell extracts containing 1% Triton X-100 were prepared from transfected COS-1 cells, using procedures described previously (Kukowska-Latallo et al, *Genes Devel.*, 4:1288–1303, 1990). Fucosyltransferase assays were performed in a total volume of 20 μl, and contained 50 mM sodium cacodylate, pH 6.2, 5 mM ATP, 10 mM fucose, 20 mM $MnCl_2$, 3 μM GDP-$^{14}$C-fucose, and 5 μl (30 μg protein) of cell extract. Acceptor substrates were added to a final concentration of 20 mM. Reactions were incubated at 37° C. for 1 hour and terminated by addition of 20 μl ethanol, followed by addition of 600 μl of distilled water. An aliquot of each reaction (50 μl) was subjected to scintillation counting to determine total radioactivity in the reaction. Another aliquot (200 μl) was applied to a column containing 400 μl of Dowex 1X2–400, formate form (Rajan et al, *J. Biol. Chem.*, 264:11158–11167, 1989). The flow through fraction, and 2 μl of a subsequent water elution, were collected and pooled, and an aliquot was subjected to scintillation counting to quantitate incorporation of radioactive fucose into neutral product.

TABLE 4

Substrate Utilzation Properties of Human α(1,3)Fucosyltransferases

| Acceptor substrate | Product Name | Relative Activity (%) with each α(1,3)Fucosyltransferase | | | |
| --- | --- | --- | --- | --- | --- |
| | | Fuc-TIII | Fuc-TIV | Fuc-TV | Fuc-TVI |
| N-acetyllactosamine (20 mM) | Lewis x | 100 | 100 | 100 | 100 |
| lactose (20 mM) | Lewis x | 145 | 3 | 11 | <1 |
| α(2,3)sialyllactosamine (20 mM) | sialyl Lewis x | 56 | <1 | 115 | 110 |

TABLE 4-continued

Substrate Utilzation Properties of Human α(1,3)Fucosyltransferases

| Acceptor substrate | Product Name | Relative Activity (%) with each α(1,3)Fucosyltransferase | | | |
|---|---|---|---|---|---|
| | | Fuc-TIII | Fuc-TIV | Fuc-TV | Fuc-TVI |
| 2'-fucosyllactose (5 mM) | Lewis y | 254 | 6 | 42 | <1 |
| lacto-N-biose I (20 mM) | Lewis a | 420 | <1 | 10 | <1 |

Table 2 presents the relative product formation rates obtained with low molecular weight acceptor substrates using cell extracts containing recombinant human α(1,3) fucosyltransferases expressed in transfected COS-1 cells, as described in the preceding sections. Fucosyltransferase assays were performed as described in detail in Lowe et al, *J. Biol. Chem.*, (1991), 266:17467–17477; Weston et al, *J. Biol. Chem.* (1992), 267:4152–4160; and Kukowska-Latallo et al, *Genes. Devel.*, (1990), 4:1288–1303. For each enzyme, the same extract was used, with saturating amounts of each acceptor oligosaccharide (20 mM, except for 2'-fucosylactose which was used at 5 mM), and GDP-[$^{14}$C] fucose was present at 3 μM. Reaction times and enzyme amounts were adjusted to ensure a linear rate of product formation (less than 15% of the GDP-fucose substrate consumed). Products were separated by column chromatography and quantitated by liquid scintillation counting, and their structures were confirmed by high performance liquid chromatography, as described in Lowe et al, *J. Biol. Chem.*, (1991), 266:17467–17477; Weston et al, *J. Biol. Chem.* (1992), 267:4152–4160; and Kukowska-Latallo et al, *Genes. Devel.*, (1990), 4:1288–1303.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. An isolated DNA fragment, comprising a nucleotide sequence which encodes the amino acid sequence of SEQ ID NO:11.

2. The DNA fragment of claim 1, wherein said nucleotide sequence has the sequence of SEQ ID NO:10.

3. The DNA fragment of claim 1, wherein said nucleotide sequence has the sequence of from position 247 to position 1111 of SEQ ID NO:10.

4. A vector, comprising a DNA sequence which encodes the amino acid sequence of SEQ ID NO:11.

5. The vector of claim 4, wherein said DNA sequence comprises from base 247 to base 1111 of SEQ ID NO:10.

6. The vector of claim 4, wherein said DNA sequence comprises SEQ ID NO:10.

7. A transformed microorganism, comprising a vector, said vector comprising a DNA sequence which encodes the amino acid sequence of SEQ ID NO:11.

8. The transformed microorganism of claim 7, wherein said DNA sequence comprises from base 247 to base 1111 of SEQ ID NO:10.

9. The transformed microorganism of claim 7, wherein said DNA sequence comprises SEQ ID NO:10.

10. An isolated DNA fragment, comprising a nucleotide sequence which encodes the amino acid sequence of from position 43 to position 374 of SEQ ID NO:11.

11. The DNA fragment of claim 10, wherein said nucleotide sequence has the sequence of SEQ ID NO:10.

12. The DNA fragment of claim 10, wherein said nucleotide sequence has the sequence of from position 247 to position 1111 of SEQ ID NO:10.

13. A vector, comprising a DNA sequence which encodes the amino acid sequence of from position 43 to position 374 of SEQ ID NO:11.

14. The vector of claim 13, wherein said DNA sequence comprises from base 247 to base 1111 of SEQ ID NO:10.

15. The vector of claim 13, wherein said DNA sequence comprises SEQ ID NO:10.

16. A transformed microorganism, comprising a vector, said vector comprising a DNA sequence which encodes the amino acid sequence of from position 43 to position 374 SEQ ID NO:11.

17. The transformed microorganism of claim 16, wherein said DNA sequence comprises from base 247 to base 1111 of SEQ ID NO:10.

18. The transformed microorganism of claim 16, wherein said DNA sequence comprises SEQ ID NO:10.

* * * * *

UNITED STATES PATENT AND TRADEMARK OFFICE
CERTIFICATE OF CORRECTION

PATENT NO. : 5,955,347

DATED : September 21, 1999

INVENTOR(S): John B. LOWE

It is certified that an error appears in the above-identified patent and that said Letters Patent is hereby corrected as shown below:

Column 1, before line 8, insert:
--This invention is supported by the National Institutes of Health under Grant No. GM 47455. The U.S. Government may have certain rights to this invention.--

Column 15, line 28, "wbich" should read --which--.

Column 33, line 8, "residues residues" should read --residues--.

Column 64, line 39, "Glvcosylated" should read --Glycosylated--.

Column 65, line 40, "transqlycosylation" should read --transglycosylation--.

Column 66, line 44, "withchromatographic" should read --with chromatographic--.

Column 69, line 53, "GDP-[$^{14}$C fucose," should read --GDP-[$^{14}$C] fucose,--.

Column 73, line 48, "presentce" should read --presence--.

Column 74, line 19, "exhbited" should read --exhibited--.

Column 79, line 28, "Fucosvltransferase" should read --Fucosyltransferase--.

UNITED STATES PATENT AND TRADEMARK OFFICE
CERTIFICATE OF CORRECTION

PATENT NO. : 5,955,347
DATED : September 21, 1999
INVENTOR(S): John B. LOWE

It is certified that an error appears in the above-identified patent and that said Letters Patent is hereby corrected as shown below:

Column 84, line 12, "sectment" should read --segment--; and
line 14, "cDNA As" should read --cDNA - As--.

Column 85, line 16, "monocional" should read --monoclonal--.

Column 88, line 8, "prmnoter" should read --promoter--.

Signed and Sealed this

Seventeenth Day of April, 2001

Attest:

NICHOLAS P. GODICI

Attesting Officer

Acting Director of the United States Patent and Trademark Office